（12） United States Patent
Shen et al.

(10) Patent No.: US 11,104,690 B2
(45) Date of Patent: *Aug. 31, 2021

(54) INDAZOLE DERIVATIVES USEFUL AS INHIBITORS OF DIACYLGLYCERIDE O-ACYLTRANSFERASE 2

(71) Applicants: Merck Sharp & Dohme Corp., Rahway, NJ (US); Dong-Ming Shen, Edison, NJ (US); Thomas H. Graham, Quincy, MA (US); Wensheng Liu, Edison, NJ (US); Clare Tudge, Wayne, PA (US); Andreas Verras, New York, NY (US); Jinlong Jiang, Scotch Plains, NJ (US)

(72) Inventors: Dong-Ming Shen, Edison, NJ (US); Thomas H. Graham, Quincy, MA (US); Wensheng Liu, Edison, NJ (US); Clare Tudge, Wayne, PA (US); Andreas Verras, New York, NY (US); Jinlong Jiang, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/461,902

(22) PCT Filed: Nov. 13, 2017

(86) PCT No.: PCT/US2017/061223
§ 371 (c)(1),
(2) Date: May 17, 2019

(87) PCT Pub. No.: WO2018/093696
PCT Pub. Date: May 24, 2018

(65) Prior Publication Data
US 2019/0330239 A1    Oct. 31, 2019

Related U.S. Application Data

(60) Provisional application No. 62/424,066, filed on Nov. 18, 2016.

(51) Int. Cl.
| | |
|---|---|
| *C07D 515/08* | (2006.01) |
| *C07D 409/12* | (2006.01) |
| *C07D 401/12* | (2006.01) |
| *C07D 403/12* | (2006.01) |
| *C07D 231/56* | (2006.01) |
| *C07D 405/12* | (2006.01) |
| *C07D 487/04* | (2006.01) |
| *C07D 417/12* | (2006.01) |
| *C07D 413/12* | (2006.01) |
| *C07D 409/14* | (2006.01) |

(52) U.S. Cl.
CPC ......... *C07D 515/08* (2013.01); *C07D 231/56* (2013.01); *C07D 401/12* (2013.01); *C07D 403/12* (2013.01); *C07D 405/12* (2013.01); *C07D 409/12* (2013.01); *C07D 409/14* (2013.01); *C07D 413/12* (2013.01); *C07D 417/12* (2013.01); *C07D 487/04* (2013.01)

(58) Field of Classification Search
CPC .................................................... C07D 231/56
See application file for complete search history.

(56) References Cited

U.S. PATENT DOCUMENTS

| 6,262,040 B1 | 7/2001 | Marfat | |
| 8,569,512 B2 * | 10/2013 | Burgey | ............... A61K 31/415 548/361.1 |

(Continued)

FOREIGN PATENT DOCUMENTS

| EP | 2210891 A1 | 7/2010 |
| EP | 2884977 B1 | 10/2017 |

(Continued)

OTHER PUBLICATIONS

International Search Report, PCTUS17061223, dated Feb. 14, 2018, 16 pages.
Belikov, V.G., Pharmaceutical Chemistry, Moscow MEDpress—inform, 2007, 27-29, 4th Edition.
Sato, Kenjiro et al., Discovery of a Novel Series of N-Phenylindoline-5-sulfonamide Derivatives as Potent, Selective, and Orally Bioavailable Acyl CoA:Monoacylglycerol Acyltransferas-2 Inhibitors, Journal of Medicinal Chemistry, 2015, 3892-3909, 58(9).

*Primary Examiner* — Kamal A Saeed
(74) *Attorney, Agent, or Firm* — Sarah L. Hooson; Catherine D. Fitch

(57) ABSTRACT

The present invention relates to a compound represented by formula I': and pharmaceutically acceptable salts thereof. The compounds of formula I are inhibitors of diacylglyceride O-acyltransferase 2 ("DGAT2") and may be useful in the treatment, prevention and suppression of diseases mediated by DGAT2. The compounds of the present invention may be useful in the treatment of hepatic steatosis, diabetes mellitus, obesity, hyperlipidemia, hypercholesterolemia, atherosclerosis, cardiorenal diseases such as chronic kidney diseases and heart failure and related diseases and conditions.

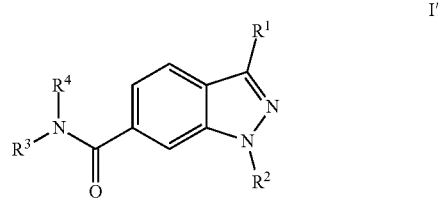

9 Claims, No Drawings

(56) References Cited

U.S. PATENT DOCUMENTS

| | | |
|---|---|---|
| 2006/0189606 A1 | 8/2006 | Karp et al. |
| 2009/0286791 A1 | 11/2009 | Kitamura et al. |
| 2013/0184261 A1 | 7/2013 | Dorsch et al. |

FOREIGN PATENT DOCUMENTS

| | | |
|---|---|---|
| RU | 2015108935 A | 10/2016 |
| WO | 2006019831 A1 | 2/2006 |
| WO | 2006117314 | 11/2006 |
| WO | 2007084413 | 7/2007 |
| WO | 2007084435 | 7/2007 |
| WO | 2008015125 | 2/2008 |
| WO | 2008088692 | 7/2008 |
| WO | 2009058298 | 5/2009 |
| WO | 2009058299 | 5/2009 |
| WO | 2010051188 | 5/2010 |
| WO | 2010107765 | 9/2010 |
| WO | 2010111058 | 9/2010 |
| WO | 2010111059 | 9/2010 |
| WO | 2010111060 | 9/2010 |
| WO | 2010118009 | 10/2010 |
| WO | 2016036633 | 3/2016 |
| WO | 2016036636 | 3/2016 |
| WO | 2016036638 | 3/2016 |
| WO | 2016187384 | 11/2016 |

\* cited by examiner

INDAZOLE DERIVATIVES USEFUL AS INHIBITORS OF DIACYLGLYCERIDE O-ACYLTRANSFERASE 2

CROSS-REFERENCE TO RELATED APPLICATIONS

This application is a U.S. National Phase application under 35 U.S.C. § 371 of PCT/US2017/061223 filed on Nov. 13, 2017, which claims priority to US 62/424,066 filed on Nov. 18, 2016, the contents of which are hereby incorporated by reference in their entireties.

FIELD OF THE INVENTION

The present invention is directed to indazole derivative compounds which inhibit diacylglyceride O-acyltransferase 2 ("DGAT2"), and may be useful for preventing, treating or acting as a remedial agent for hepatic steatosis, type-2 diabetic mellitus, obesity, hyperlipidemia, hypercholesterolemia, atherosclerosis, nonalcoholic steatohepatitis (NASH), cardiorenal diseases such as chronic kidney diseases and heart failure, and related diseases and conditions, as well as methods of making such compounds and pharmaceutical compositions comprising such a compound and a pharmaceutical carrier.

BACKGROUND OF THE INVENTION

Triacylglycerols ("TGs") serve several functions in living organisms. One such function of TGs is in the storage of energy. TGs also play a role in the synthesis of membrane lipids. TG synthesis in cells may protect them from the potentially toxic effects of excess fatty acid ("FA"). In enterocytes and hepatocytes, TGs are synthesized for the assembly and secretion of lipoproteins which transport FA between tissues. TGs play a role in the skin's surface water barrier, and TGs in adipose tissue provide insulation for organisms.

The glycerol phosphate and the monoacylglycerol pathways are the major pathways for the biosynthesis of TG. However, the last step in the synthesis of TG involves the reaction of a fatty acyl-CoA and diacylglycerol ("DG") to form TG. The reaction is catalyzed by acyl-CoA:diacylglycerol acyltransferase ("DGAT") enzymes. There have been identified two DGAT enzymes, DGAT1 and DGAT2, Although DGAT1 and DGAT2 catalyze the same reaction, they differ significantly at the level of DNA and protein sequences.

DGAT2 is an integral membrane protein of the endoplasmic reticulum ("ER") and is expressed strongly in adipose tissue and the liver. DGAT2 appears to be the dominant DGAT enzyme controlling TG homeostasis in vivo. DGAT2 deficient mice survive for only a few hours after birth. On the other hand, DGAT1 deficient mice are viable.

In a study, DGAT2 knockdown in ob/ob mice with a DGAT2 gene-specific antisense oligonucleotide resulted in a dose dependent decrease in very low density lipoprotein ("VLDL") and a reduction in plasma TG, total cholesterol, and ApoB. Liu, et al., *Biochim. Biophys Acta* 2008, 1781, 97. In the same study, DGAT2 antisense oligonucleotide treatment of ob/ob mice showed a decrease in weight gain, adipose weight and hepatic TG content. Id. In another study, antisense treatment of ob/ob mice improved hepatic steatosis and hyperlipidemia. Yu, et al., *Hepatology*, 2005, 42, 362. In another study, diet-induced hepatic steatosis and insulin resistance was improved by knocking down DGAT2 in rats. Choi et al., *J. Bio. Chem.*, 2007, 282, 22678.

In light of the above description, inhibitors of DGAT2 may be considered useful as agents for treating and/or preventing hepatic steatosis, diabetes mellitus, obesity, hyperlipidemia, hypercholesterolemia, atherosclerosis, non-alcoholic steatohepatitis (NASH), cardiorenal diseases such as chronic kidney diseases and heart failure and related diseases and conditions.

SUMMARY OF THE INVENTION

The present invention relates to compounds represented by Formula I:

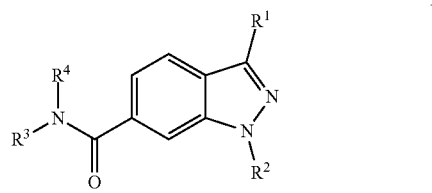

as well as pharmaceutically acceptable salts thereof, and pharmaceutical compositions comprising a compound of Formula I.

The present invention further relates to methods of treating hepatic steatosis, diabetes mellitus, obesity, hyperlipidemia, hypercholesterolemia, atherosclerosis, nonalcoholic steatohepatitis (NASH), cardiorenal diseases such as chronic kidney diseases and heart failure and related diseases and conditions, comprising administering a compound of formula I to a patient in need thereof.

DETAILED DESCRIPTION OF THE INVENTION

The present invention is directed to compounds having structural Formula I:

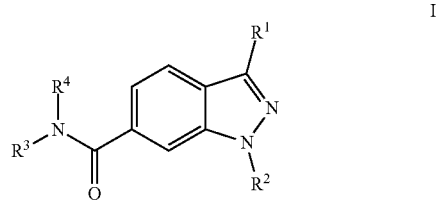

or pharmaceutically acceptable salts thereof wherein:
$R^1$ is
  (1) aryl unsubstituted or substituted by 1, 2, or 3 $R^5$, or
  (2) 5- or 6-membered heteroaryl containing 1, 2 or 3 heteroatoms independently selected from N, O, and S, wherein the heteroaryl is unsubstituted or substituted by 1, 2, or 3 $R^5$;
$R^2$ is
  (1) aryl unsubstituted or substituted by 1, 2, or 3 $R^5$,
  (2) 5- or 6-membered heteroaryl containing 1, 2 or 3 heteroatoms independently selected from N, O, and S, wherein the heteroaryl is unsubstituted or substituted by 1, 2, or 3 $R^7$,
  (3) $(C_{1-6})$alkyl, (4) 4- to 6-membered heterocyclyl containing 1 or 2 heteroatoms independently selected from N, O and S, or
(5) —CH$_2$-aryl, wherein the aryl is unsubstituted or substituted by 1, 2, or 3 R$^1$;

R$^3$ is
(1) 4- to 7-membered heterocyclyl containing 1 or 2 heteroatoms independently selected from N, O and S,
(2) 5- or 6-membered heteroaryl containing 1, 2 or 3 heteroatoms independently selected from N, O, and S,
(3) —(C$_{1-6}$)alkyl-heteroaryl, wherein the heteroaryl is a 5- or 6-membered heteroaryl containing 1, 2 or 3 heteroatoms independently selected from N, O and S,
(4) —(C$_{1-6}$)alkyl-aryl,
(5) —(C$_{1-6}$)alkyl-heterocyclyl, wherein the heterocyclyl is a 3- to 6-membered ring containing 1 or 2 heteroatoms independently selected from N, O and S,
(6) (C$_{1-6}$)alkyl,
(7) —(C$_{1-6}$)alkyl-C(O)O—(C$_{1-4}$)alkyl,
(8) —(C$_{1-6}$)alkyl-S(O)$_2$—NR$^{9a}$R$^{9b}$,
(9) —(C$_{1-6}$)alkyl-S(O)$_2$—(C$_{1-3}$)alkyl,
(10) —(C$_{1-3}$)alkyl-heteroaryl, wherein the heteroaryl is a 8- to 10-membered fused ring, and wherein the heteroaryl contains 1, 2, 3, or 4 heteroatoms independently selected from N, O, and S,
(11) —(C$_{1-6}$)alkyl-S(O)$_2$—(C$_{3-6}$)cycloalkyl,
(12) —(C$_{1-6}$)alkyl-(C$_{3-6}$)cycloalkyl,
(13) (C$_{3-6}$)cycloalkyl, or
(14) fused aryl,
wherein each aryl, heteroaryl, cycloalkyl, or heterocyclyl are unsubstituted or substituted by 1, 2, or 3 R$^6$, and wherein each alkyl is unsubstituted or substituted by R$^8$;

R$^4$ is
(1) hydrogen,
(2) (C$_{1-3}$)alkyl,
or R$^3$ and R$^4$ combine along with the nitrogen atom to which they are attached to form a mono- or bicyclic heterocyclyl ring containing 1 or 2 heteroatoms independently selected from N, O and S, wherein the heterocyclyl ring is unsubstituted or substituted by 1, 2, or 3 R$^6$;

R$^5$ is
(1) cyano,
(2) halo,
(3) (C$_{1-6}$)alkyl,
(4) —C(O)NH$_2$,
(5) (C$_{3-6}$)cycloalkyl,
(6) hydroxy,
(7) (C$_{1-6}$)alkoxy-,
(8) —NR$^{10a}$R$^{10b}$,
(9) halo(C$_{1-6}$)alkyl-, or
(10) halo(C$_{1-6}$)alkoxy-;

R$^6$ is
(1) (C$_{1-3}$)alkyl,
(2) halo(C$_{1-3}$)alkyl-,
(3) oxo,
(4) (C$_{3-6}$)cycloalkyl,
(5) —C(O)O—(C$_4$)alkyl,
(6) NH$_2$,
(7) hydroxy,
(8) phenyl unsubstituted or substituted by halo,
(9) hydroxy(C$_{1-3}$)alkyl-,
(10) cyano, or
(11) halo;

R$^7$ is
(1) (C$_{1-6}$)alkyl,
(2) halo,
(3) (C$_{1-3}$)alkoxy-,
(4) halo(C$_{1-3}$)alkyl-,
(5) (C$_{3-6}$)cycloalkyl, or
(6) —C(O)O—(C$_{1-3}$)alkyl;

R$^8$ is
(1) (C$_{1-3}$)alkyl,
(2) hydroxy(C$_{1-3}$)alkyl-,
(3) (C$_{1-3}$)alkoxy-,
(4) hydroxy,
(5) halo(C$_{1-3}$)alkyl-,
(6) (C$_{1-3}$)alkyl-S—, or
(7) phenyl;

R$^{9a}$ and R$^{9b}$ are independently
(1) hydrogen,
(2) (C$_{1-3}$)alkyl,
(3) —(C$_{1-3}$)alkyl-phenyl,
(4) 5- or 6-membered heteroaryl containing 1, 2, or 3 heteroatoms independently selected from N, O, and S, or
(5) phenyl;

R$^{10a}$ and R$^{10b}$ are independently
(1) hydrogen, or
(2) (C$_{1-3}$)alkyl.

The present invention is directed to compounds having structural Formula I':

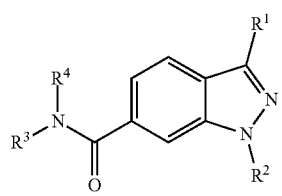

or pharmaceutically acceptable salts thereof wherein:
R$^1$ is
(1) 6-membered aryl unsubstituted or substituted by 1, 2, or 3 R$^5$, or
(2) 5-, 6- or 9-membered heteroaryl or 9-membered bicyclic heterocycle, containing 1, 2 or 3 heteroatoms independently selected from N, O, and S, wherein the heteroaryl is unsubstituted or substituted by 1, 2, or 3 R$^5$;

R$^2$ is
(1) 6-membered aryl unsubstituted or substituted by 1, 2, or 3 R$^7$,
(2) 5- or 6-membered heteroaryl containing 1, 2 or 3 heteroatoms independently selected from N, O, and S, wherein the heteroaryl is unsubstituted or substituted by 1, 2, or 3 R$^7$,
(3) (C$_{1-6}$)alkyl,
(4) 4- to 6-membered heterocyclyl containing 1 or 2 heteroatoms independently selected from N, O and S, or
(5) —CH$_2$-6-membered aryl, wherein the aryl is unsubstituted or substituted by 1, 2, or 3 R$^7$;

R$^3$ is
(1) 4- to 7-membered heterocyclyl containing 1 or 2 heteroatoms independently selected from N, O and S,
(2) 5- or 6-membered heteroaryl containing 1, 2 or 3 heteroatoms independently selected from N, O, and S,
(3) —(C$_{1-6}$)alkyl-heteroaryl, wherein the heteroaryl is a 5- or 6-membered heteroaryl containing 1, 2 or 3 heteroatoms independently selected from N, O and S,
(4) —(C$_{1-6}$)alkyl-6-membered aryl, (5) —(C$_{1-6}$)alkyl-heterocyclyl, wherein the heterocyclyl is a 3- to 6-membered ring containing 1 or 2 heteroatoms independently selected from N, O and S,
(6) (C$_{1-6}$)alkyl,
(7) —(C$_{1-6}$)alkyl-C(O)O—(C$_{1-4}$)alkyl,
(8) —(C$_{1-6}$)alkyl-S(O)$_2$—NR$^{9a}$R$^{9b}$,
(9) —(C$_{1-6}$)alkyl-S(O)$_2$—(C$_{1-3}$)alkyl,
(10) —(C$_{1-3}$)alkyl-heteroaryl, wherein the heteroaryl is a 8- to 10-membered fused ring, and wherein the heteroaryl contains 1, 2, 3, or 4 heteroatoms independently selected from N, O, and S,
(11) —(C$_{1-6}$)alkyl-S(O)$_2$—(C$_{3-6}$)cycloalkyl,
(12) —(C$_{1-6}$)alkyl-S(O)$_2$—NR$^{9a}$—(C$_{3-6}$ cycloalkyl,
(13) —(C$_{1-6}$)alkyl-(C$_{3-6}$)cycloalkyl,
(14) (C$_{3-6}$)cycloalkyl, or
(15) 9- to 10-membered fused aryl,
wherein each aryl, heteroaryl, cycloalkyl, or heterocyclyl are unsubstituted or substituted by 1, 2, or 3 R$^6$, and wherein each alkyl is unsubstituted or substituted by 1-3 R$^8$;
R$^4$ is
(1) hydrogen,
(2) (C$_{1-3}$)alkyl,
or R$^3$ and R$^4$ combine along with the nitrogen atom to which they are attached to form a 4- to 7-membered mono- or 6- to 10-membered bicyclic heterocyclyl ring containing 1 or 2 heteroatoms independently selected from N, O and S, wherein the heterocyclyl ring is unsubstituted or substituted by 1, 2, or 3 R$^6$;
R$^5$ is
(1) cyano,
(2) halo,
(3) (C$_{1-6}$)alkyl,
(4) —C(O)NH$_2$,
(5) —C(O)NR$^{10a}$R$^{10b}$,
(6) (C$_{3-6}$)cycloalkyl,
(7) hydroxy,
(8) hydroxy(C$_{1-3}$)alkyl-,
(9) (C$_{1-6}$)alkoxy-,
(10) —NR$^{10a}$R$^{10b}$,
(11) 5-membered heteroaryl containing 1, 2 or 3 heteroatoms independently selected from N, O, and S, wherein the heteroaryl is unsubstituted or substituted by 1-2 R$^7$;
(12) halo(C$_{1-6}$)alkyl-, or
(13) halo(C$_{1-6}$)alkoxy-;
R$^6$ is
(1) (C$_{1-3}$)alkyl,
(2) halo(C$_{1-3}$)alkyl-,
(3) oxo,
(4) (C$_{3-6}$)cycloalkyl,
(5) —C(O)O—(C$_{1-4}$)alkyl,
(6) NH$_2$,
(7) hydroxy,
(8) phenyl unsubstituted or substituted by halo,
(9) hydroxy(C$_{1-3}$)alkyl-,
(10) (C$_{1-6}$)alkoxy-,
(11) halo(C$_{1-6}$)alkoxy-,
(12) cyano, or
(13) halo;
R$^7$ is
(1) (C$_{1-6}$)alkyl,
(2) halo,
(3) (C$_{1-3}$)alkoxy-,
(4) halo(C$_{1-3}$)alkyl-,
(5) (C$_{3-6}$)cycloalkyl, or
(6) —C(O)O—(C$_{1-3}$)alkyl;
R$^8$ is
(1) (C$_{1-3}$)alkyl,
(2) hydroxy(C$_{1-3}$)alkyl-,
(3) (C$_{1-3}$)alkoxy-,
(4) hydroxy,
(5) halo(C$_{1-3}$)alkyl-,
(6) (C$_{1-3}$)alkyl-S—,
(7) —C(O)—NR$^{9a}$R$^{9b}$, or
(8) phenyl;
R$^{9a}$ and R$^{9b}$ are independently
(1) hydrogen,
(2) (C$_{1-3}$)alkyl,
(3) —(C$_{1-3}$)alkyl-phenyl,
(4) 5- or 6-membered heteroaryl containing 1, 2, or 3 heteroatoms independently selected from N, O, and S, or
(5) phenyl;
R$^{10a}$ and R$^{10b}$ are independently
(1) hydrogen, or
(2) (C$_{1-3}$)alkyl.
In one embodiment of Formula I or I', R$^1$ is aryl unsubstituted or substituted by 1, 2 or 3 R$^4$. In one class of this embodiment, R$^1$ is phenyl unsubstituted or substituted with 1, 2, or 3 R$^4$.

In one embodiment of Formula I or I'. R$^1$ is 5- or 6-membered heteroaryl containing 1, 2, or 3 heteroatoms independently selected from N, O, and S, wherein the heteroaryl is unsubstituted or substituted by 1, 2, or 3 R$^4$. In one class of this embodiment, R$^1$ is pyridinyl unsubstituted or substituted with 1, 2, or 3 R$^4$. In one class of this embodiment, R$^1$ is pyrimidinyl unsubstituted or substituted with 1, 2, or 3 R$^4$.

In one embodiment of Formula I or I', R$^1$ is

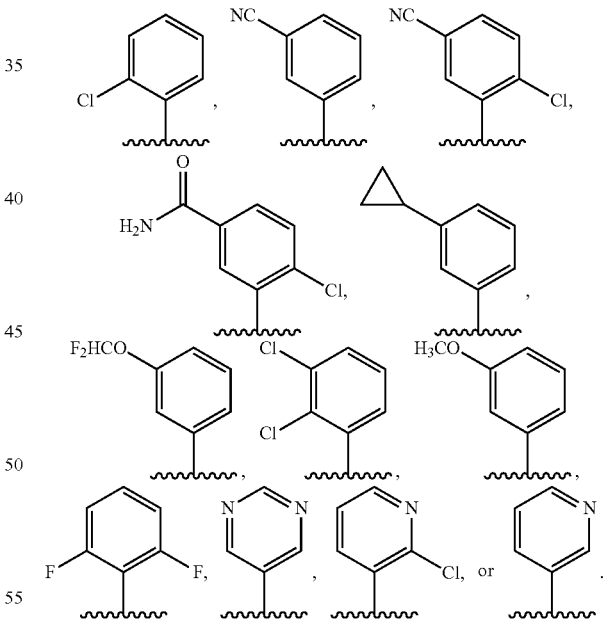

In one embodiment of Formula I or I', R$^1$ is

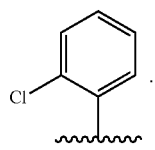 [SMILES: *c1ccccc1Cl]

In one class of this embodiment, $R^2$ is
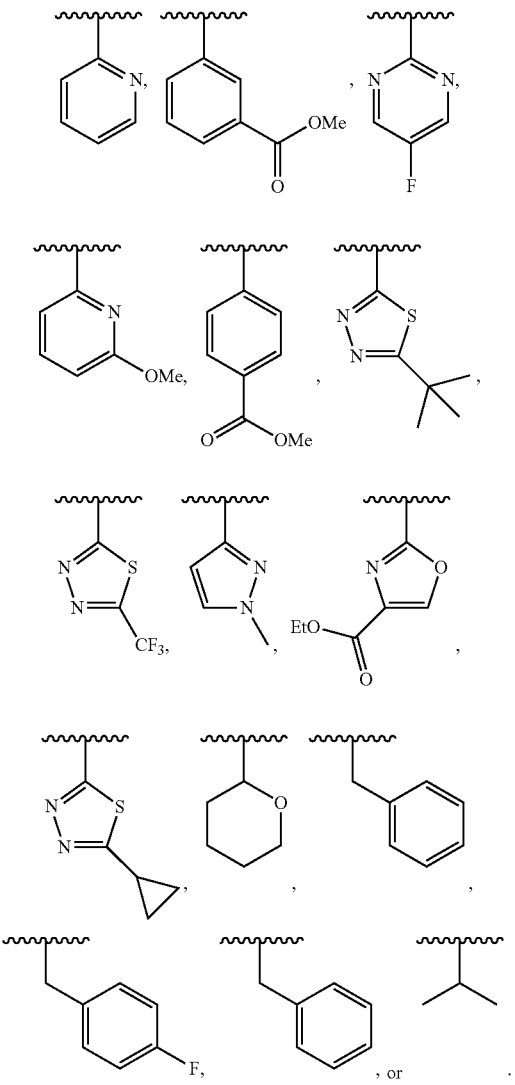
In one embodiment of Formula I or I', $R^1$ is
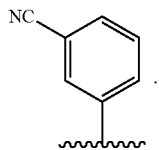
In one class of this embodiment, $R^2$ is
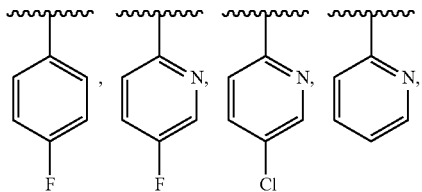
-continued
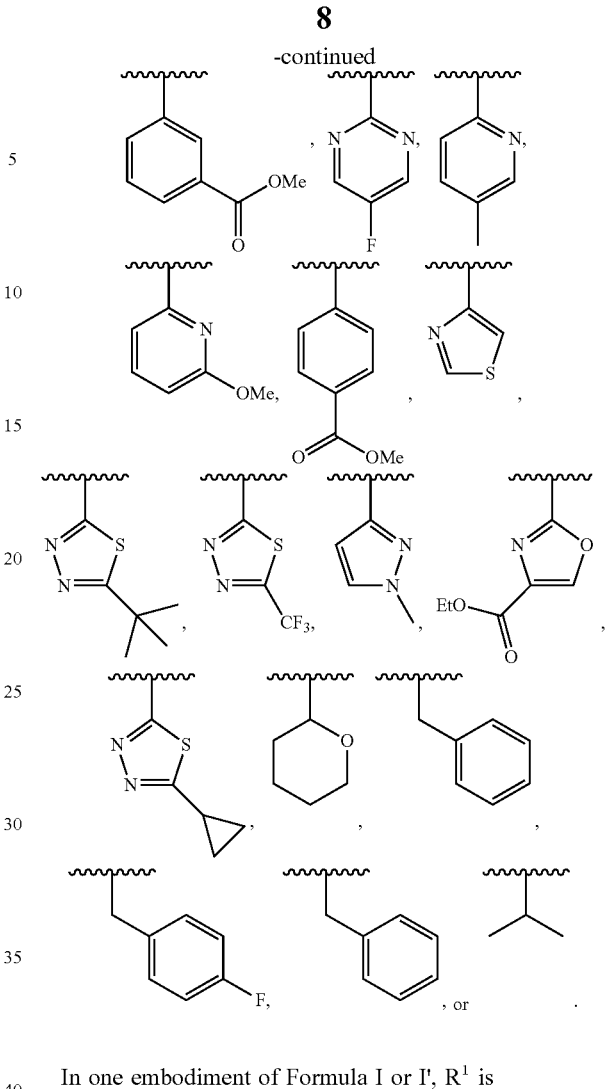
In one embodiment of Formula I or I', $R^1$ is
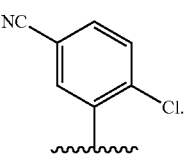
In one class of this embodiment, $R^2$ is
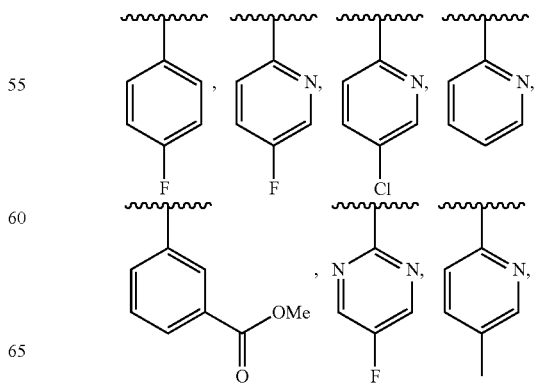

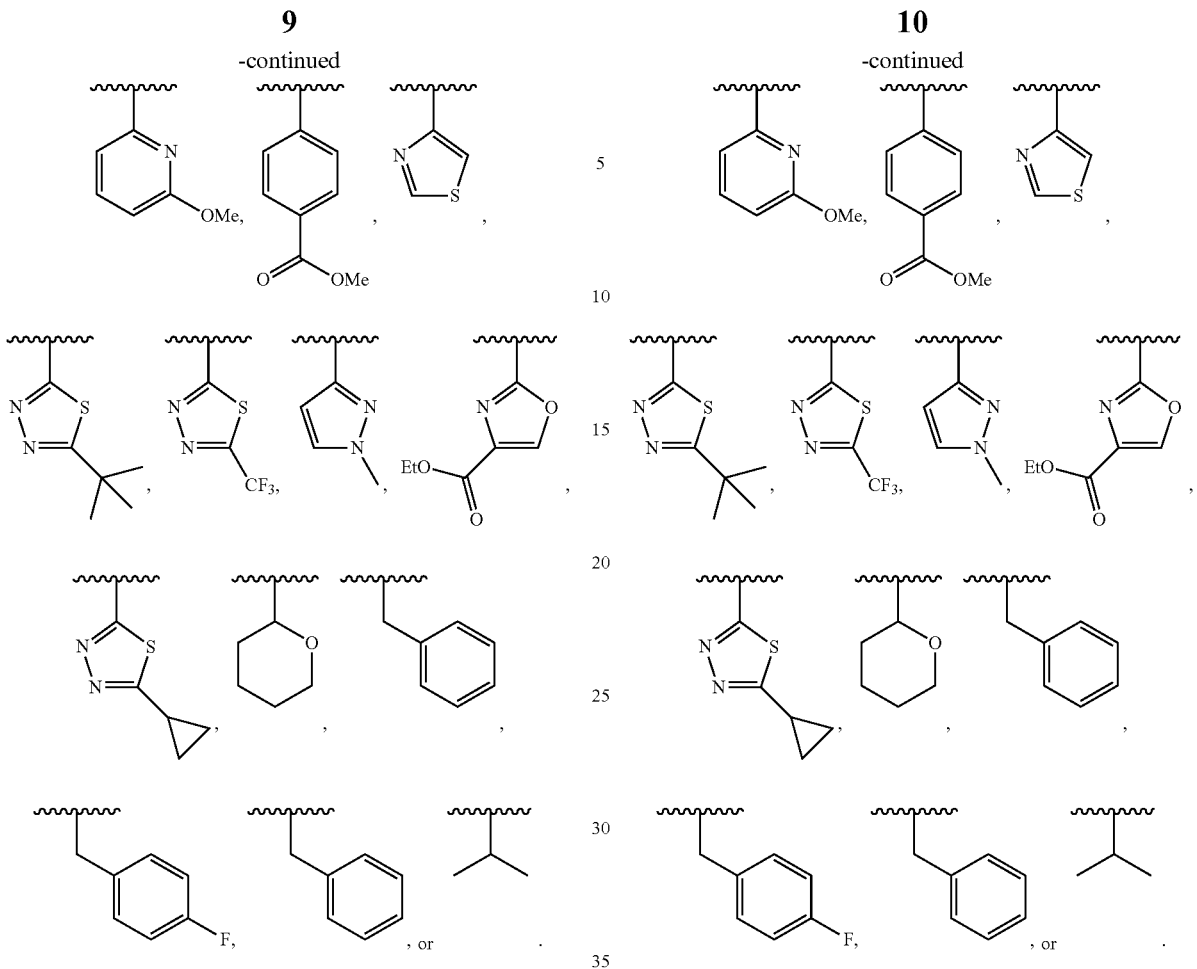
In one embodiment of Formula I or I', $R^1$ is
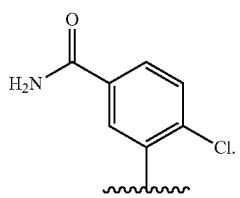 [SMILES: *c1cc(C(N)=O)ccc1Cl]
In one class of this embodiment, $R^2$ is
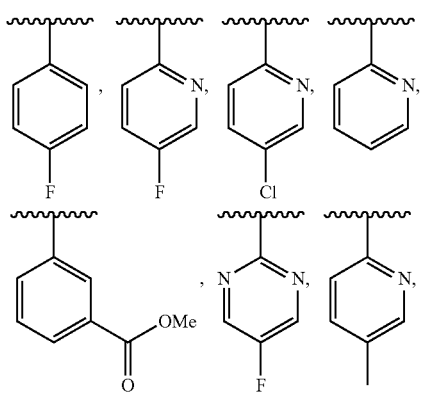
In one embodiment of Formula I or I', $R^1$ is
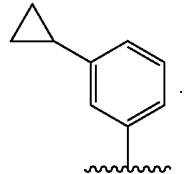 [SMILES: *c1cccc(C2CC2)c1]
In one class of this embodiment, $R^2$ is
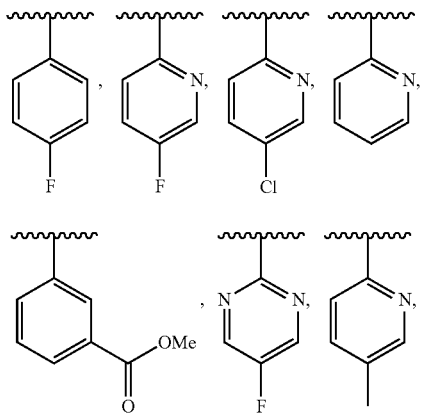

-continued
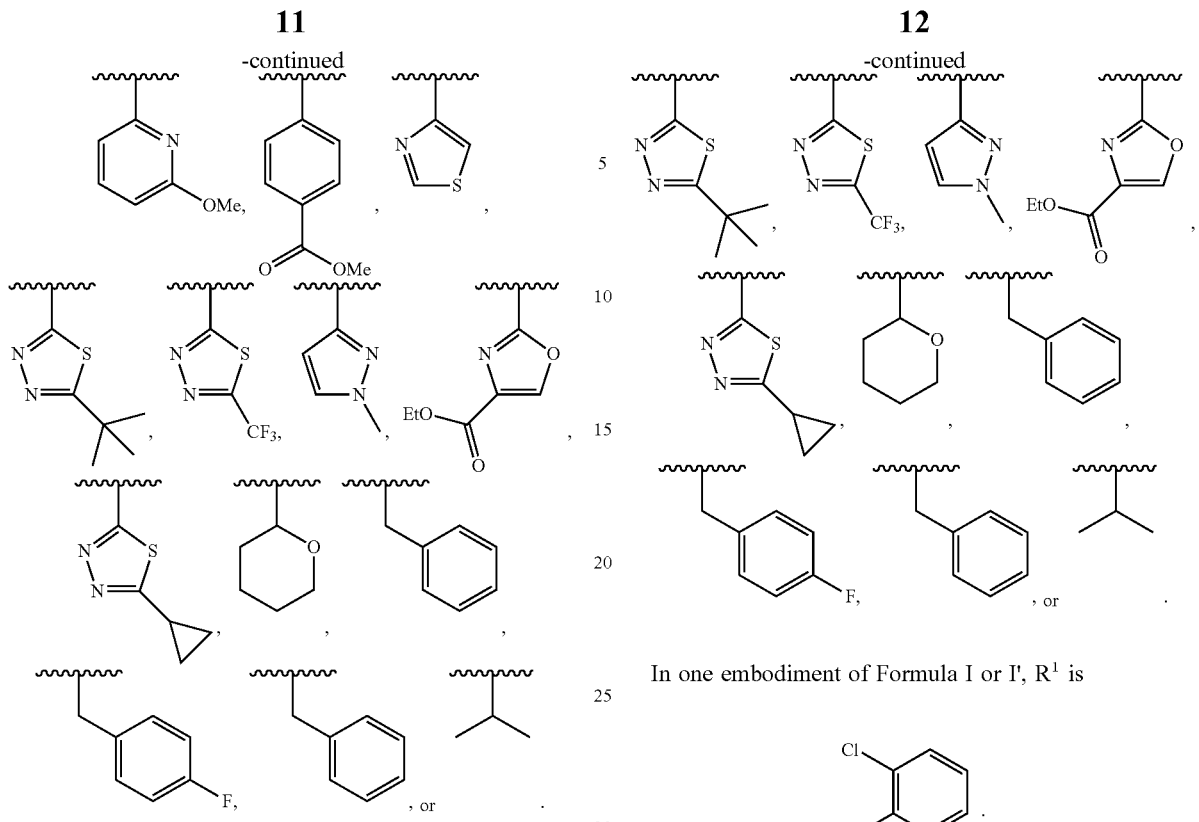
In one embodiment of Formula I or I', $R^1$ is
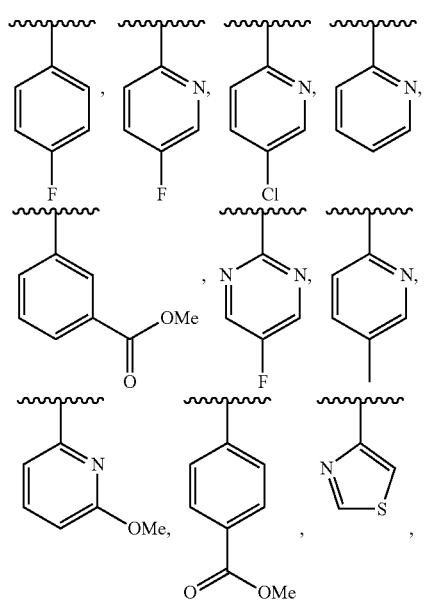
In one class of this embodiment, $R^2$ is
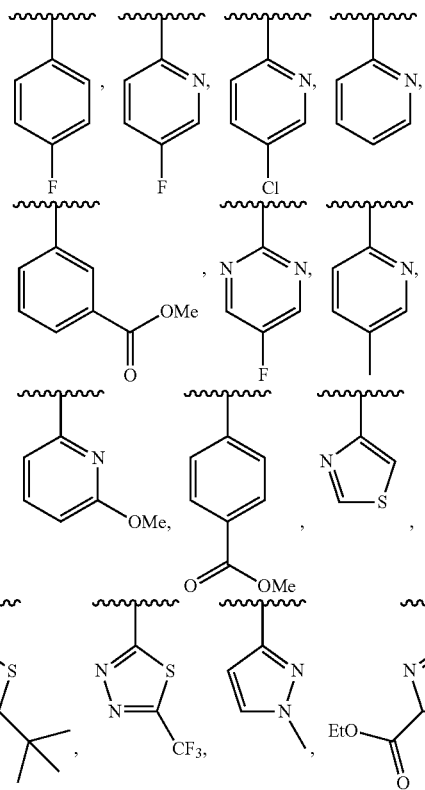

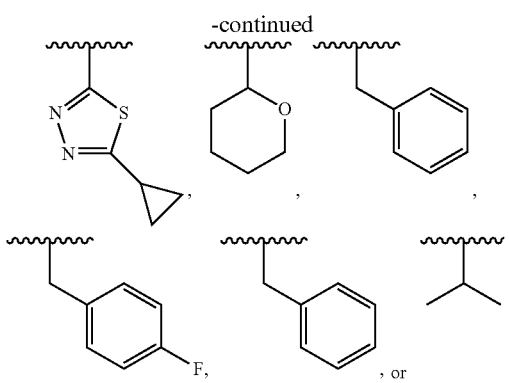
In one embodiment of Formula I or I', R[1] is
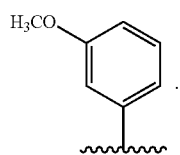
In one class of this embodiment R[2] is
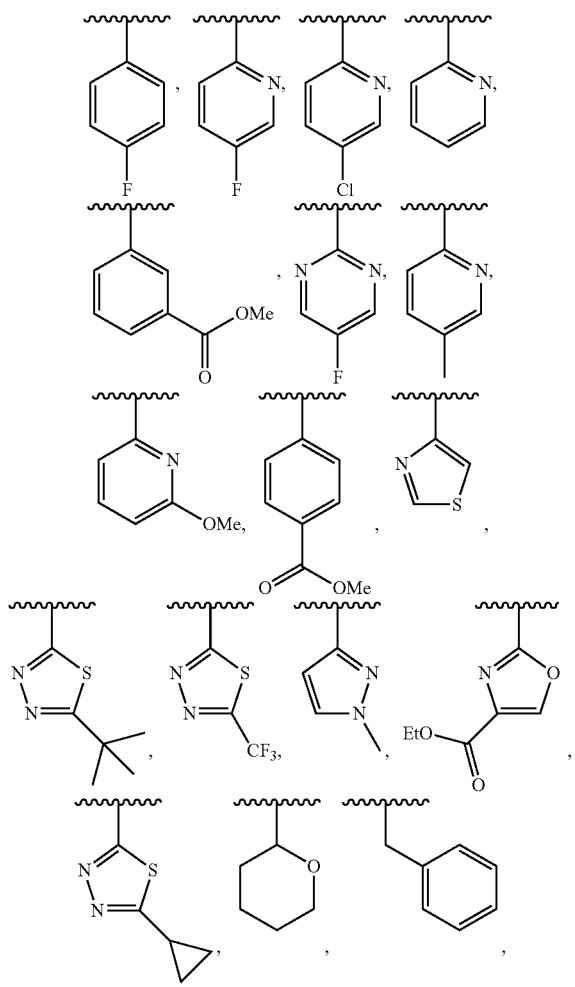
In one embodiment of Formula I or I', R[1] is
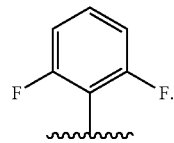
In one class of this embodiment R[2] is
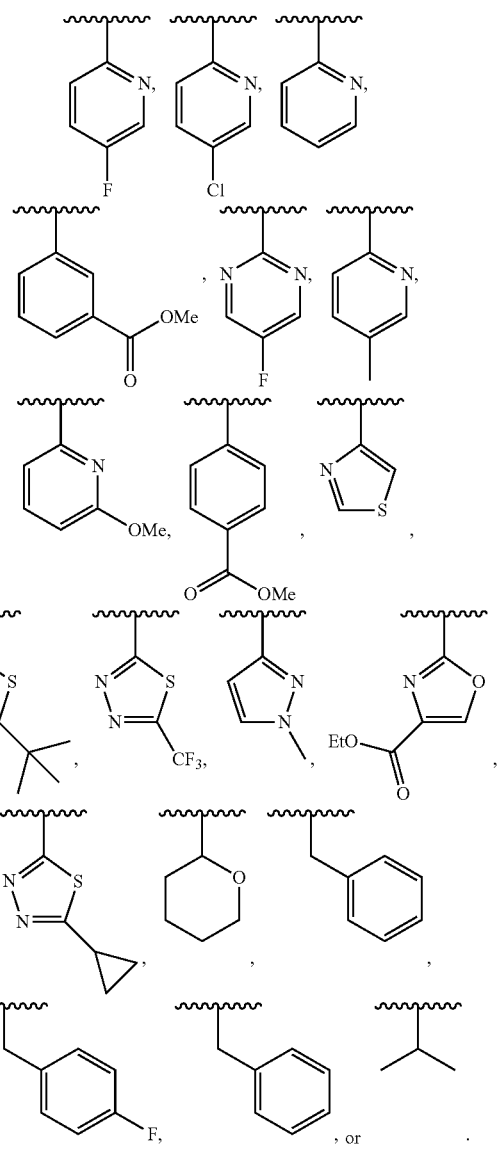

In one embodiment of Formula I or I', $R^1$ is
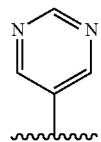
In one class of this embodiment, $R^2$ is
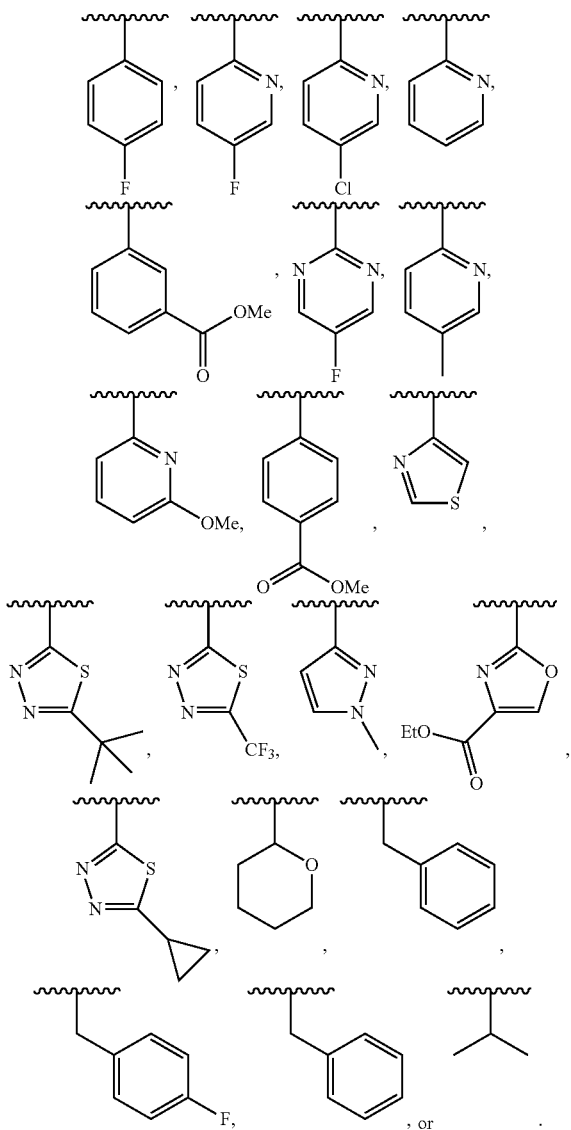
In one embodiment of Formula I or I', $R^1$ is
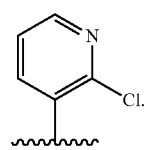
In one class of this embodiment, $R^2$ is
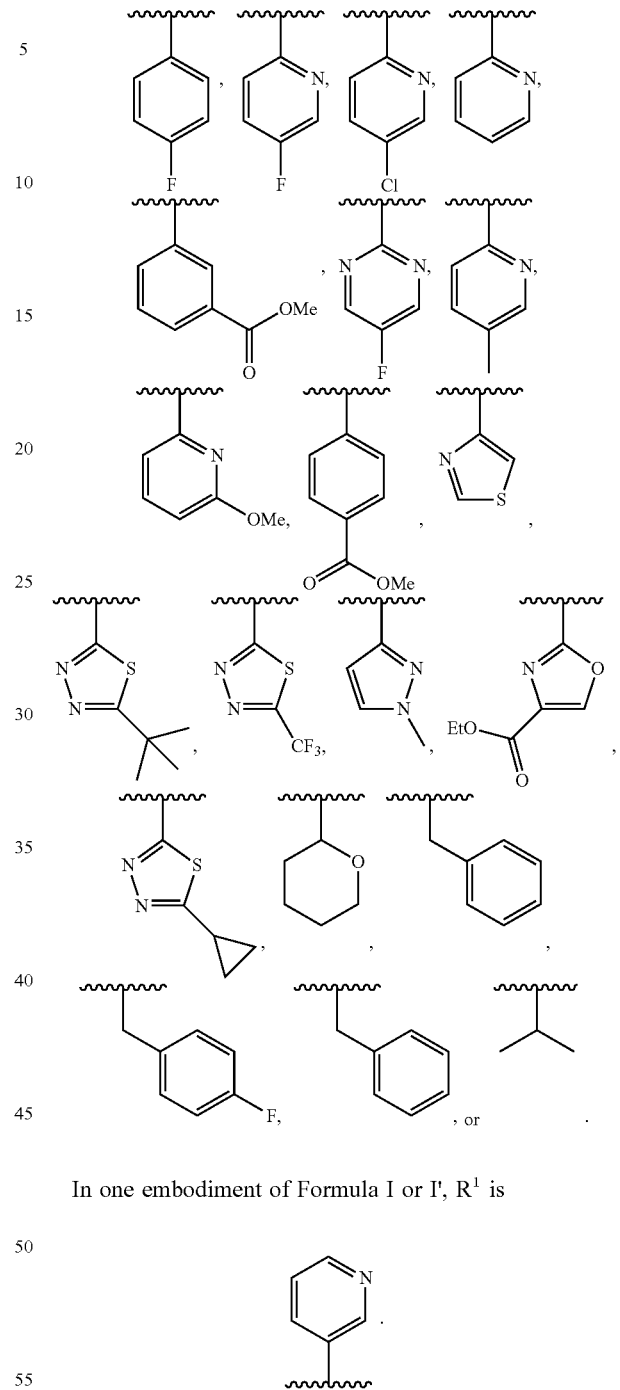
In one embodiment of Formula I or I', $R^1$ is
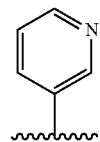
In one class of this embodiment, $R^2$ is
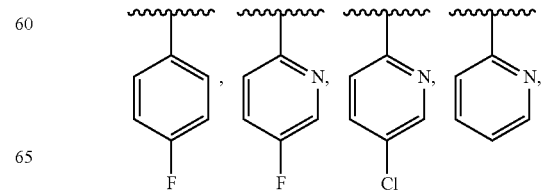

-continued

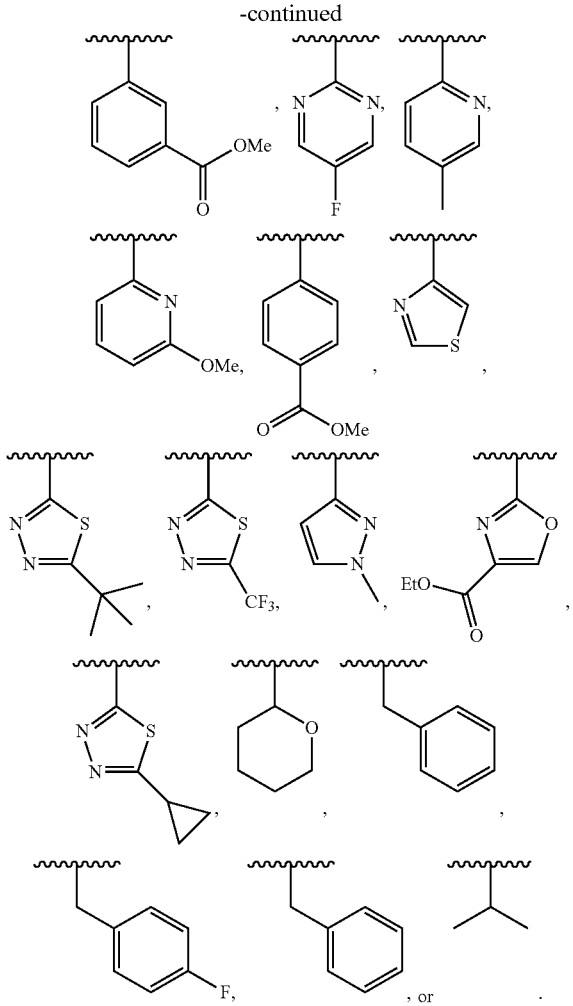

In one embodiment of Formula I or I', $R^1$ is aryl unsubstituted or substituted by 1, 2, or 3 $R^6$. In one class of this embodiment, $R^2$ is phenyl unsubstituted or substituted with 1 or 2 $R^6$.

In one embodiment of Formula I or I', $R^2$ is 5- or 6-membered heteroaryl containing 1, 2, or 3 heteroatoms independently selected from N, O, and S, and wherein the heteroaryl is unsubstituted or substituted by 1, 2, or 3 $R^6$. In one class of this embodiment, $R^2$ is thiazolyl, pyridinyl, pyrimidinyl, oxazolyl, thiadiazolyl, or pyrazolyl, wherein each ring is unsubstituted or substituted by 1, 2, or 3 $R^6$. In one subclass of this class, $R^2$ is thiazolyl unsubstituted or substituted by 1 or 2 $R^6$. In one subclass of this class, $R^2$ is pyridinyl unsubstituted or substituted by 1, 2, or 3 $R^6$. In one subclass of this class, $R^2$ is pyrimidinyl unsubstituted or substituted by 1, 2, or 3 $R^6$. In one subclass of this class, $R^2$ is oxazolyl unsubstituted or substituted by 1 or 2 $R^6$. In one subclass of this class, $R^2$ is thiadiazolyl unsubstituted or substituted by 1 $R^6$. In one subclass of this class, $R^2$ is pyrazolyl unsubstituted or substituted by 1 or 2 $R^6$ In one embodiment of Formula I or I', $R^2$ is $(C_{1-6})$alkyl.

In one embodiment of Formula I or I', $R^2$ is 4- to 6-membered heterocyclyl containing 1 or 2 heteroatoms independently selected from N, O and S. In one class of this embodiment, $R^2$ is tetrahydropyranyl.

In one embodiment of Formula I or I', $R^2$ is

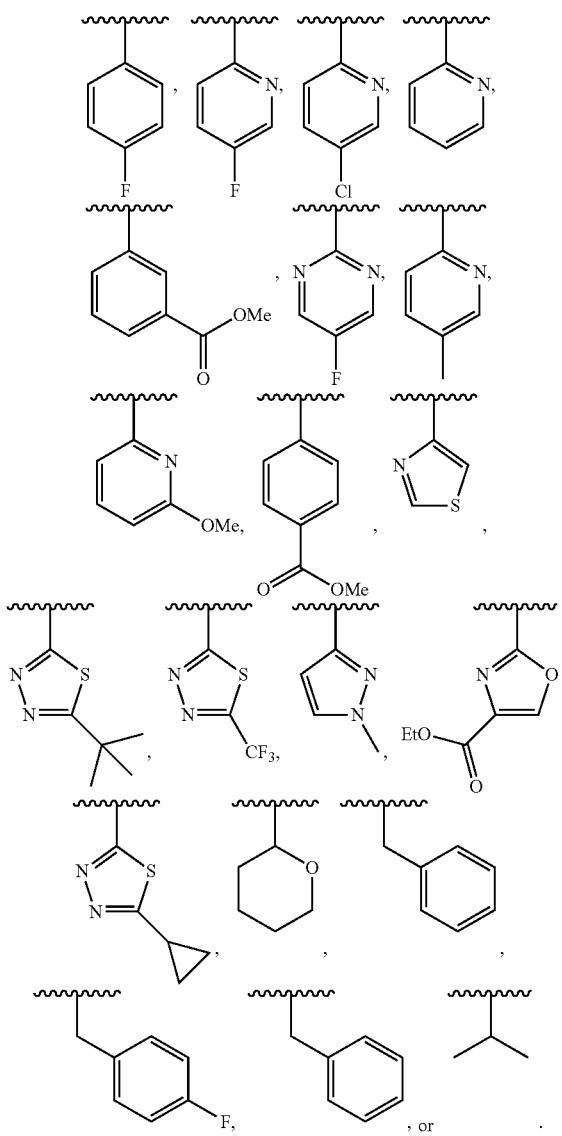

In one embodiment of Formula I or I', $R^3$ is 4- to 7-membered heterocyclyl containing 1 or 2 heteroatoms independently selected from N, O and S, wherein the heterocyclyl unsubstituted or substituted by 1, 2, or 3 $R^6$. In one class of this embodiment, $R^1$ is

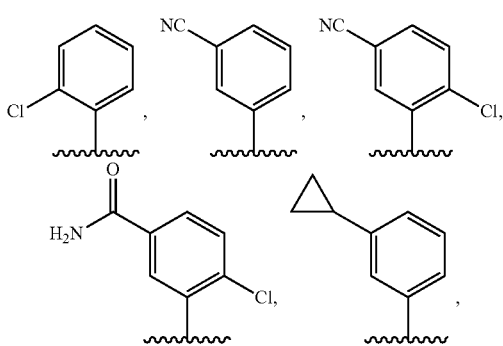

-continued

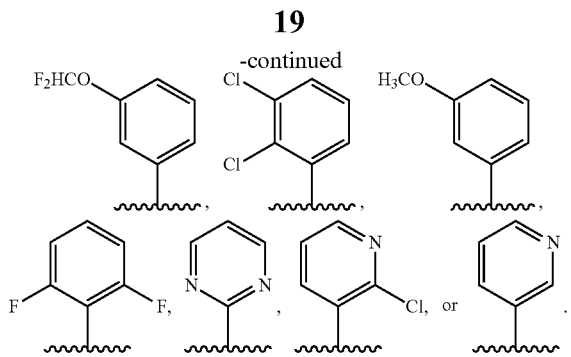

In one embodiment of Formula I or I'. $R^3$ is 5- or 6-membered heteroaryl containing 1, 2, or 3 heteroatoms independently selected from N, O, and S, wherein the heteroaryl is unsubstituted or substituted by 1, 2, or 3 $R^6$. In one class of this embodiment, $R^1$ is

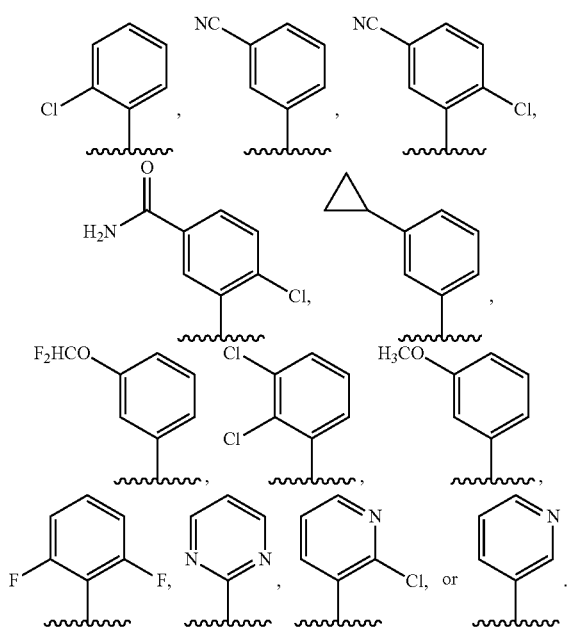

In one embodiment of Formula I or I', $R^3$ is —(C$_{1-6}$)alkyl-heteroaryl, wherein the heteroaryl is a 5- or 6-membered heteroaryl containing 1, 2, or 3 heteroatoms independently selected from N, O and S, wherein the heteroaryl is unsubstituted or substituted by 1, 2, or 3 $R^6$, and wherein the alkyl is unsubstituted or substituted by $R^8$. In one class of this embodiment, $R^1$ is

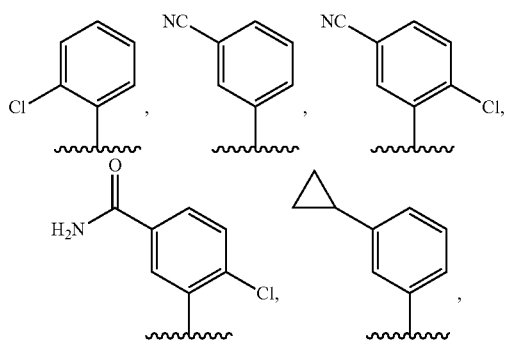

-continued

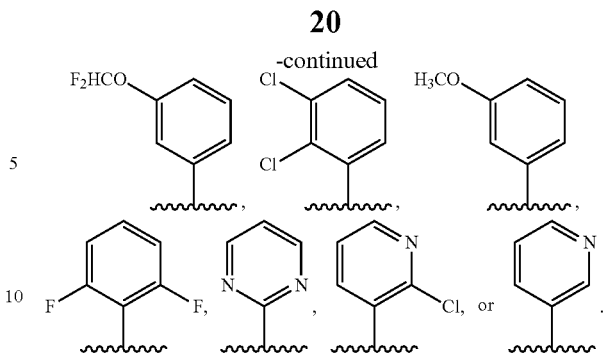

In one embodiment of Formula I or I', $R^3$ is —(C$_{1-6}$)alkyl-aryl, wherein the aryl is unsubstituted or substituted by 1, 2, or 3 $R^6$, and wherein the alkyl is unsubstituted or substituted by $R^8$. In one class of this embodiment, $R^1$ is

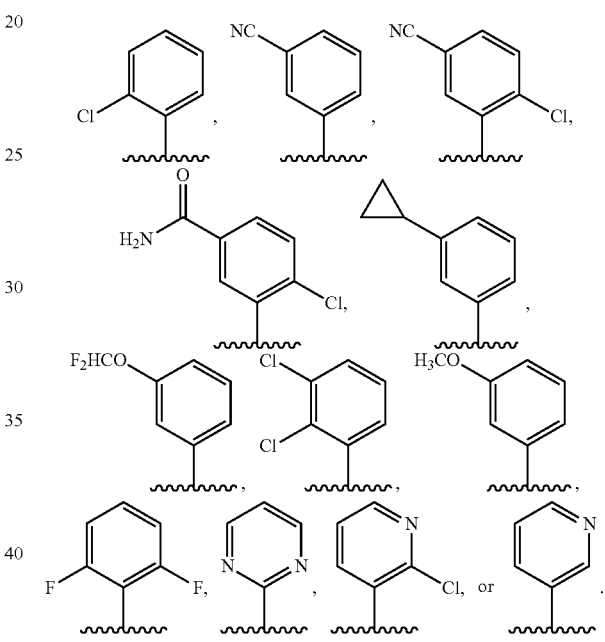

In one embodiment of Formula I or I', $R^3$ is —(C$_{1-6}$)alkyl-heterocyclyl, wherein the heterocyclyl is a 3- to 6-membered ring containing 1 or 2 heteroatoms independently selected from N, O and S, and wherein the heterocyclyl is unsubstituted or substituted by 1, 2, or 3 $R^6$, and wherein the alkyl is unsubstituted or substituted by $R^8$. In one class of this embodiment, $R^1$ is

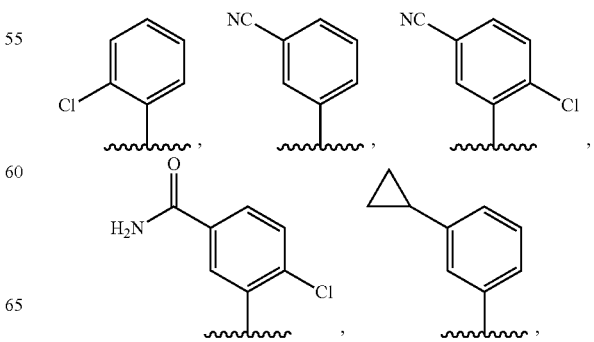

-continued

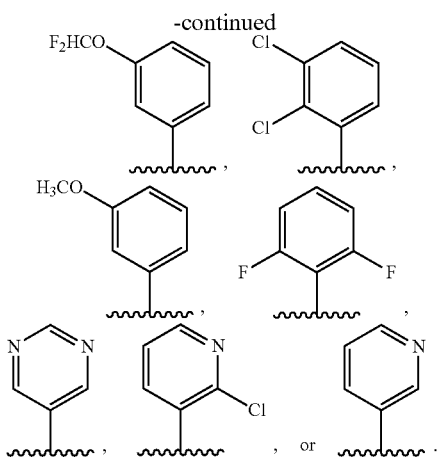

In one embodiment of Formula I or I', $R^3$ is $(C_{1-6})$alkyl unsubstituted or substituted by $R^8$. In one embodiment, $R^3$ is —$(C_{1-6})$alkyl-C(O)O—$(C_{1-4})$alkyl wherein the $(C_{1-6})$alkyl is unsubstituted or substituted by $R^8$. In one class of this embodiment, $R^1$ is

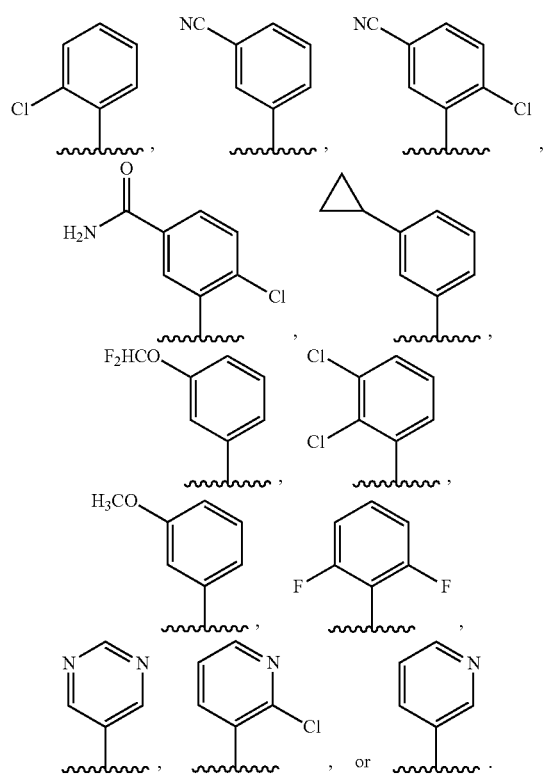

In one embodiment of Formula I or I', $R^3$ is —$(C_{1-6})$alkyl-S(O)$_2$—NR$^{9a}$R$^{9b}$, wherein the alkyl is unsubstituted or substituted by $R^8$. In one class of this embodiment, $R^1$ is

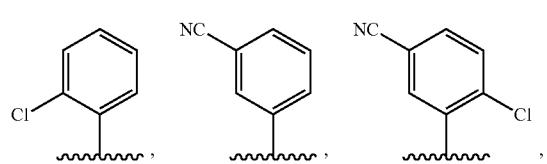

-continued

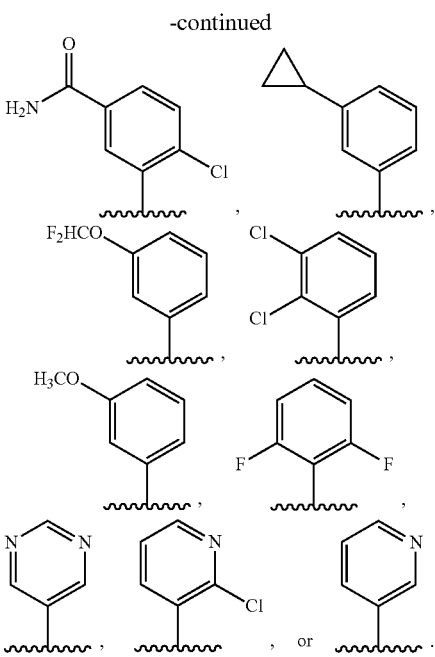

In one embodiment of Formula I or I', $R^3$ is —$(C_{1-6})$alkyl-S(O)$_2$—$(C_{1-3})$alkyl, wherein the $(C_1C_{1-6})$alkyl is unsubstituted or substituted by $R^8$. In one class of this embodiment, $R^1$ is

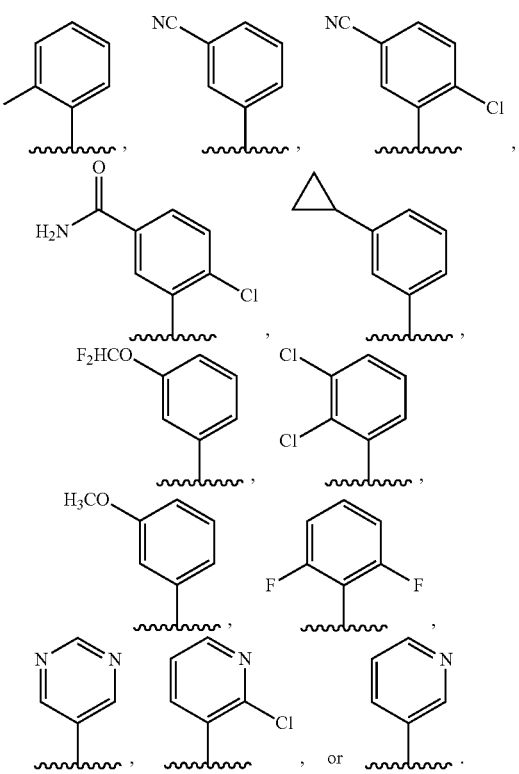

In one embodiment of Formula I or I', $R^3$ is —$(C_{1-3})$alkyl-heteroaryl, wherein the heteroaryl is fused, and wherein the heteroaryl contains 1, 2, 3 or 4 heteroatoms independently selected from N, O, and S, and wherein the heteroaryl is unsubstituted or substituted by 1, 2, or 3 $R^6$, and wherein the alkyl is unsubstituted or substituted by $R^8$. In one class of this embodiment, $R^1$ is

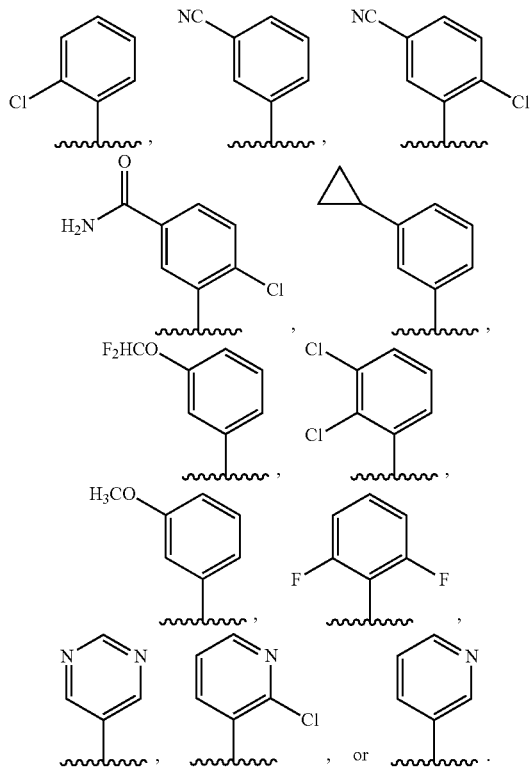

In one embodiment of Formula I or I', $R^3$ is —($C_{1-6}$)alkyl-S(O)$_2$—($C_{3-6}$)cycloalkyl, wherein the cycloalkyl is unsubstituted or substituted by 1, 2, or 3 $R^6$, and wherein the alkyl is unsubstituted or substituted by $R^8$. In one class of this embodiment, $R^1$ is

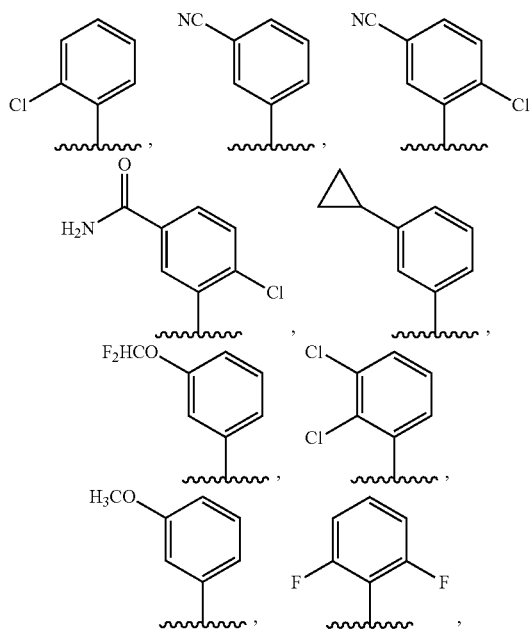

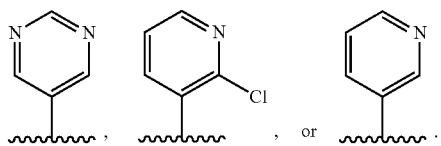

In one embodiment of Formula I or I', $R^3$ is —($C_{1-6}$)alkyl-($C_{3-6}$)cycloalkyl wherein the cycloalkyl is unsubstituted or substituted by 1, 2, or 3 $R^6$, and wherein the alkyl is unsubstituted or substituted by $R^8$. In one class of this embodiment, $R^1$ is

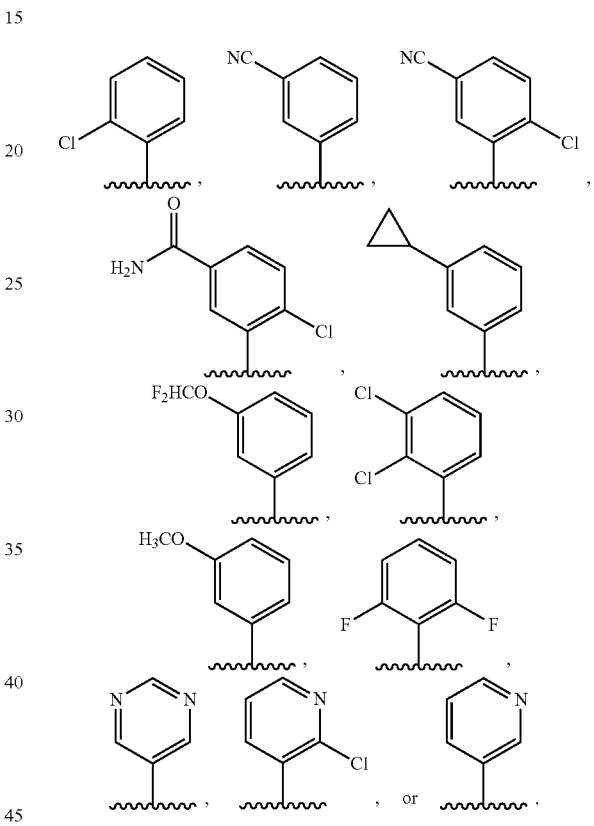

In one embodiment of Formula I or I', $R^3$ is ($C_{3-6}$) cycloalkyl unsubstituted or substituted by 1, 2, or 3 $R^6$. In one embodiment, $R^3$ is fused aryl unsubstituted or substituted by 1, 2, or 3 $R^6$. In one class of this embodiment $R^1$ is

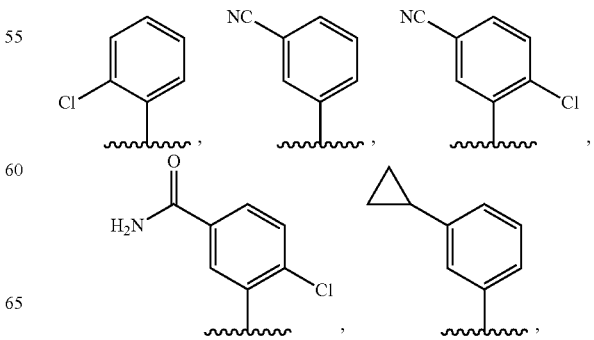

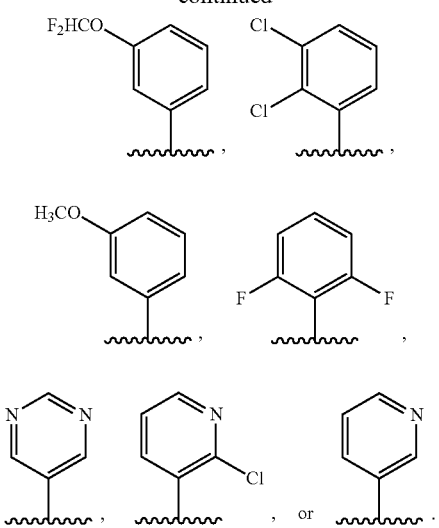
In one embodiment of Formula I or I', R³ is
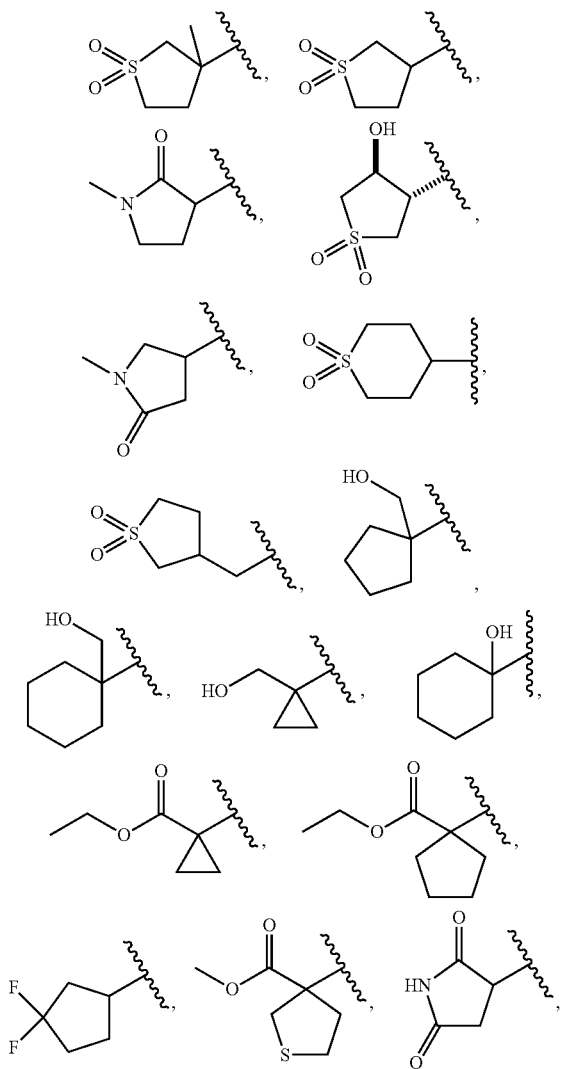
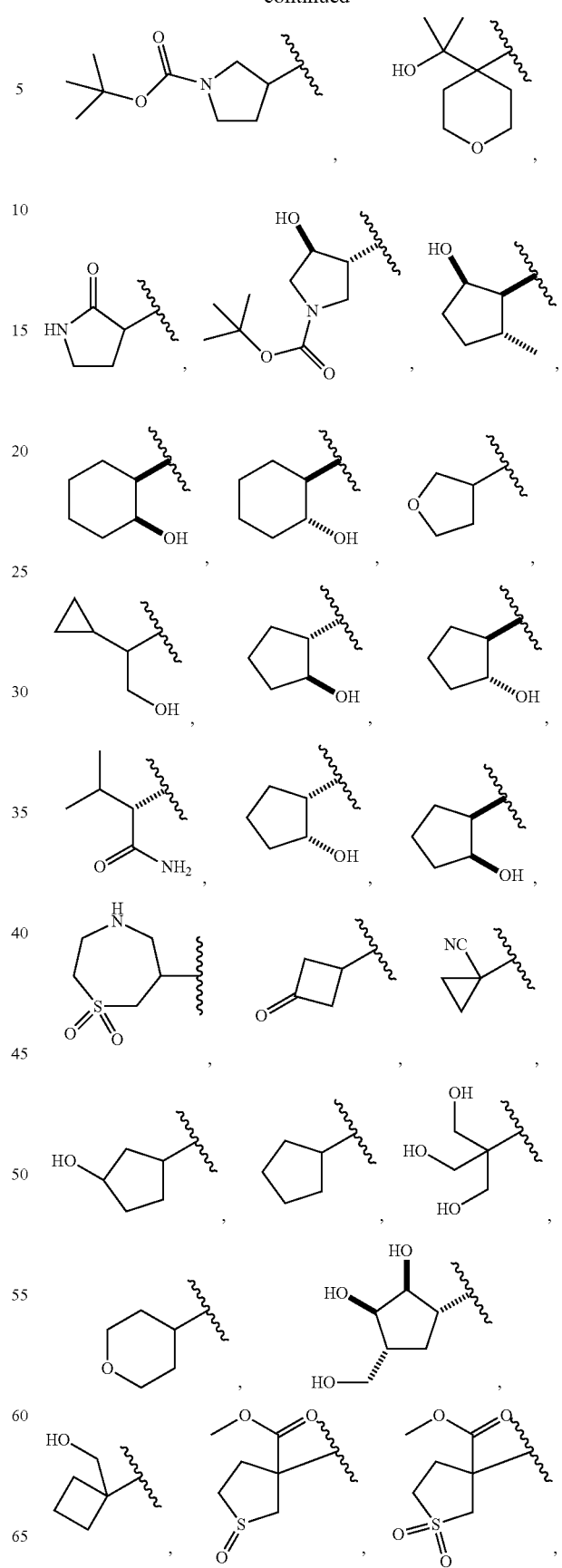

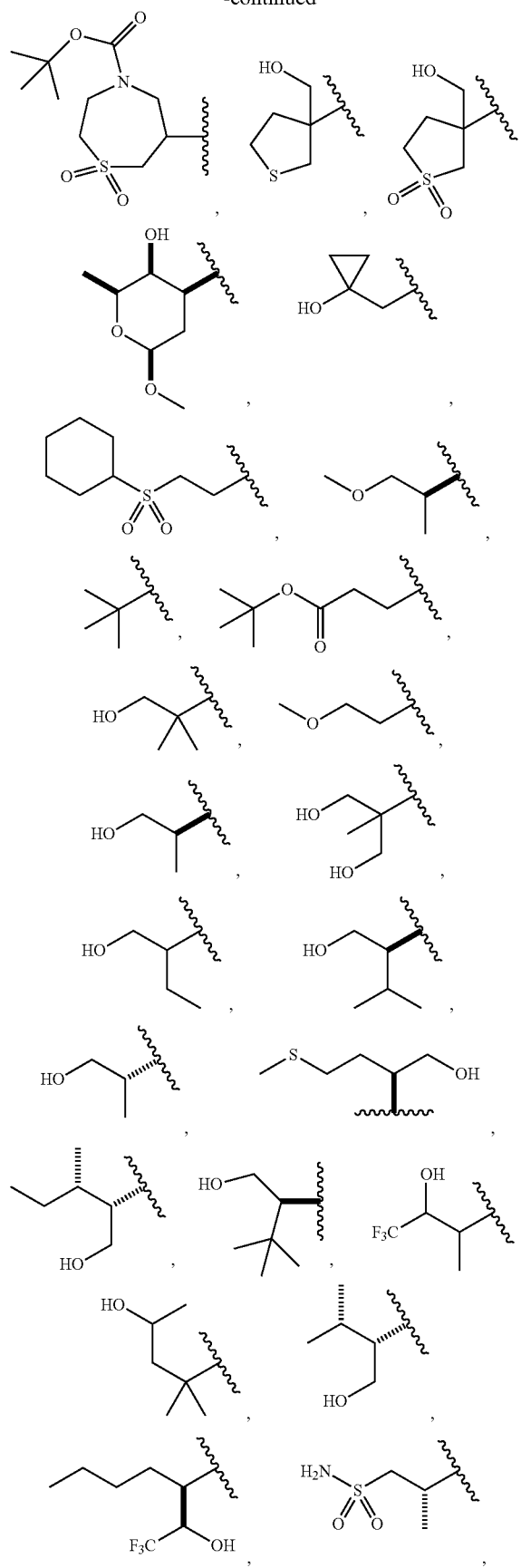
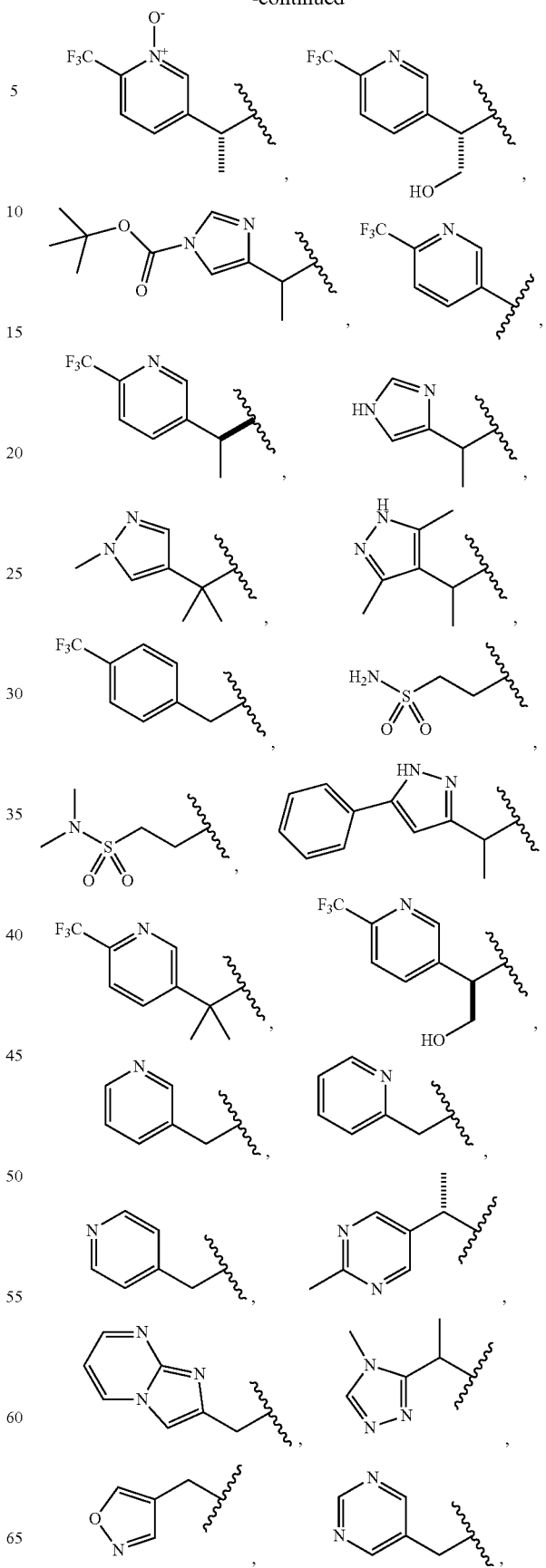

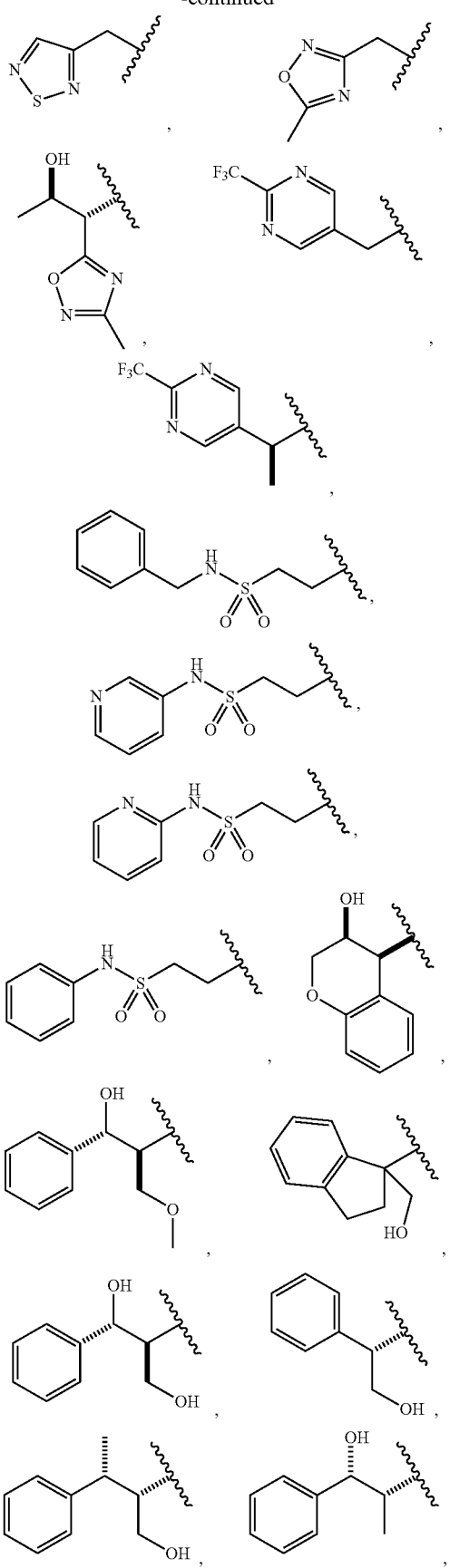
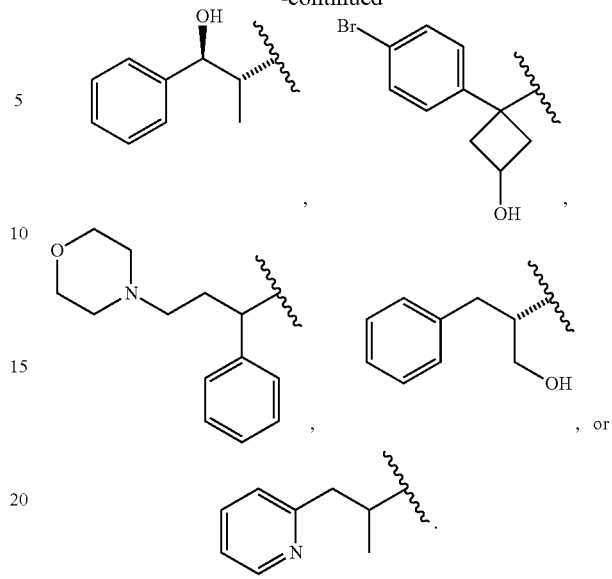
In one embodiment of Formula I', the invention relates to compounds of Formula I-a:
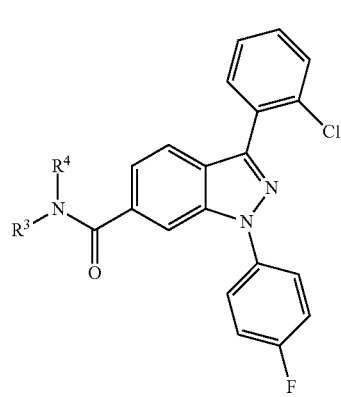
I-a
or a pharmaceutically acceptable salt thereof, wherein $R^3$ and $R^4$ are as previously defined for Formula I.
In one embodiment of Formula I', the invention relates to compounds of Formula I-a':
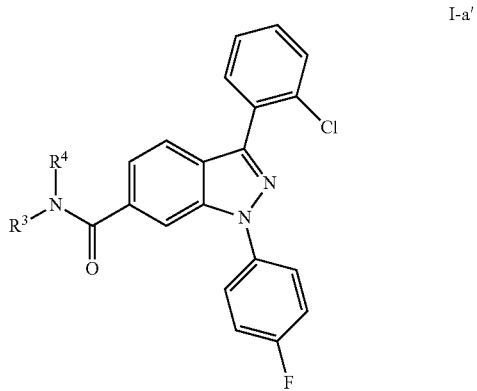
I-a' or a pharmaceutically acceptable salt thereof, wherein R³ and R⁴ are as previously defined for Formula I'.
In one class of Formula I-a or I-a', R³ is
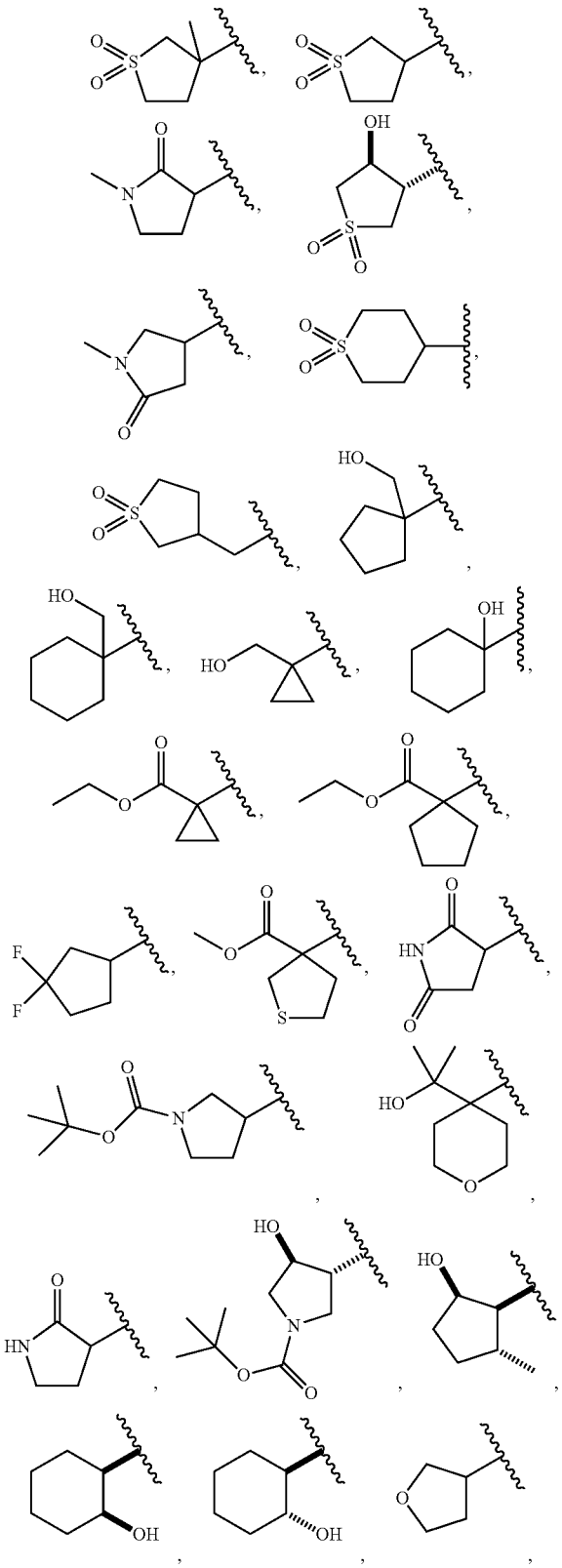
-continued
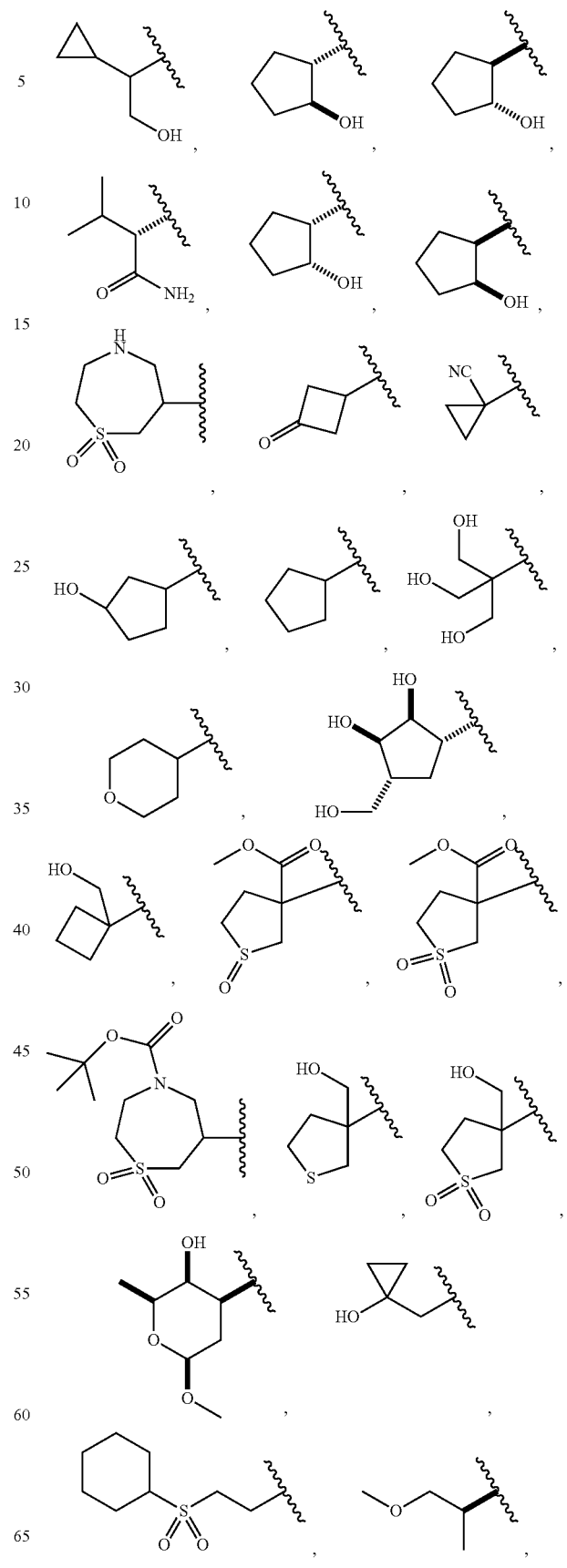

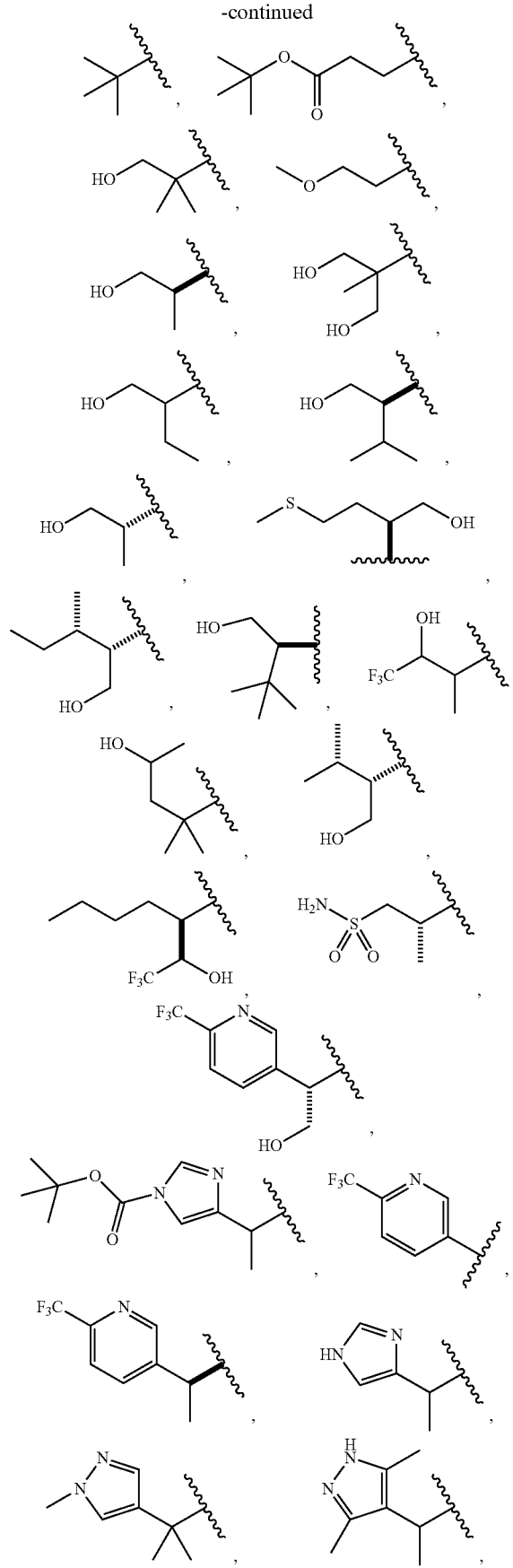
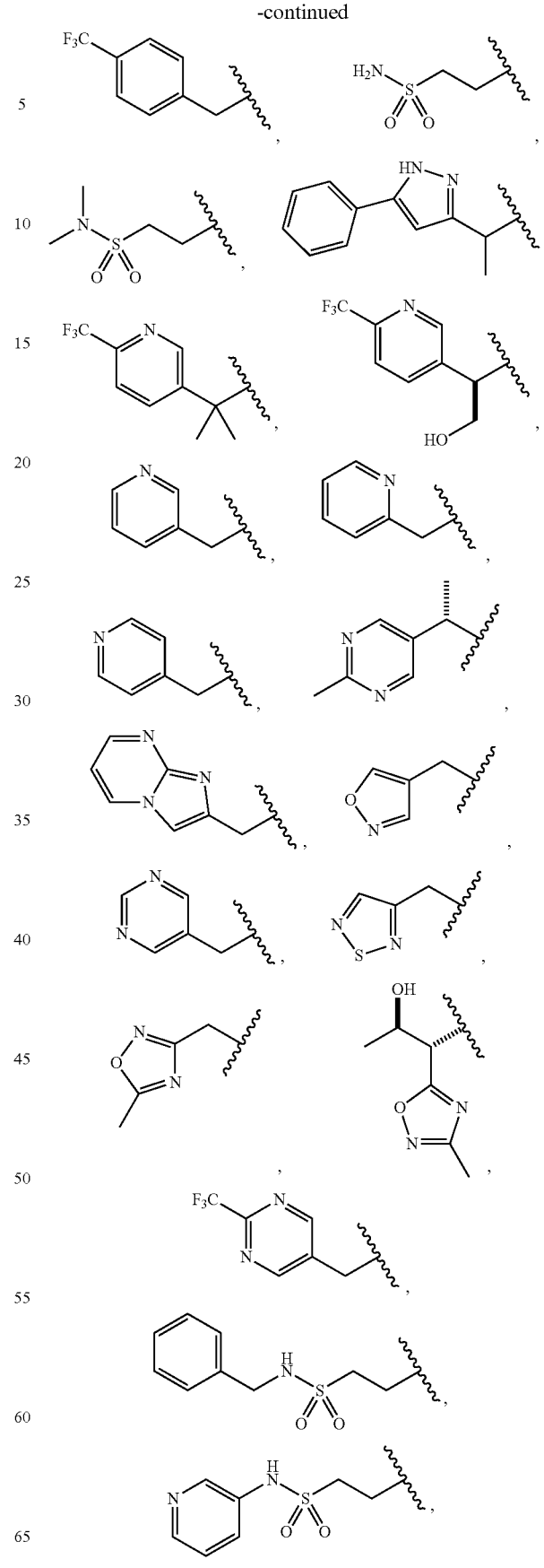

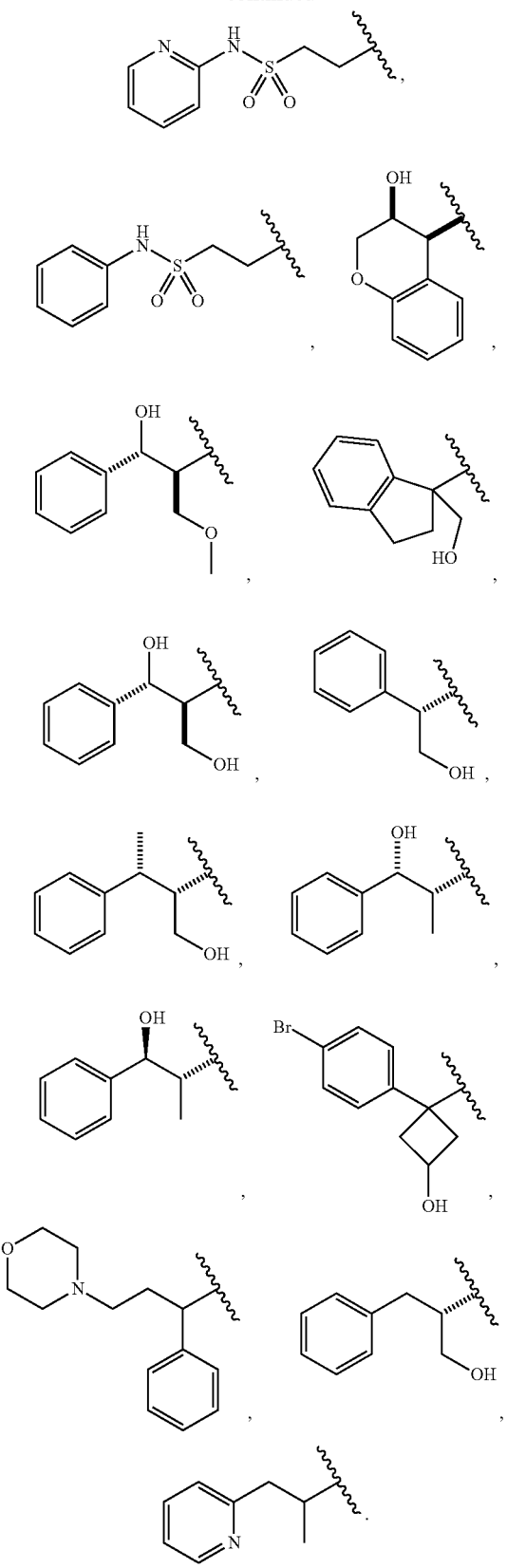

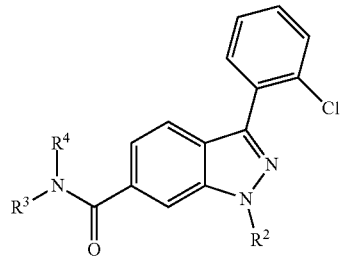

or a pharmaceutically acceptable salt thereof, wherein R², R³ and R⁴ are as previously defined for Formula I.

In one embodiment of Formula I', the invention relates to compounds of Formula I-b':

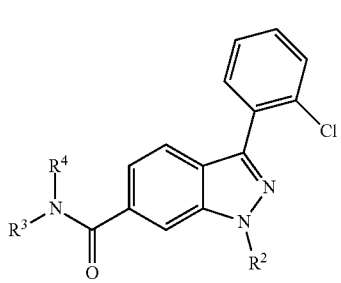

or a pharmaceutically acceptable salt thereof, wherein R², R³ and R⁴ are as previously defined for Formula I'.

In one class of Formula I-b or I-b', R² is

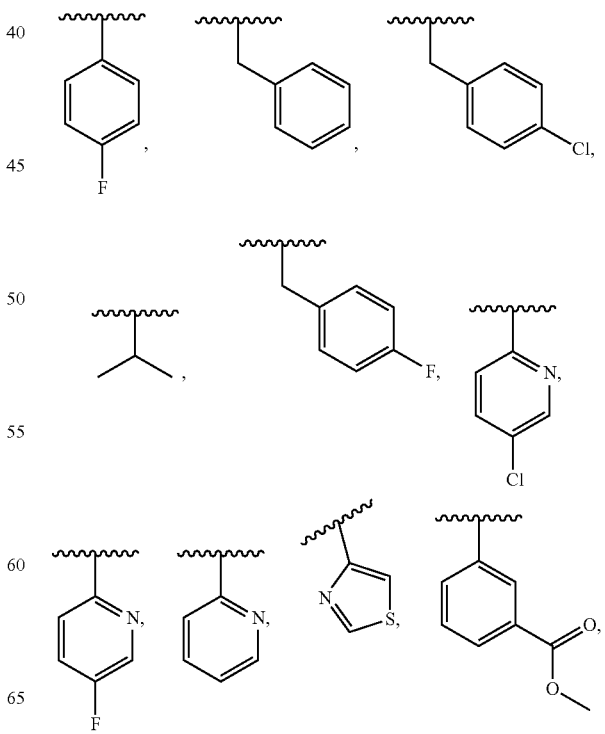

In one embodiment of Formula I, the invention relates to compounds of Formula I-b:

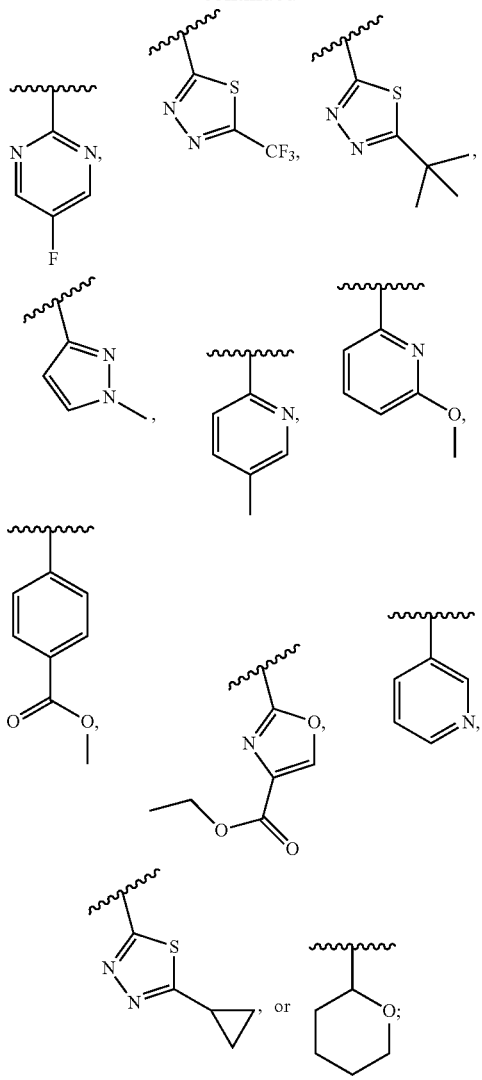
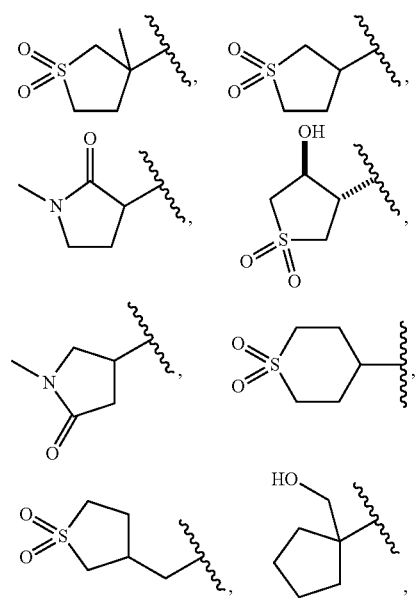
$R^3$ is
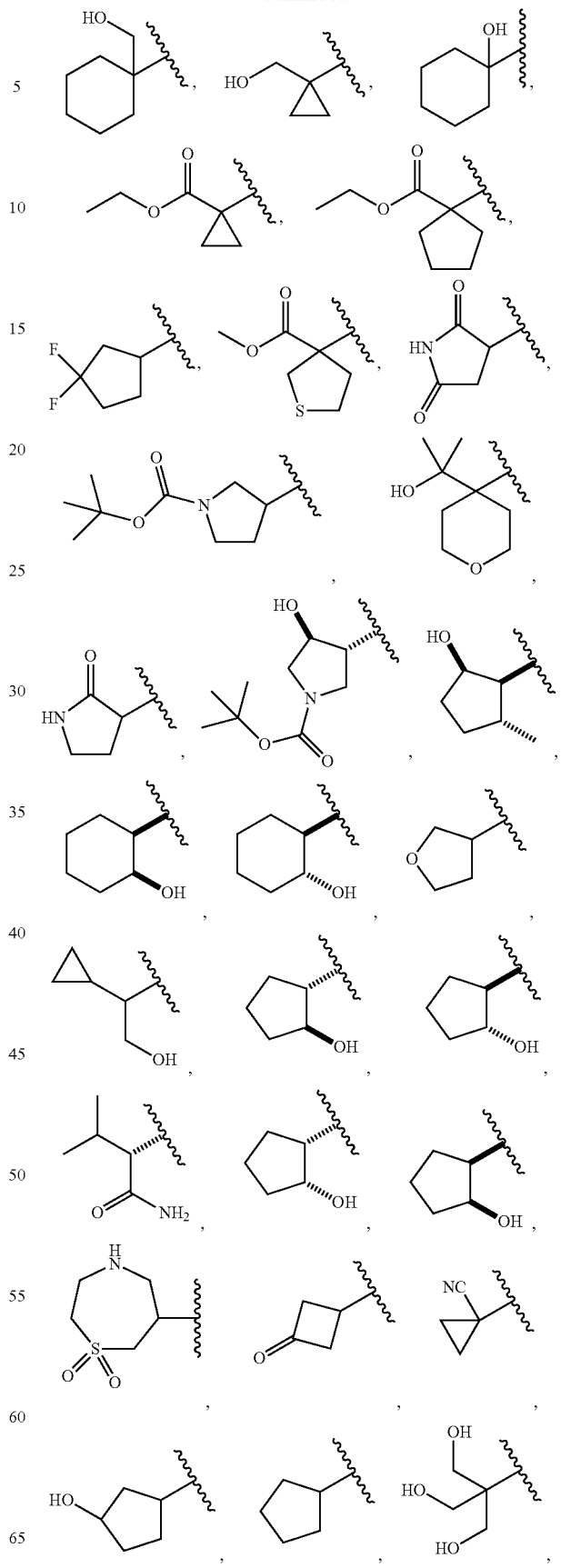

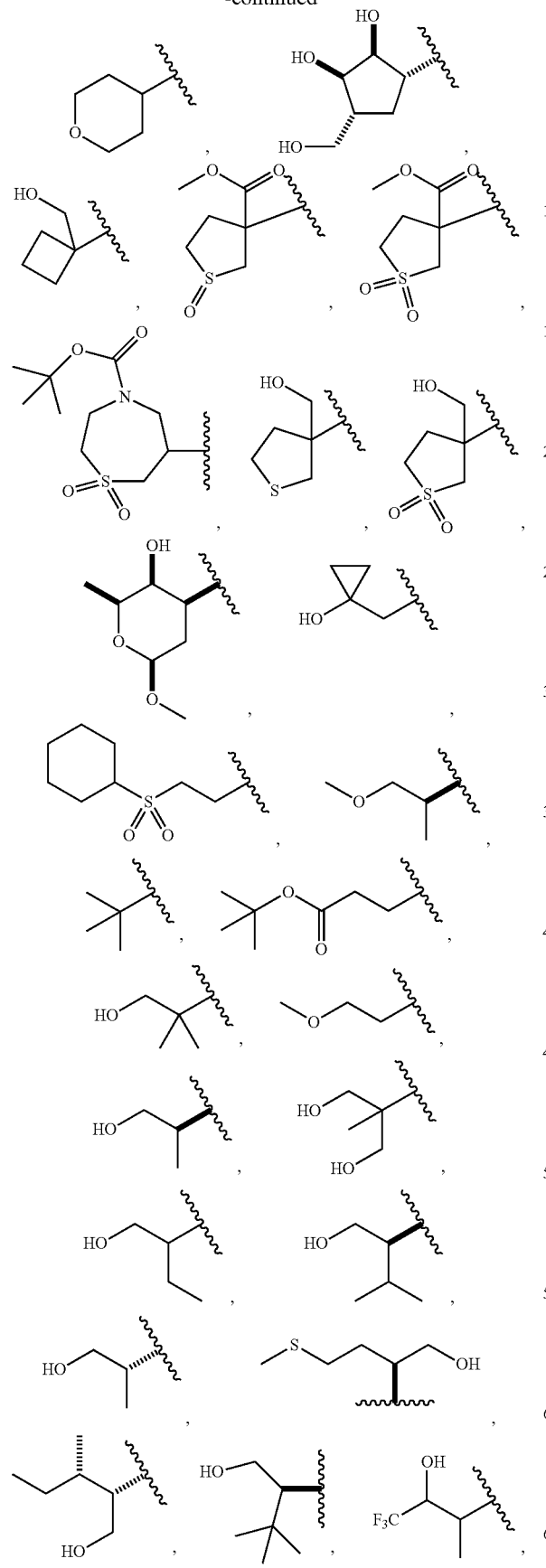
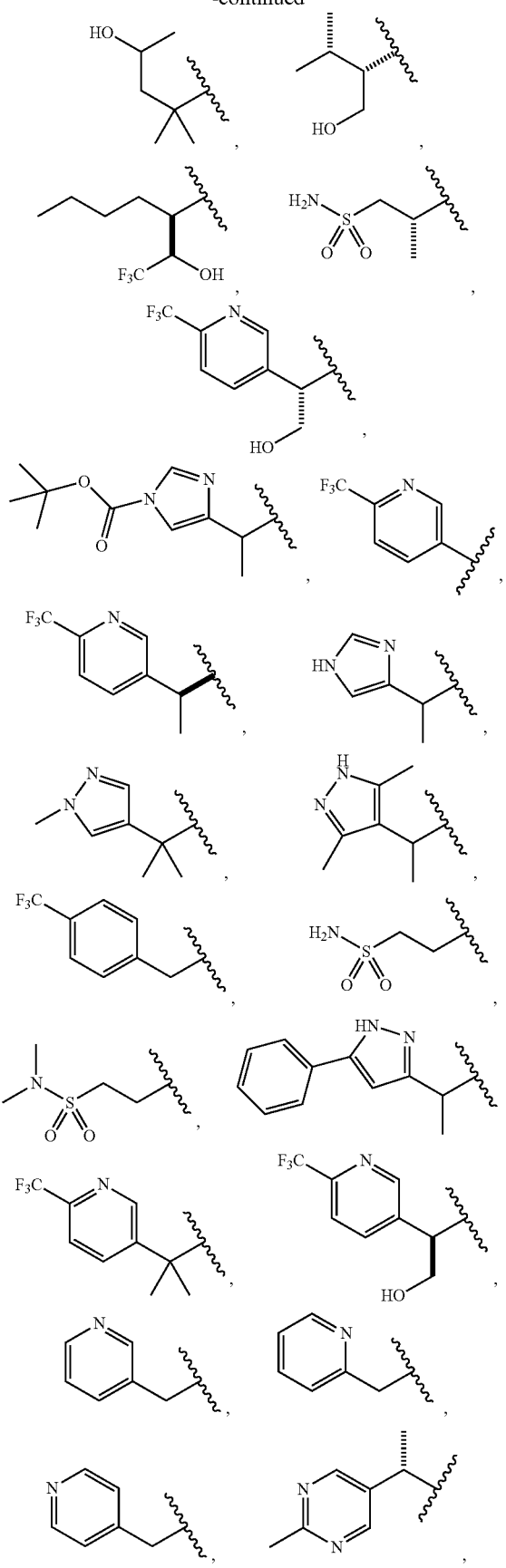

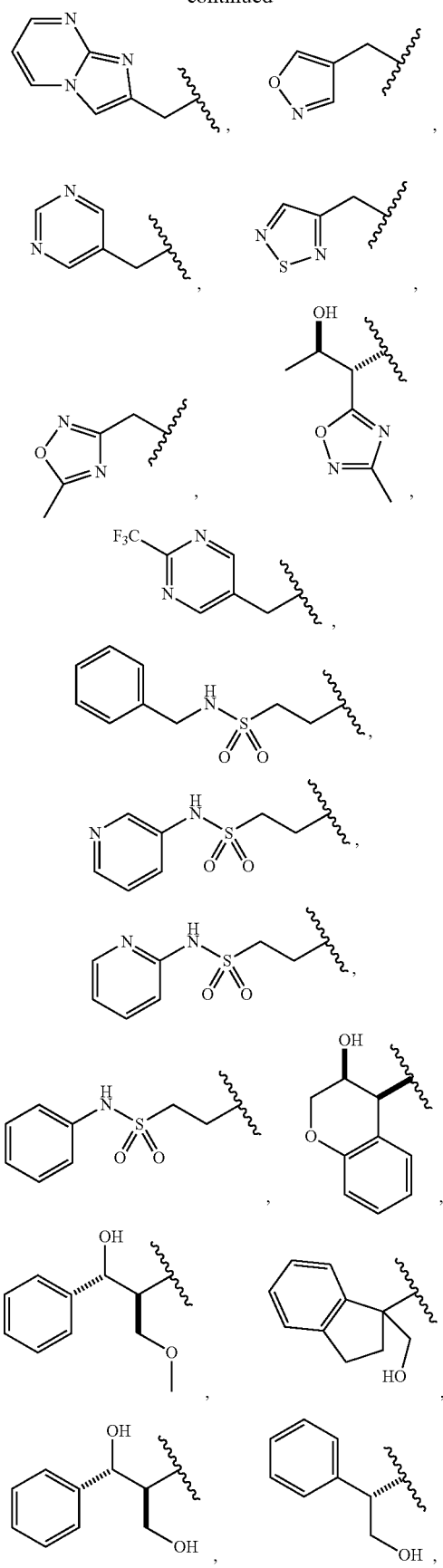

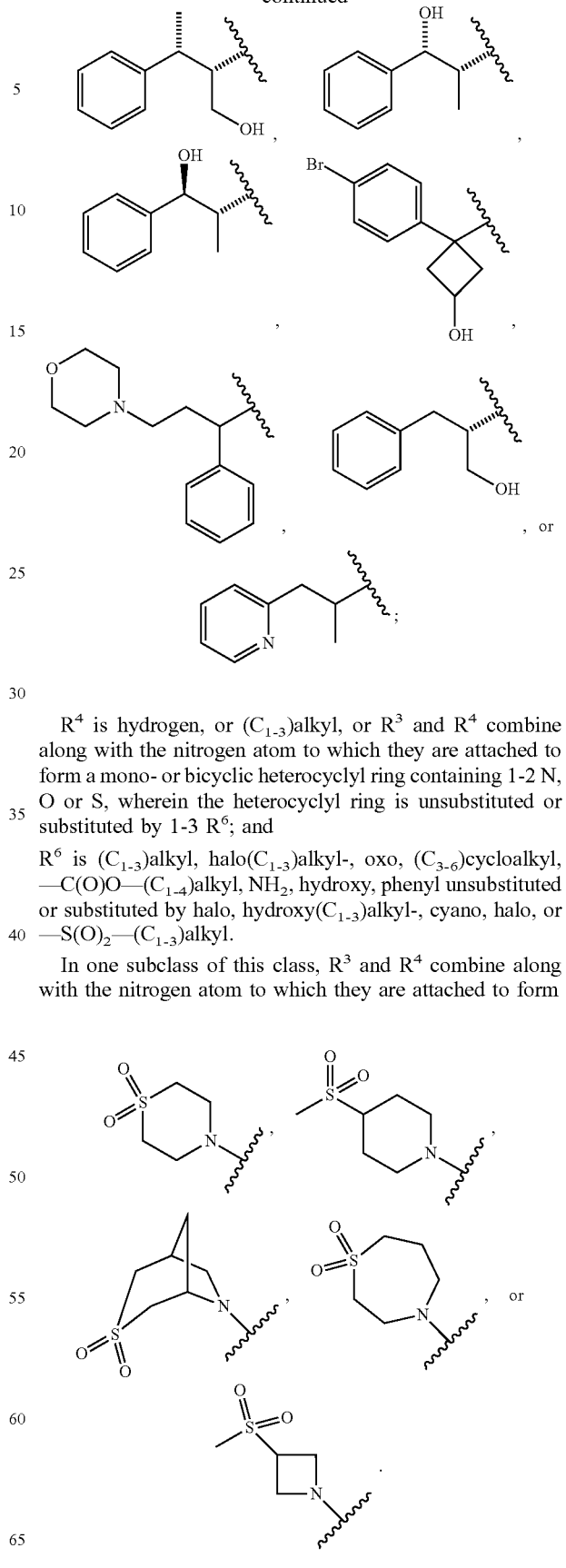

R[4] is hydrogen, or (C$_{1-3}$)alkyl, or R[3] and R[4] combine along with the nitrogen atom to which they are attached to form a mono- or bicyclic heterocyclyl ring containing 1-2 N, O or S, wherein the heterocyclyl ring is unsubstituted or substituted by 1-3 R[6]; and R[6] is (C$_{1-3}$)alkyl, halo(C$_{1-3}$)alkyl-, oxo, (C$_{3-6}$)cycloalkyl, —C(O)O—(C$_{1-4}$)alkyl, NH$_2$, hydroxy, phenyl unsubstituted or substituted by halo, hydroxy(C$_{1-3}$)alkyl-, cyano, halo, or —S(O)$_2$—(C$_{1-3}$)alkyl.

In one subclass of this class, R[3] and R[4] combine along with the nitrogen atom to which they are attached to form In one class of this embodiment, $R^2$ is
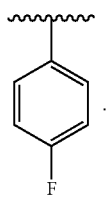 [SMILES: *c1ccc(F)cc1]
In one subclass of this class, $R^3$ is
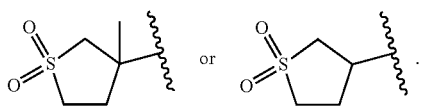
In one class of Formula I-b', $R^2$ is
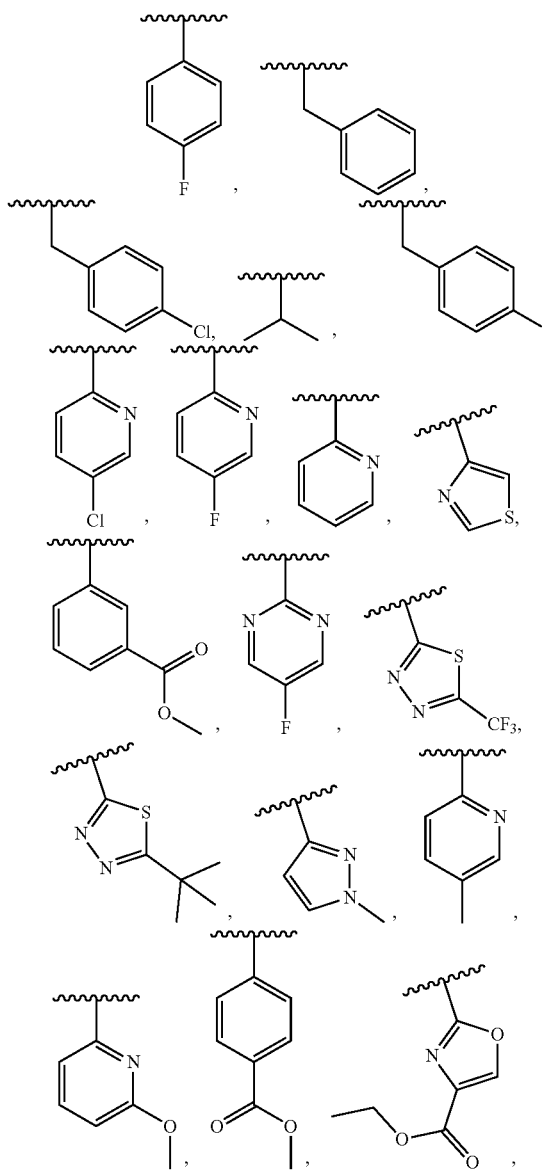
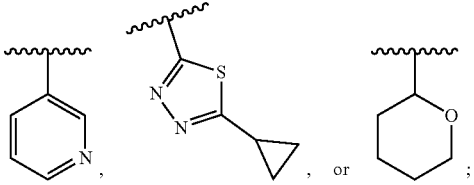
$R^3$ is
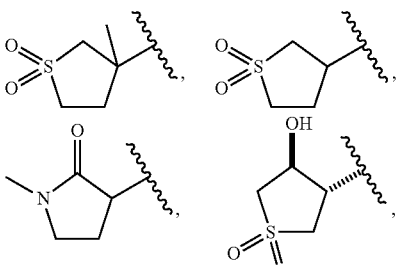
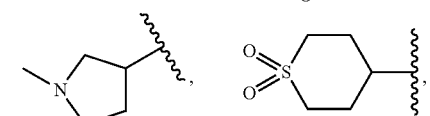
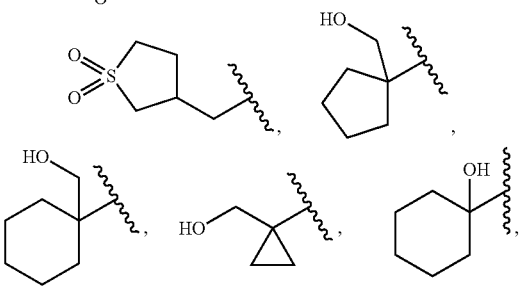
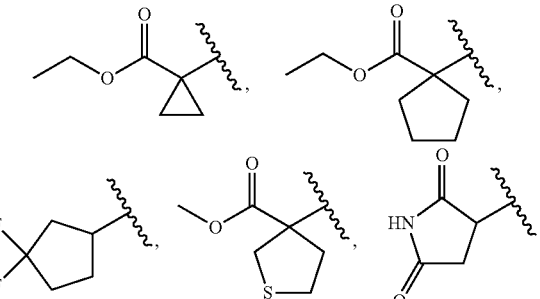
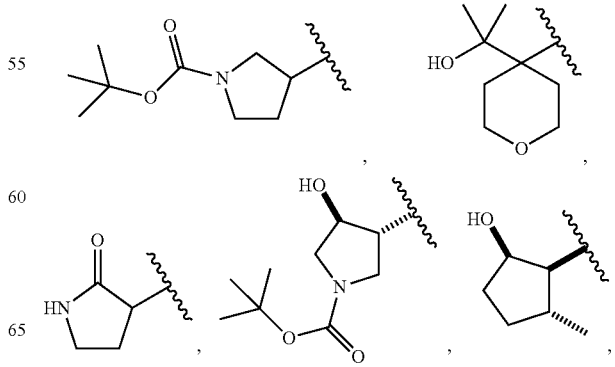

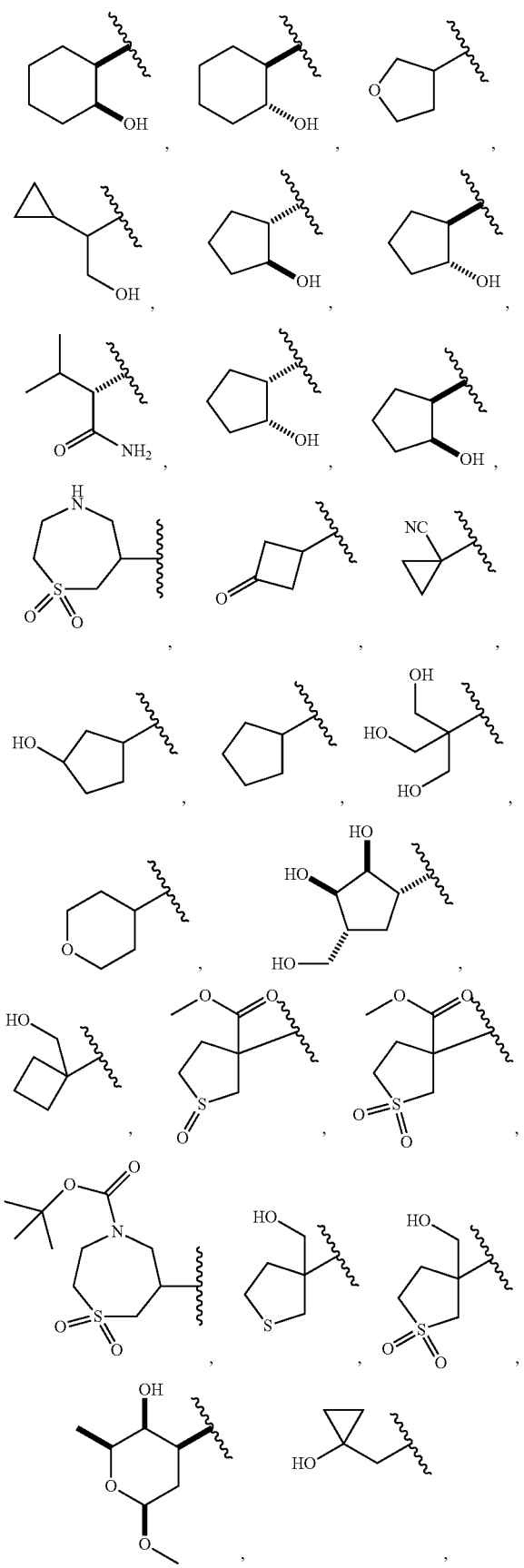
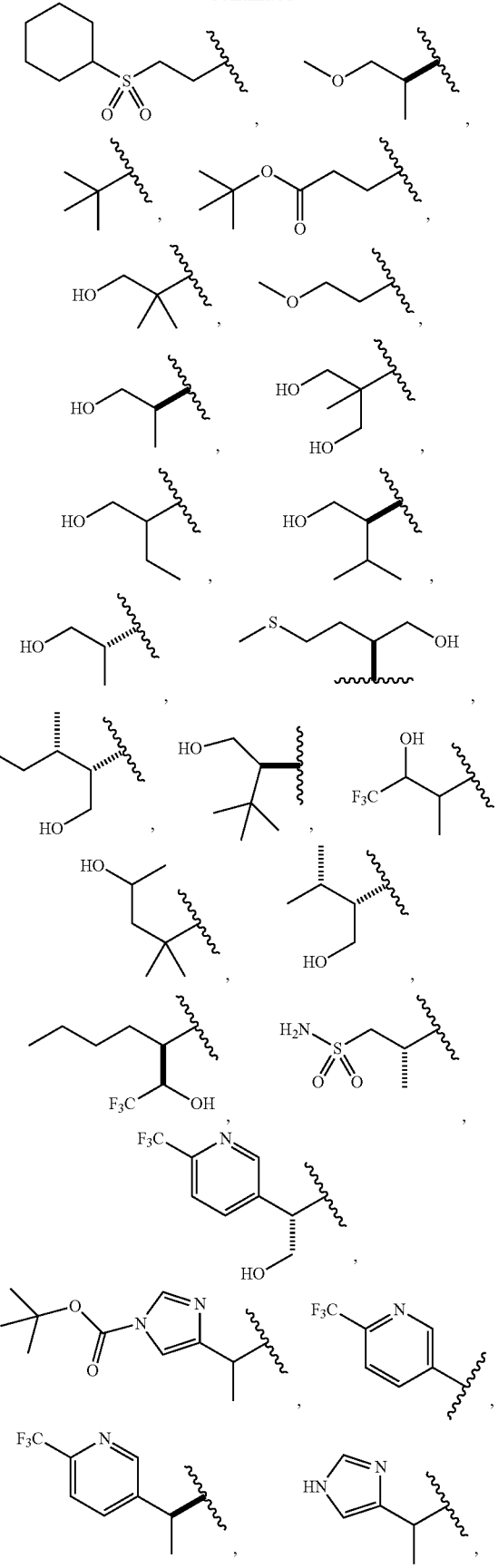

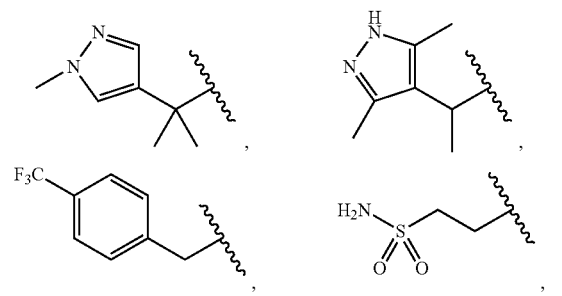
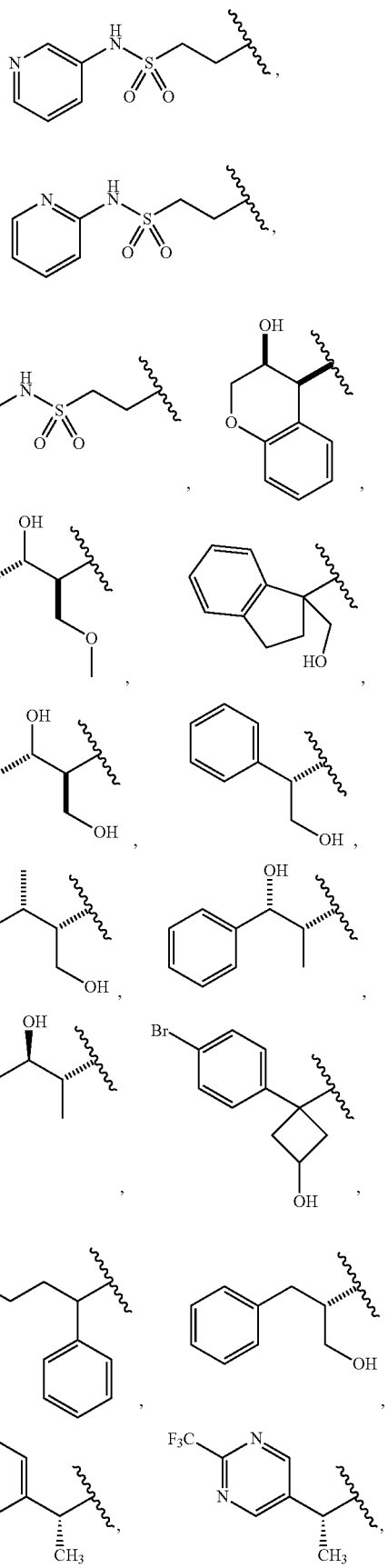

-continued

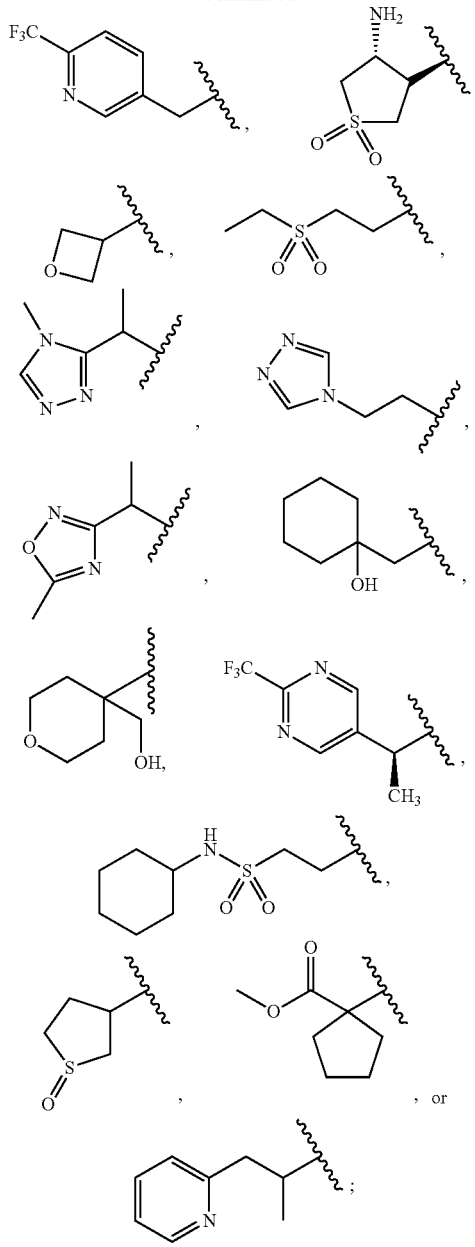

R⁴ is
(1) hydrogen, or
(2) (C$_{1-3}$)alkyl,
or R³ and R⁴ combine along with the nitrogen atom to which they are attached to form a 4- to 7-membered mono- or 6- to 10-membered bicyclic heterocyclyl ring, containing 1 or 2 heteroatoms independently selected from N, O and S, wherein the heterocyclyl ring is unsubstituted or substituted by 1-3 R⁶; and
R⁶ is
(1) (C$_{1-3}$)alkyl,
(2) halo(C$_{1-3}$)alkyl-,
(3) oxo,
(4) (C$_{3-6}$)cycloalkyl,
(5) —C(O)O—(C$_{1-4}$)alkyl,
(6) NH$_2$,
(7) hydroxy,
(8) phenyl unsubstituted or substituted by halo,
(9) hydroxy(C$_{1-3}$)alkyl-,
(10) cyano,
(11) halo, or
(12) —S(O)$_2$—(C$_{1-3}$)alkyl.

In one subclass of this class, R³ and R⁴ combine along with the nitrogen atom to which they are attached to form

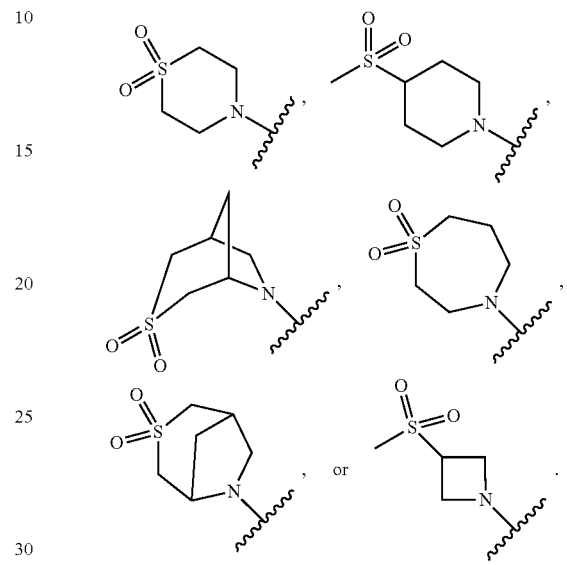

In one class of this embodiment, R² is

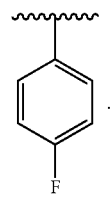

In one subclass of this class, R³ is

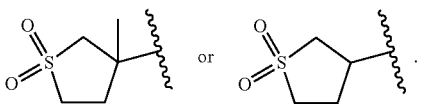

In one embodiment of Formula I, the invention relates to compounds of Formula I-c:

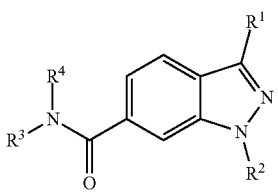

I-c or a pharmaceutically acceptable salt thereof, wherein R¹, R², R³ and R⁴ are as previously defined for Formula I.

In one embodiment of Formula I', the invention relates to compounds of Formula I-c':
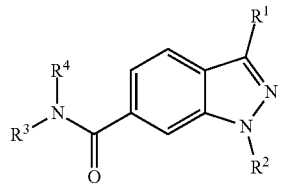
I-c'
or a pharmaceutically acceptable salt thereof, wherein $R^1$, $R^2$, $R^3$ and $R^4$ are as previously defined for Formula I'.
In one class of Formula I-c or I-c', $R^1$ is
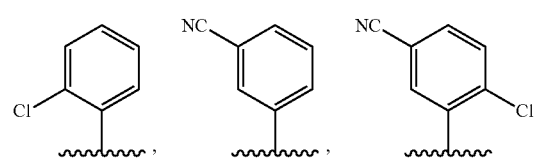
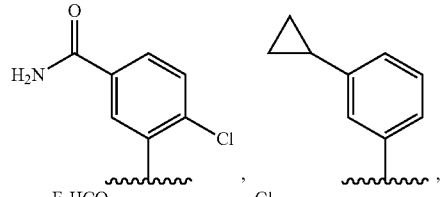
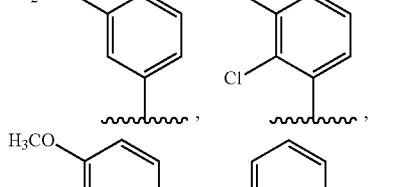
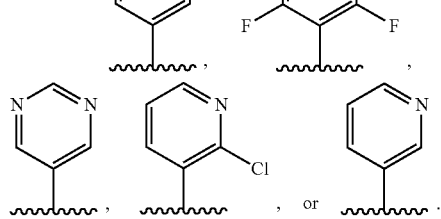
, or
In one class of Formula I-c or I-c', $R^1$ is
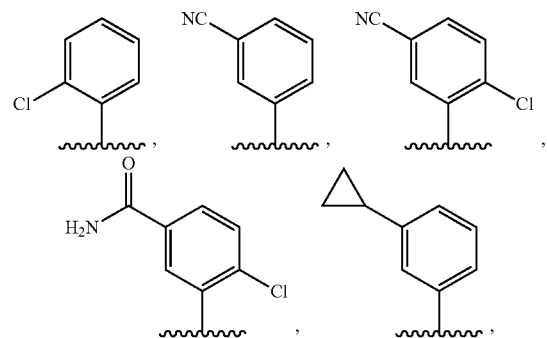
-continued
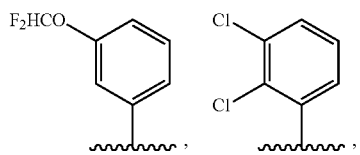
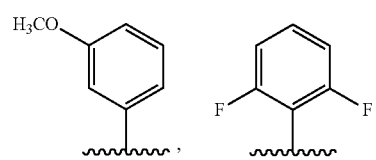
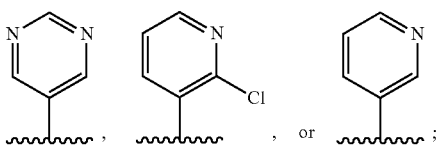
, or
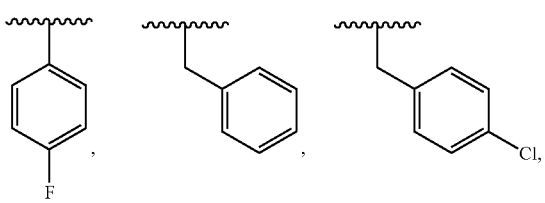
;
$R^2$ is
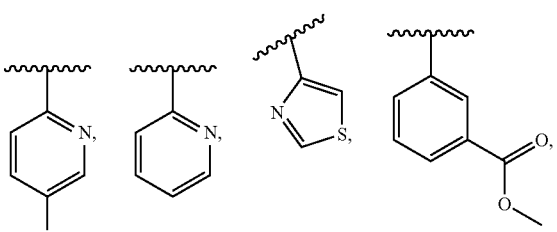
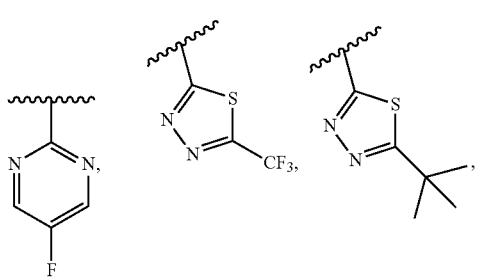

-continued
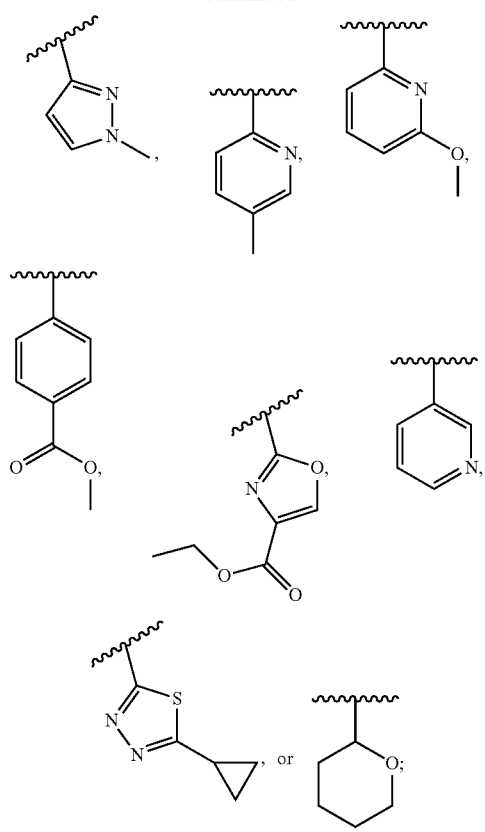
R³ is
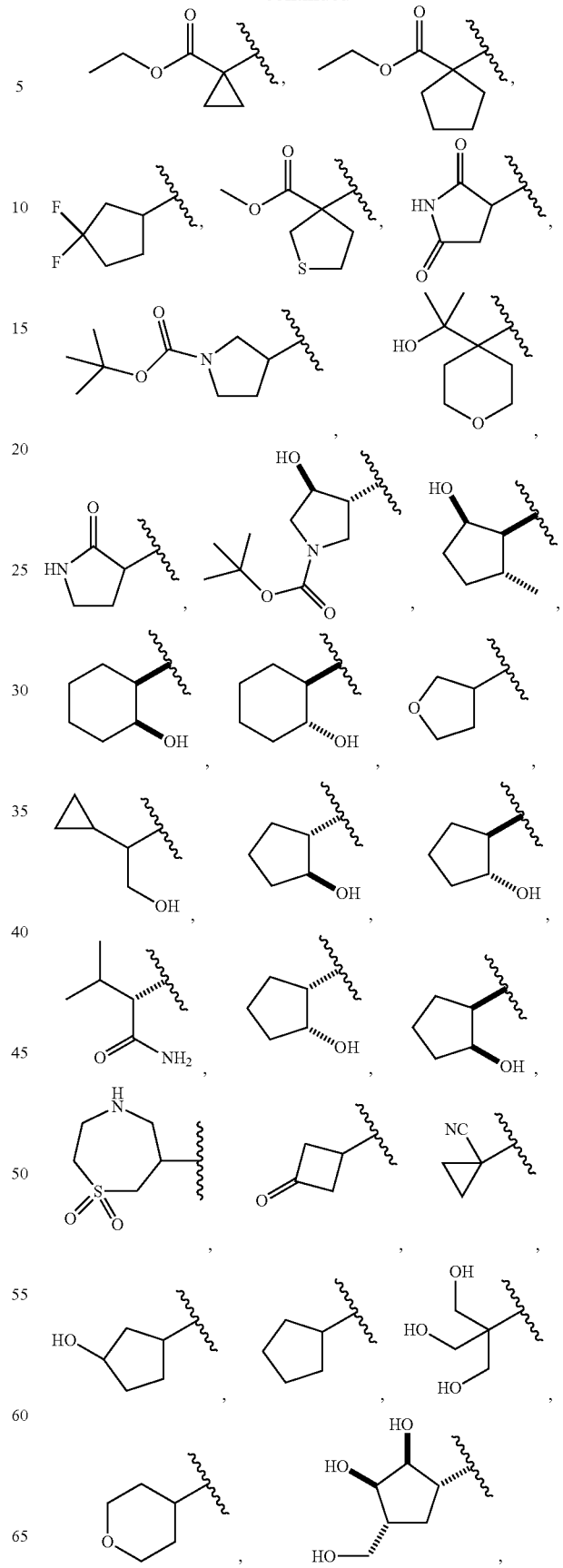

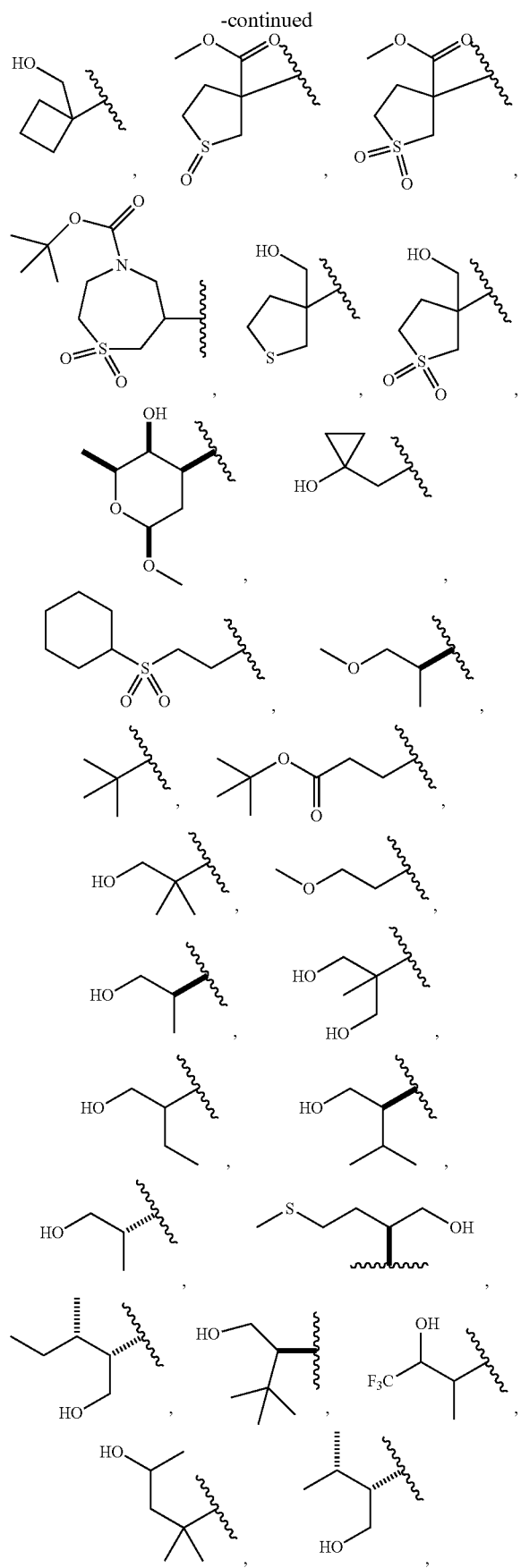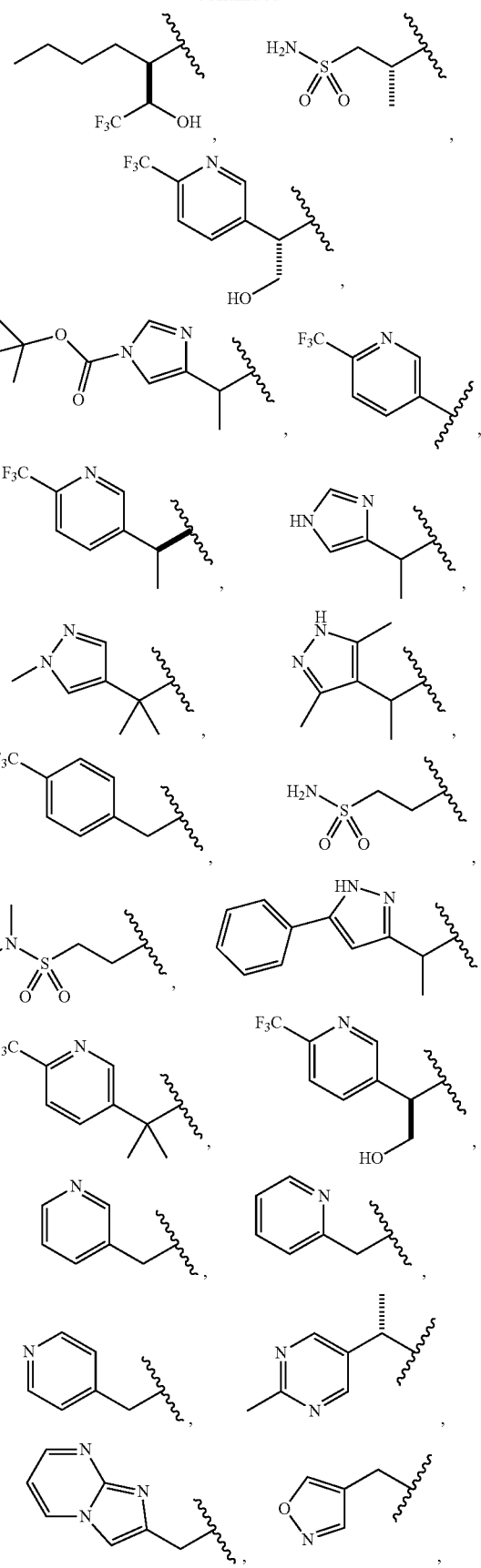

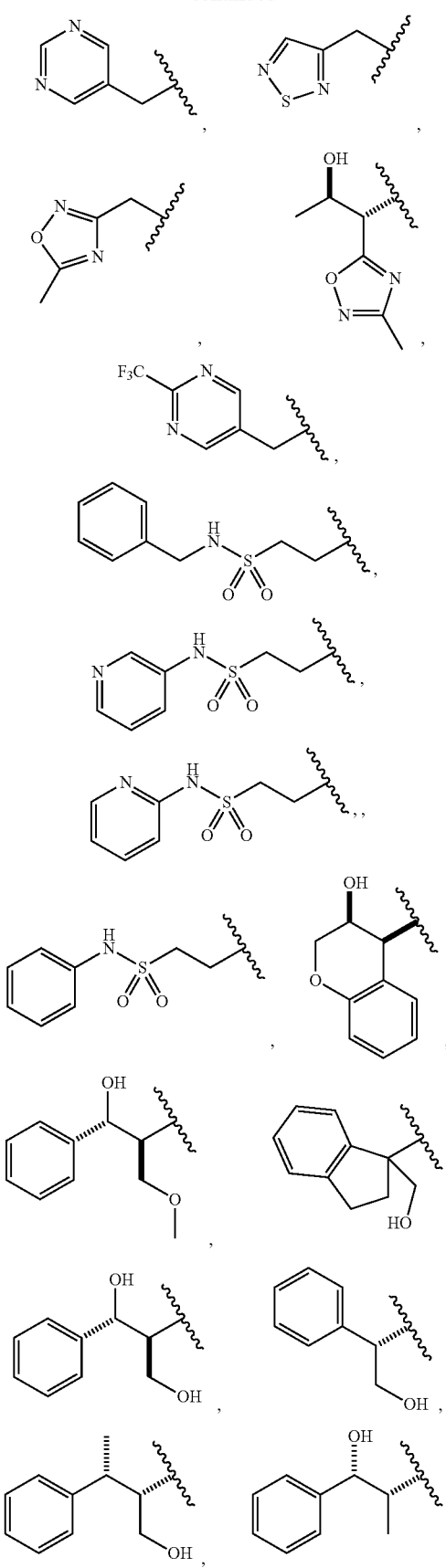

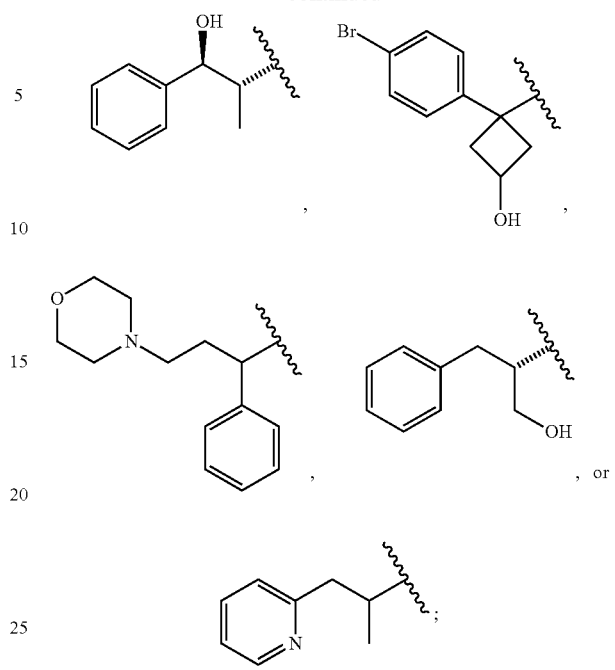

R⁴ is hydrogen, or $(C_{1-3})$alkyl, or R³ and R⁴ combine along with the nitrogen atom to which they are attached to form a mono- or bicyclic heterocyclyl ring containing 1-2 N, O or S, wherein the heterocyclyl ring is unsubstituted or substituted by 1-3 R⁶; and R⁶ is $(C_{1-3})$alkyl, halo$(C_{1-3})$alkyl-, oxo, $(C_{3-6})$cycloalkyl, —C(O)O—$(C_{1-4})$alkyl, NH₂, hydroxy, phenyl unsubstituted or substituted by halo, hydroxy$(C_{1-3})$alkyl-, cyano, halo, or —S(O)₂—$(C_{1-3})$alkyl.

In one subclass of this class, R³ and R⁴ combine along with the nitrogen atom to which they are attached to form

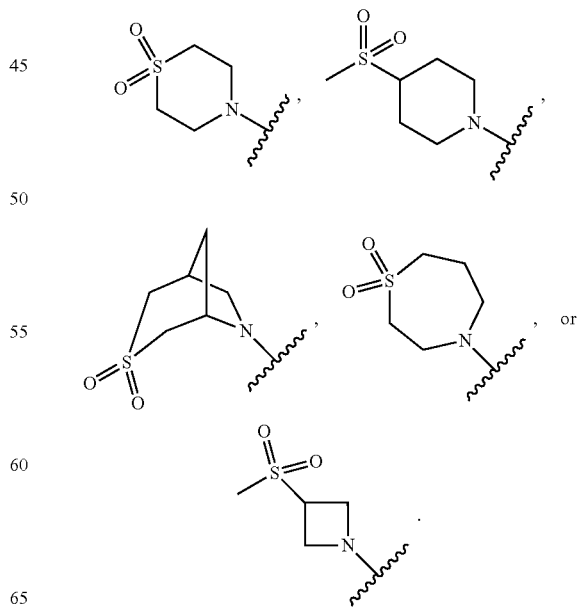

In one class of this embodiment, $R^2$ is
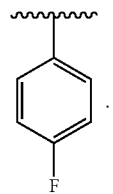 [SMILES: *c1ccc(F)cc1]
In one subclass of this class, $R^3$ is
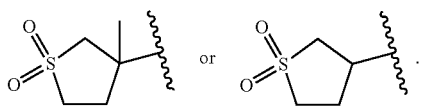
In one class of Formula I-c', $R^1$ is
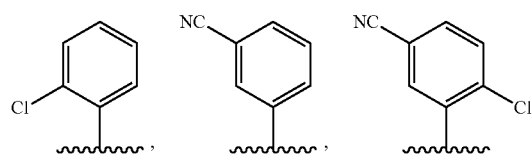
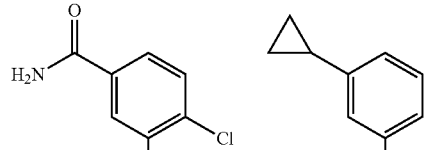
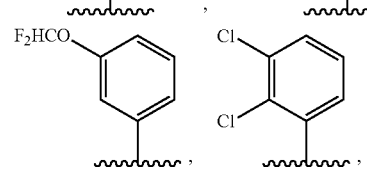
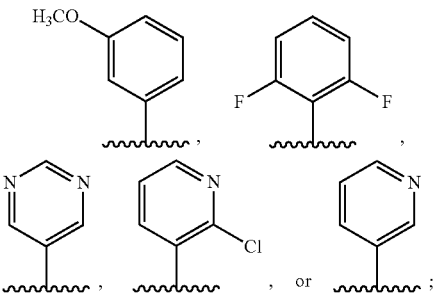
$R^2$ is
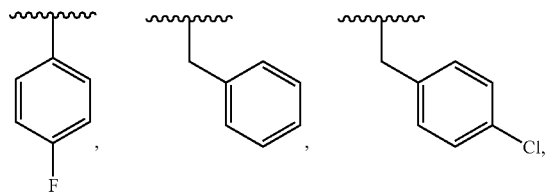
-continued
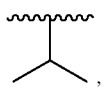 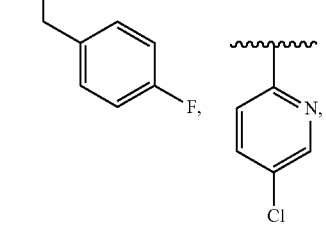
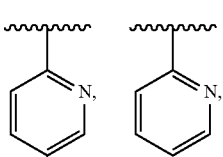 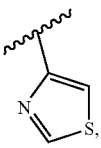 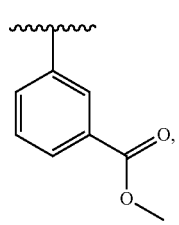
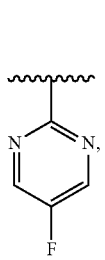 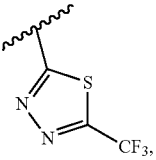 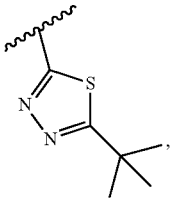
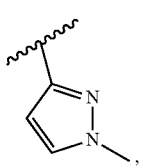 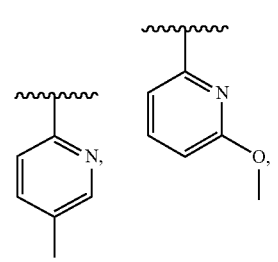
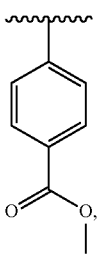  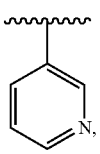
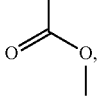 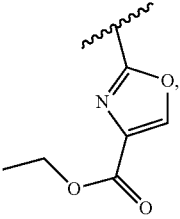
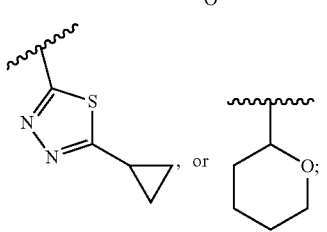

$R^3$
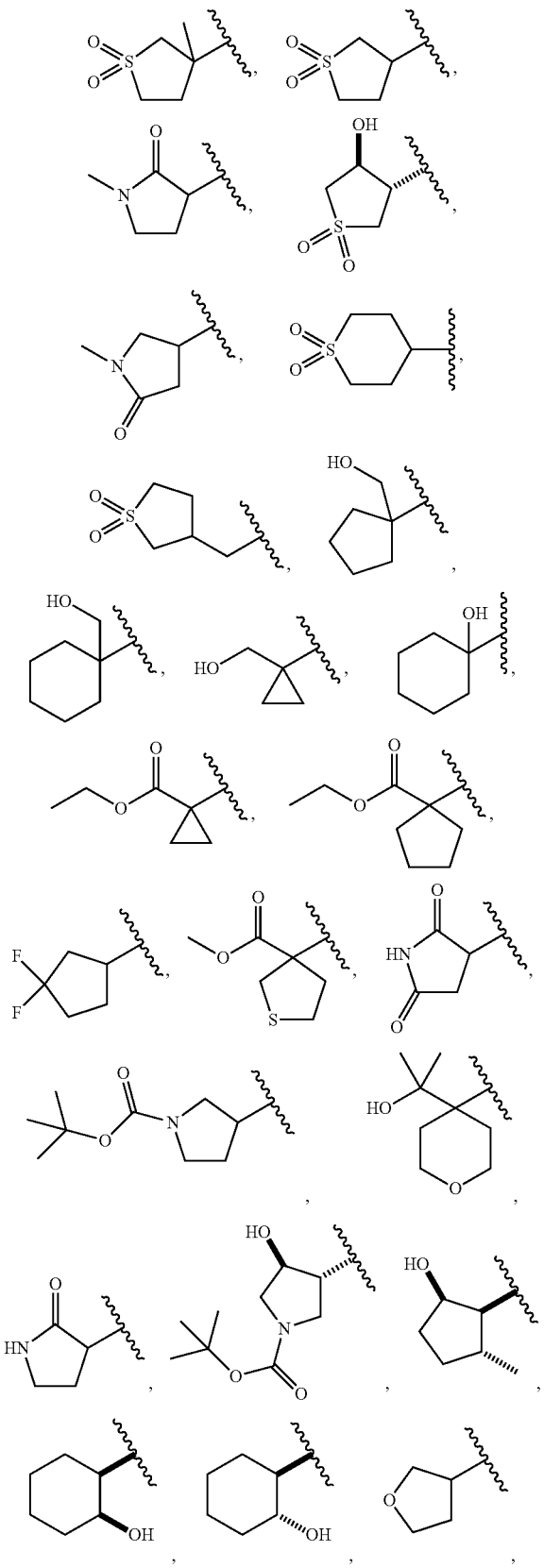
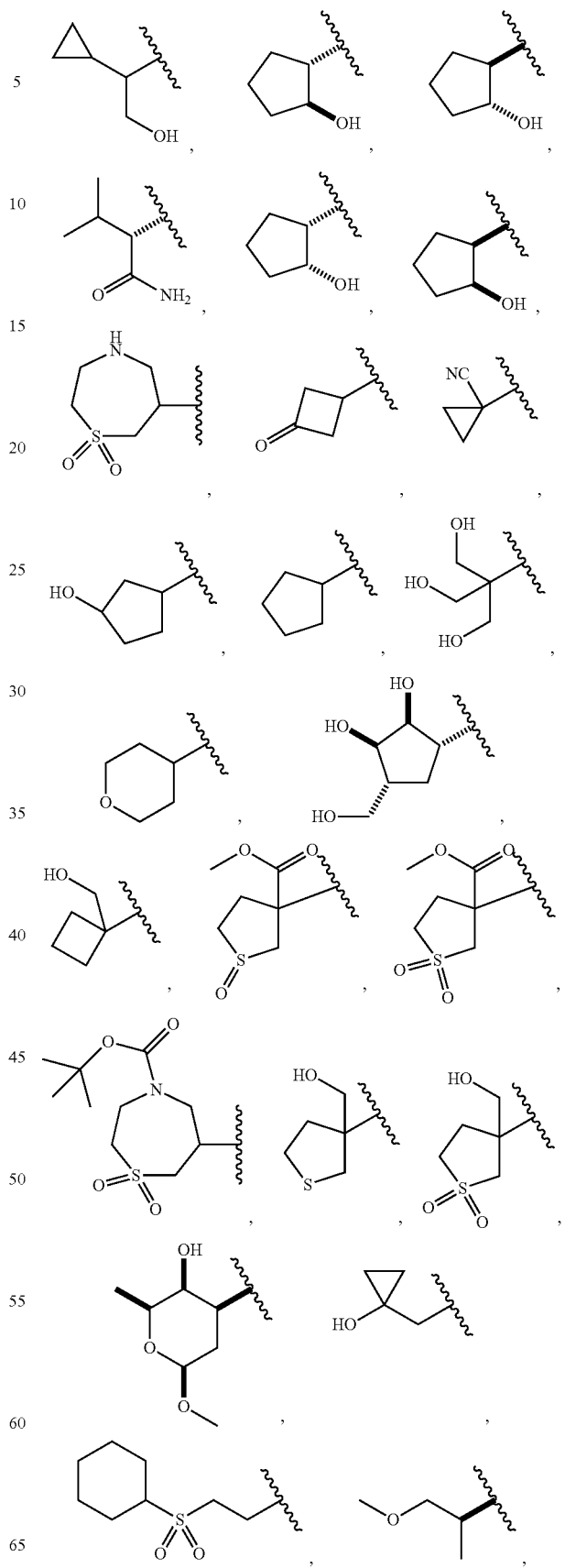

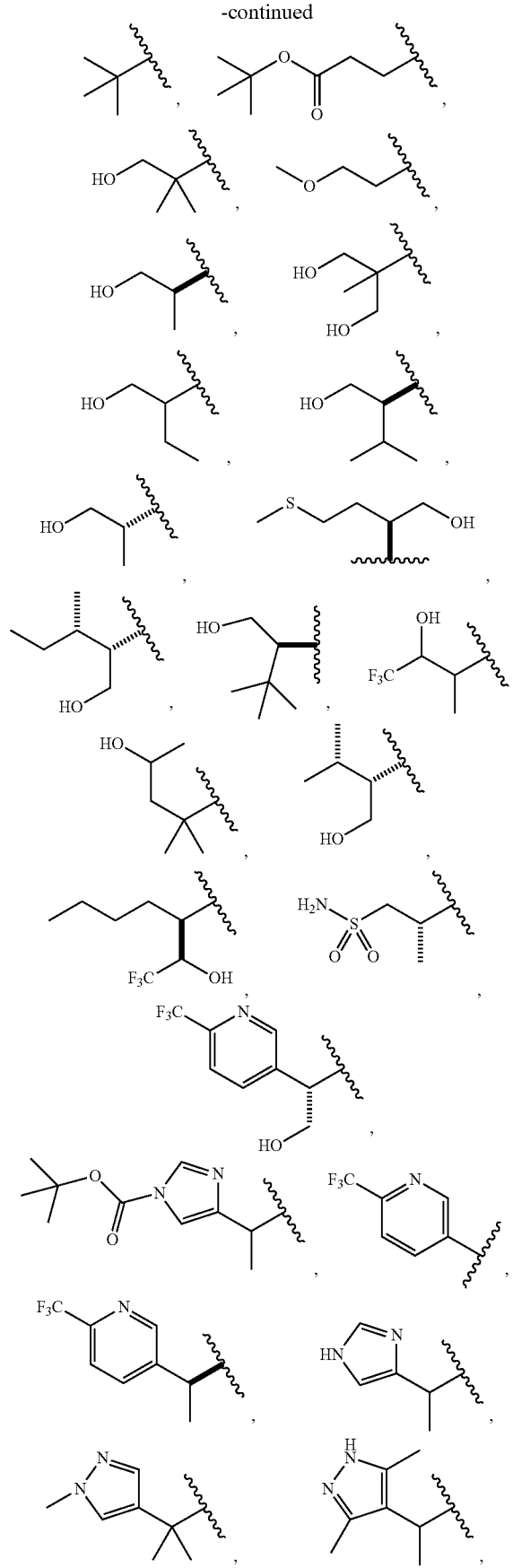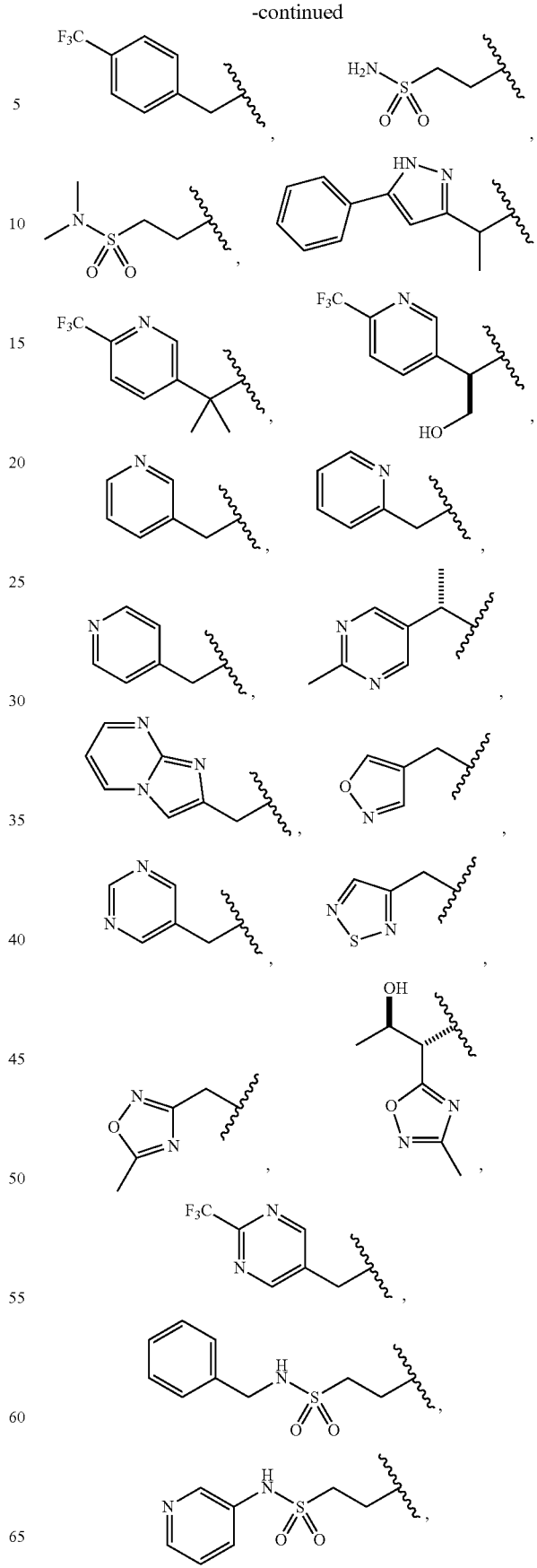

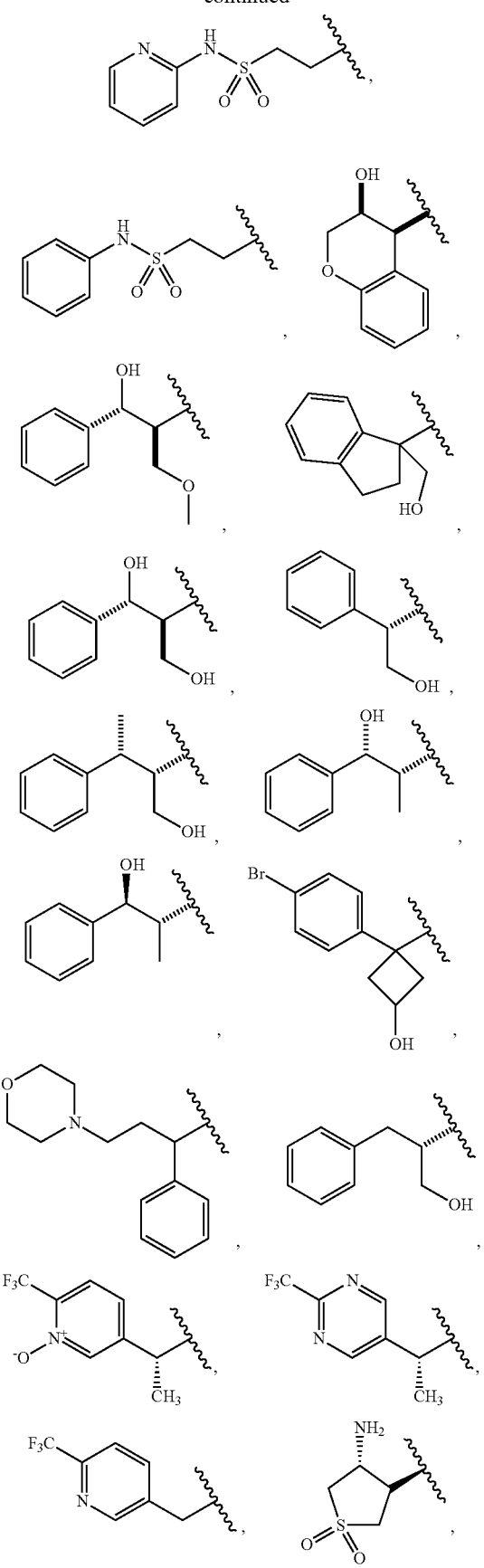
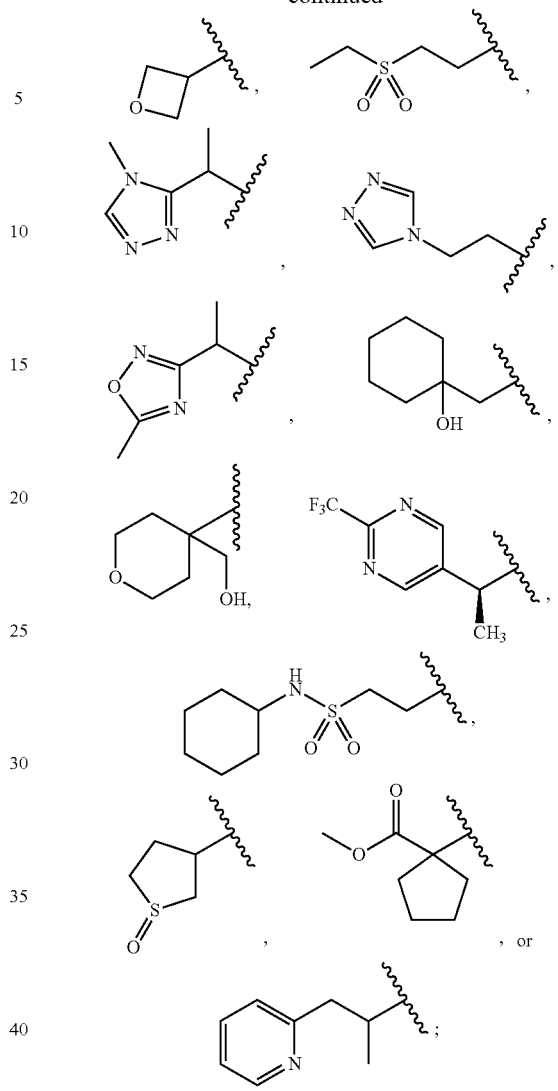

$R^4$ is
(1) hydrogen, or
(2) $(C_{1-3})$alkyl,
or $R^3$ and $R^4$ combine along with the nitrogen atom to which they are attached to form a 4- to 7-membered mono- or 6- to 10-membered bicyclic heterocyclyl ring, containing 1 or 2 heteroatoms independently selected from N, O and S, wherein the heterocyclyl ring is unsubstituted or substituted by 1-3 $R^6$; and $R^6$ is
(1) $(C_{1-3})$alkyl,
(2) halo$(C_{1-3})$alkyl-,
(3) oxo,
(4) $(C_{3-6})$cycloalkyl,
(5) —C(O)O—$(C_{1-4})$alkyl,
(6) $NH_2$,
(7) hydroxy,
(8) phenyl unsubstituted or substituted by halo,
(9) hydroxy$(C_{1-3})$alkyl-,
(10) cyano,
(11) halo, or
(12) —S(O)$_2$—$(C_{1-3})$alkyl.

In one subclass of this class, $R^3$ and $R^4$ combine along with the nitrogen atom to which they are attached to form

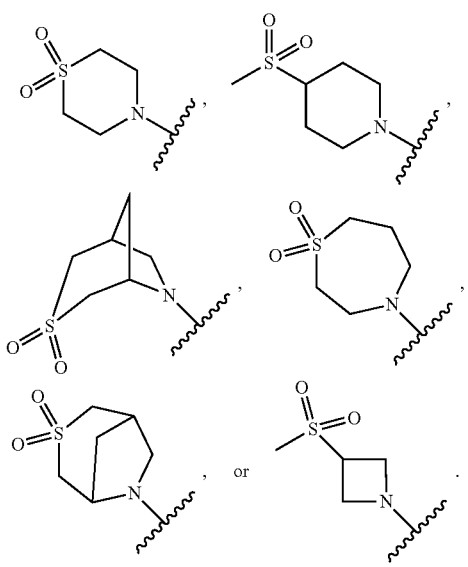

In one class of this embodiment R² is

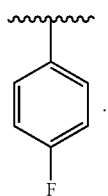 [SMILES: *c1ccc(F)cc1]

In one subclass of this class, R³ is

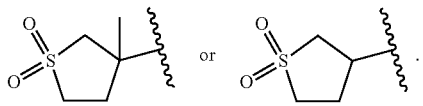

The present invention includes the pharmaceutically acceptable salts of the compounds defined therein. Reference to the compounds of structural Formulas I, I', I-a, I-a', I-b and I-b' (hereinafter "Formulas I to I-b'") includes the compounds of other generic structural Formulas and embodiments that fall within the scope scope of Formulas I to I-b'.

"Alkyl" means branched- and straight-chain saturated aliphatic hydrocarbon groups having the specified number of carbon atoms when noted. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, octyl, nonyl, and the like.

"Alkoxy" refers to an alkyl group linked to oxygen. Examples of alkoxy groups include methoxy, ethoxy, propoxy and the like.

"Aryl" means phenyl or naphthyl.

"Fused aryl" means a phenyl ring fused with heterocyclyl or cycloalkyl. Examples include 1,2,3,4-tetrahydronaphthalene, 1,2,3,4-tetrahydroquinoline, and indoline.

"Halogen" (halo) includes fluorine, chlorine, bromine and iodine.

"Cycloalkyl" means a saturated cyclic hydrocarbon radical having the number of carbon atoms designated. If no number of atoms is specified, 3-10 carbon atoms are intended. Cycloalkyl may also be fused, forming 1-3 carbocyclic rings. Examples of cycloalkyl include cyclopropyl, cyclobutyl, cyclopentyl, cyclohexyl, cycloheptyl, tetrahydronaphthyl, decahydronaphthyl, indanyl and the like.

Alkyl and cycloalkyl are each intended to include such carbon moieties containing isotopic forms of hydrogen (H) such as proton ($^1$H), for example but not limited to —CH₃, and/or deuterium ($^2$H, also denoted herein as D), for example but not limited to —CD₃.

"Haloalkyl" and derivatives such as "halo($C_{1-6}$)alkyl" include mono-substituted as well as multiple halo substituted alkyl groups, up to perhalo substituted alkyl. For example, trifluoromethyl is included.

"Haloalkoxy," "haloalkyl-O" and derivatives such as "halo($C_{1-6}$)alkoxy" are used interchangeably and refer to halo substituted alkyl groups linked through the oxygen atom. Haloalkoxy include mono-substituted as well as multiple halo substituted alkoxy groups, up to perhalo substituted alkoxy. For example trifluoromethoxy, chloromethoxy, and bromomethoxy are included.

"Heterocyclyl," "heterocycle" or "heterocyclic" refers to nonaromatic monocyclic ring structures in which one or more atoms in the ring, the heteroatom(s), is an element other than carbon. Heteroatoms are typically O, S or N atoms. Examples of heterocyclyl groups include: piperidine, piperazine, morpholine, pyrrolidine, tetrahydrofuran, azetidine, oxirane, or aziridine, and the like.

"Bicyclic heterocyclyl," "bicyclic heterocycle" or "bicyclic heterocyclic" refers to a heterocyclic ring fused to another ring system. The fusion may be bridged or unbridged.

"Heteroaryl" unless otherwise indicated, means a monocyclic-aromatic ring or ring system, wherein the ring or ring system is made up of a specified number of atoms when noted, and which contains at least one heteroatom selected from O, S and N or a specified number and selection of heteroatoms when noted. Examples include, but are not limited to, pyrrolyl, isoxazolyl, isothiazolyl, pyrazolyl, pyridyl, oxazolyl, oxadiazolyl, 1,3,4-oxadiazolyl-2(3H)-one, thiadiazolyl, thiazolyl, imidazolyl, triazolyl, tetrazolyl, furanyl, triazinyl, thienyl, pyridinyl, pyrimidinyl, pyridazinyl, pyrazinyl, and the like.

"Fused heteroaryl" is heteroaryl fused with a heteroaryl.

"Oxo" means an oxygen linked to an atom by a double bond. An example of an oxo group is a doubly bonded oxygen in a ketone, sulfoxide, sulfone and sulfate.

"Hydroxyalkyl" means an alkyl group having one or more hydrogen atoms replaced by hydroxyl groups.

When any variable (e.g., $R^6$ etc.) occurs more than one time in any constituent or in Formulas I to I-b' or other generic Formula herein, its definition on each occurrence is independent of its definition at every other occurrence. Combinations of substituents and/or variables are permissible only if such combinations result in stable compounds. In choosing compounds of the present invention, one of ordinary skill in the art will recognize that the various substituents, i.e. $R^6$ etc., are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of structural Formulas I to I-b' may contain one or more asymmetric centers and can thus occur as racemates and racemic mixtures, single enantiomers, diastereoisomeric mixtures and individual diastereoisomers. Centers of asymmetry that are present in the compounds of Formulas I to I-b' can all independently of one another have S configuration or R configuration. The compounds of this invention include all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The present invention is meant to comprehend all such stereo-isomeric forms of the compounds of structural Formulas I to I-b'.

Compounds of structural Formulas I to I-b' may be separated into their individual diastereoisomers by, for example, fractional crystallization from a suitable solvent, for example MeOH or EtOAc or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Alternatively, any stereoisomer or isomers of a compound of Formulas I to I-b' may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formulas I to I-b' described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formulas I to I-b' of the present invention.

In the compounds of structural Formulas I to I-b', the atoms may exhibit their natural isotopic abundances, or one or more of the atoms may be artificially enriched in a particular isotope having the same atomic number, but an atomic mass or mass number different from the atomic mass or mass number predominately found in nature. The present invention as described and claimed herein is meant to include all suitable isotopic variations of the compounds of structural Formulas I to I-b' and embodiments thereof. For example, different isotopic forms of hydrogen (H) include protium ($^1$H) and deuterium ($^2$H, also denoted herein as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples, Isotopically-enriched compounds within structural Formulas I to I-b', can be prepared without undue experimentation by conventional techniques well known to those skilled in the art or by processes analogous to those described in the Schemes and Examples herein using appropriate isotopically-enriched reagents and/or intermediates.

It will be understood that the compounds of structural Formulas I to I-b' may be prepared as pharmaceutically acceptable salts or as salts that are not pharmaceutically acceptable when they are used as precursors to the free compounds or their pharmaceutically acceptable salts or in other synthetic manipulations. The compounds of the present invention, including the compounds of the Examples, may also include all salts of the compounds of Formulas I to I-b' which, owing to low physiological compatibility, are not directly suitable for use in pharmaceuticals but which can be used, for example, as intermediates for chemical reactions or for the preparation of physiologically acceptable salts.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, bromide, butyrate, camphorate, camphorsulfonate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, methanesulfonate, mucate, napsylate, nitrate, N-methylglucamine ammonium salt, oleate, oxalate, pamoate (embonate), palmitate, pantothenate, phosphate/diphosphate, polygalacturonate, propionate, salicylate, stearate, sulfate, subacetate, succinate, tannate, tartrate, teoclate, thiocyanate, tosylate, triethiodide, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. In one embodiment, the salts of acidic compounds are as follows, the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. If the compounds of Formulas I to I-b' simultaneously contain acidic and basic groups in the molecule the invention also includes, in addition to the salt forms mentioned, inner salts or betaines (zwitterions). Salts can be obtained from the compounds of Formulas I to I-b' by customary methods which are known to the person skilled in the art, for example by combination with an organic or inorganic acid or base in a solvent or dispersant, or by anion exchange or cation exchange from other salts.

Furthermore, compounds of the present invention may exist in amorphous form and/or one or more crystalline forms, and as such all amorphous and crystalline forms and mixtures thereof of the compounds of Formulas I to I-b', including the Examples, are intended to be included within the scope of the present invention. In addition, some of the compounds of the instant invention may form solvates with water (i.e., a hydrate) or common organic solvents such as but not limited to EtOAc. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid (—COOH) group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Included are those esters and acyl groups known in the art for modifying the solubility or hydrolysis characteristics for use as sustained-release or prodrug formulations. Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed.

Accordingly, the compounds within the generic structural formulas, embodiments and specific compounds described in the Examples and claimed herein encompass salts, all possible stereoisomers and tautomers, physical forms (e.g., amorphous and crystalline forms), solvate and hydrate forms thereof and any combination of these forms, as well as the salts, pro-drug forms thereof, and salts of pro-drug forms thereof, where such forms are possible unless specified otherwise, The present invention also relates to processes for the preparation of the compounds of Formulas I to I-b' which are described in the following and by which the compounds of the invention are obtainable.

The terms "therapeutically effective (or efficacious) amount" and similar descriptions such as "an amount efficacious for treatment" are intended to mean that amount of a pharmaceutical drug that will alleviate the symptoms of the disorder, condition or disease being treated (i.e., disorder, condition or disease associated with DGAT2 activity) in an animal or human. The terms "prophylactically effective (or efficacious) amount" and similar descriptions such as "an amount efficacious for prevention" are intended to mean that amount of a pharmaceutical drug that will prevent or reduce the symptoms or occurrence of the disorder, condition or disease being treated (i.e., disorder, condition or disease associated with DGAT2 activity) in an animal or human. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of hepatic steatosis, diabetes mellitus, obesity, hyperlipidemia, hypercholesterolemia, and a prophylactically effective amount, e.g., for prevention of atherosclerosis.

Disorders, conditions and diseases which can be treated or prevented by inhibiting DGAT2 by using the compounds of Formulas I to I-b' are, for example, diseases such as hyperlipidemia, type I diabetes, type II diabetes mellitus, coronary heart disease, ischemic stroke, restenosis, peripheral vascular disease, intermittent claudication, myocardial infarction, dyslipidemia, post-prandial lipemia, obesity, osteoporosis, hypertension, congestive heart failure, left ventricular hypertrophy, peripheral arterial disease, diabetic retinopathy, diabetic nephropathy, glomerulosclerosis, chronic renal failure, diabetic neuropathy, metabolic syndrome, syndrome X, coronary heart disease, angina pectoris, thrombosis, atherosclerosis, myocardial infarction, transient ischemic attacks, stroke, hyperglycemia, hyperinsulinemia, hypertriglyceridemia, hypertriglyceridemia, insulin resistance, impaired glucose tolerance, erectile dysfunction, skin and connective tissue disorders, hyper-apo B lipoproteinemia, non-alcoholic steatohepatitis (NASH), non-alcoholic fatty liver disease, cardiorenal diseases such as chronic kidney diseases and heart failure, and related diseases and conditions.

The compounds of Formulas I to I-b' and their pharmaceutically acceptable salts can be administered to animals, preferably to mammals, and in particular to humans, as pharmaceuticals by themselves, in mixtures with one another or in the form of pharmaceutical preparations. The term "patient" includes animals, preferably mammals and especially humans, who use the instant active agents for the prevention or treatment of a medical condition. Administering of the drug to the patient includes both self-administration and administration to the patient by another person. The patient may be in need of, or desire, treatment for an existing disease or medical condition, or may be in need of or desire prophylactic treatment to prevent or reduce the risk of occurrence of said disease or medical condition. As used herein, a patient "in need" of treatment of an existing condition or of prophylactic treatment encompasses both a determination of need by a medical professional as well as the desire of a patient for such treatment.

Furthermore, a subject of the present invention are pharmaceutical preparations (or pharmaceutical compositions) which comprise as active component a therapeutically effective dose of at least one compound of Formulas I to I-b' and/or a pharmaceutically acceptable salt thereof and a customary pharmaceutically acceptable carrier, i.e., one or more pharmaceutically acceptable carrier substances and/or additives.

Thus, a subject of the invention is, for example, said compound and its pharmaceutically acceptable salts for use as a pharmaceutical, pharmaceutical preparations which comprise as active component a therapeutically effective dose of said compound and/or a pharmaceutically acceptable salt thereof and a customary pharmaceutically acceptable carrier, and the uses of said compound and/or a pharmaceutically acceptable salt thereof in the therapy or prophylaxis of the above mentioned syndromes as well as their use for preparing medicaments for these purposes.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of Formulas I to I-b' and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of Formulas I to I-b' and/or of a pharmaceutically acceptable salt thereof to be administered depends on the individual case and is, as is customary, to be adapted to the individual circumstances to achieve an optimum effect. Thus, it depends on the nature and the severity of the disorder, condition or disease to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formulas I to I-b'.

One or more additional pharmacologically active agents may be administered in combination with a compound of Formulas I to I-b'. An additional active agent (or agents) is intended to mean a pharmaceutically active agent (or agents) that is active in the body, including pro-drugs that convert to pharmaceutically active form after administration, which are different from the compound of Formulas I to I-b', and also includes free-acid, free-base and pharmaceutically acceptable salts of said additional active agents. Generally, any suitable additional active agent or agents, including but not limited to anti-hypertensive agents, anti-atherosclerotic agents such as a lipid modifying compound, anti-diabetic agents and/or antiobesity agents may be used in any combination with the compound of Formulas I to I-b' in a single dosage formulation (a fixed dose drug combination), or may be administered to the patient in one or more separate dosage formulations which allows for concurrent or sequential administration of the active agents (co-administration of the separate active agents).

Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides, amino acids and derivatives, amino acid chains linked by non-peptidic bonds, di- and tri-peptide derivatives, peptidyl amino diols and peptidyl beta-aminoacyl aminodiol carbamates; also, and small molecule renin inhibitors (including diol sulfonamides and, N-morpholino derivatives, N-heterocyclic alcohols and pyrolirnidazolones; also, pepstatin derivatives and fluoro- and chloro-derivatives of statone-containing peptides, enalkrein, RO 42-5892, A 65317, CP 80794, ES 1005, ES 8891, SQ 34017, aliskiren (2(S),4(S), 5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazosin, prazosin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR@ and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), fluvastatin (particularly the sodium salt sold in LESCOL®), cerivastatin, and pitavastatin; a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and/or with an HMG-CoA reductase inhibitor; niacin receptor agonists such as acipimox and acifran, as well as niacin receptor partial agonists; metabolic altering agents including insulin and insulin mimetics (e.g., insulin degludec, insulin glargine, insulin lispro), dipeptidyl peptidase-IV (DPP-4) inhibitors (e.g., sitagliptin, alogliptin, omarigliptin, linagliptin, vildagliptin); insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); insulin or insulin analogs (e.g., insulin detemir, insulin glulisine, insulin degludec, insulin glargine, insulin lispro and inhalable formulations of each); leptin and leptin derivatives and agonists; amylin and amylin analogs (e.g., pramlintide); sulfonylurea and non-sulfonylurea insulin secretagogues (e.g., tolbutamide, glyburide, glipizide, glimepiride, mitiglinide, meglitinides, nateglinide and repaglinide); α-glucosidase inhibitors (e.g., acarbose, voglibose and miglitol); glucagon receptor antagonists (e.g., MK-3577, MK-0893, LY-2409021 and KT6-971); incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof), bile acid sequestering agents (e.g., colestilan, colestimide, colesevalam hydrochloride, colestipol, cholestyramine, and dialkylaminoalkyl derivatives of a cross-linked dextran), acyl CoA:cholesterol acyltransferase inhibitors, (e.g., avasimibe); antiobesity compounds; agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199); CETP inhibitors (e.g., anacetrapib, torcetrapib, and evacetrapib); inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2); AMP-activated Protein Kinase (AMPK) activators; other agonists of the G-protein-coupled receptors: (i) GPR-109, (ii) GPR-119 (e.g., MBX2982 and PSN821), and (iii) GPR-40 (e.g., TAK875); SSTR3 antagonists (e.g., such as those disclosed in WO 2009/001836); neuromedin U receptor agonists (e.g., such as those disclosed in WO 2009/042053, including, but not limited to, neuromedin S (NMS)); SCD modulators; GPR-105 antagonists (e.g., such as those disclosed in WO 2009/000087); SGLT inhibitors (e.g., ASP1941, SGLT-3, empagliflozin, dapagliflozin, canagliflozin, BI-10773, ertugliflozin, remogliflozin, TS-071, tofogliflozin, ipragliflozin, and LX-4211); inhibitors of acyl coenzyme A:diacylglycerol acyltransferase 1 and 2 (DGAT-1 and DGAT-2); inhibitors of fatty acid synthase; inhibitors of acyl coenzyme A:monoacylglycerol acyltransferase 1 and 2 (MGAT-1 and MGAT-2); agonists of the TGR5 receptor (also known as GPBAR1, BG37, GPCR19, GPR131, and M-BAR); ileal bile acid transporter inhibitors; PACAP, PACAP mimetics, and PACAP receptor 3 agonists; PPAR agonists; protein tyrosine phosphatase-1B (PTP-1B) inhibitors; IL-1b antibodies, (e.g., XOMA052 and canakinumab); and bromocriptine mesylate and rapid-release formulations thereof; or with other drugs beneficial for the prevention or the treatment of the above-mentioned diseases including nitroprusside and diazoxide the free-acid, free-base, and pharmaceutically acceptable salt forms of the above active agents where chemically possible.

The following examples are provided so that the invention might be more fully understood. Unless otherwise indicated, the starting materials are commercially available. They should not be construed as limiting the invention in any way.

Several methods for preparing the compounds of this invention are described in the following Schemes and Examples. Starting materials and intermediates are purchased, made from known procedures, or as otherwise illustrated. Some frequently applied routes to the compounds of Formulas I to I-b' are also described by the Schemes as follows. In some cases the order of carrying out the steps of reaction schemes may be varied to facilitate the reaction or to avoid unwanted reaction products. For stereoisomers, enantiomer A refers to the faster/earlier eluting enantiomer and enantiomer B refers to the slower/later eluting enantiomer at the point of separation and this nomenclature is maintained through the remainder of a synthetic sequence for a given enantiomeric series regardless of the possibility that subsequent intermediates and final compounds may have the same or opposite orders of elution.

Throughout the synthetic schemes and examples, abbreviations and acronyms may be used with the following meanings unless otherwise indicated: ACN, MeCN=acetonitrile, AcOH=acetic acid, aq.=aqueous, Bn=benzyl, Bn-Br=benzyl bromide, CBZ=carbobenzyloxy, CBZ-Cl=benzylchloroformate, ° C.=degrees Celsius, CoA=coenzyme A, DIPEA=diethylpropylamine, DMA=N,N-dimethylacetamide, DMF=N,N-dimethylformamide, DMSO=dimethylsulfoxide, DME=1,2-dimethoxyethane, EDC=N-(3-Dimethylaminopropyl)-N'-ethylcarbodiimide hydrochloride; EDTA=ethylenediaminetetraacetic acid, Et=ethyl, EtOAc=ethyl acetate, HBTU=N,N,N',N'-Tetramethyl-O-(1H-benzotriazol-1-yl)uronium hexafluorophosphate, O-(Benzotriazol-1-yl)-N,N,N',N'-tetramethyluronium hexafluorophosphate, HATU=(1-[Bis(dimethylamino)methylene]-1H-1,2,3-triazolo[4,5-b]pyridinium 3-oxid hexafluorophosphate), HBTU=N,N,N',N'-Tetramethyl-O-(1H-benzotriazol-1-yl)uronium hexafluorophosphate; HOBT=hydroxybenzotriazole, h or hr=hour, HPLC=High pressure liquid chromatography, Int=intermediate, L=liter, LC=liquid chromatography, Me=methyl, MeOH=methanol, M=molar, mCPBA=meta-chloroperoxybenzoic acid, m/z=minutes, mL=milliliter, MS=mass spectrometry, MTBE=methyl tertiary butyl ether, mmol=millimole or millimolar, NMR=nuclear magnetic resonance, Pd/C=palladium on carbon, Pd(PPh₃)₄=tetrakis(triphenylphosphine)palladium(0); RP=reverse phase, rt=room temperature, TEA, Et₃N=triethylamine, p-TsOH=para-toluene sulfonic acid, THF=tetrahydrofuran, CELITE=diatomaceous earth, TFA=trifluoroacetic acid, Ti(OEt)₄=titanium(4-+) ethoxide, TPP=potassium phosphate tribasic, V=volt.

1. General Synthetic Schemes

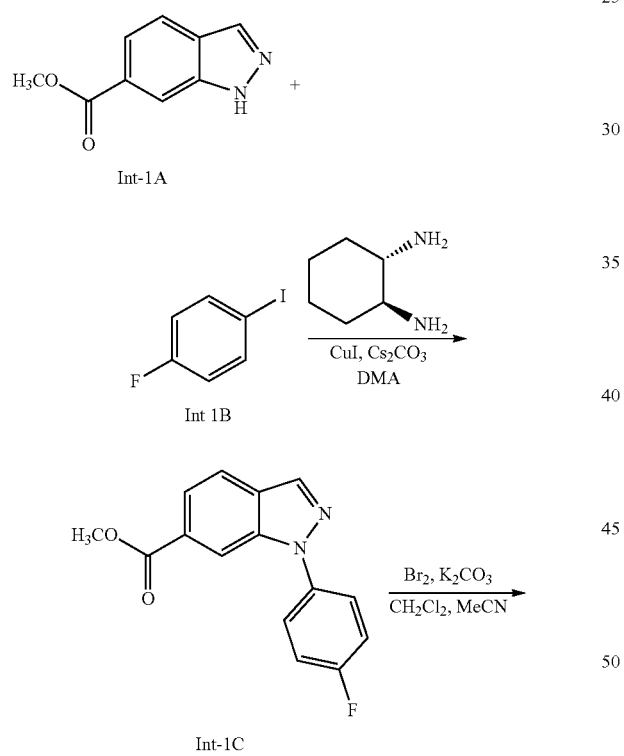

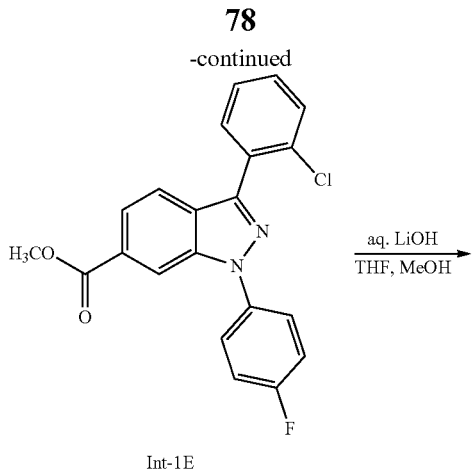

Scheme A shows the preparation of Int-1, which starts with a copper catalyzed N-arylation of indazole Int-1A with 1-fluoro-4-iodobenzene Int-1B. The resulting Int-1C is selectively brominated to furnish Int-1D. A Suzuki coupling affords ester Int-1E, which is hydrolyzed to provide Int-1.

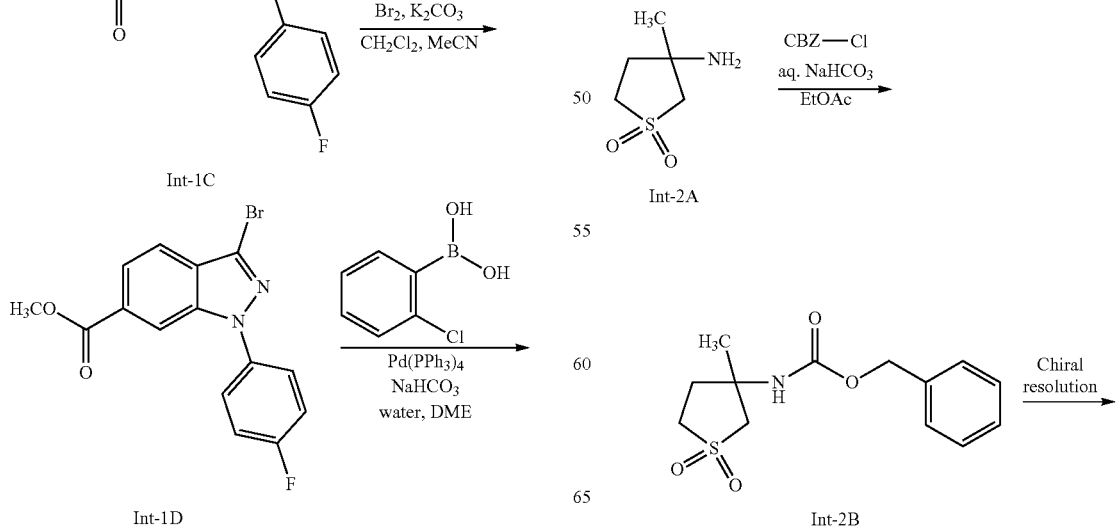

-continued

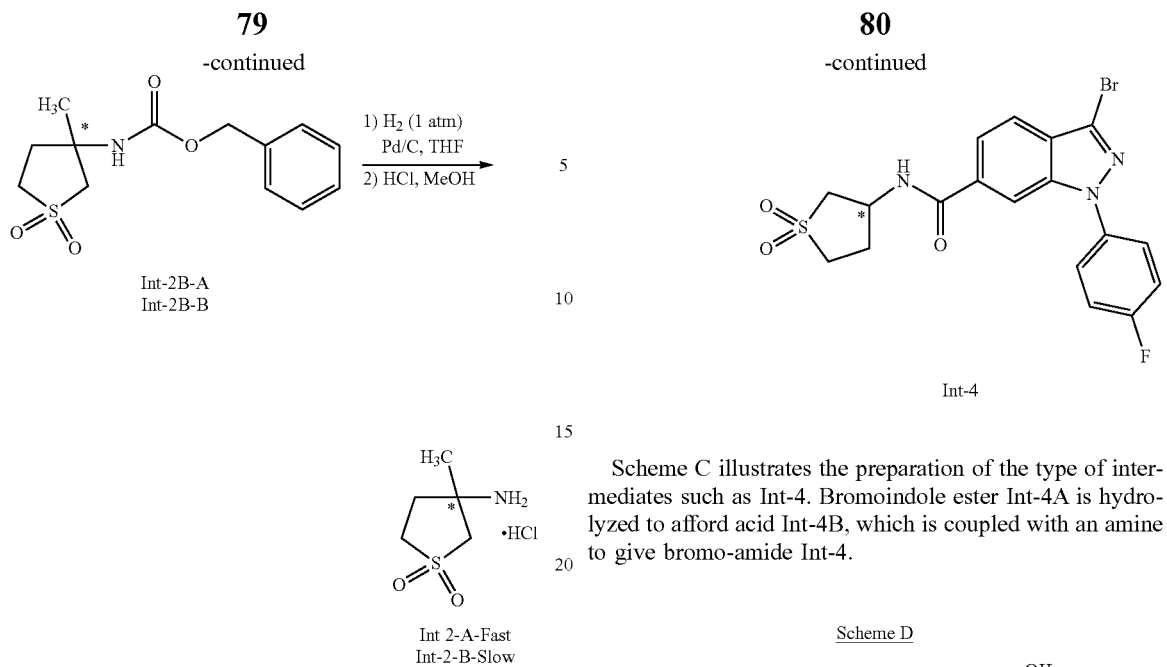

Int-2B-A
Int-2B-B

Int 2-A-Fast
Int-2-B-Slow

In Scheme B, racemic amine Int-2A is protected with CBZ to afford Int-2B, which is resolved to give two enantiomers (Int-2B-A and Int-2B-B). Each of these enantiomers is deprotected to give Int-2-A (fast eluting, enantiomer A) and Int-2-B (slow-eluting, enantiomer B). The same general scheme is used to obtain enantiomers of the des-methyl analog Int-3.

Scheme C

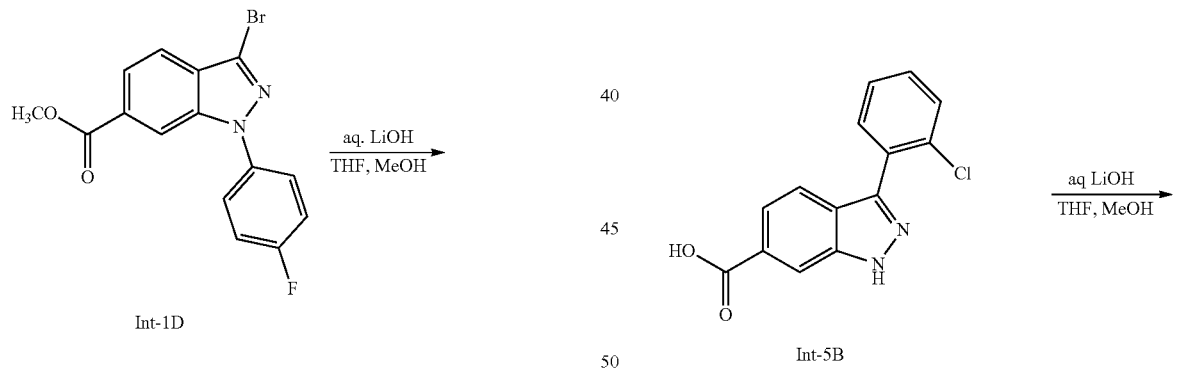

Int-1D

Int-4A

-continued

Int-4

Scheme C illustrates the preparation of the type of intermediates such as Int-4. Bromoindole ester Int-4A is hydrolyzed to afford acid Int-4B, which is coupled with an amine to give bromo-amide Int-4.

Scheme D

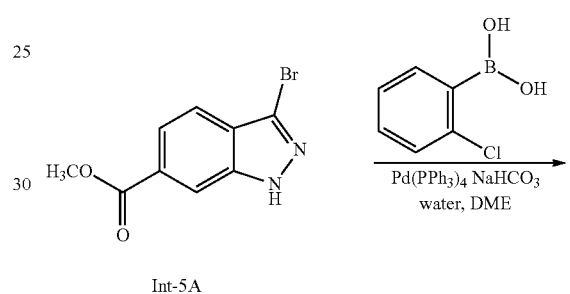

Int-5A

Int-5B

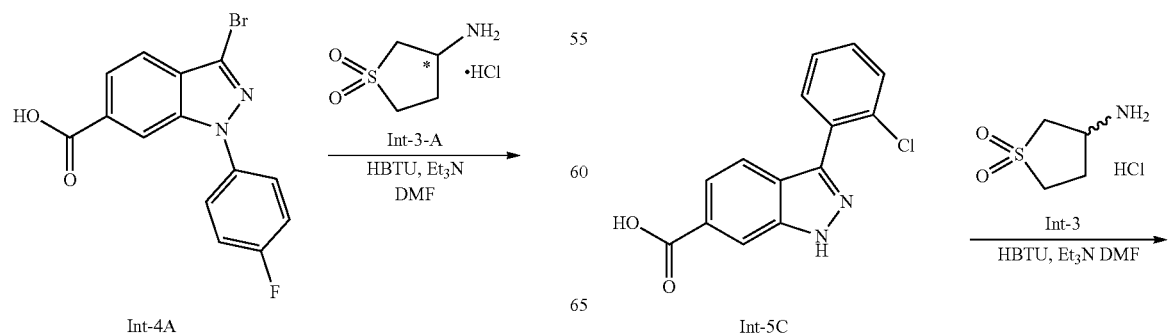

Int-5C

-continued

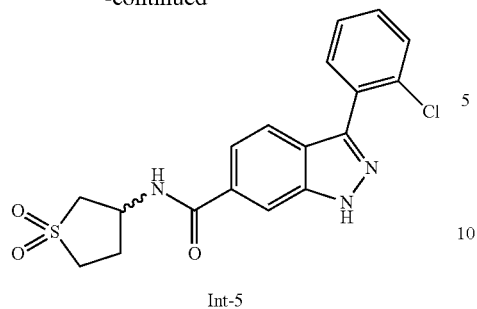

Int-5

Scheme D illustrates the procedures for the synthesis of Int-5. Bromo-indazole ester Int-5A is coupled with an aryl boronic acid to furnish Int-5B, which is in turn hydrolyzed to acid Int-5C and coupled with an amine to afford Int-5.

Scheme E

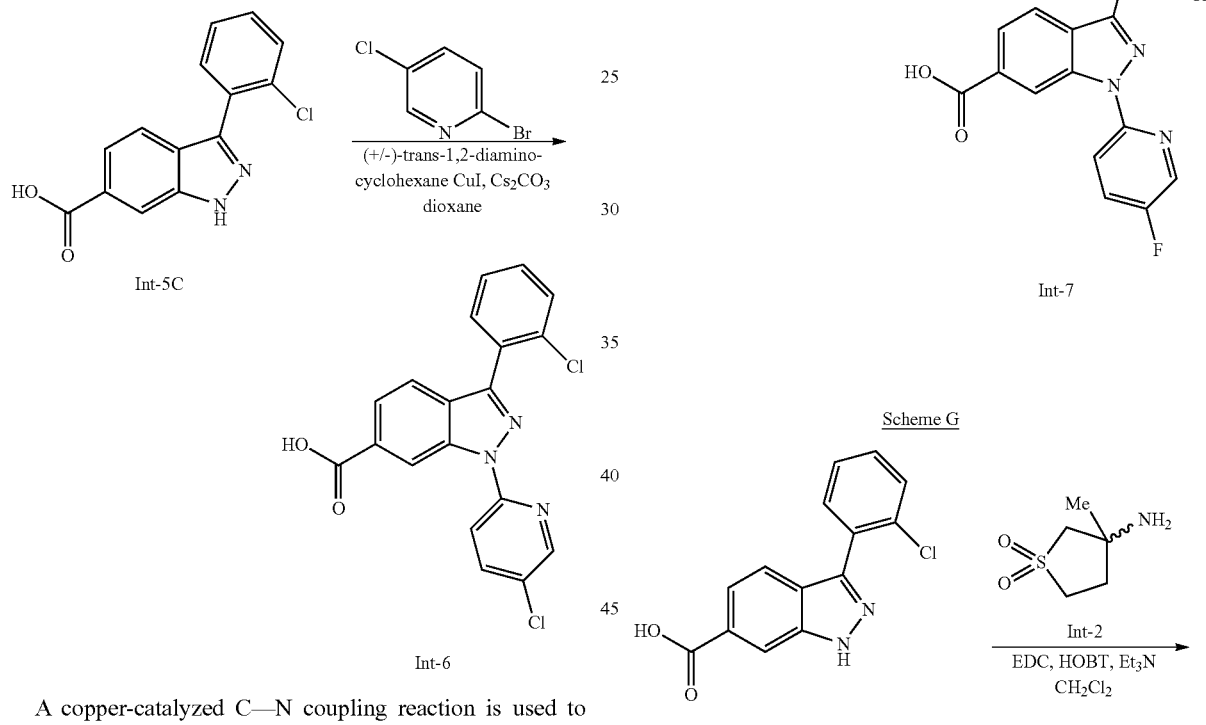

Int-5C

Int-6

A copper-catalyzed C—N coupling reaction is used to prepare Int-6 (Scheme E). A similar reaction is used in the key step for the synthesis of Int-7 (Scheme F).

Scheme F

Int-5B

-continued

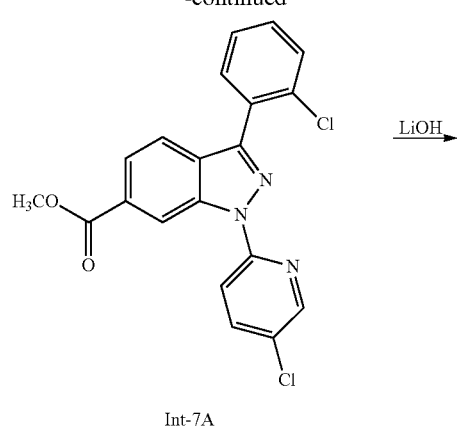

Int-7A

Int-7

Scheme G

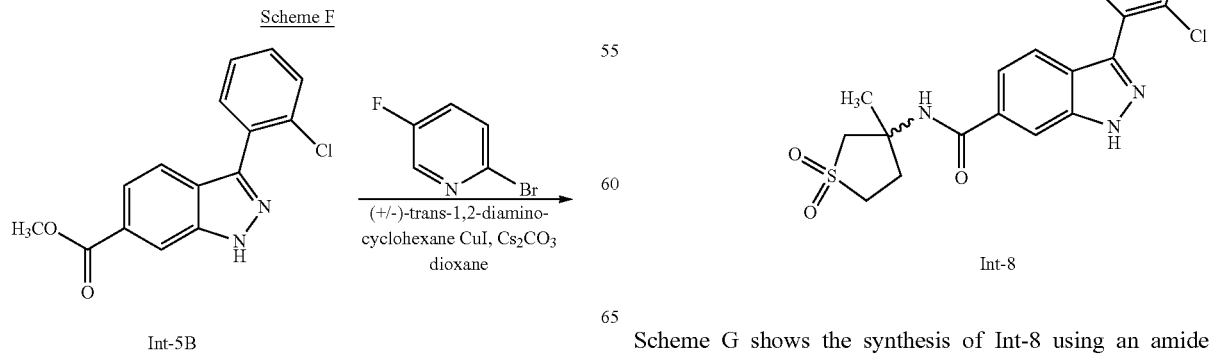

Int-5C

Int-8

Scheme G shows the synthesis of Int-8 using an amide coupling reaction from indazole Int-5C.

Schemes H~M illustrate several methods used to prepare the compounds of this invention.
Scheme H
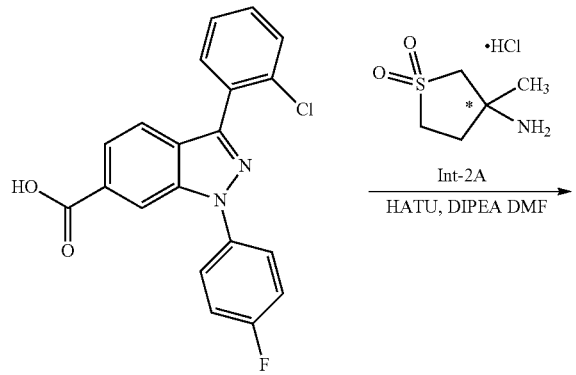
Int-1
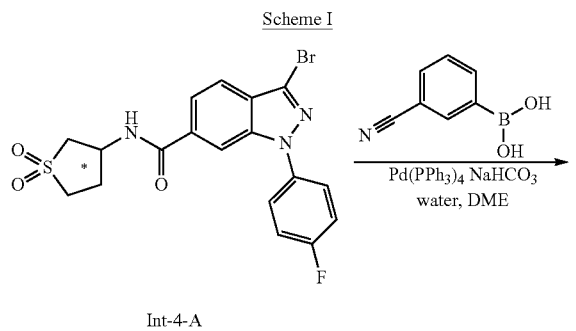
Ex. 1
Scheme I
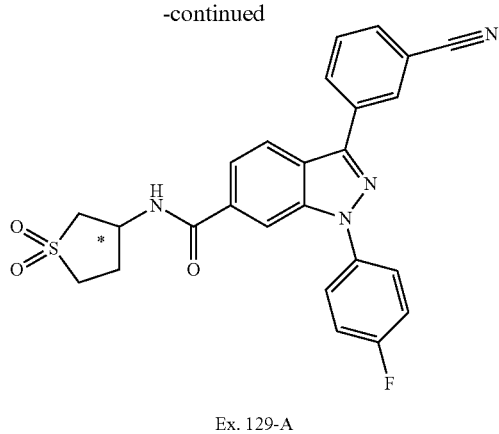
Ex. 129-A
Scheme J
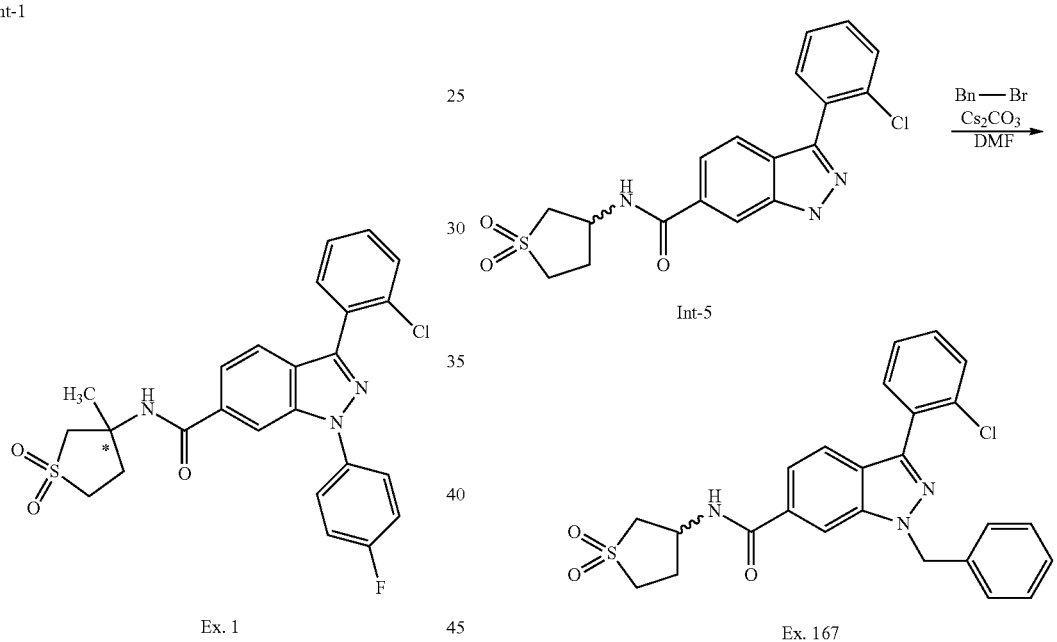
Int-5
Ex. 167
Scheme K
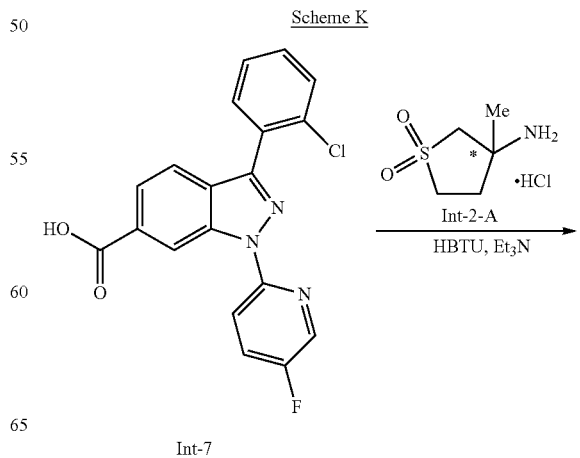
Int-7

85
-continued
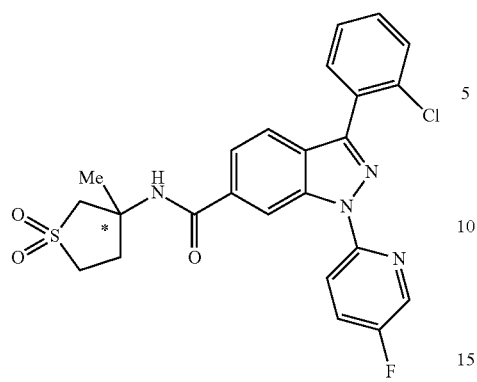
Ex. 172-A
86
-continued
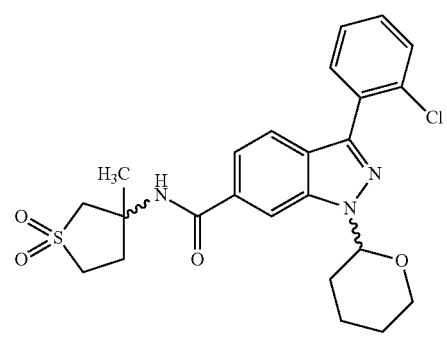
Ex. 191
Scheme L
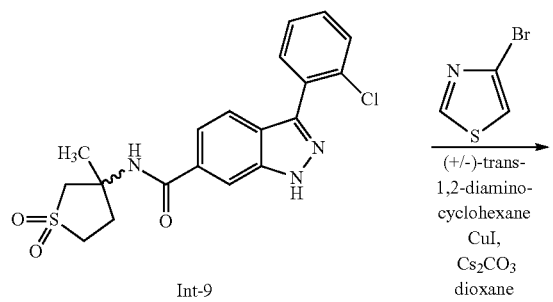
Int-9
Scheme M
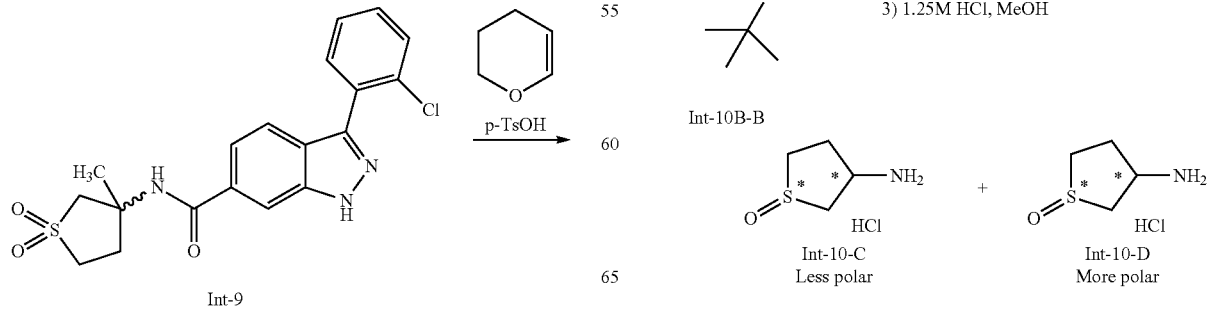
Int-9
Scheme N
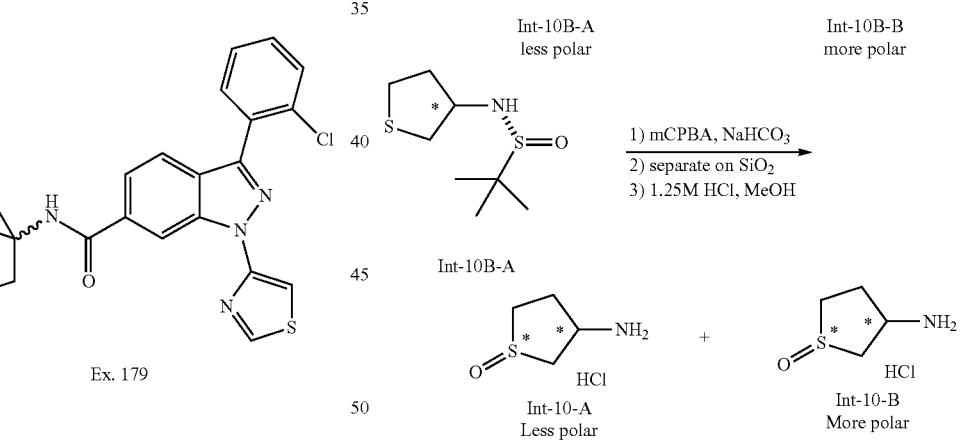

Scheme N shows the syntheses of Intermediates 10-A, 10-B, 10-C, and 10-D. Commercially available Int-10A is condensed with enantiomerically pure 2-methylpropane-2-sulfinamide to give a diastereomeric mixture of Int-10B, which is separated by chromatography on silica gel to give less polar Int-10B-A (fast eluting) and more polar (slow eluting) Int-10B-B. The single diastereomer Int-10B-A is then oxidized to give yet another pair of diastereomers which are separated by chromatography on silica gel to give two single diastereomers. Each of these separated diastereomers is deprotected to Intermediates 10-A and 10-B, respectively. Applying the same sequence to Int-10B affords Intermediates 10-C and 10-D. The absolute stereochemistry of any of Intermediates 10-A, 10-B, 10-C or 10-D was not determined.

Intermediate 1

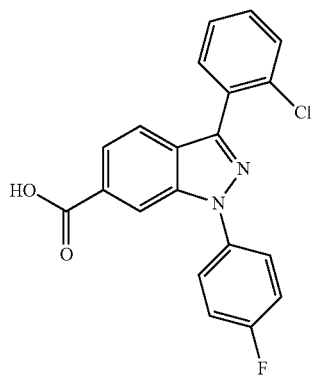 [SMILES: O=C(O)c1ccc2c(-c3ccccc3Cl)nn(-c3ccc(F)cc3)c2c1]

3-(2-Chlorophenyl)-1-(4-fluorophenyl)-1H-indazole-6-carboxylic Acid

Step A. Methyl 1-(4-fluorophenyl)-1H-indazole-6-carboxylate

A mixture of methyl 1H-indazole-6-carboxylate (1.0 g, 5.68 mmol), 1-fluoro-4-iodobenzene (1.309 ml, 11.35 mmol), trans-cyclohexane-1,2-diamine (0.136 ml, 1.135 mmol), copper(I) iodide (108 mg, 0.568 mmol) and cesium carbonate (3.70 g, 11.35 mmol) in DMA (15 ml) was heated at 100° C. for 18 hr. The mixture was cooled to rt, poured into water and extracted with MTBE. The combined organic layers were washed with brine, dried over anhydrous sodium sulfate, filtered and the filtrate was concentrated in vacuo. The resulting residue was purified by column chromatography on silica gel (0 to 30?% EtOAc in hexanes) to afford the title compound. m/z=271.0 [M+H]$^+$. $^1$H NMR (500 MHz, CDCl$_3$): δ 8.37 (s, 1H), 8.23 (s, 1H), 7.89 (dd, J=8.5, 1.3 Hz, 1H), 7.84 (d, J=8.5 Hz, 11-t), 7.67-7.70 (m, 2H), 7.24-7.28 (m, 2H), 3.96 (s, 3H).

Step B. Methyl 3-bromo-1-(4-fluorophenyl)-1H-indazole-6-carboxylate

Methyl 1-(4-fluorophenyl)-1H-indazole-6-carboxylate (1.178 g, 4.36 mmol) in DCM (30 ml) and ACN (10 ml) was treated at rt with potassium carbonate (3.01 g, 21.79 mmol) and bromine (1.123 ml, 21.79 mmol). The mixture was stirred at rt for 6 h, poured into aq. Na$_2$S$_2$O$_3$ and extracted with MTBE. The combined organic portions were concentrated to afford the title compound that was used without further purification. m/z=348.9/350.8 [M+H]$^+$. $^1$H NMR (500 MHz, CDCl$_3$): δ 8.34 (s, 1H), 7.96 (dd, J=8.5, 1.2 Hz, 1H), 7.75 (d, J=8.5 Hz, 1H), 7.65-7.68 (m, 2H), 7.25-7.28 (m, 2H), 3.97 (s, 3H).

Step C. Methyl 3-(2-chlorophenyl)-1-(4-fluorophenyl)-1H-indazole-6-carboxylate

A mixture of methyl 3-bromo-1-(4-fluorophenyl)-1H-indazole-6-carboxylate (529.6 mg, 1.517 mmol) and 2-chlorophenylboronic acid (429.1 mg, 2.74 mmol) in DME (10 ml) was treated with tetrakis(triphenylphosphine)palladium (202.3 mg, 0.175 mmol) and sub-surface sparged with nitrogen for 5 min. The mixture was treated with aq. sodium bicarbonate (397.3 mg, 4.73 mmol) in water (5.00 ml) with continued sparging. The mixture was capped and heated at 90° C. overnight, cooled to rt, and diluted with water. The mixture was extracted with EtOAc, and the combined organic fractions were washed with water and then concentrated in vacuo. The residue was purified by column chromatography on silica gel (0 to 15% EtOAc in hexanes) to afford the title compound. m/z=381.1/382.9 [M+H]$^+$.

Step D. 3-(2-Chlorophenyl)-1-(4-fluorophenyl-1H-indazole-6-carboxylic Acid

Methyl 3-(2-chlorophenyl)-1-(4-fluorophenyl)-1H-indazole-6-carboxylate (257.6 mg, 0.676 mmol) was dissolved in THF (10 mL) and treated with 1 M aq. LiOH (1.353 mL, 1.353 mmol). The mixture was heated at 50° C. for 16 h, cooled to rt and treated with 1 M aq. HCl (1.353 mL, 1.353 mmol). The resulting mixture was diluted with EtOAc and the organic phase was washed with water and then concentrated in vacuo. The residue was purified by column chromatography on silica gel (5% to 20% MeOH in DCM) to afford the title compound. m/z=367.1 [M+H]$^+$.

Intermediates 2-A (Fast Eluting) and 2-B (Slow Eluting)

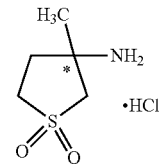

(3R)-3-Amino-3-methyltetrahydrothiophene-1,1-dioxide Hydrogen Chloride and (3 S)-3-amino-3-methyltetrahydrothiophene-1,1-dioxide Hydrogen Chloride Step A: Benzyl (3-methyl-1,1-dioxidotetrahydrothiophen-3-yl)carbamates Int-2A 3-Amino-3-methyltetrahydrothiophene-1,1-dioxide (5.018 g, 27.0 mmol) in EtOAc (25 ml) was treated with saturated aq. NaHCO$_3$ (20 mL) and CBZ-Cl (4.63 ml, 32.4 mmol). The mixture was stirred at rt for 4 h. The organic portion was separated, washed with brine, dried with anhydrous sodium sulfate, and filtered. The filtrate was concentrated in vacuo. The residue was purified on silica gel (0 to 100% EtOAc/hexanes) to afford the title compound Int-2B. $^1$H NMR (500 MHz, CD$_3$OD)) 7.29-7.35 (m, 5H), 5.08 (s, 2H), 3.85 (s, 1H), 3.82 (s, 1H), 3.19-3.24 (m, 1H), 3.07 (d, J=13.8 Hz, 1H), 2.58 (br s, 1H), 2.20 (ddd, J=13.9, 10.54, 7.9 Hz, 1H), 1.53 (s, 3H). Chiral resolution using SFC conditions (15% 2:1 MeOH:ACN on an OD or IA column) afforded Int-2B-A (fast eluting) and Int-2B-B (slow eluting).

Step B: 3-Amino-3-methyltetrahydrothiophene-1,1-dioxide Hydrogen Chloride (Int-2-A (Fast-Eluting Enantiomer) and Int-2-B (Slow-Eluting Enantiomer)

A flask was charged with benzyl (3-methyl-1,1-dioxidotetrahydrothiophen-3-yl)carbamate (Int-2B-A, fast-eluting on an OD or IA column) (6.52 g, 23.01 mmol), 10% Pd/C (1.20 g) and EtOAc (100 ml). The flask was purged with nitrogen and then hydrogen. The mixture was stirred under hydrogen (1 atm.) for 24 h, filtered through CELITE, and the filtrate was concentrated in vacuo to give the crude product that was treated with 1.25 M HCl in MeOH (50 mL). The reaction mixture was then concentrated in vacuo to afford 3-amino-3-methyltetrahydrothiophene-1,1-dioxide hydrogen chloride Int-2-A (fast-eluting enantiomer). $^1$H NMR (500 MHz, D$_2$O) δ 4.76 (s, 3H), 3.47-3.54 (m, 41H), 2.49 (t, J=7.7 Hz, 2H), 1.60 (s, 3H). m/z=150.0 [M+H]$^+$. The same procedure was used to synthesize Int-2-B (slow eluting enantiomer) from benzyl (3-methyl-1,1-dioxidotetrahydrothiophen-3-yl)carbamate Int-2B-B (slow eluting on an OD or IA column). Note that the designation of fast- and slow-eluting isomers lint-2 refer to the elution order for enantiomers of their CBZ precursors on the columns specified and not those of Int-2.

Intermediates 3-A (Fast Eluting) and 3-B (Slow Eluting)

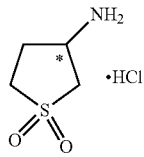

(3R)-3-Aminotetrahydrothiophene-1,1-dioxide Hydrogen Chloride and (3S)-3-aminotetrahydrothiophene-dioxide Hydrogen Chloride

Step A: Benzyl (1,1-dioxidotetrahydrothiophen-3-yl)carbamates

A flask was charged with 3-aminotetrahydrothiophene-1,1-dioxide hydrochloride (11.6 g, 67.8 mmol), EtOAc (100 ml) and sodium bicarbonate (21.63 g, 257 mmol). Water (100 ml) was added portion-wise over 10 min. at rt. The CBZ-Cl (14.70 ml, 103 mmol) was added at rt, and the mixture was stirred at rt for 16 h. The aq. layer was separated from the organic layer, and the organic layer was washed with brine, dried with anhydrous sodium sulfate, and filtered, and the filtrate was concentrated in vacuo. Purification on silica gel (10 to 100% EtOAc/hexanes) afforded the title compound $^1$H NMR (500 MHz, CDCl$_3$) δ 7.33-7.37 (n, 5H), 5.33 (s, 1H), 5.11 (s, 2H), 4.55 (s, 1H), 3.37 (dd, J=13.7 and 7.4 Hz, 1H), 3.20-3.26 (m, 1H), 3.06-3.12 (m, 1H), 3.00 (d, J=13.6 Hz, 1H), 2.51 (dq, 1=13.7 and 7.1 Hz, 1H), 2.26 (br s, 1H). Chiral resolution using SFC conditions (25% 2:1 MeOH:ACN in CO$_2$ on an OJ column) afforded Int-3A-A (fast eluting) and Int-3A-B (slow eluting).

Step B: 3-Aminotetrahydrothiophene-1,1-dioxide Int-3-A (Fast-Eluting) Int-3-B (Slow-Eluting)

A solution of benzyl (1,1-dioxidotetrahydrothiophen-3-yl)carbamate Int-3A-A (fast eluting on OJ) (2.856 g, 10.60 mmol) in EtOAc (15 ml) was charged into a flask containing 10% Pd/C (300 mg) under N$_2$, The flask was purged with nitrogen and then hydrogen. The mixture was stirred under hydrogen (1 atm.) for 48 h, filtered through CELITE, and the filtrate was concentrated in vacuo to give the crude product that was treated with 1.25 M HCl in MeOH (50 mL), aged 10 min, and then concentrated in vacuo to afford 3-aminotetrahydrothiophene-1,1-dioxide hydrogen chloride Int-3-A (fast eluting). $^1$H NMR (500 MHz, D$_2$O) δ 4.76 (s, 3H), 4.27 (p, J=7.8 Hz, 1H), 3.75 (dd, J=14.4, 8.5 Hz, 1H), 3.49-3.54 (m, 1H), 3.32-3.38 (m, 2H), 2.75-2.82 (m, 1H), 2.32-2.40 (m, 1H). The same procedure was used to synthesize Int-3-B (slow eluting) from benzyl (1,1-dioxidotetrahydrothiophen-3-yl)carbamate Int-3-B (slow eluting). Note that the designation of fast- and slow-eluting isomers of Int-3 refers to the elution order for enantiomers of their benzyl precursors (Int-3A-A and Int-3A-B) on the OJ column and not those of Int-3-A (fast eluting) and Int-3-B (slow eluting).

Intermediate 4-A

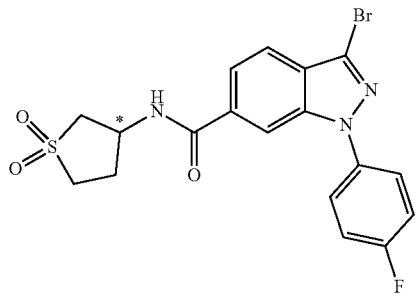 [SMILES: O=C(NC1CCS(=O)(=O)C1)c1ccc2c(Br)nn(-c3ccc(F)cc3)c2c1]

3-Bromo-N-(1,1-dioxidotetrahydrothiophen-3-yl)-1-(4-fluorophenyl)-1H-indazole-6-carboxamide (Enantiomer A)

Step A. 3-Bromo-1-(4-fluorophenyl)-1H-indazole-6-carboxylic Acid

Methyl 3-bromo-1-(4-fluorophenyl)-1H-indazole-6-carboxylate (285 mg, 0.816 mmol) in MeOH (2.5 ml) and THF (2.5 ml) was treated at rt with 1 M aq. lithium hydroxide (2.449 ml, 2.449 mmol). The mixture was heated at 50° C. for 30 min, cooled to rt and partitioned between MTBE (10 mL) and water (10 mL). The organic and aq. layers were separated. The organic layer was washed with water (10 mL), and the organic layer was discarded. The combined aq. portions were acidified (pH<2) with 2 M aq. NaHSO$_4$ (5 mL) and extracted with MTBE. The combined organic portions were dried over anhydrous sodium sulfate, filtered, and the filtrate was concentrated in vacuo to afford the title compound that was used without further purification. m/z=334.8/336.8 [M+H]+.

Step B. 3-Bromo-N-(1,1-dioxidotetrahydrothiophen-3-yl)-1-(4-fluorophenyl-1)-1H-indazole-6-carboxamide 3-Bromo-1-(4-fluorophenyl)-1H-indazole-6-carboxylic acid (224 mg, 0.668 mmol) and 3-aminotetrahydrothiophene 1,1-dioxide hydrochloride Int-3-A (115 mg, 0.668 mmol) in DMF (3 mL) was treated with HBTU (304 mg, 0.802 mmol) and TEA (186 µl, 1.337 mmol), and stirred at rt for 12 h. The reaction mixture was directly purified by RP-HPLC (ACN/water with 0.05% TFA) to afford the title compound. m/z=451.8/453.8 [M+H]+.

Intermediate 5

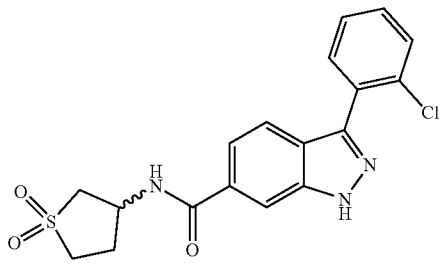 [SMILES: O=C(NC1CCS(=O)(=O)C1)c1ccc2c(-c3ccccc3Cl)n[nH]c2c1]

(±)-3-(2-Chlorophenyl)-N-(1,1-dioxidotetrahydrothiophen-3-yl)-1H-indazole-6-carboxamide Step A. Methyl 3-(2-chlorophenyl)-1H-indazole-6-carboxylate A mixture of methyl 3-bromo-1H-indazole-6-carboxylate (1.0483 g, 4.11 mmol), 2-chlorophenylboronic acid (0.964 g, 6.16 mmol) and tetrakis(triphenylphosphine)palladium (508.6 mg, 0.440 mmol) in DME (15 ml) was sub-surface sparged with nitrogen for 5 min, and then treated with sodium bicarbonate (1.0758 g, 12.81 mmol) in water (7.5 ml) with continued sparging. The reaction mixture was heated for 16 h under a nitrogen atmosphere, cooled to rt, and diluted with water. The reaction mixture was extracted with EtOAc (20 mL), and the combined organic fractions were washed with water and concentrated in vacuo. The residue was purified by preparative RP-HPLC (ACN/water with 0.1° % TFA) to afford the title compound. m/z=287.0/2890 [M+H]+.

Step B. 3-(2-chlorophenyl)-1H-indazole-6-carboxylic Acid

A mixture of methyl 3-(2-chlorophenyl)-1H-indazole-6-carboxylate (333 mg, 1.161 mmol) in THF (3.0 ml) and MeOH (1.0 ml) was treated at rt with LiOH (1M aq.) (2.90 ml, 2.90 mmol), stirred at rt for 16 h, neutralized with AcOH, and purified by RP-HPLC (ACN water with m/z 0.05% TFA) to afford the title compound that was used without further purification. m/z=273.0 [M+H]+. 1H NMR (500 MHz, CD3OD): δ 8.31 (s, 1H), 7.82 (d, J=8.6 Hz, 1H), 7.67 (d, J=8.5 Hz, 1H), 7.58-7.61 (m, 2H), 7.44-7.50 (m, 2H)

Step C. 3-(2-Chlorophenyl-N-(1-dioxidotetrahydrothiophen-3-yl)-1H-indazole-6-carboxamide A mixture of 3-(2-chlorophenyl)-1H-indazole-6-carboxylic acid (100 mg, 0.367 mmol), 3-aminotetrahydrothiophene 1,1-dioxide hydrochloride (racemic; 126 mg, 0.733 mmol) and HBTU (278 mg, 0.733 mmol) in DMF (1.0 ml) was treated with TEA (0.102 ml, 0.733 mmol) and stirred at rt for 16 h. The reaction mixture was neutralized with aq. AcOH and directly purified by RP-HPLC (ACN/water with 0.05% TFA) to afforded the title compound. m/z=390.0/391.9 [M+H]+.

Intermediate 6

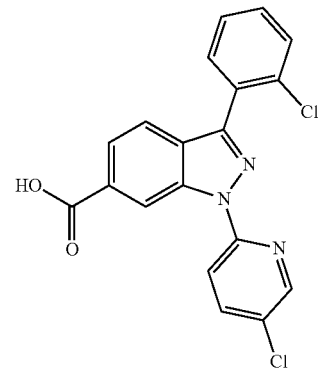 [SMILES: O=C(O)c1ccc2c(-c3ccccc3Cl)nn(-c3ccc(Cl)cn3)c2c1]

3-(2-Chlorophenyl)-1-(5-chloropyridin-2-yl)-1H-indazole-6-carboxylic Acid

A mixture of 3-(2-chlorophenyl)-1H-indazole-6-carboxylic acid (75 mg, 0.275 mmol), 2-bromo-5-chloropyridine (106 mg, 0.550 mmol), (+/−)-trans-1,2-diaminocyclohexane (31.4 mg, 0.275 mmol), copper (I) iodide (26.2 mg, 0.138 mmol) and TPP (175 rag, 0.825 mmol) in dioxane (2.0 mil) was sub-surface sparged with nitrogen for 2 min., and then reaction mixture was stirred at 100° C. for 12 h under a nitrogen atmosphere. The reaction mixture was cooled to rt, diluted with aq. AcOH and DMSO, and directly purified by RP-HPLC (ACN/water with 0.05% TFA) to afford the title compound, m/z=384.0/385.9 [M+H]+.

Intermediate 7

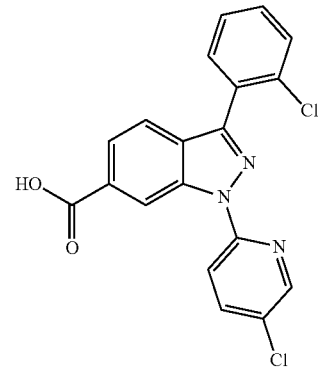 [SMILES: O=C(O)c1ccc2c(-c3ccccc3Cl)nn(-c3ccc(Cl)cn3)c2c1]

3-(2-chlorophenyl)-1-(5-fluoropyridin-2-yl)-1H-indazole-6-carboxylic Acid

Step A. Methyl 3-(2-chlorophenyl)-1-(5-fluoropyridin-2-yl)-1H-indazole-6-carboxylate A mixture of methyl 3-(2-chlorophenyl)-1H-indazole-6-carboxylate (500 mg, 1.744 mmol), 2-bromo-5-fluoropyridine, (+/−)-trans-1,2-diaminocyclohexane (0.084 ml, 0.70 mmol), copper (I) iodide (66.4 mg, 0.349 mmol) and TPP (370 mg, 1.74 mmol) in dioxane (15 ml) was heated at 100° C. for 18 hr, cooled to rt, and poured into water. The mixture was extracted with MTBE. The combined organic portion was washed with brine, dried over anhydrous sodium sulfate, and filtered, and the filtrate was concentrated in vacuo. The residue was purified by RP-HPLC (ACN/water with 0.05% TFA) to afford the title compound. m/z=382.1/384.0 [M+H]+.

Step B. 3-(2-chlorophenyl)-1-(5-fluoropyridin-2-yl)-1H-indazole-6-carboxylic Acid A solution of methyl 3-(2-chlorophenyl)-1-(5-fluoropyridin-2-yl)-1H-indazole-6-carboxylate (226 mg, 0.592 mmol) in THF (1 mL) and MeOH (1.0 ml) was treated with 1M aq. LiOH (0.6 mL, 0.6 mmol). The mixture was heated at 60° C. for 4 h, cooled to rt, poured into 2M aq. NaHSO4 (10 mL), and extracted with MTBE. The combined organic layers were concentrated in vacuo to afford the title compound that was used without further purification. m/z=367.9/369.9 [M+H]+.

Intermediates 10-A, 10-B, 10-C, AND 10-D

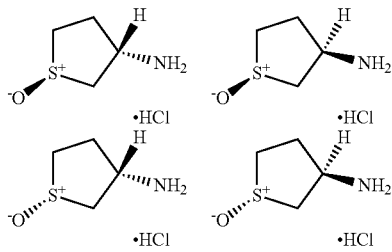

(1S,3S)-3-aminotetrahydrothiophene 1-oxide Hydrochloride, (1S,3R)-3-aminotetrahydrothiophene 1-oxide Hydrochloride, (1R,3S)-3-aminotetrahydrothiophene 1-oxide Hydrochloride, and (1R,3R)-3-aminotetrahydrothiophene 1-oxide Hydrochloride Step A. (R)-2-methyl-N—((S)-tetrahydrothiophen-3-yl)propane-2-sulfinamide and (R)-2-methyl N—((R)-tetrahydrothiophen-3-yl)propane-2-sulfinamide To a mixture of (R)-2-methylpropane-2-sulfinamide (1558 mg, 12.86 mmol) and Ti(OEt)4 (5.332 g, 23.38 mmol) was added THF (20 ml) and tetrahydrothiophen-3-one (1.00 ml, 11.69 mmol). The resulting mixture was heated at 60° C. for 12 h, cooled to 0° C. The cooled reaction mixture was added drop-wise to a suspension of sodium borohydride (1769 mg, 46.8 mmol) in THF (10 mL+10 mL rinse). The resulting mixture was stirred at 0° C. for 1 h, and then warmed to rt and carefully treated with MeOH. The mixture was poured into water and extracted with EtOAc. The combined organic layer was dried over anhydrous sodium sulfate, filtered, and concentrated in vacuo. Purification on SiO2 (50 to 100% EtOAc/hexanes) afforded the separated diastereomers. m/z=208.0 [M+H]+.

Step B. Individual Diastereomers of 3-Aminotetrahydrothiophene 1-oxide Hydrochloride The less polar diastereomer of (R)-2-methyl-N-(tetrahydrothiophen-3-yl)propane-2-sulfinamide from Step A above (150 mg, 0.723 mmol) in DCM (3.0 ml) was treated at −78° C. with sodium bicarbonate (182 mg, 2.170 mmol) and mCPBA (162 mg, 0.723 mmol). The mixture was stirred for 10 min, and then warmed to 0° C. After 15 min, solid sodium thiosulfate (100 mg) was added and the mixture was stirred for 15 min at rt, treated with TEA (0.05 mL), and the mixture was loaded onto a silica gel column. Gradient elution with 0 to 10% MeOH/DCM afforded less polar (R)-2-methyl-N-(1-oxidotetrahydrothiophen-3-yl)propane-2-sulfinamide. [1H NMR (500 MHz, CDCl3): δ 1.21 (s, 9H), 2.52-2.45 (m, 1H), 2.66-2.59 (m, 1H), 2.94-2.85 (m, 1H), 3.26-3.05 (m, 2H), 3.42 (d, J=15.1 Hz, 1H), 4.37 (s, 1H), 4.85 (d, J=8.9 Hz, 1H)] followed by more polar (R)-2-methyl-N-(1-oxidotetrahydrothiophen-3-yl)propane-2-sulfinamide [1H NMR (500 MHz, CDCl3): δ 1.21 (s, 9H), 2.30-2.24 (m, 1H). 2.78-2.71 (m, 1H), 2.97-2.89 (min, 1H), 3.21-3.12 (m, 3H), 4.14 (s, 1H), 4.60-4.57 (m, 1H)]. Each diastereomer was treated separately with 1.25 M HCl in MeOH, stirred at rt for 18 h, and then concentrated in vacuo and dried under vacuum to afford Int-10-A (fast eluting) and Int-10-B (slow eluting). Each was used without further purification.

A similar procedure was used to convert the more polar (R)-2-methyl-N-(tetrahydrothiophen-3-yl)propane-2-sulfinamide from Step A to afford Int-10-C (from fast eluting (R)-2-methyl-N-(1-oxidotetrahydrothiophen-3-yl)propane-2-sulfinamide): 1H NMR (500 MHz, CDCl3): δ 1.13-1.11 (m, 9H), 2.34 (d, J=11.4 Hz, 1H), 282 (dd, J=114.2, 6.9 Hz, 1H), 3.07-2.96 (min, 4H), 4.26 (br s, 1H), 4.84 (d, J=9.6 Hz, 1H) and Int-10-1) (from slow eluting (R)-2-methyl-N-1-oxidotetrahydrothiophen-3-yl)propane-2-sulfinamide): 1H NMR (500 MHz, CDCl3): δ 1.17 (s, 9H), 2.14-2.08 (n, 1H), 2.92-2.80 (min, 1H), 3.04 (dd, J=14.3, 5.8 Hz, 1H), 3.20-3.12 (min 2H), 3.38 (s, 2H), 4.56-4.53 (m, 1H).

Intermediate 11

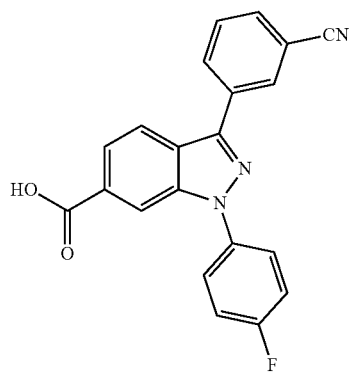 [SMILES: N#Cc1cccc(-c2nn(-c3ccc(F)cc3)c3cc(C(=O)O)ccc23)c1]

3-(3-Cyanophenyl)-1-(4-fluorophenyl)-1H-indazole-6-carboxylic Acid

The title compound was prepared by adapting the synthetic procedure for the synthesis of Int-1 from Int-1D. m/z=358.0 [M+H]+.

Intermediate 12 and 13

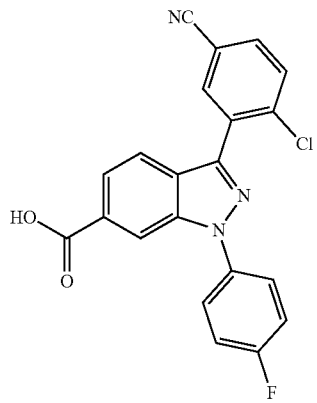 [SMILES: N#Cc1ccc(Cl)c(-c2nn(-c3ccc(F)cn3)c3cc(C(=O)O)ccc23)c1]

3-(2-Chloro-5-cyanophenyl)-1-(4-fluorophenyl)-1H-indazole-6-carboxylic Acid

The title compound was prepared from methyl 3-bromo-1-(4-fluorophenyl)-1H-indazole-6-carboxylate (Step B, for synthesis of Int-1) by adapting the synthetic procedure for the synthesis of Int-1 with partial hydrolysis of the nitrile occurring during the Suzuki cross-coupling reaction.

Int-12: m/z=392.1 [M+H]+. Int-13: m/z=410.1 [M+H]+. Intermediates 12 and 13 were used as the mixture for the subsequent steps and separated at the final compounds.

Intermediate 14

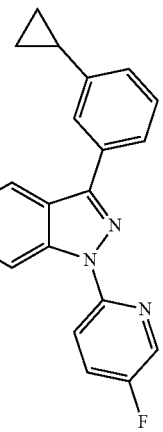

3-(3-Cyclopropylphenyl)-1-(5-fluoropyridin-2-yl)-1H-indazole-6-carboxylic Acid The title compound was prepared from methyl 3-bromo-1-(4-fluorophenyl)-1H-indazole-6-carboxylate (Step A, for synthesis of Int-1) by adapting the synthetic procedure for the synthesis of Int-1. m/z=388.1 [M+H]+.

Intermediate 15

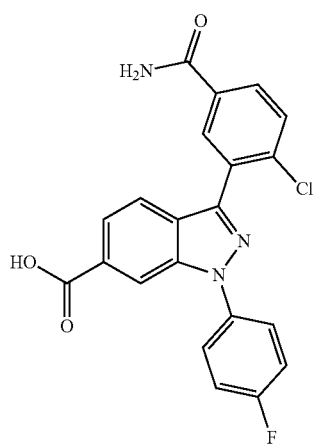

3-(2-Chloro-5-cyanophenyl)-1-(5-fluoropyridin-2-yl)-1H-indazole-6-carboxylic Acid The title compound was prepared from methyl 3-bromo-1-(4-fluorophenyl)-1H-indazole-6-carboxylate (Step B, for synthesis of Int-1) by adapting the synthetic procedure for the synthesis of Int-1. m/z=393.1 [M+H]+.

Intermediate 16

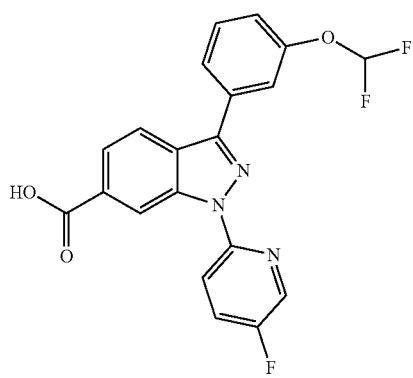 [SMILES: O=C(O)c1ccc2c(-c3cccc(OC(F)F)c3)nn(-c3ccc(F)cn3)c2c1]

3-(3-(Difluoromethoxy)phenyl)-1-(5-fluoropyridin-2-yl)-1H-indazole-6-carboxylic Acid The title compound was prepared from methyl 3-bromo-1-(4-fluorophenyl)-1H-indazole-6-carboxylate (Step B, for synthesis of Int-1) by adapting the synthetic procedure for the synthesis of Int-1. m/z=400.1 [M+H]⁺.

Intermediate 17

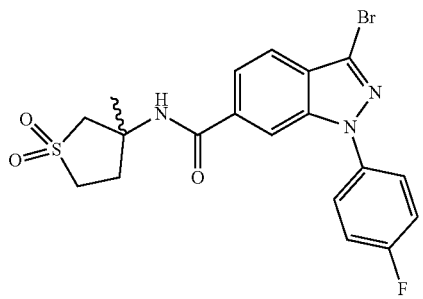 [SMILES: CC1(NC(=O)c2ccc3c(Br)nn(-c4ccc(F)cc4)c3c2)CCS(=O)(=O)C1]

3-Bromo-1-(4-fluorophenyl)-N-(3-methyl-1,1-dioxidotetrahydrothiophen-3-yl)-1H-indazole-6-carboxamide (Racemic)

The title compound was prepared by adapting the synthetic procedure for the synthesis of Int-4 using racemic 3-amino-3-methyltetrahydrothiophene-1,1-dioxide by adapting the synthetic procedure for the synthesis of Int-4. m/z=466.0/467.9 [M+H]⁺.

Intermediate 18-A

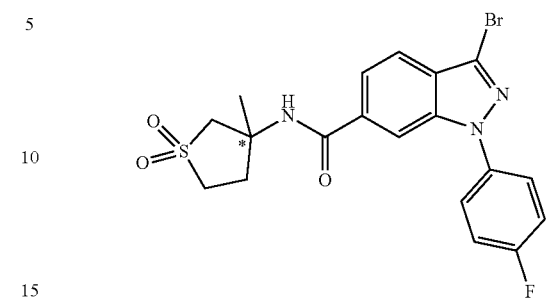

3-Bromo-1-(4-fluorophenyl)-N-(3-methyl-1,1-dioxidotetrahydrothiophen-3-yl)-1H-indazole-6-carboxamide (Enantiomer A)

The title compound was prepared by adapting the synthetic procedure for the synthesis of Int-4 using Int-2-A. m/z=466.0/467.9 [M+H]⁺.

Intermediate 18-B

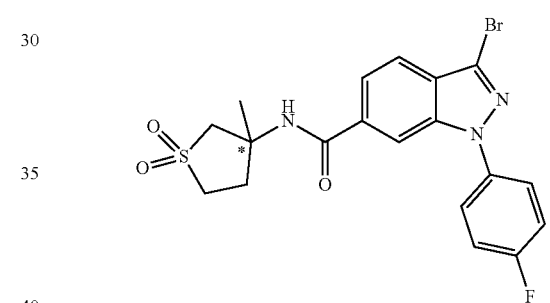

3-Bromo-1-(4-fluorophenyl)-N-(3-methyl-1,1-dioxidotetrahydrothiophen-3-yl)-1H-indazole-6-carboxamide (Enantiomer B)

The title compound was prepared by adapting the synthetic procedure for the synthesis of Int-4 using Int-2-B. m/z [M+H]⁺ 466.0/467.8 [M+H]+.

Intermediate 19

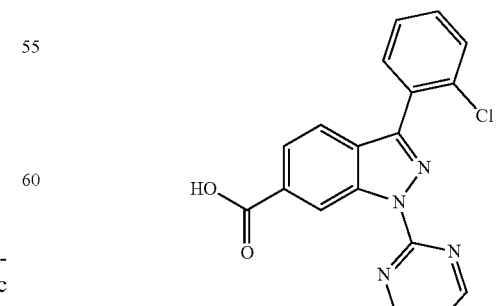

3-(2-Chlorophenyl)-1-(pyrimidin-2-yl)-1H-indazole-6-carboxylic Acid

The title compound was prepared by adapting the synthetic procedure for the synthesis of Int-7. m/z=351.0 [M+H]⁺.

Intermediate 20

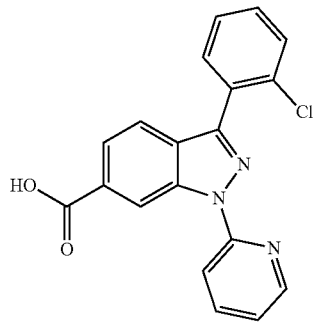 [SMILES: O=C(O)c1ccc2c(-c3ccccc3Cl)nn(-c3ccccn3)c2c1]

3-(2-Chlorophenyl)-1-(pyridin-2-yl)-1H-indazol-6-carboxylic Acid

The title compound was prepared by adapting the synthetic procedure for the synthesis of Int-7. m/z=350.0 [M+H]⁺.

Intermediate 21

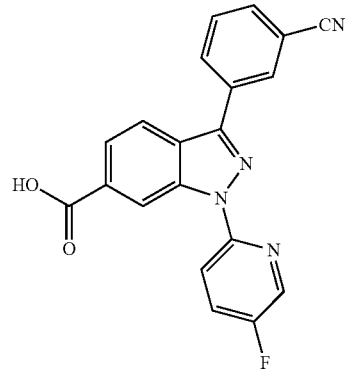 [SMILES: N#Cc1cccc(-c2nn(-c3ccc(F)cn3)c3cc(C(=O)O)ccc23)c1]

3-(3-Cyanophenyl)-1-(5-fluoropyridin-2-yl)-1H-indazole-6-carboxylic Acid

The title compound was prepared by adapting the synthetic procedure for the synthesis of Int-7. m/z (methyl ester precursor)=373.1 [M+H]⁺.

Intermediate 22

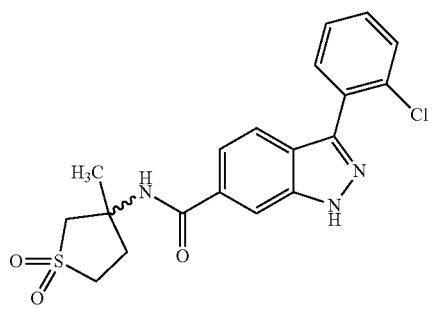 [SMILES: CC1(NC(=O)c2ccc3c(-c4ccccc4Cl)n[nH]c3c2)CCS(=O)(=O)C1]

3-(2-Chlorophenyl)-N-(3-methyl-1,1-dioxidotetrahydrothiophen-3-yl)-1H-indazole-6-carboxamide 3-(2-Chlorophenyl)-1H-indazole-6-carboxylic acid (2.00 g, 7.33 mmol) and 3-amino-3-methyl-tetrahydrothiophene 1,1-dioxide hydrochloride (1.498 g, 8.07 mmol) in DCM (15 ml) treated at rt with HOBT (1.123 g, 7.33 mmol), TEA (1.125 ml, 8.07 mmol), and EDC (1.547 g, 8.07 mmol). The reaction mixture was stirred at rt for 14 h, poured into water, and extracted with DCM. The combined organic layer was dried over anhydrous sodium sulfate, filtered, and the filtrate was concentrated in vacuo. The residue was purified by column chromatography on silica gel (EtOAc) to afford the title compound. m/z=404.0/405.9 [M+H]⁺. ¹H NMR (500 MHz, DMSO-d₆): δ 8.51 (s, 1H), 8.05 (s, 1H), 7.61-7.65 (m, 3H), 7.58 (d, J=8.6 Hz, 1H), 7.47-7.52 (m, 2H), 5.74 (s, 1H), 4.01 (d, J=13.7 Hz, 1H), 3.33-3.39 (m, 21H), 3.21 (d, J=13.7 Hz, 1H), 2.76-2.83 (m, 1H), 2.18-2.25 (m, 1H), 1.59 (s, 3H).

The designation of A and B for the examples (e.g., Example 1-A) is based on the designation of the intermediate used (e.g., Int-2-A (fast eluting) or Int-2-B (slow eluting)). If for example, Int-2-A is used in the synthesis of Example 1, the designation will be Example 1-A.

Example 1-A

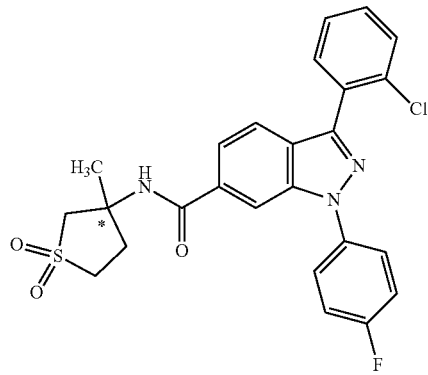 [SMILES: CC1(NC(=O)c2ccc3c(-c4ccccc4Cl)nn(-c4ccc(F)cc4)c3c2)CCS(=O)(=O)C1]

3-(2-Chlorophenyl)-1-(4-fluorophenyl)-N-(3-methyl-1,1-dioxidotetrahydrothiophen-3-yl)-1H-indazole-6-carboxamide (Enantiomer A)

A mixture of 3-(2-chlorophenyl)-1-(4-fluorophenyl)-1H-indazole-6-carboxylic acid from Int-1 (107.8 mg, 0.294 mmol) and HATU (180.1 mg, 0.474 mmol) in DMF (2 ml) was treated with 3-amino-3-methyltetrahydrothiophene-1,1-dioxide hydrochloride from Int-2-A (72.2 mg, 0.389 mmol) and DIPEA (0.35 ml, 2.004 mmol). The reaction mixture was aged at rt for 16 h. The volatiles were removed under vacuum, and the residue was purified by preparative RP-HPLC (ACN/water with 0.1% TFA) to afford the title compound. m/z=498.0 [M+H]⁺. $^1$H NMR (500 MHz, CD$_3$OD): δ 8.21 (s, 1H), 7.85-7.88 (m, 2H), 7.77 (d, J=8.5 Hz, 1H), 7.68-7.70 (m, 2H), 7.64 (dd, J=7.6, 1.7 Hz, 1H), 7.48-7.54 (m, 2H), 7.37-7.40 (m, 2H), 3.97-4.00 (m, 1H), 3.41 (m, 1H), 3.28-3.33 (m, 1H), 3.24 (d, J=13.8 Hz, 1H), 2.86-2.89 (m, 1H), 2.33 (ddd, J=14.0, 10.2, 8.2 Hz, 1H), 1.70 (s, 3H).

Example 2-A

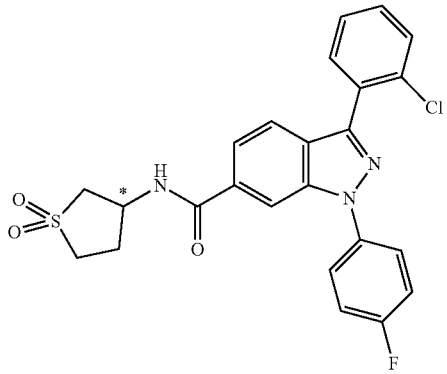 [SMILES: O=C(NC1CCS(=O)(=O)C1)c1ccc2c(-c3ccccc3Cl)nn(-c3ccc(F)cc3)c2c1]

3-(2-Chlorophenyl-N-(1,1-dioxidotetrahydrothiophen-3-yl)-1-(4-fluorophenyl)-1H-indazole-6-carboxamide (Enantiomer A)

A mixture of 3-(2-chlorophenyl)-1-(4-fluorophenyl)-1H-indazole-6-carboxylic acid (66 mg, 0.18 mmol), HATU (103 mg, 0.271 mmol) in DMF (1 ml) was treated with Int-3-A (37.2 mg, 0.22 mmol) and DIPEA (0.189 ml, 1.085 mmol) was added to the solution, and the reaction mixture was stirred for 16 h. The volatiles were removed under vacuum, and the residue was dissolved in DMSO and purified by preparative RP-HPLC (ACN/water with 0.1% TFA) to afford the title compound. m/z=484.0/486.1 [M+H]⁺. $^1$H NMR (500 MHz, CD$_3$OD): δ 8.93 (d, J=6.7 Hz, 1H), 8.26 (s, 1H), 7.84-7.87 (m, 2H), 7.73-7.79 (m, 2H), 7.63-7.69 (m, 2H), 7.48-7.54 (n, 2H), 7.39 (t, J=8.6 Hz, 2-1), 3.58 (dd, J=13.5, 7.8 Hz, 1H), 3.36 (ddd, J=13.4, 7.9, 4.7 Hz, 1H), 3.12-3.24 (m, 2H), 2.60-2.66 (m, 1H), 2.35 (dq, J=13.4, 8.8 Hz, 1H).

TABLE 1

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]⁺ |
|---|---|---|---|
| 1-B | 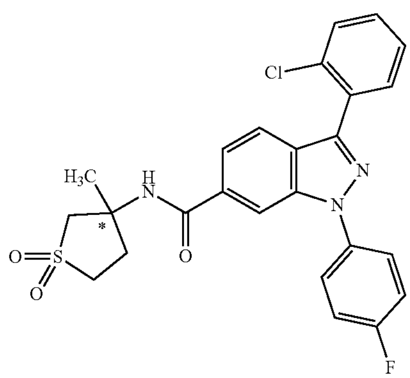 [SMILES: CC1(NC(=O)c2ccc3c(-c4ccccc4Cl)nn(-c4ccc(F)cc4)c3c2)CCS(=O)(=O)C1] | 3-(2-chlorophenyl)-1-(4-fluorophenyl)-N-(3-methyl-1,1-dioxidotetrahydrothiophen-3-yl)-1H-indazole-6-carboxamide (Enantiomer B) | 498.0 |
| 2-B | 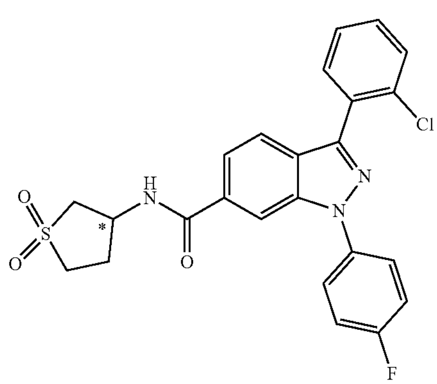 [SMILES: O=C(NC1CCS(=O)(=O)C1)c1ccc2c(-c3ccccc3Cl)nn(-c3ccc(F)cc3)c2c1] | 3-(2-chlorophenyl)-N-(1,1-dioxidotetrahydrothiophen-3-yl)-1-(4-fluorophenyl)-1H-indazole-6-carboxamide (Enantiomer B) | 484.1 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 3 | 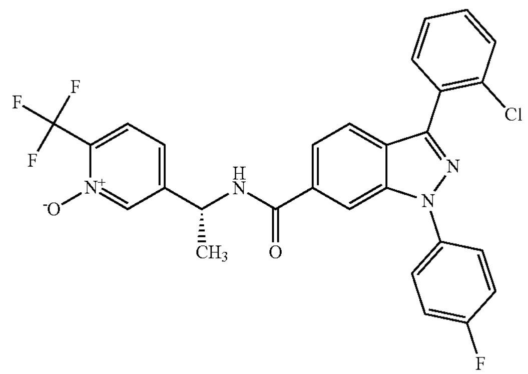 | 3-(2-chlorophenyl)-1-(4-fluorophenyl)-N-{(1R)-1-[1-oxido-6-(trifluoromethyl)pyridin-3-yl]ethyl}-1H-indazole-6-carboxamide | 555.0 |
| 4 | 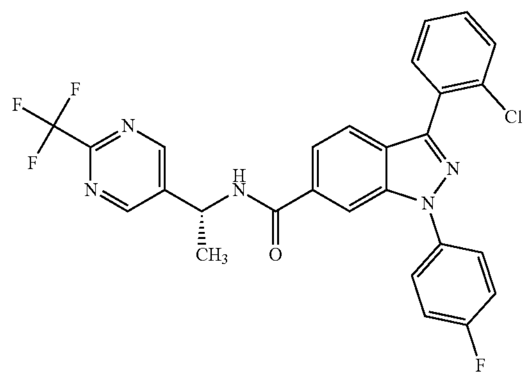 [SMILES: C[C@@H](NC(=O)c1ccc2c(-c3ccccc3Cl)nn(-c3ccc(F)cc3)c2c1)c1cnc(C(F)(F)F)nc1] | 3-(2-chlorophenyl)-1-(4-fluorophenyl)-N-{(1R)-1-[2-(trifluoromethyl)pyrimidin-5-yl]ethyl}-1H-indazole-6-carboxamide | 540.0 |
| 5 | 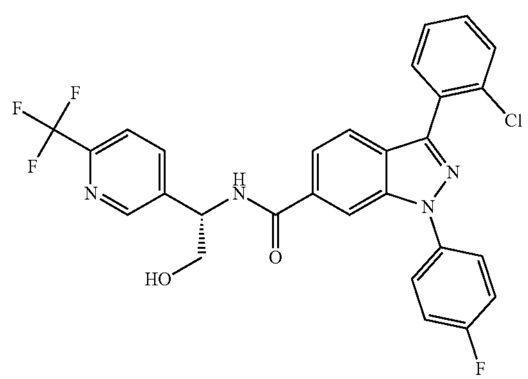 [SMILES: O=C(N[C@H](CO)c1ccc(C(F)(F)F)nc1)c1ccc2c(-c3ccccc3Cl)nn(-c3ccc(F)cc3)c2c1] | 3-(2-chlorophenyl)-1-(4-fluorophenyl)-N-{(1S)-2-hydroxy-1-[6-(trifluoromethyl)pyridin-3-yl]ethyl}-1H-indazole-6-carboxamide | 555.0 |
| 6 | 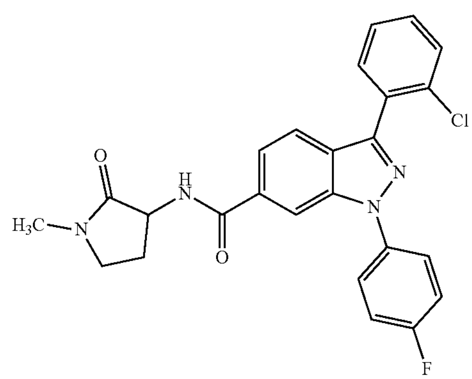 [SMILES: CN1CCC(NC(=O)c2ccc3c(-c4ccccc4Cl)nn(-c4ccc(F)cc4)c3c2)C1=O] | 3-(2-chlorophenyl)-1-(4-fluorophenyl)-N-(1-methyl-2-oxopyrrolidin-3-yl)-1H-indazole-6-carboxamide (racemic) | 463.1 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 7 | 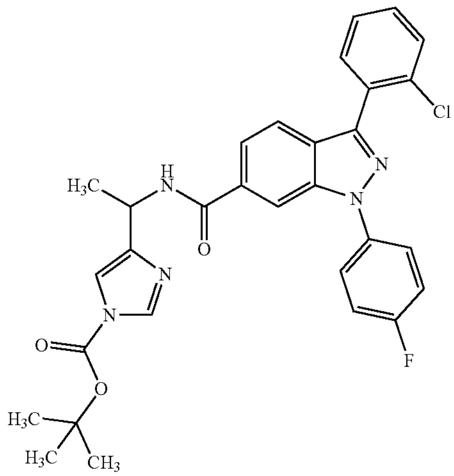 [SMILES: CC(NC(=O)c1ccc2c(-c3ccccc3Cl)nn(-c3ccc(F)cc3)c2c1)c1cn(C(=O)OC(C)(C)C)cn1] | tert-butyl 4-[1-({[3-(2-chlorophenyl)-1-(4-fluorophenyl)-1H-indazol-6-yl]carbonyl}amino)ethyl]-1H-imidazole-1-carboxylate (racemic) | 460.1 (-Boc) |
| 8 | 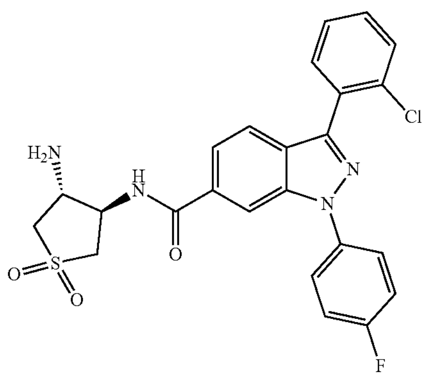 [SMILES: N[C@H]1CS(=O)(=O)C[C@@H]1NC(=O)c1ccc2c(-c3ccccc3Cl)nn(-c3ccc(F)cc3)c2c1] | N-[(3R,4R)-4-amino-1,1-dioxidotetrahydrothiophen-3-yl]-3-(2-chlorophenyl)-1-(4-fluorophenyl)-1H-indazole-6-carboxamide | 499.0 |
| 9 | 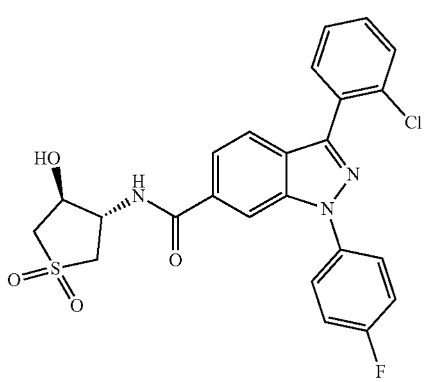 [SMILES: O=C(N[C@@H]1CS(=O)(=O)C[C@H]1O)c1ccc2c(-c3ccccc3Cl)nn(-c3ccc(F)cc3)c2c1] | 3-(2-chlorophenyl)-1-(4-fluorophenyl)-N-[(3S,4S)-4-hydroxy-1,1-dioxidotetrahydrothiophen-3-yl]-1H-indazole-6-carboxamide | 500.0 |

TABLE 1-continued

Examples 1-B through 128-A in the following table were prepared from
appropriate acid and amine starting materials described previously or commercially available
starting materials using procedures described for the synthesis of Examples 1-A and 2-A.

| Ex # | Structure | Chemical Name | m/z[M + H]+ |
| --- | --- | --- | --- |
| 10 | 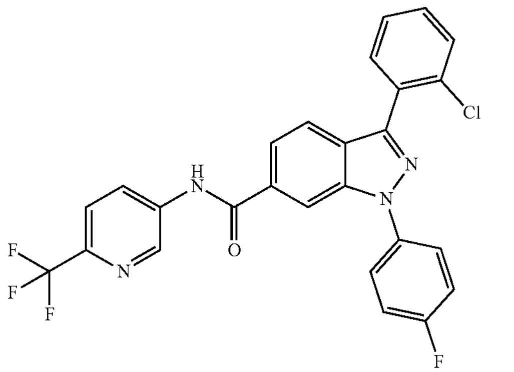 [SMILES: O=C(Nc1ccc(C(F)(F)F)nc1)c1ccc2c(-c3ccccc3Cl)nn(-c3ccc(F)cc3)c2c1] | 3-(2-chlorophenyl)-1-(4-fluorophenyl)-N-[6-(trifluoromethyl)pyridin-3-yl]-1H-indazole-6-carboxamide | 511.1 |
| 11 | 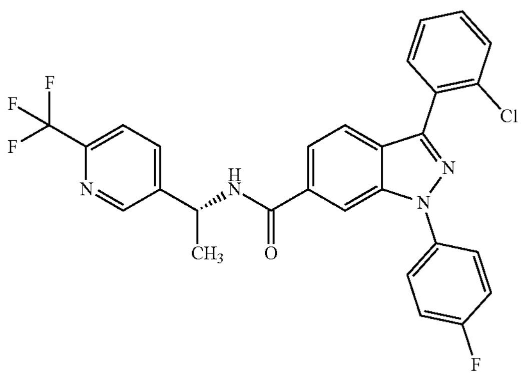 [SMILES: C[C@@H](NC(=O)c1ccc2c(-c3ccccc3Cl)nn(-c3ccc(F)cc3)c2c1)c1ccc(C(F)(F)F)nc1] | 3-(2-chlorophenyl)-1-(4-fluorophenyl)-N-{(1R)-1-[6-(trifluoromethyl)pyridin-3-yl]ethyl}-1H-indazole-6-carboxamide | 538.8 |
| 12 | 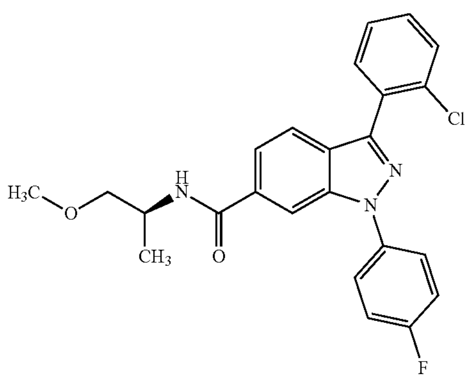 [SMILES: COC[C@H](C)NC(=O)c1ccc2c(-c3ccccc3Cl)nn(-c3ccc(F)cc3)c2c1] | 3-(2-chlorophenyl)-1-(4-fluorophenyl)-N-[(1S)-2-methoxy-1-methylethyl]-1H-indazole-6-carboxamide | 437.8 |
| 13 | 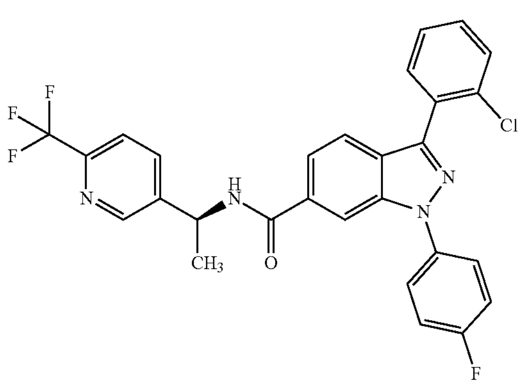 [SMILES: C[C@H](NC(=O)c1ccc2c(-c3ccccc3Cl)nn(-c3ccc(F)cc3)c2c1)c1ccc(C(F)(F)F)nc1] | 3-(2-chlorophenyl)-1-(4-fluorophenyl)-N-{(1S)-1-[6-(trifluoromethyl)pyridin-3-yl]ethyl}-1H-indazole-6-carboxamide | 539.1 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 14 | 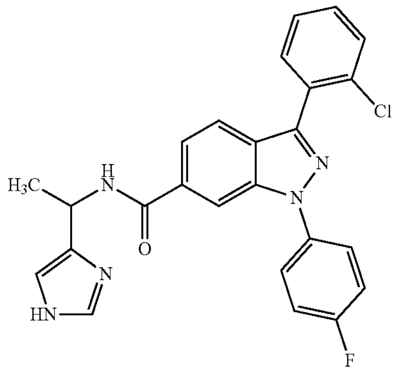 [SMILES: CC(NC(=O)c1ccc2c(-c3ccccc3Cl)nn(-c3ccc(F)cc3)c2c1)c1c[nH]cn1] | 3-(2-chlorophenyl)-1-(4-fluorophenyl)-N-[1-(1H-imidazol-4-yl)ethyl]-1H-indazole-6-carboxamide (racemic) | 459.9 |
| 15 | 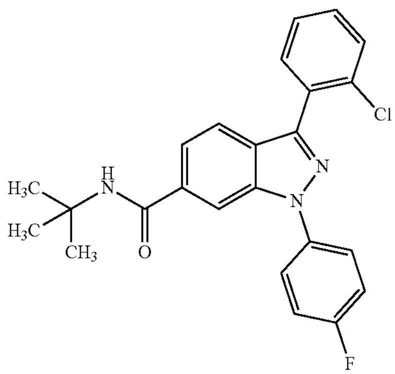 [SMILES: CC(C)(C)NC(=O)c1ccc2c(-c3ccccc3Cl)nn(-c3ccc(F)cc3)c2c1] | N-tert-butyl-3-(2-chlorophenyl)-1-(4-fluorophenyl)-1H-indazole-6-carboxamide | 422.1 |
| 16 | 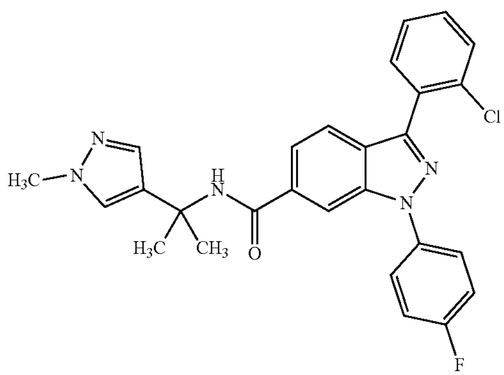 [SMILES: Cn1cc(C(C)(C)NC(=O)c2ccc3c(-c4ccccc4Cl)nn(-c4ccc(F)cc4)c3c2)cn1] | 3-(2-chlorophenyl)-1-(4-fluorophenyl)-N-[1-methyl-1-(1-methyl-1H-pyrazol-4-yl)ethyl]-1H-indazole-6-carboxamide | 488.1 |
| 17 | 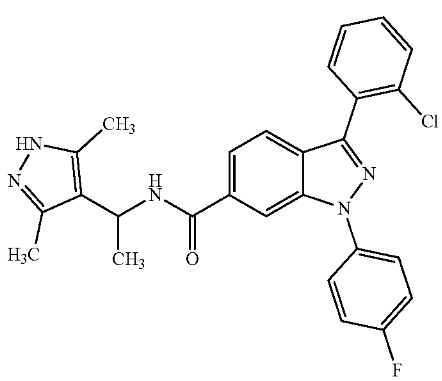 [SMILES: Cc1n[nH]c(C)c1C(C)NC(=O)c1ccc2c(-c3ccccc3Cl)nn(-c3ccc(F)cc3)c2c1] | 3-(2-chlorophenyl)-N-[1-(3,5-dimethyl-1H-pyrazol-4-yl)ethyl]-1-(4-fluorophenyl)-1H-indazole-6-carboxamide (racemic) | 488.1 |

TABLE 1-continued

Examples 1-B through 128-A in the following table were prepared from
appropriate acid and amine starting materials described previously or commercially available
starting materials using procedures described for the synthesis of Examples 1-A and 2-A.

| Ex # | Structure | Chemical Name | m/z[M + H]+ |
|---|---|---|---|
| 18 | 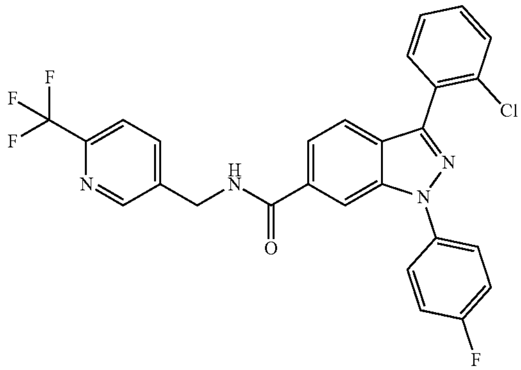 [SMILES: O=C(NCc1ccc(C(F)(F)F)nc1)c1ccc2c(-c3ccccc3Cl)nn(-c3ccc(F)cc3)c2c1] | 3-(2-chlorophenyl)-1-(4-fluorophenyl)-N-{[6-(trifluoromethyl)pyridin-3-yl]methyl}-1H-indazole-6-carboxamide | 525.1 |
| 19 | 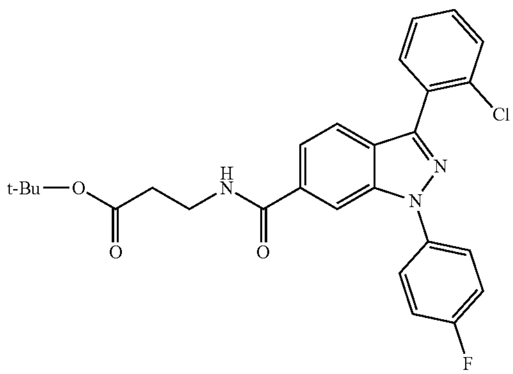 [SMILES: CC(C)(C)OC(=O)CCNC(=O)c1ccc2c(-c3ccccc3Cl)nn(-c3ccc(F)cc3)c2c1] | tert-butyl N-{[3-(2-chlorophenyl)-1-(4-fluorophenyl)-1H-indazol-6-yl]carbonyl}-beta-alaninate | 494.1 |
| 20 | 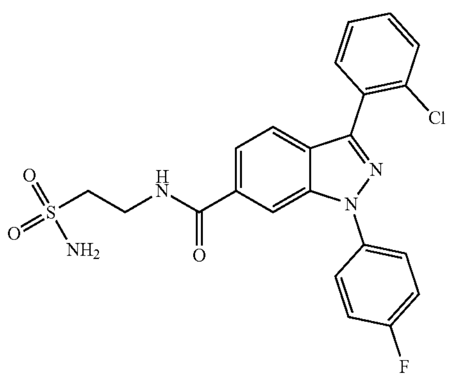 [SMILES: NS(=O)(=O)CCNC(=O)c1ccc2c(-c3ccccc3Cl)nn(-c3ccc(F)cc3)c2c1] | 3-(2-chlorophenyl)-1-(4-fluorophenyl)-N-(2-sulfamoylethyl)-1H-indazole-6-carboxamide | 473.0 |
| 21 | 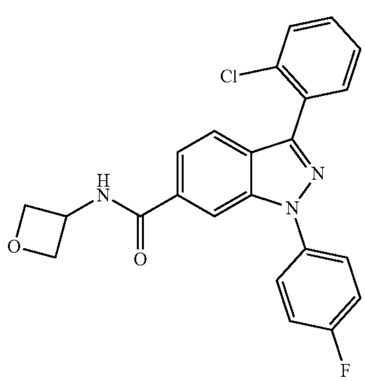 [SMILES: O=C(NC1COC1)c1ccc2c(-c3ccccc3Cl)nn(-c3ccc(F)cc3)c2c1] | 3-(2-chlorophenyl)-1-(4-fluorophenyl)-N-oxetan-3-yl-1H-indazole-6-carboxamide | 422.1 |

TABLE 1-continued

Examples 1-B through 128-A in the following table were prepared from
appropriate acid and amine starting materials described previously or commercially available
starting materials using procedures described for the synthesis of Examples 1-A and 2-A.

| Ex # | Structure | Chemical Name | m/z[M + H]+ |
|---|---|---|---|
| 22 | 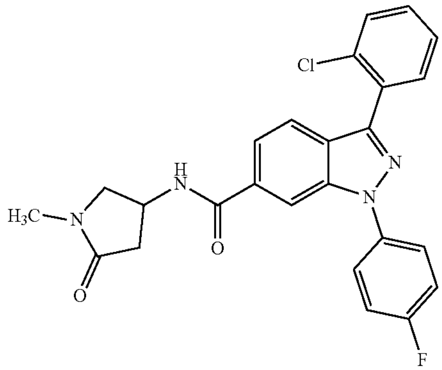 [SMILES: CN1CC(NC(=O)c2ccc3c(-c4ccccc4Cl)nn(-c4ccc(F)cc4)c3c2)CC1=O] | 3-(2-chlorophenyl)-1-(4-fluorophenyl)-N-(1-methyl-5-oxopyrrolidin-3-yl)-1H-indazole-6-carboxamide (racemic) | 463.1 |
| 23 | 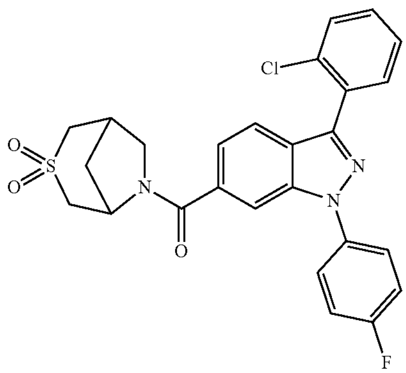 [SMILES: O=C(c1ccc2c(-c3ccccc3Cl)nn(-c3ccc(F)cc3)c2c1)N1CC2CC1CS(=O)(=O)C2] | 3-(2-chlorophenyl)-6-[(3,3-dioxido-3-thia-6-azabicyclo[3.2.1]oct-6-yl)carbonyl]-1-(4-fluorophenyl)-1H-indazole (racemic) | 510.1 |
| 24 | 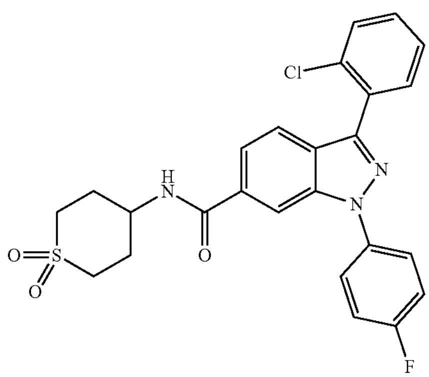 [SMILES: O=C(NC1CCS(=O)(=O)CC1)c1ccc2c(-c3ccccc3Cl)nn(-c3ccc(F)cc3)c2c1] | 3-(2-chlorophenyl)-N-(1,1-dioxidotetrahydro-2H-thiopyran-4-yl)-1-(4-fluorophenyl)-1H-indazole-6-carboxamide | 498.1 |
| 25 | 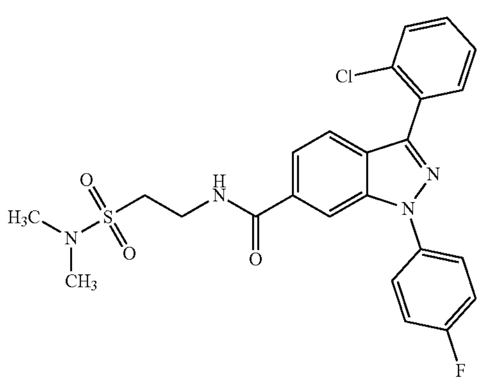 [SMILES: CN(C)S(=O)(=O)CCNC(=O)c1ccc2c(-c3ccccc3Cl)nn(-c3ccc(F)cc3)c2c1] | 3-(2-chlorophenyl)-N-[2-(dimethylsulfamoyl)ethyl]-1-(4-fluorophenyl)-1H-indazole-6-carboxamide | 501.1 |

TABLE 1-continued

Examples 1-B through 128-A in the following table were prepared from
appropriate acid and amine starting materials described previously or commercially available
starting materials using procedures described for the synthesis of Examples 1-A and 2-A.

| Ex # | Structure | Chemical Name | m/z[M + H]+ |
|---|---|---|---|
| 26 | 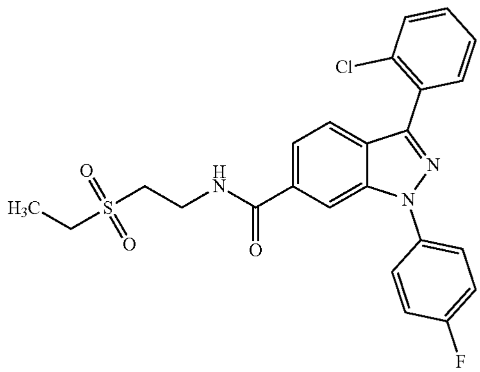 [SMILES: CCS(=O)(=O)CCNC(=O)c1ccc2c(-c3ccccc3Cl)nn(-c3ccc(F)cc3)c2c1] | 3-(2-chlorophenyl)-N-[2-(ethylsulfonyl)ethyl]-1-(4-fluorophenyl)-1H-indazole-6-carboxamide | 486.0 |
| 27 | 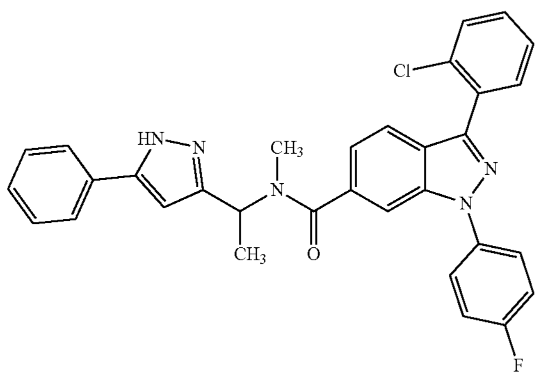 [SMILES: CC(c1cc(-c2ccccc2)[nH]n1)N(C)C(=O)c1ccc2c(-c3ccccc3Cl)nn(-c3ccc(F)cc3)c2c1] | 3-(2-chlorophenyl)-1-(4-fluorophenyl)-N-methyl-N-[1-(5-phenyl-1H-pyrazol-3-yl)ethyl]-1H-indazole-6-carboxamide (racemic) | 550.2 |
| 28 | 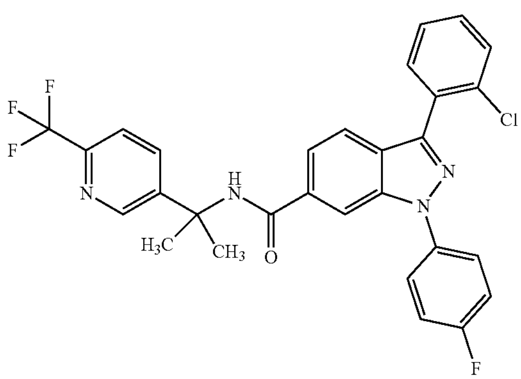 [SMILES: CC(C)(NC(=O)c1ccc2c(-c3ccccc3Cl)nn(-c3ccc(F)cc3)c2c1)c1ccc(C(F)(F)F)nc1] | 3-(2-chlorophenyl)-1-(4-fluorophenyl)-N-{1-methyl-1-[6-(trifluoromethyl)pyridin-3-yl]ethyl}-1H-indazole-6-carboxamide | 553.1 |
| 29 | 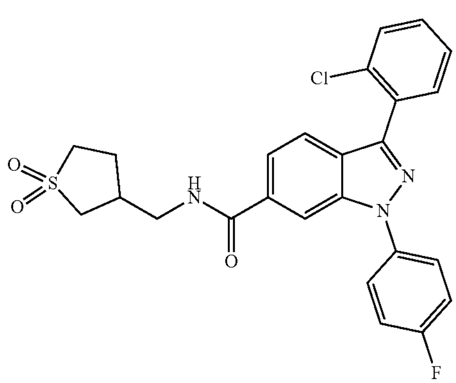 [SMILES: O=C(NCC1CCS(=O)(=O)C1)c1ccc2c(-c3ccccc3Cl)nn(-c3ccc(F)cc3)c2c1] | 3-(2-chlorophenyl)-N-[(1,1-dioxidotetrahydrothiophen-3-yl)methyl]-1-(4-fluorophenyl)-1H-indazole-6-carboxamide (racemic) | 498.1 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 30 | 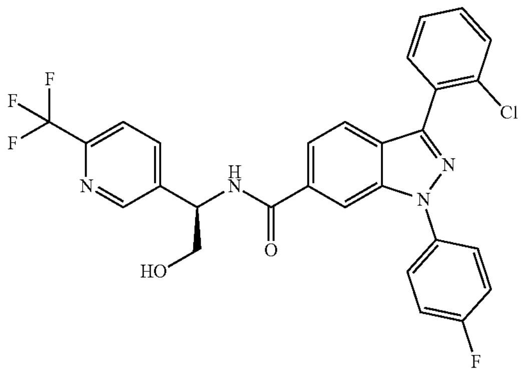 [SMILES: O=C(N[C@@H](CO)c1ccc(C(F)(F)F)nc1)c1ccc2c(-c3ccccc3Cl)nn(-c3ccc(F)cc3)c2c1] | 3-(2-chlorophenyl)-1-(4-fluorophenyl)-N-{(1R)-2-hydroxy-1-[6-(trifluoromethyl)pyridin-3-yl]ethyl}-1H-indazole-6-carboxamide | 555.1 |
| 31 | 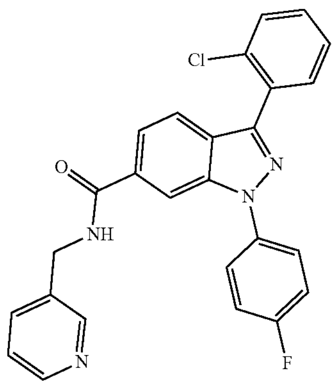 [SMILES: O=C(NCc1cccnc1)c1ccc2c(-c3ccccc3Cl)nn(-c3ccc(F)cc3)c2c1] | 3-(2-chlorophenyl)-1-(4-fluorophenyl)-N-(pyridin-3-ylmethyl)-1H-indazole-6-carboxamide | 457.1 |
| 32 | 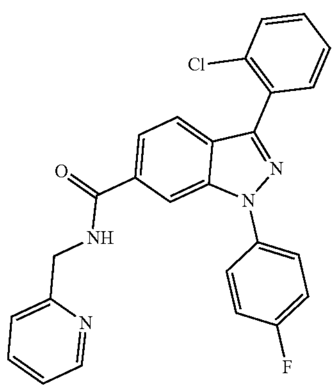 [SMILES: O=C(NCc1ccccn1)c1ccc2c(-c3ccccc3Cl)nn(-c3ccc(F)cc3)c2c1] | 3-(2-chlorophenyl)-1-(4-fluorophenyl)-N-(pyridin-2-ylmethyl)-1H-indazole-6-carboxamide | 457.1 |
| 33 | 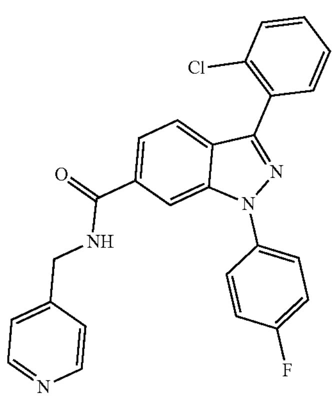 [SMILES: O=C(NCc1ccncc1)c1ccc2c(-c3ccccc3Cl)nn(-c3ccc(F)cc3)c2c1] | 3-(2-chlorophenyl)-1-(4-fluorophenyl)-N-(pyridin-4-ylmethyl)-1H-indazole-6-carboxamide | 457.1 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 34 | 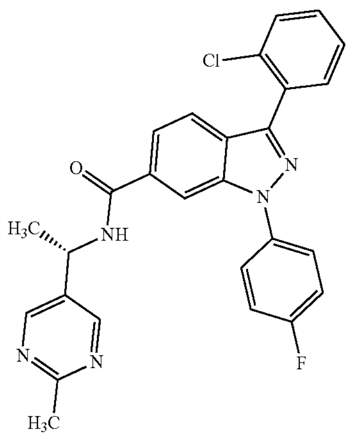 [SMILES: Cc1ncc([C@H](C)NC(=O)c2ccc3c(-c4ccccc4Cl)nn(-c4ccc(F)cc4)c3c2)cn1] | 3-(2-chlorophenyl)-1-(4-fluorophenyl)-N-[(1S)-1-(2-methylpyrimidin-5-yl)ethyl]-1H-indazole-6-carboxamide | 486.1 |
| 35 | 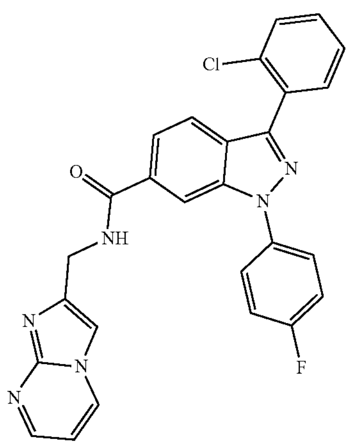 [SMILES: O=C(NCc1cn2cccnc2n1)c1ccc2c(-c3ccccc3Cl)nn(-c3ccc(F)cc3)c2c1] | 3-(2-chlorophenyl)-1-(4-fluorophenyl)-N-(imidazo[1,2-a]pyrimidin-2-ylmethyl)-1H-indazole-6-carboxamide | 497.1 |
| 36 | 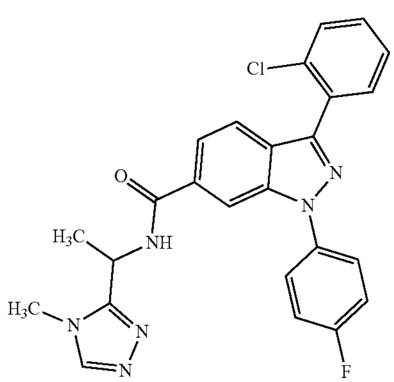 [SMILES: CC(NC(=O)c1ccc2c(-c3ccccc3Cl)nn(-c3ccc(F)cc3)c2c1)c1nncn1C] | 3-(2-chlorophenyl)-1-(4-fluorophenyl)-N-[1-(4-methyl-4H-1,2,4-triazol-3-yl)ethyl]-1H-indazole-6-carboxamide (racemic) | 475.2/477.1 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 37 | 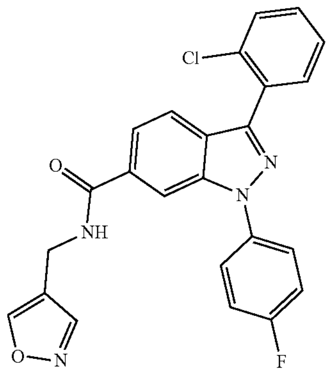 [SMILES: O=C(NCc1cnoc1)c1ccc2c(-c3ccccc3Cl)nn(-c3ccc(F)cc3)c2c1] | 3-(2-chlorophenyl)-1-(4-fluorophenyl)-N-(isoxazol-4-ylmethyl)-1H-indazole-6-carboxamide | 447.1 |
| 38 | 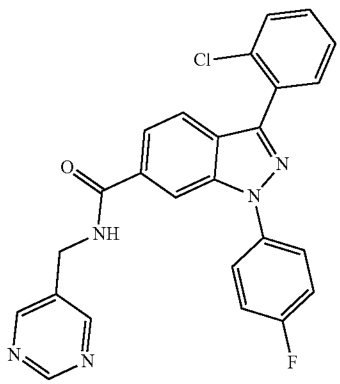 [SMILES: O=C(NCc1cncnc1)c1ccc2c(-c3ccccc3Cl)nn(-c3ccc(F)cc3)c2c1] | 3-(2-chlorophenyl)-1-(4-fluorophenyl)-N-(pyrimidin-5-ylmethyl)-1H-indazole-6-carboxamide | 458.1 |
| 39 | 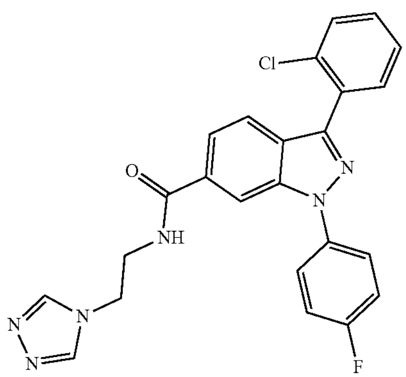 [SMILES: O=C(NCCn1cnnc1)c1ccc2c(-c3ccccc3Cl)nn(-c3ccc(F)cc3)c2c1] | 3-(2-chlorophenyl)-1-(4-fluorophenyl)-N-[2-(4H-1,2,4-triazol-4-yl)ethyl]-1H-indazole-6-carboxamide | 461.1 |
| 40 | 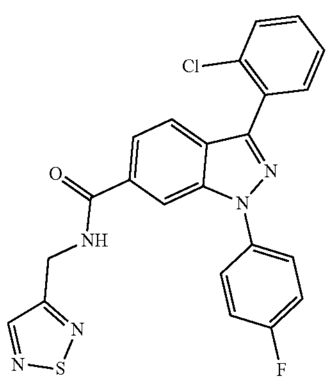 [SMILES: O=C(NCc1cnsn1)c1ccc2c(-c3ccccc3Cl)nn(-c3ccc(F)cc3)c2c1] | 3-(2-chlorophenyl)-1-(4-fluorophenyl)-N-(1,2,5-thiadiazol-3-ylmethyl)-1H-indazole-6-carboxamide | 464.1 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 41 | 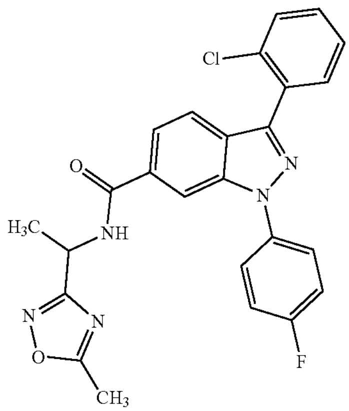 [SMILES: Cc1nc(C(C)NC(=O)c2ccc3c(-c4ccccc4Cl)nn(-c4ccc(F)cc4)c3c2)no1] | 3-(2-chlorophenyl)-1-(4-fluorophenyl)-N-[1-(5-methyl-1,2,4-oxadiazol-3-yl)ethyl]-1H-indazole-6-carboxamide (racemic) | 476.1 |
| 42 | 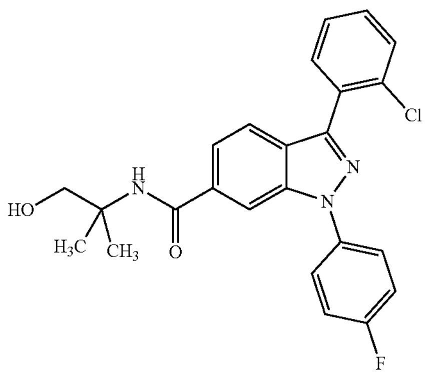 [SMILES: CC(C)(CO)NC(=O)c1ccc2c(-c3ccccc3Cl)nn(-c3ccc(F)cc3)c2c1] | 3-(2-chlorophenyl)-1-(4-fluorophenyl)-N-(2-hydroxy-1,1-dimethylethyl)-1H-indazole-6-carboxamide | 438.1 |
| 43 | 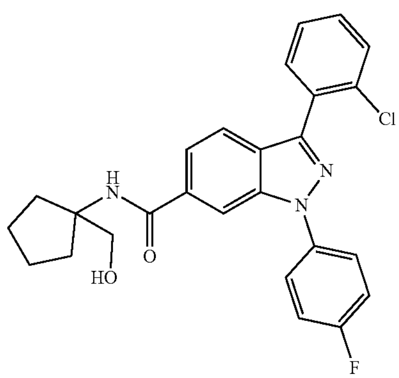 [SMILES: O=C(NC1(CO)CCCC1)c1ccc2c(-c3ccccc3Cl)nn(-c3ccc(F)cc3)c2c1] | 3-(2-chlorophenyl)-1-(4-fluorophenyl)-N-[1-(hydroxymethyl)cyclopentyl]-1H-indazole-6-carboxamide | 464.0 |
| 44 | 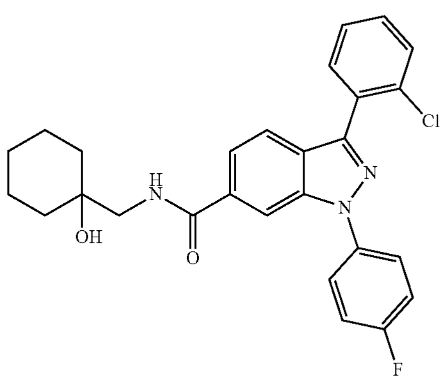 [SMILES: O=C(NCC1(O)CCCCC1)c1ccc2c(-c3ccccc3Cl)nn(-c3ccc(F)cc3)c2c1] | 3-(2-chlorophenyl)-1-(4-fluorophenyl)-N-[(1-hydroxycyclohexyl)methyl]-1H-indazole-6-carboxamide | 478.1 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 45 | 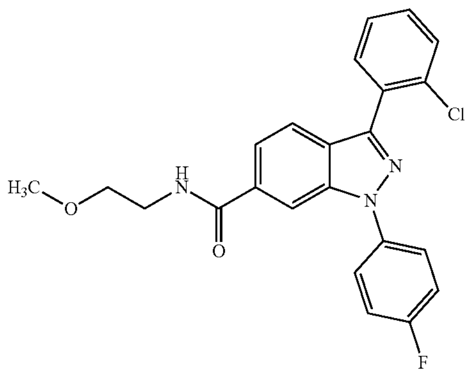 [SMILES: COCCNC(=O)c1ccc2c(-c3ccccc3Cl)nn(-c3ccc(F)cc3)c2c1] | 3-(2-chlorophenyl)-1-(4-fluorophenyl)-N-(2-methoxyethyl)-1H-indazole-6-carboxamide | 424.0 |
| 46 | 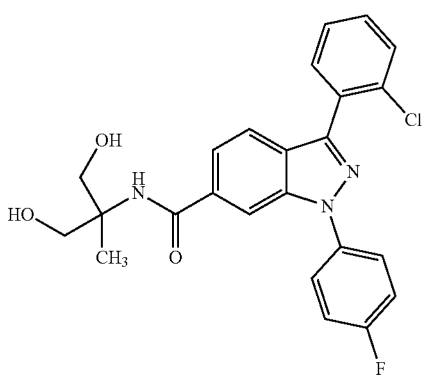 [SMILES: CC(CO)(CO)NC(=O)c1ccc2c(-c3ccccc3Cl)nn(-c3ccc(F)cc3)c2c1] | 3-(2-chlorophenyl)-1-(4-fluorophenyl)-N-[2-hydroxy-1-(hydroxymethyl)-1-methylethyl]-1H-indazole-6-carboxamide | 454.0 |
| 47 | 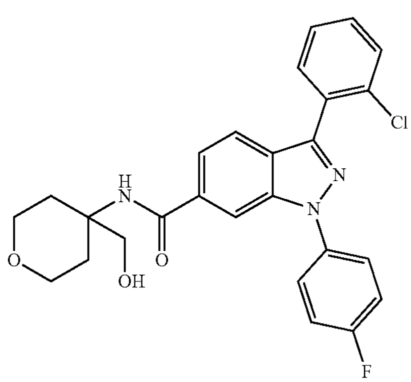 [SMILES: O=C(NC1(CO)CCOCC1)c1ccc2c(-c3ccccc3Cl)nn(-c3ccc(F)cc3)c2c1] | 3-(2-chlorophenyl)-1-(4-fluorophenyl)-N-[4-(hydroxymethyl)tetrahydro-2H-pyran-4-yl]-1H-indazole-6-carboxamide | 480.0 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]⁺ |
|---|---|---|---|
| 48 | 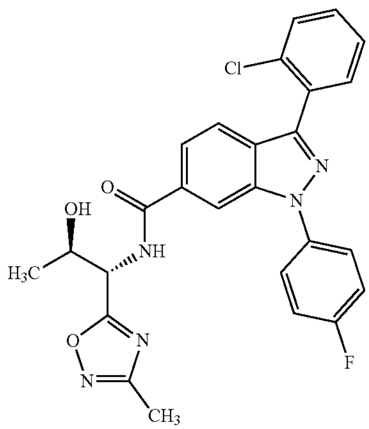 [SMILES: Cc1noc([C@@H](NC(=O)c2ccc3c(-c4ccccc4Cl)nn(-c4ccc(F)cc4)c3c2)[C@@H](C)O)n1] | 3-(2-chlorophenyl)-1-(4-fluorophenyl)-N-[(1R,2S)-2-hydroxy-1-(3-methyl-1,2,4-oxadiazol-5-yl)propyl]-1H-indazole-6-carboxamide | 506.0 |
| 49 | 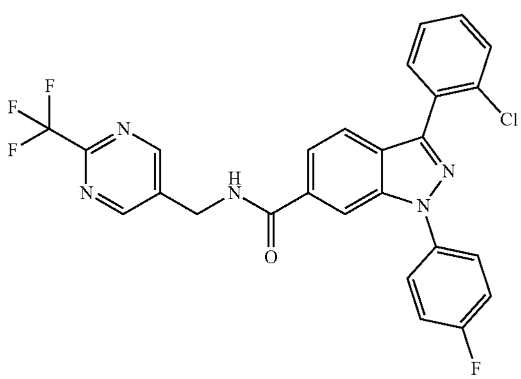 [SMILES: O=C(NCc1cnc(C(F)(F)F)nc1)c1ccc2c(-c3ccccc3Cl)nn(-c3ccc(F)cc3)c2c1] | 3-(2-chlorophenyl)-1-(4-fluorophenyl)-N-{[2-(trifluoromethyl)pyrimidin-5-yl]methyl}-1H-indazole-6-carboxamide | 526.0 |
| 50 | 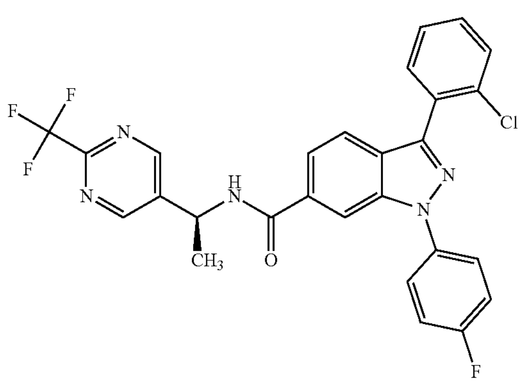 [SMILES: C[C@H](NC(=O)c1ccc2c(-c3ccccc3Cl)nn(-c3ccc(F)cc3)c2c1)c1cnc(C(F)(F)F)nc1] | 3-(2-chlorophenyl)-1-(4-fluorophenyl)-N-{(1S)-1-[2-(trifluoromethyl)pyrimidin-5-yl]ethyl}-1H-indazole-6-carboxamide | 540.0 |

TABLE 1-continued

Examples 1-B through 128-A in the following table were prepared from
appropriate acid and amine starting materials described previously or commercially available
starting materials using procedures described for the synthesis of Examples 1-A and 2-A.

| Ex # | Structure | Chemical Name | m/z[M + H]+ |
|---|---|---|---|
| 51 | 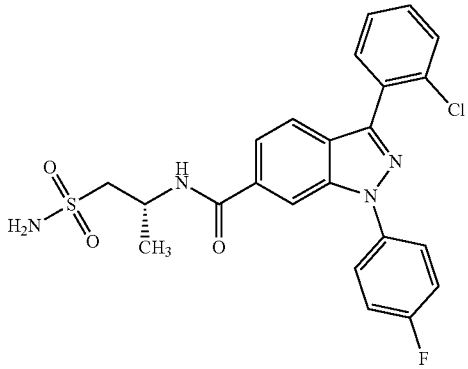 [SMILES: C[C@H](CS(N)(=O)=O)NC(=O)c1ccc2c(-c3ccccc3Cl)nn(-c3ccc(F)cc3)c2c1] | 3-(2-chlorophenyl)-1-(4-fluorophenyl)-N-[(1R)-1-methyl-2-sulfamoylethyl]-1H-indazole-6-carboxamide | 487.0 |
| 52 | 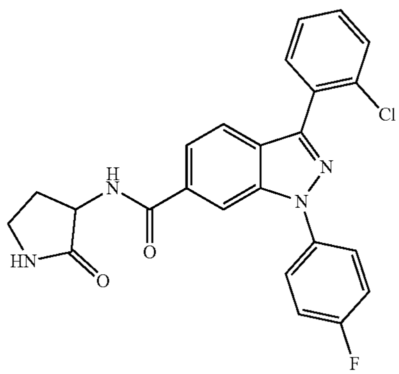 [SMILES: O=C(NC1CCNC1=O)c1ccc2c(-c3ccccc3Cl)nn(-c3ccc(F)cc3)c2c1] | 3-(2-chlorophenyl)-1-(4-fluorophenyl)-N-(2-oxopyrrolidin-3-yl)-1H-indazole-6-carboxamide (racemic) | 449.0 |
| 53 | 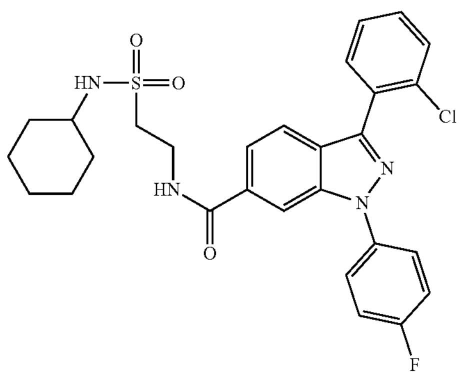 [SMILES: O=C(NCCS(=O)(=O)NC1CCCCC1)c1ccc2c(-c3ccccc3Cl)nn(-c3ccc(F)cc3)c2c1] | 3-(2-chlorophenyl)-N-[2-(cyclohexylsulfamoyl)ethyl]-1-(4-fluorophenyl)-1H-indazole-6-carboxamide | 555.0 |
| 54 | 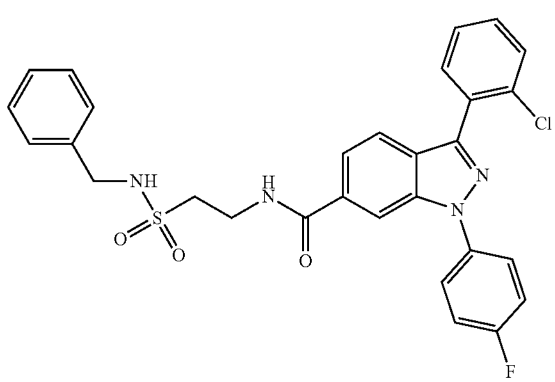 [SMILES: O=C(NCCS(=O)(=O)NCc1ccccc1)c1ccc2c(-c3ccccc3Cl)nn(-c3ccc(F)cc3)c2c1] | N-[2-(benzylsulfamoyl)ethyl]-3-(2-chlorophenyl)-1-(4-fluorophenyl)-1H-indazole-6-carboxamide | 563.0 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 55 | 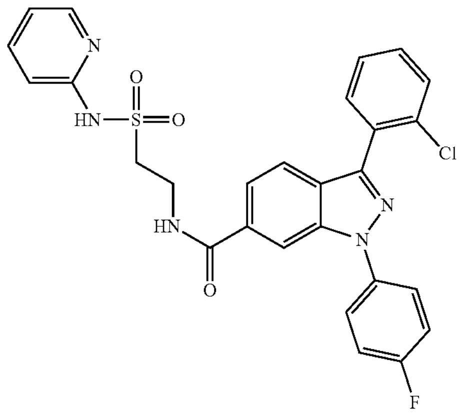 [SMILES: O=C(NCCS(=O)(=O)Nc1ccccn1)c1ccc2c(-c3ccccc3Cl)nn(-c3ccc(F)cc3)c2c1] | 3-(2-chlorophenyl)-1-(4-fluorophenyl)-N-[2-(pyridin-2-ylsulfamoyl)ethyl]-1H-indazole-6-carboxamide | 550.0 |
| 56 | 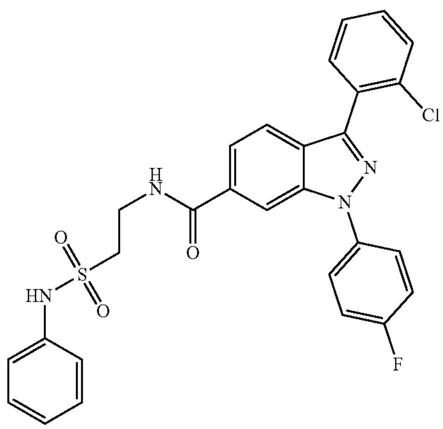 [SMILES: O=C(NCCS(=O)(=O)Nc1ccccc1)c1ccc2c(-c3ccccc3Cl)nn(-c3ccc(F)cc3)c2c1] | 3-(2-chlorophenyl)-1-(4-fluorophenyl)-N-[2-(phenylsulfamoyl)ethyl]-1H-indazole-6-carboxamide | 548.9 |
| 57 | 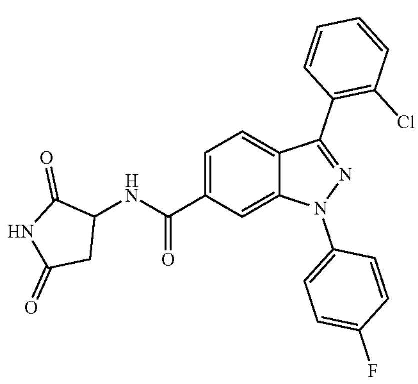 [SMILES: O=C1CC(NC(=O)c2ccc3c(-c4ccccc4Cl)nn(-c4ccc(F)cc4)c3c2)C(=O)N1] | 3-(2-chlorophenyl)-N-(2,5-dioxopyrrolidin-3-yl)-1-(4-fluorophenyl)-1H-indazole-6-carboxamide (racemic) | 463.1 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 58-A | 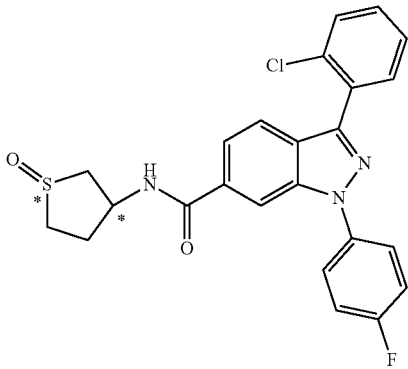 [SMILES: O=C(NC1CCS(=O)C1)c1ccc2c(-c3ccccc3Cl)nn(-c3ccc(F)cc3)c2c1] | 3-(2-chlorophenyl)-1-(4-fluorophenyl)-N-(1-oxidotetrahydrothiophen-3-yl)-1H-indazole-6-carboxamide (a single diastereomer) | 468.0 |
| 58-B | 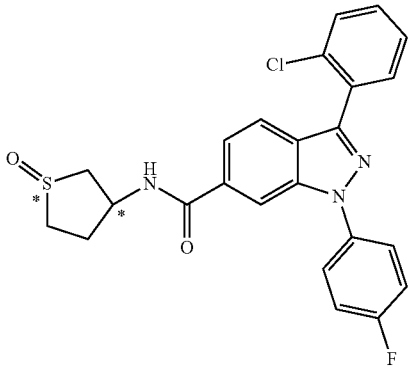 [SMILES: O=C(NC1CCS(=O)C1)c1ccc2c(-c3ccccc3Cl)nn(-c3ccc(F)cc3)c2c1] | 3-(2-chlorophenyl)-1-(4-fluorophenyl)-N-(1-oxidotetrahydrothiophen-3-yl)-1H-indazole-6-carboxamide (a single diastereomer) | 468.0 |
| 59 | 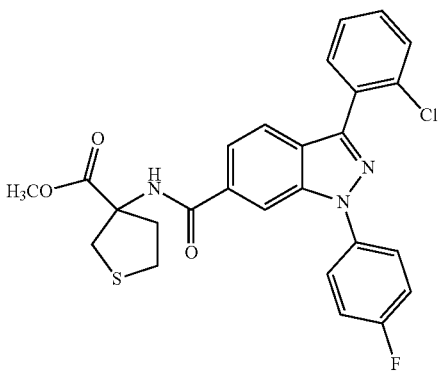 [SMILES: COC(=O)C1(NC(=O)c2ccc3c(-c4ccccc4Cl)nn(-c4ccc(F)cc4)c3c2)CCSC1] | methyl 3-({[3-(2-chlorophenyl)-1-(4-fluorophenyl)-1H-indazol-6-yl]carbonyl}amino)tetrahydrothiophene-3-carboxylate (racemic) | 510.0 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 60 | 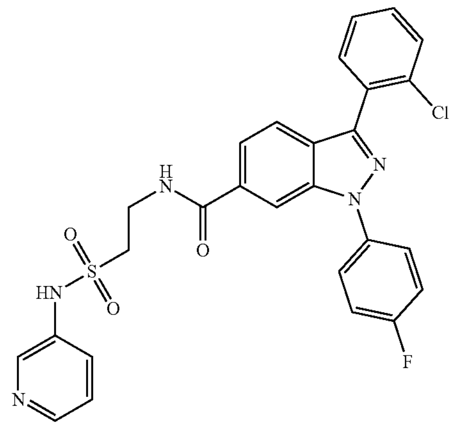 [SMILES: O=C(NCCS(=O)(=O)Nc1cccnc1)c1ccc2c(-c3ccccc3Cl)nn(-c3ccc(F)cc3)c2c1] | 3-(2-chlorophenyl)-1-(4-fluorophenyl)-N-[2-(pyridin-3-ylsulfamoyl)ethyl]-1H-indazole-6-carboxamide | 550.1 |
| 61 | 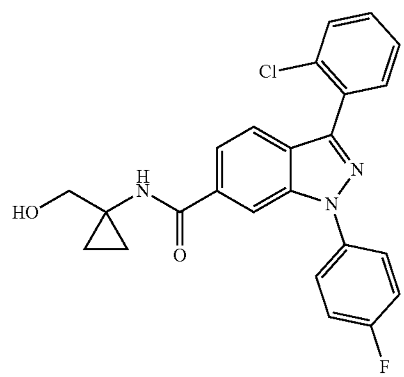 [SMILES: O=C(NC1(CO)CC1)c1ccc2c(-c3ccccc3Cl)nn(-c3ccc(F)cc3)c2c1] | 3-(2-chlorophenyl)-1-(4-fluorophenyl)-N-[1-(hydroxymethyl)cyclopropyl]-1H-indazole-6-carboxamide | 436.0 |
| 62 | 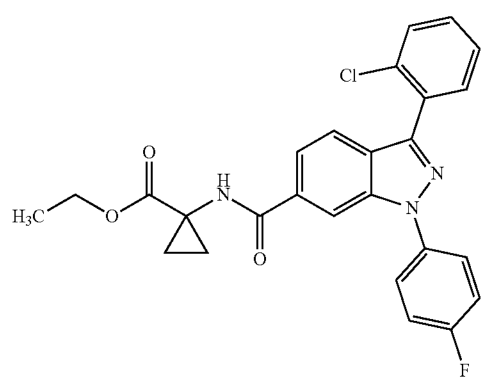 [SMILES: CCOC(=O)C1(NC(=O)c2ccc3c(-c4ccccc4Cl)nn(-c4ccc(F)cc4)c3c2)CC1] | ethyl 1-({[3-(2-chlorophenyl)-1-(4-fluorophenyl)-1H-indazol-6-yl]carbonyl}amino)cyclopropane carboxylate | 478.0 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 63 | 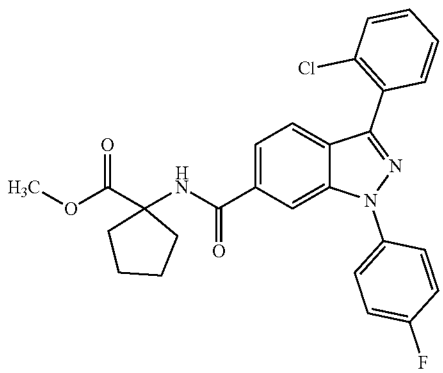 [SMILES: COC(=O)C1(NC(=O)c2ccc3c(-c4ccccc4Cl)nn(-c4ccc(F)cc4)c3c2)CCCC1] | methyl 1-({[3-(2-chlorophenyl)-1-(4-fluorophenyl)-1H-indazol-6-yl]carbonyl}amino)cyclopentanecarboxylate | 492.0 |
| 64 | 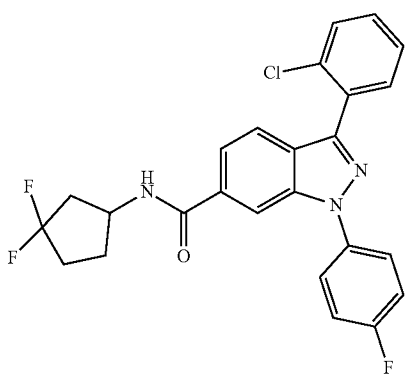 [SMILES: O=C(NC1CCC(F)(F)C1)c1ccc2c(-c3ccccc3Cl)nn(-c3ccc(F)cc3)c2c1] | 3-(2-chlorophenyl)-N-(3,3-difluorocyclopentyl)-1-(4-fluorophenyl)-1H-indazole-6-carboxamide (racemic) | 470.2 |
| 65 | 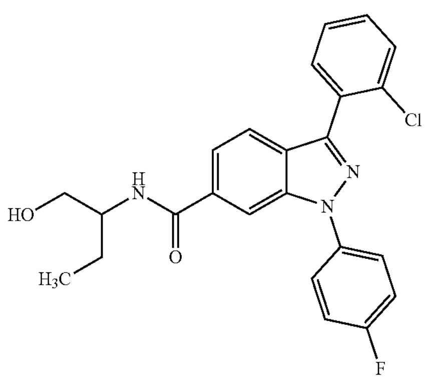 [SMILES: CCC(CO)NC(=O)c1ccc2c(-c3ccccc3Cl)nn(-c3ccc(F)cc3)c2c1] | 3-(2-chlorophenyl)-1-(4-fluorophenyl)-N-[1-(hydroxymethyl)propyl]-1H-indazole-6-carboxamide (racemic) | 438.2 |
| 66 | 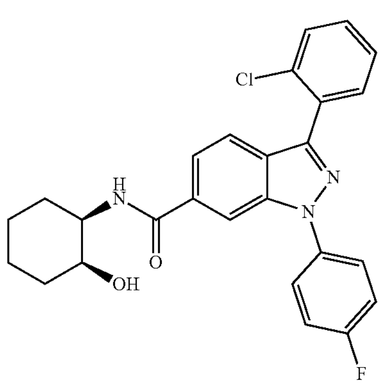 [SMILES: O=C(N[C@@H]1CCCC[C@@H]1O)c1ccc2c(-c3ccccc3Cl)nn(-c3ccc(F)cc3)c2c1] | 3-(2-chlorophenyl)-1-(4-fluorophenyl)-N-2-hydroxycyclohexyl]-1H-indazole-6-carboxamide (cis, racemic) | 464.2 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 67 | 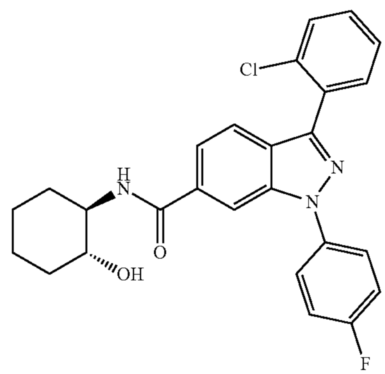 [SMILES: O=C(N[C@@H]1CCCC[C@H]1O)c1ccc2c(-c3ccccc3Cl)nn(-c3ccc(F)cc3)c2c1] | 3-(2-chlorophenyl)-1-(4-fluorophenyl)-N-2-hydroxycyclohexyl]-1H-indazole-6-carboxamide (trans, racemic) | 464.2 |
| 68 | 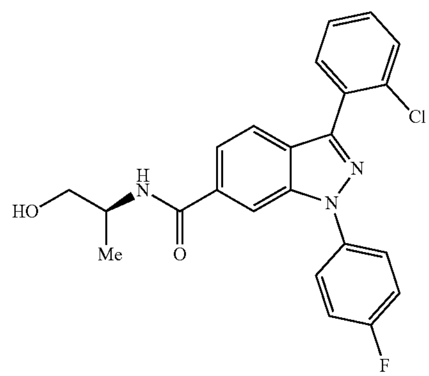 [SMILES: C[C@@H](CO)NC(=O)c1ccc2c(-c3ccccc3Cl)nn(-c3ccc(F)cc3)c2c1] | 3-(2-chlorophenyl)-1-(4-fluorophenyl)-N-[(1S)-2-hydroxy-1-methylethyl]-1H-indazole-6-carboxamide | 424.2 |
| 69 | 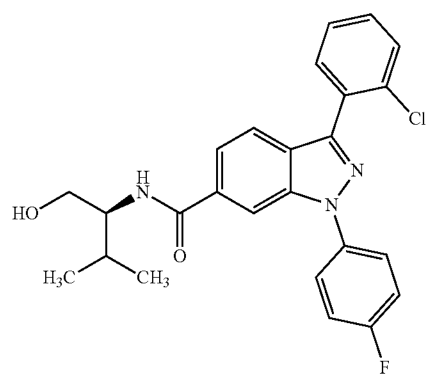 [SMILES: CC(C)[C@@H](CO)NC(=O)c1ccc2c(-c3ccccc3Cl)nn(-c3ccc(F)cc3)c2c1] | 3-(2-chlorophenyl)-1-(4-fluorophenyl)-N-[(1S)-1-(hydroxymethyl)-2-methylpropyl]-1H-indazole-6-carboxamide | 452.1 |
| 70 | 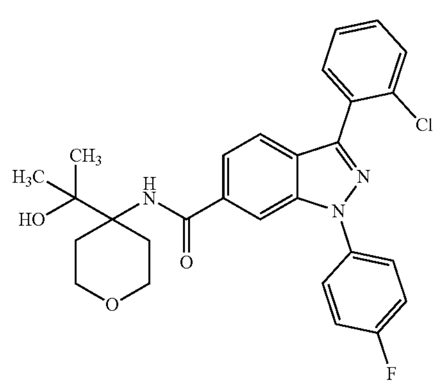 [SMILES: CC(C)(O)C1(NC(=O)c2ccc3c(-c4ccccc4Cl)nn(-c4ccc(F)cc4)c3c2)CCOCC1] | 3-(2-chlorophenyl)-1-(4-fluorophenyl)-N-[4-(1-hydroxy-1-methylethyl)tetrahydro-2H-pyran-4-yl]-1H-indazole-6-carboxamide | 508.3 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]⁺ |
|---|---|---|---|
| 71 | 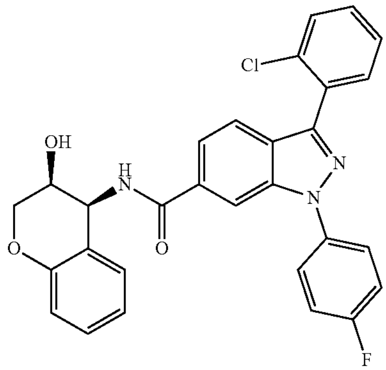 [SMILES: O=C(N[C@H]1c2ccccc2OC[C@H]1O)c1ccc2c(-c3ccccc3Cl)nn(-c3ccc(F)cc3)c2c1] | 3-(2-chlorophenyl)-1-(4-fluorophenyl)-N-[(3S,4S)-3-hydroxy-3,4-dihydro-2H-chromen-4-yl]-1H-indazole-6-carboxamide | 514.3 |
| 72 | 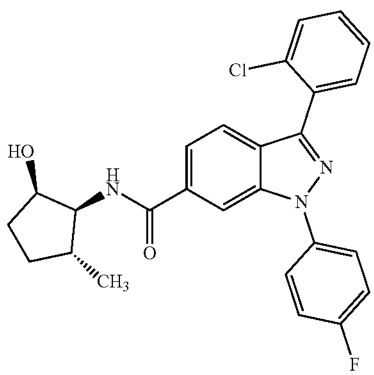 [SMILES: C[C@@H]1CC[C@@H](O)[C@H]1NC(=O)c1ccc2c(-c3ccccc3Cl)nn(-c3ccc(F)cc3)c2c1] | 3-(2-chlorophenyl)-1-(4-fluorophenyl)-N-[(1S,2R,5R)-2-hydroxy-5-methylcyclopentyl]-1H-indazole-6-carboxamide | 464.1 |
| 73 | 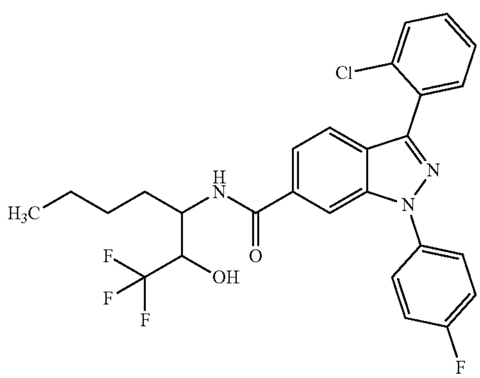 [SMILES: CCCCC(NC(=O)c1ccc2c(-c3ccccc3Cl)nn(-c3ccc(F)cc3)c2c1)C(O)C(F)(F)F] | 3-(2-chlorophenyl)-1-(4-fluorophenyl)-N-[1-(2,2,2-trifluoro-1-hydroxyethyl)pentyl]-1H-indazole-6-carboxamide (one diastereomer) | 534.3 |
| 74 | 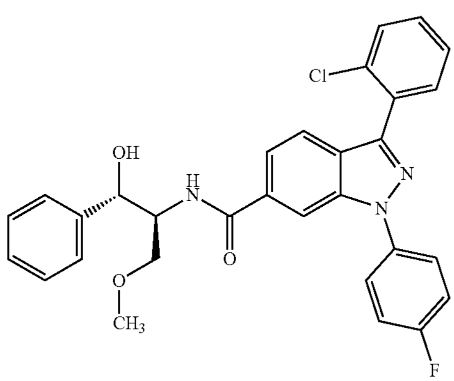 [SMILES: COC[C@H](NC(=O)c1ccc2c(-c3ccccc3Cl)nn(-c3ccc(F)cc3)c2c1)[C@@H](O)c1ccccc1] | 3-(2-chlorophenyl)-1-(4-fluorophenyl)-N-[(1S,2S)-2-hydroxy-1-(methoxymethyl)-2-phenylethyl]-1H-indazole-6-carboxamide | 530.3 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 75 | 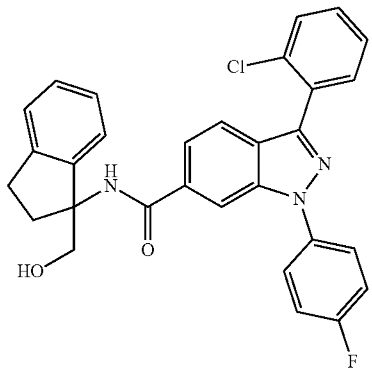 [SMILES: O=C(NC1(CO)CCc2ccccc21)c1ccc2c(-c3ccccc3Cl)nn(-c3ccc(F)cc3)c2c1] | 3-(2-chlorophenyl)-1-(4-fluorophenyl)-N-[1-(hydroxymethyl)-2,3-dihydro-1H-inden-1-yl]-1H-indazole-6-carboxamide (racemic) | 512.3 |
| 76 | 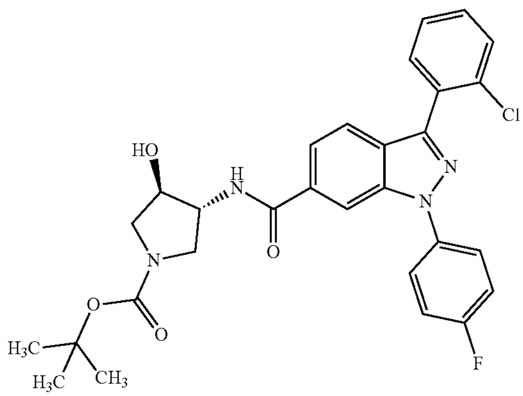 [SMILES: CC(C)(C)OC(=O)N1C[C@@H](O)[C@H](NC(=O)c2ccc3c(-c4ccccc4Cl)nn(-c4ccc(F)cc4)c3c2)C1] | tert-butyl (3R,4R)-3-({[3-(2-chlorophenyl)-1-(4-fluorophenyl)-1H-indazol-6-yl]carbonyl}amino)-4-hydroxypyrrolidine-1-carboxylate | 550.2 |
| 77 | 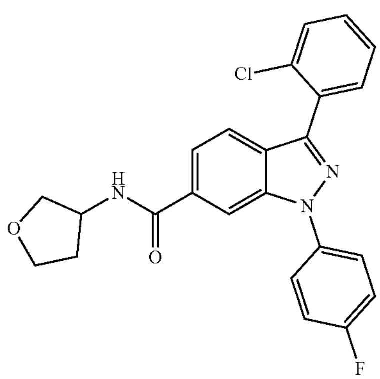 [SMILES: O=C(NC1CCOC1)c1ccc2c(-c3ccccc3Cl)nn(-c3ccc(F)cc3)c2c1] | 3-(2-chlorophenyl)-1-(4-fluorophenyl)-N-(tetrahydrofuran-3-yl)-1H-indazole-6-carboxamide (racemic) | 436.2 |
| 78 | 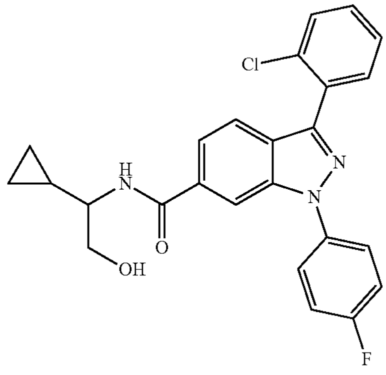 [SMILES: O=C(NC(CO)C1CC1)c1ccc2c(-c3ccccc3Cl)nn(-c3ccc(F)cc3)c2c1] | 3-(2-chlorophenyl)-N-(1-cyclopropyl-2-hydroxyethyl)-1-(4-fluorophenyl)-1H-indazole-6-carboxamide (racemic) | 450.2 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 79 | 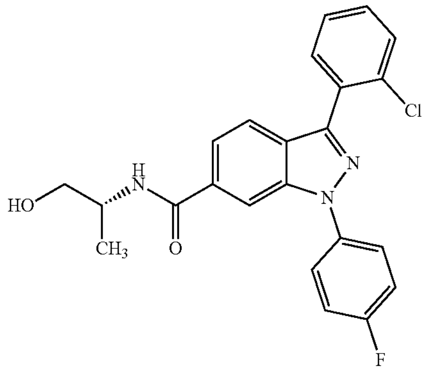 [SMILES: C[C@H](CO)NC(=O)c1ccc2c(-c3ccccc3Cl)nn(-c3ccc(F)cc3)c2c1] | 3-(2-chlorophenyl)-1-(4-fluorophenyl)-N-[(1R)-hydroxy-1-methylethyl]-1H-indazole-6-carboxamide | 424.2 |
| 80 | 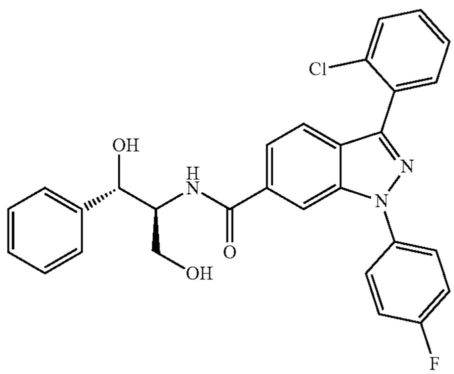 [SMILES: O=C(N[C@@H](CO)[C@@H](O)c1ccccc1)c1ccc2c(-c3ccccc3Cl)nn(-c3ccc(F)cc3)c2c1] | 3-(2-chlorophenyl)-1-(4-fluorophenyl)-N-[(1S,2S)-2-hydroxy-1-(hydroxymethyl)-2-phenylethyl]-1H-indazole-6-carboxamide | 516.3 |
| 81 | 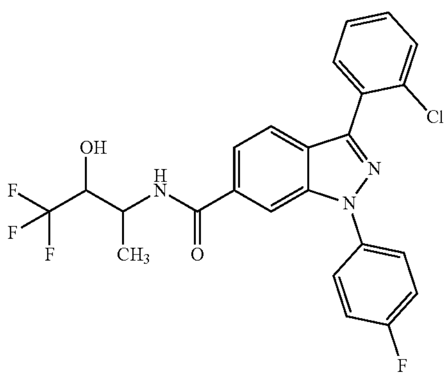 [SMILES: CC(NC(=O)c1ccc2c(-c3ccccc3Cl)nn(-c3ccc(F)cc3)c2c1)C(O)C(F)(F)F] | 3-(2-chlorophenyl)-1-(4-fluorophenyl)-N-(3,3,3-trifluoro-2-hydroxy-1-methylpropyl)-1H-indazole-6-carboxamide | 492.2 |
| 82 | 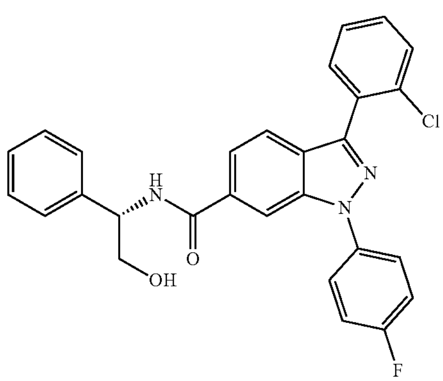 [SMILES: O=C(N[C@H](CO)c1ccccc1)c1ccc2c(-c3ccccc3Cl)nn(-c3ccc(F)cc3)c2c1] | 3-(2-chlorophenyl)-1-(4-fluorophenyl)-N-[(1S)-2-hydroxy-1-phenylethyl]-1H-indazole-6-carboxamide | 486.2 |

TABLE 1-continued

Examples 1-B through 128-A in the following table were prepared from
appropriate acid and amine starting materials described previously or commercially available
starting materials using procedures described for the synthesis of Examples 1-A and 2-A.

| Ex # | Structure | Chemical Name | m/z[M + H]+ |
|---|---|---|---|
| 83 | 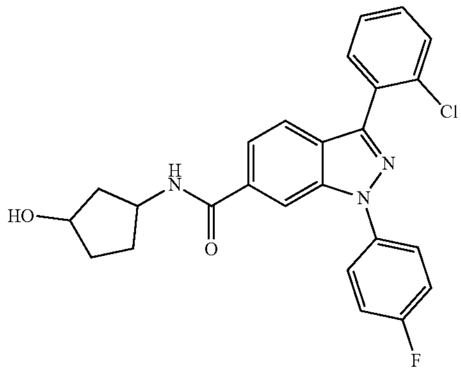 [SMILES: O=C(NC1CCC(O)C1)c1ccc2c(-c3ccccc3Cl)nn(-c3ccc(F)cc3)c2c1] | 3-(2-chlorophenyl)-1-(4-fluorophenyl)-N-(3-hydroxycyclopentyl)-1H-indazole-6-carboxamide (racemic) | 450.2 |
| 84 | 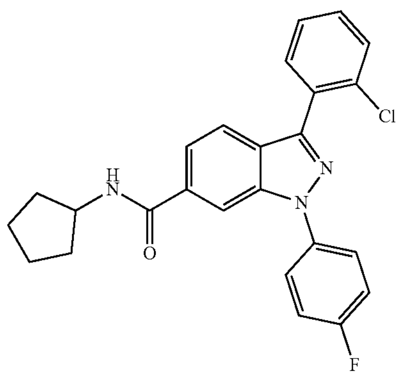 [SMILES: O=C(NC1CCCC1)c1ccc2c(-c3ccccc3Cl)nn(-c3ccc(F)cc3)c2c1] | 3-(2-chlorophenyl)-N-cyclopentyl-1-(4-fluorophenyl)-1H-indazole-6-carboxamide | 434.1 |
| 85 | 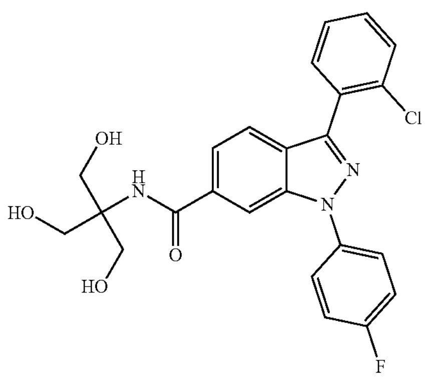 [SMILES: O=C(NC(CO)(CO)CO)c1ccc2c(-c3ccccc3Cl)nn(-c3ccc(F)cc3)c2c1] | 3-(2-chlorophenyl)-1-(4-fluorophenyl)-N-[2-hydroxy-1,1-bis(hydroxymethyl)ethyl]-1H-indazole-6-carboxamide | 470.1 |
| 86 | 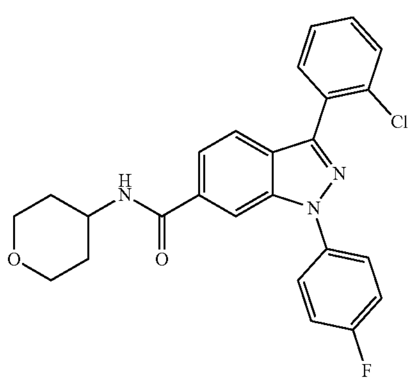 [SMILES: O=C(NC1CCOCC1)c1ccc2c(-c3ccccc3Cl)nn(-c3ccc(F)cc3)c2c1] | 3-(2-chlorophenyl)-1-(4-fluorophenyl)-N-(tetrahydro-2H-pyran-4-yl)-1H-indazole-6-carboxamide | 450.1 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 87 | 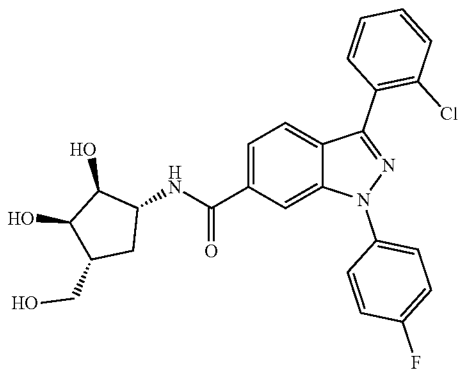 [SMILES: O=C(N[C@@H]1C[C@H](CO)[C@@H](O)[C@H]1O)c1ccc2c(-c3ccccc3Cl)nn(-c3ccc(F)cc3)c2c1] | 3-(2-chlorophenyl)-N-[(1R,2S,3R,4R)-2,3-dihydroxy-4-(hydroxymethyl)cyclopentyl]-1-(4-fluorophenyl)-1H-indazole-6-carboxamide | 496.1 |
| 88 | 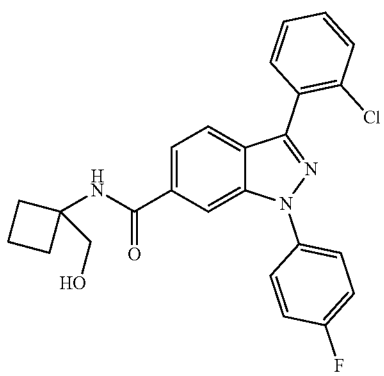 [SMILES: O=C(NC1(CO)CCC1)c1ccc2c(-c3ccccc3Cl)nn(-c3ccc(F)cc3)c2c1] | 3-(2-chlorophenyl)-1-(4-fluorophenyl)-N-[1-(hydroxymethyl)cyclobutyl]-1H-indazole-6-carboxamide | 450.1 |
| 89 | 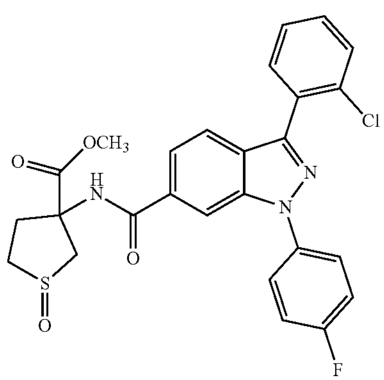 [SMILES: COC(=O)C1(NC(=O)c2ccc3c(-c4ccccc4Cl)nn(-c4ccc(F)cc4)c3c2)CCS(=O)C1] | methyl 3-({[3-(2-chlorophenyl)-1-(4-fluorophenyl)-1H-indazol-6-yl]carbonyl}amino)tetrahydrothiophene-3-carboxylate 1-oxide (racemic) | 526.0 |
| 90 | 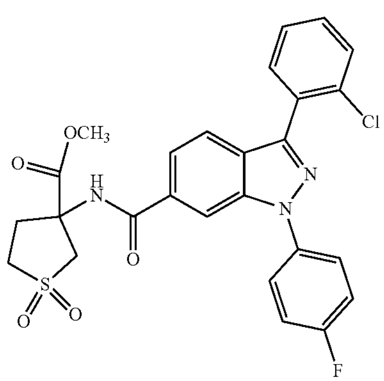 [SMILES: COC(=O)C1(NC(=O)c2ccc3c(-c4ccccc4Cl)nn(-c4ccc(F)cc4)c3c2)CCS(=O)(=O)C1] | methyl 3-({[3-(2-chlorophenyl)-1-(4-fluorophenyl)-1H-indazol-6-yl]carbonyl}amino)tetrahydrothiophene-3-carboxylate 1,1-dioxide (racemic) | 542.0 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 91 | 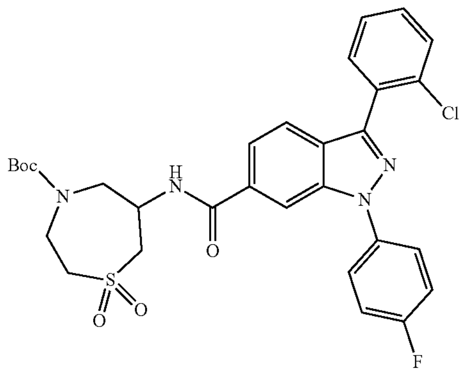 [SMILES: CC(C)(C)OC(=O)N1CCS(=O)(=O)CC(NC(=O)c2ccc3c(-c4ccccc4Cl)nn(-c4ccc(F)cc4)c3c2)C1] | tert-butyl 6-({[3-(2-chlorophenyl)-1-(4-fluorophenyl)-1H-indazol-6-yl]carbonyl}amino)-1,4-thiazepane-4-carboxylate 1,1-dioxide (racemic) | 613.1 |
| 92 | 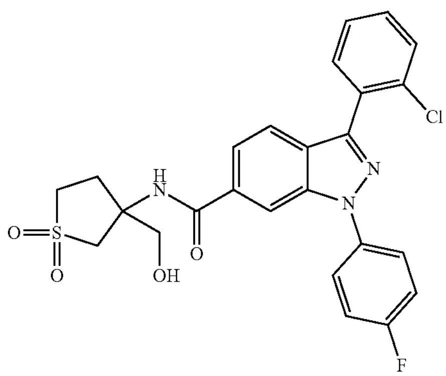 [SMILES: O=C(NC1(CO)CCS(=O)(=O)C1)c1ccc2c(-c3ccccc3Cl)nn(-c3ccc(F)cc3)c2c1] | 3-(2-chlorophenyl)-1-(4-fluorophenyl)-N-[3-(hydroxymethyl)-1,1-dioxidotetrahydrothiophen-3-yl]-1H-indazole-6-carboxamide (racemic) | 514.0 |
| 93 | 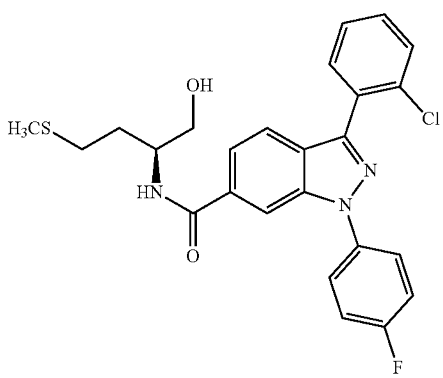 | 3-(2-chlorophenyl)-1-(4-fluorophenyl)-N-[(1S)-1-(hydroxymethyl)-3-(methylsulfanyl)propyl]-1H-indazole-6-carboxamide | 484.0 |
| 94 | 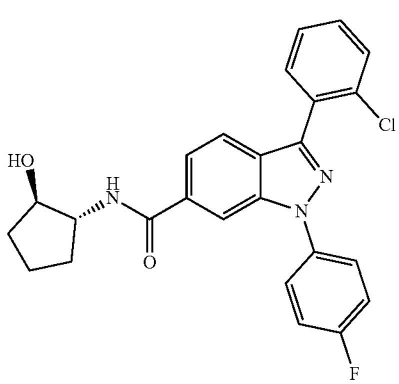 [SMILES: O=C(N[C@@H]1CCC[C@H]1O)c1ccc2c(-c3ccccc3Cl)nn(-c3ccc(F)cc3)c2c1] | 3-(2-chlorophenyl)-1-(4-fluorophenyl)-N-[(1R,2R)-2-hydroxycyclopentyl]-1H-indazole-6-carboxamide | 450.2 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 95 | 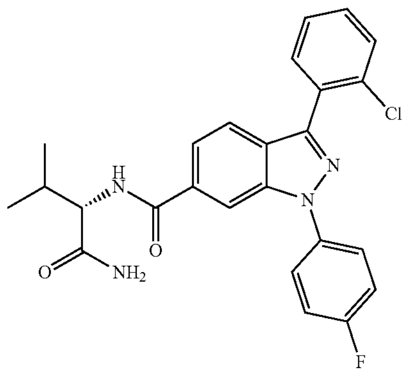 [SMILES: CC(C)[C@H](NC(=O)c1ccc2c(-c3ccccc3Cl)nn(-c3ccc(F)cc3)c2c1)C(N)=O] | N-[(1S)-1-carbamoyl-2-methylpropyl]-3-(2-chlorophenyl)-1-(4-fluorophenyl)-1H-indazole-6-carboxamide | 465.2 |
| 96 | 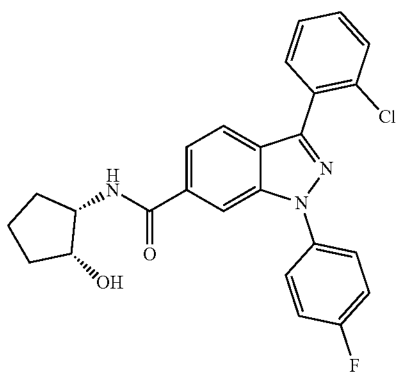 [SMILES: O=C(N[C@H]1CCC[C@H]1O)c1ccc2c(-c3ccccc3Cl)nn(-c3ccc(F)cc3)c2c1] | 3-(2-chlorophenyl)-1-(4-fluorophenyl)-N-[(1S,2R)-2-hydroxycyclopentyl]-1H-indazole-6-carboxamide | 450.2 |
| 97 | 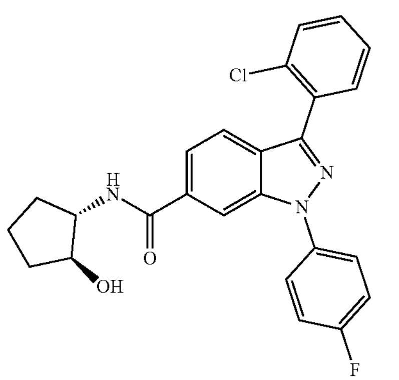 [SMILES: O=C(N[C@H]1CCC[C@@H]1O)c1ccc2c(-c3ccccc3Cl)nn(-c3ccc(F)cc3)c2c1] | 3-(2-chlorophenyl)-1-(4-fluorophenyl)-N-[(1S,2S)-2-hydroxycyclopentyl]-1H-indazole-6-carboxamide | 450.2 |
| 98 | 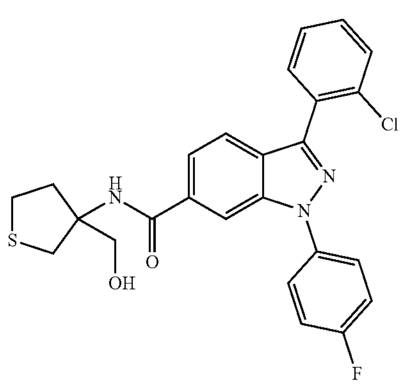 [SMILES: O=C(NC1(CO)CCSC1)c1ccc2c(-c3ccccc3Cl)nn(-c3ccc(F)cc3)c2c1] | 3-(2-chlorophenyl)-1-(4-fluorophenyl)-N-[3-(hydroxymethyl)tetrahydrothiophen-3-yl]-1H-indazole-6-carboxamide (racemic) | 482.0 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 99 | 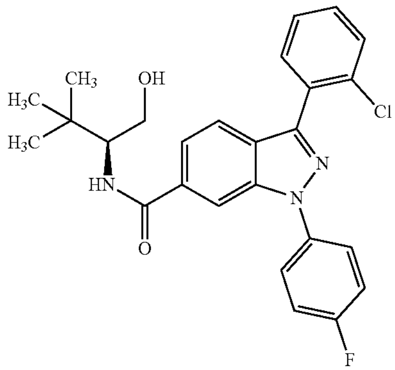 [SMILES: CC(C)(C)[C@@H](CO)NC(=O)c1ccc2c(-c3ccccc3Cl)nn(-c3ccc(F)cc3)c2c1] | 3-(2-chlorophenyl)-1-(4-fluorophenyl)-N-[(1S)-1-(hydroxymethyl)-2,2-dimethylpropyl]-1H-indazole-6-carboxamide | 466.1 |
| 100 | 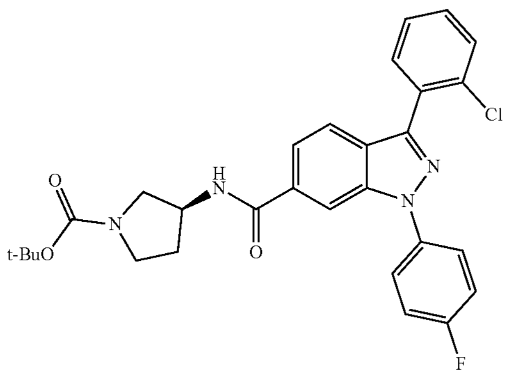 [SMILES: CC(C)(C)OC(=O)N1CC[C@H](NC(=O)c2ccc3c(-c4ccccc4Cl)nn(-c4ccc(F)cc4)c3c2)C1] | tert-butyl (3S)-3-({[3-(2-chlorophenyl)-1-(4-fluorophenyl)-1H-indazol-6-yl]carbonyl}amino)pyrrolidine-1-carboxylate | 535.0 |
| 101 | 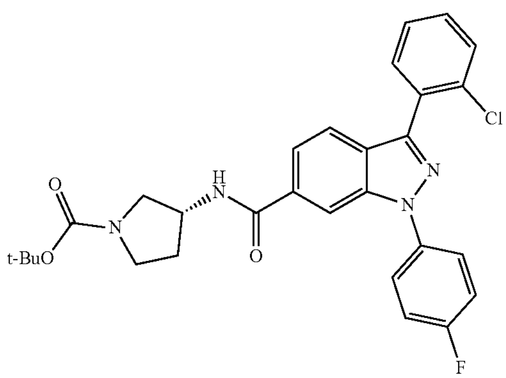 [SMILES: CC(C)(C)OC(=O)N1CC[C@@H](NC(=O)c2ccc3c(-c4ccccc4Cl)nn(-c4ccc(F)cc4)c3c2)C1] | tert-butyl (3R)-3-({[3-(2-chlorophenyl)-1-(4-fluorophenyl)-1H-indazol-6-yl]carbonyl}amino)pyrrolidine-1-carboxylate | 535.0 |
| 102 | 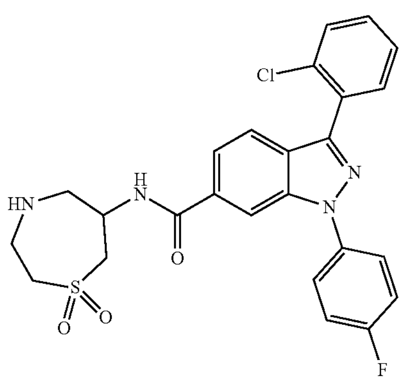 [SMILES: O=C(NC1CNCCS(=O)(=O)C1)c1ccc2c(-c3ccccc3Cl)nn(-c3ccc(F)cc3)c2c1] | 3-(2-chlorophenyl)-N-(1,1-dioxido-1,4-thiazepan-6-yl)-1-(4-fluorophenyl)-1H-indazole-6-carboxamide (racemic) | 513.0 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]$^+$ |
|---|---|---|---|
| 103 | 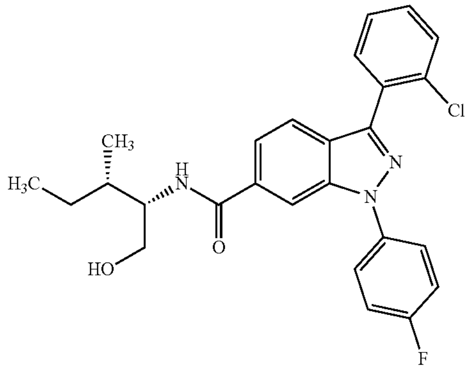 [SMILES: CC[C@H](C)[C@@H](CO)NC(=O)c1ccc2c(-c3ccccc3Cl)nn(-c3ccc(F)cc3)c2c1] | 3-(2-chlorophenyl)-1-(4-fluorophenyl)-N-[(1S,2S)-1-(hydroxymethyl)-2-methylbutyl]-1H-indazole-6-carboxamide | 466.1 |
| 104 | 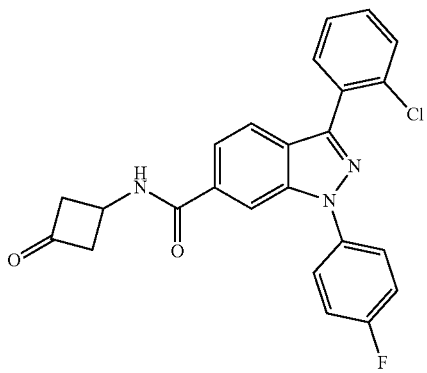 [SMILES: O=C1CC(NC(=O)c2ccc3c(-c4ccccc4Cl)nn(-c4ccc(F)cc4)c3c2)C1] | 3-(2-chlorophenyl)-1-(4-fluorophenyl)-N-(3-oxocyclobutyl)-1H-indazole-6-carboxamide | 434.2 |
| 105 | 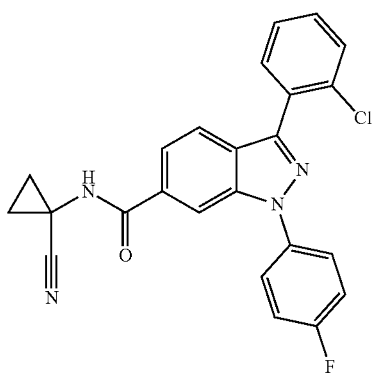 [SMILES: N#CC1(NC(=O)c2ccc3c(-c4ccccc4Cl)nn(-c4ccc(F)cc4)c3c2)CC1] | 3-(2-chlorophenyl)-N-(1-cyanocyclopropyl)-1-(4-fluorophenyl)-1H-indazole-6-carboxamide | 431.2 |
| 106 | 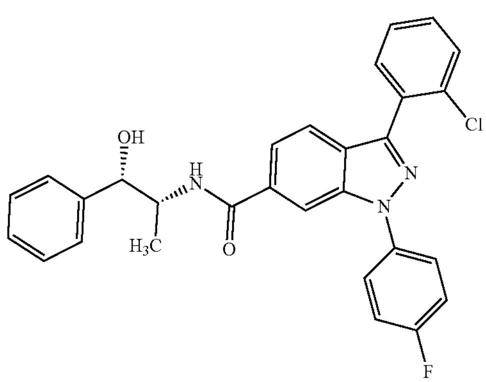 [SMILES: C[C@@H](NC(=O)c1ccc2c(-c3ccccc3Cl)nn(-c3ccc(F)cc3)c2c1)[C@@H](O)c1ccccc1] | 3-(2-chlorophenyl)-1-(4-fluorophenyl)-N-[(1R,2S)-2-hydroxy-1-methyl-2-phenylethyl]-1H-indazole-6-carboxamide | 500.2 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 107 | 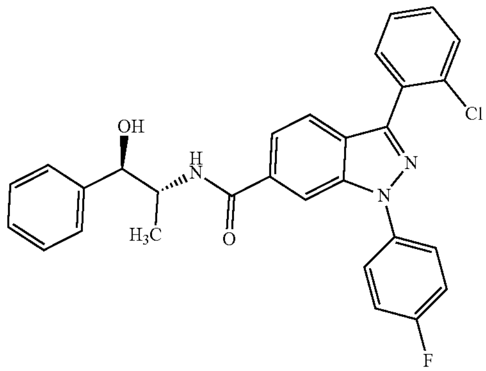 [SMILES: C[C@@H](NC(=O)c1ccc2c(-c3ccccc3Cl)nn(-c3ccc(F)cc3)c2c1)[C@H](O)c1ccccc1] | 3-(2-chlorophenyl)-1-(4-fluorophenyl)-N-[(1R,2R)-2-hydroxy-1-methyl-2-phenylethyl]-1H-indazole-6-carboxamide | 500.2 |
| 108 | 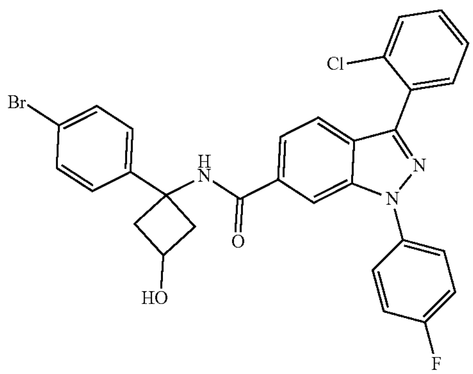 [SMILES: O=C(NC1(c2ccc(Br)cc2)CC(O)C1)c1ccc2c(-c3ccccc3Cl)nn(-c3ccc(F)cc3)c2c1] | N-[1-(4-bromophenyl)-3-hydroxycyclobutyl]-3-(2-chlorophenyl)-1-(4-fluorophenyl)-1H-indazole-6-carboxamide | 590/592.2 |
| 109 | 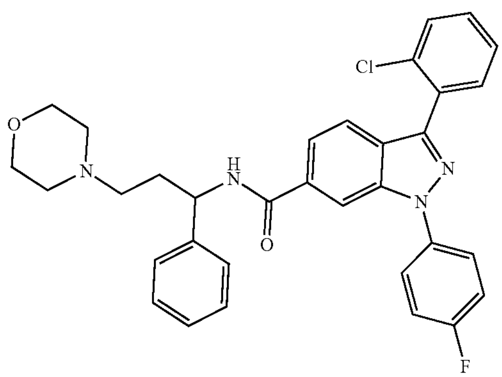 [SMILES: O=C(NC(CCN1CCOCC1)c1ccccc1)c1ccc2c(-c3ccccc3Cl)nn(-c3ccc(F)cc3)c2c1] | 3-(2-chlorophenyl)-1-(4-fluorophenyl)-N-(3-morpholin-4-yl-1-phenylpropyl)-1H-indazole-6-carboxamide (racemic) | 569.0/570.3/571.3 |
| 110 | 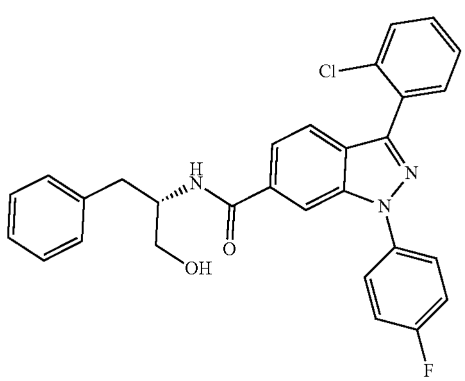 [SMILES: O=C(N[C@H](CO)Cc1ccccc1)c1ccc2c(-c3ccccc3Cl)nn(-c3ccc(F)cc3)c2c1] | N-[(1S)-1-benzyl-2-hydroxyethyl]-3-(2-chlorophenyl)-1-(4-fluorophenyl)-1H-indazole-6-carboxamide | 500.2 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 111 | 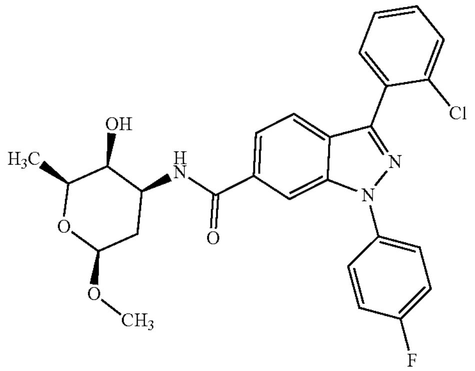 [SMILES: CO[C@@H]1C[C@H](NC(=O)c2ccc3c(-c4ccccc4Cl)nn(-c4ccc(F)cc4)c3c2)[C@H](O)[C@H](C)O1] | 3-(2-chlorophenyl)-1-(4-fluorophenyl)-N-((2S,3S,4S,6S)-3-hydroxy-6-methoxy-2-methyltetrahydro-2H-pyran-4-yl)-1H-indazole-6-carboxamide | 510.2 |
| 112 | 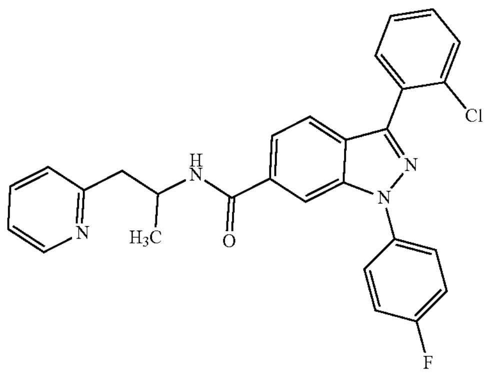 [SMILES: CC(Cc1ccccn1)NC(=O)c1ccc2c(-c3ccccc3Cl)nn(-c3ccc(F)cc3)c2c1] | 3-(2-chlorophenyl)-1-(4-fluorophenyl)-N-(1-methyl-2-pyridin-2-ylethyl)-1H-indazole-6-carboxamide (racemic) | 485.2 |
| 113 | 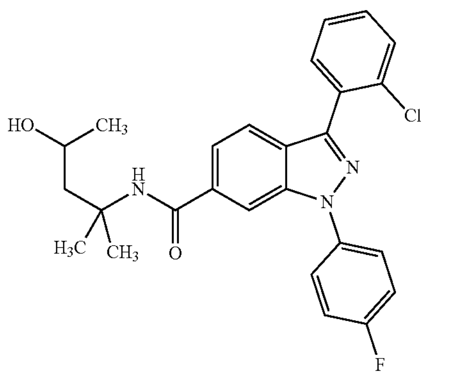 [SMILES: CC(O)CC(C)(C)NC(=O)c1ccc2c(-c3ccccc3Cl)nn(-c3ccc(F)cc3)c2c1] | 3-(2-chlorophenyl)-1-(4-fluorophenyl)-N-(3-hydroxy-1,1-dimethylbutyl)-1H-indazole-6-carboxamide (racemic) | 466.3 |
| 114 | 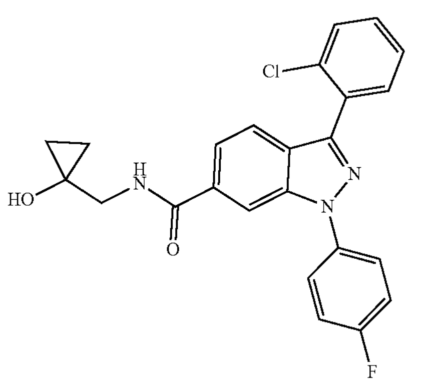 [SMILES: O=C(NCC1(O)CC1)c1ccc2c(-c3ccccc3Cl)nn(-c3ccc(F)cc3)c2c1] | 3-(2-chlorophenyl)-1-(4-fluorophenyl)-N-[(1-hydroxycyclopropyl)methyl]-1H-indazole-6-carboxamide | 436.2/438.2 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 115 | 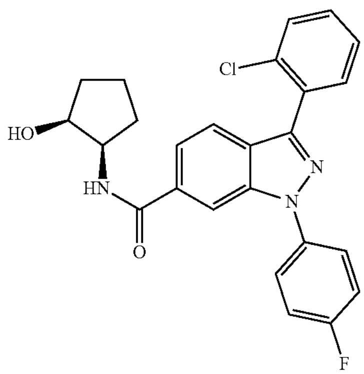 [SMILES: O=C(N[C@@H]1CCC[C@@H]1O)c1ccc2c(-c3ccccc3Cl)nn(-c3ccc(F)cc3)c2c1] | 3-(2-chlorophenyl)-1-(4-fluorophenyl)-N-[(1R,2S)-2-hydroxycyclopentyl]-1H-indazole-6-carboxamide | 450.1 |
| 116 | 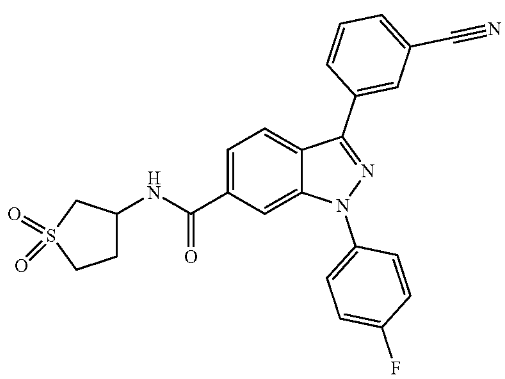 [SMILES: N#Cc1cccc(-c2nn(-c3ccc(F)cc3)c3cc(C(=O)NC4CCS(=O)(=O)C4)ccc23)c1] | 3-(3-cyanophenyl)-N-(1,1-dioxidotetrahydrothiophen-3-yl)-1-(4-fluorophenyl)-1H-indazole-6-carboxamide | 475.0 |
| 117 | 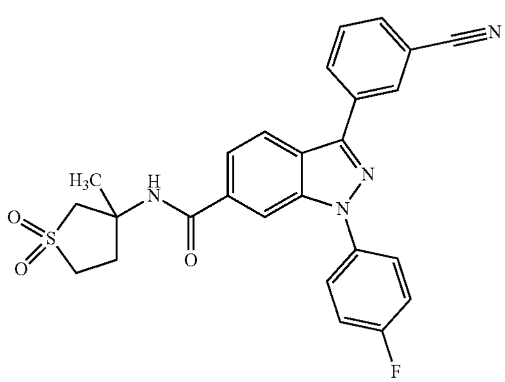 [SMILES: CC1(NC(=O)c2ccc3c(-c4cccc(C#N)c4)nn(-c4ccc(F)cc4)c3c2)CCS(=O)(=O)C1] | 3-(3-cyanophenyl)-1-(4-fluorophenyl)-N-(3-methyl-1,1-dioxidotetrahydrothiophen-3-yl)-1H-indazole-6-carboxamide | 489.0 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 118 | 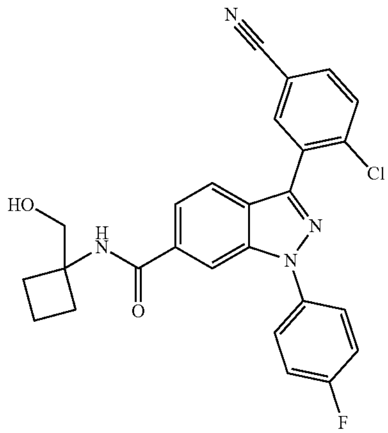 [SMILES: N#Cc1ccc(Cl)c(-c2nn(-c3ccc(F)cc3)c3cc(C(=O)NC4(CO)CCC4)ccc23)c1] | 3-(2-chloro-5-cyanophenyl)-1-(4-fluorophenyl)-N-[1-(hydroxymethyl)cyclobutyl]-1H-indazole-6-carboxamide | 475.1 |
| 119-A | 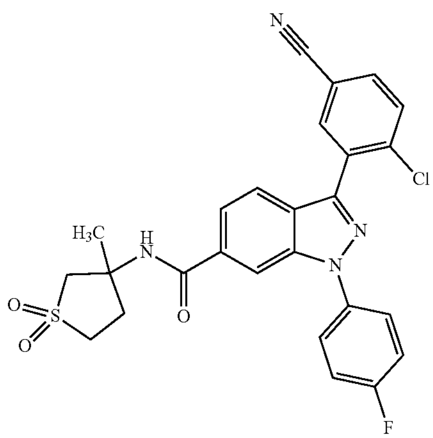 [SMILES: CC1(NC(=O)c2ccc3c(-c4cc(C#N)ccc4Cl)nn(-c4ccc(F)cc4)c3c2)CCS(=O)(=O)C1] | 3-(2-chloro-5-cyanophenyl)-1-(4-fluorophenyl)-N-(3-methyl-1,1-dioxidotetrahydrothiophen-3-yl)-1H-indazole-6-carboxamide (enantiomer A) | 523.0 |
| 120-A | 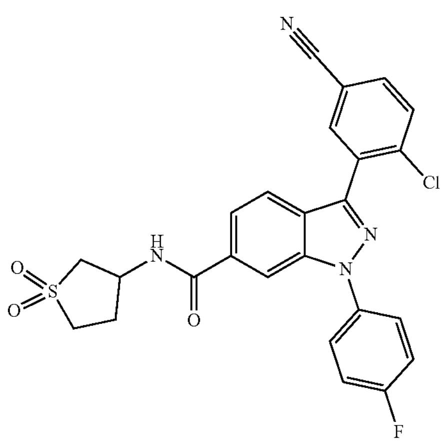 [SMILES: N#Cc1ccc(Cl)c(-c2nn(-c3ccc(F)cc3)c3cc(C(=O)NC4CCS(=O)(=O)C4)ccc23)c1] | 3-(2-chloro-5-cyanophenyl)-N-(1,1-dioxidotetrahydrothiophen-3-yl)-1-(4-fluorophenyl)-1H-indazole-6-carboxamide (enantiomer A) | 508.9 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 121-A | 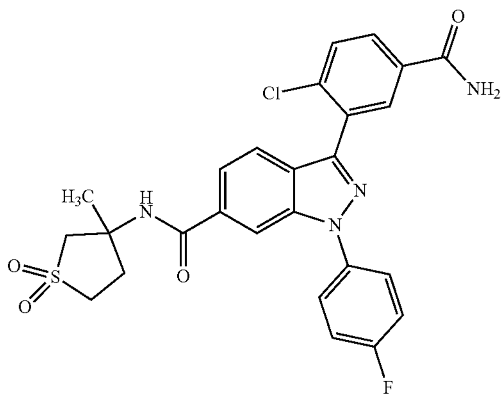 [SMILES: CC1(NC(=O)c2ccc3c(-c4cc(C(N)=O)ccc4Cl)nn(-c4ccc(F)cc4)c3c2)CCS(=O)(=O)C1] | 3-(5-carbamoyl-2-chlorophenyl)-1-(4-fluorophenyl)-N-(3-methyl-1,1-dioxidotetrahydrothiophen-3-yl)-1H-indazole-6-carboxamide (enantiomer A) | 541.0 |
| 119-B | 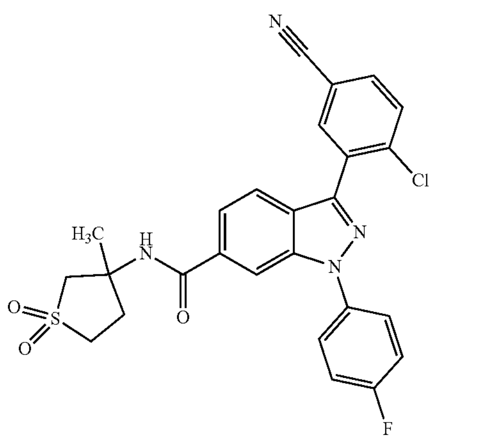 [SMILES: CC1(NC(=O)c2ccc3c(-c4cc(C#N)ccc4Cl)nn(-c4ccc(F)cc4)c3c2)CCS(=O)(=O)C1] | 3-(2-chloro-5-cyanophenyl)-1-(4-fluorophenyl)-N-(3-methyl-1,1-dioxidotetrahydrothiophen-3-yl)-1H-indazole-6-carboxamide (enantiomer B) | 523.0 |
| 121-B | 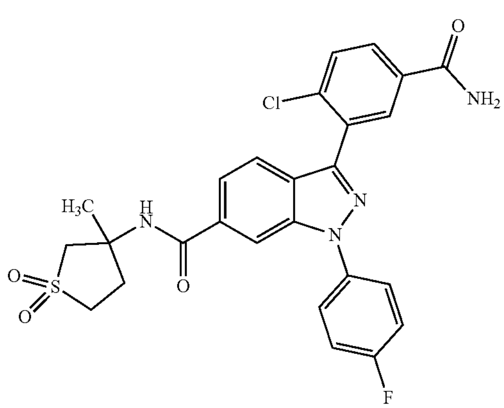 [SMILES: CC1(NC(=O)c2ccc3c(-c4cc(C(N)=O)ccc4Cl)nn(-c4ccc(F)cc4)c3c2)CCS(=O)(=O)C1] | 3-(5-carbamoyl-2-chlorophenyl)-1-(4-fluorophenyl)-N-(3-methyl-1,1-dioxidotetrahydrothiophen-3-yl)-1H-indazole-6-carboxamide (enantiomer B) | 541.1 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 122-A | 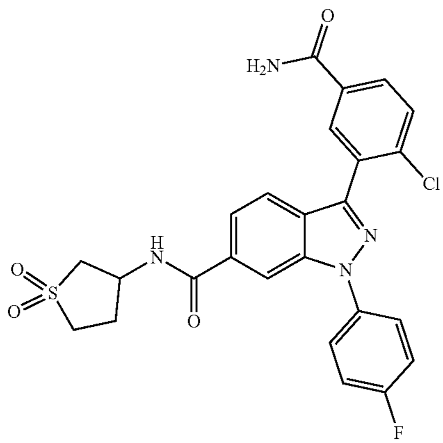 [SMILES: NC(=O)c1ccc(Cl)c(-c2nn(-c3ccc(F)cc3)c3cc(C(=O)NC4CCS(=O)(=O)C4)ccc23)c1] | 3-(5-carbamoyl-2-chlorophenyl)-N-(1,1-dioxidotetrahydrothiophen-3-yl)-1-(4-fluorophenyl)-1H-indazole-6-carboxamide (enantiomer A) | 527.1 |
| 123 | 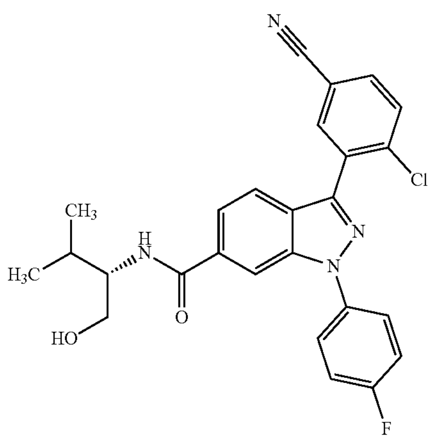 [SMILES: CC(C)[C@@H](CO)NC(=O)c1ccc2c(-c3cc(C#N)ccc3Cl)nn(-c3ccc(F)cc3)c2c1] | 3-(2-chloro-5-cyanophenyl)-1-(4-fluorophenyl)-N-[(1S)-1-(hydroxymethyl)-2-methylpropyl]-1H-indazole-6-carboxamide | 477.1 |
| 117-B | 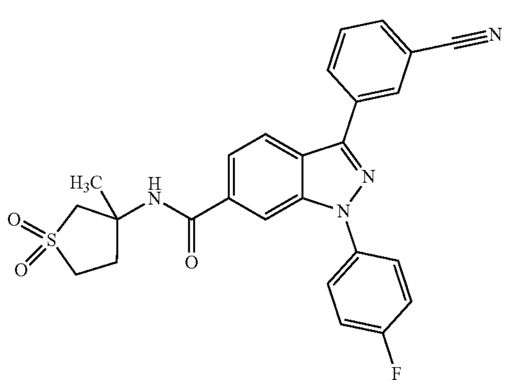 [SMILES: CC1(NC(=O)c2ccc3c(-c4cccc(C#N)c4)nn(-c4ccc(F)cc4)c3c2)CCS(=O)(=O)C1] | 3-(3-cyanophenyl)-1-(4-fluorophenyl)-N-(3-methyl-1,1-dioxidotetrahydrothiophen-3-yl)-1H-indazole-6-carboxamide (enantiomer B) | 489.0 |

TABLE 1-continued

Examples 1-B through 128-A in the following table were prepared from
appropriate acid and amine starting materials described previously or commercially available
starting materials using procedures described for the synthesis of Examples 1-A and 2-A.

| Ex # | Structure | Chemical Name | m/z[M + H]+ |
|---|---|---|---|
| 124 | 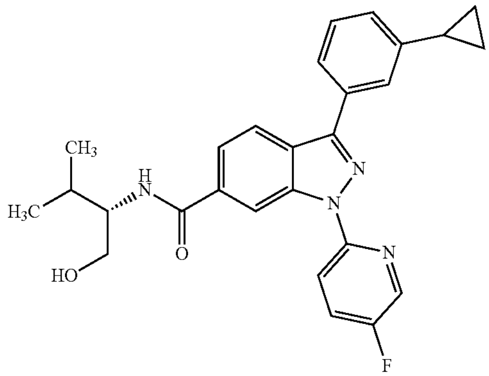 [SMILES: CC(C)[C@@H](CO)NC(=O)c1ccc2c(-c3cccc(C4CC4)c3)nn(-c3ccc(F)cn3)c2c1] | 3-(3-cyclopropylphenyl)-1-(5-fluoropyridin-2-yl)-N-[(1S)-1-(hydroxymethyl)-2-methylpropyl]-1H-indazole-6-carboxamide | 459.2 |
| 125-A | 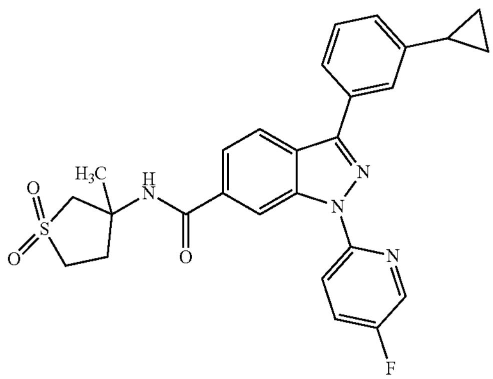 [SMILES: CC1(NC(=O)c2ccc3c(-c4cccc(C5CC5)c4)nn(-c4ccc(F)cn4)c3c2)CCS(=O)(=O)C1] | 3-(3-cyclopropylphenyl)-1-(5-fluoropyridin-2-yl)-N-(3-methyl-1,1-dioxidotetrahydrothiophen-3-yl)-1H-indazole-6-carboxamide (enantiomer A) | 505.1 |
| 125-B | 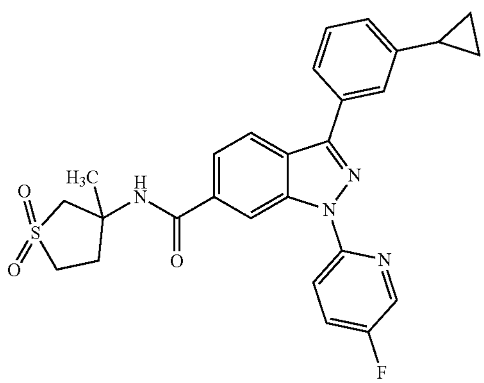 [SMILES: CC1(NC(=O)c2ccc3c(-c4cccc(C5CC5)c4)nn(-c4ccc(F)cn4)c3c2)CCS(=O)(=O)C1] | 3-(3-cyclopropylphenyl)-1-(5-fluoropyridin-2-yl)-N-(3-methyl-1,1-dioxidotetrahydrothiophen-3-yl)-1H-indazole-6-carboxamide (enantiomer B) | 505.1 |
| 126-A | 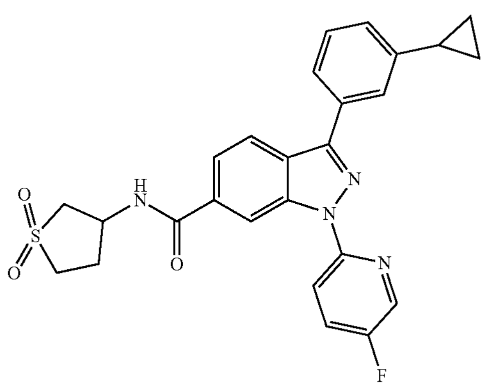 [SMILES: O=C(NC1CCS(=O)(=O)C1)c1ccc2c(-c3cccc(C4CC4)c3)nn(-c3ccc(F)cn3)c2c1] | 3-(3-cyclopropylphenyl)-N-(1,1-dioxidotetrahydrothiophen-3-yl)-1-(5-fluoropyridin-2-yl)-1H-indazole-6-carboxamide (enantiomer A) | 491.1 |

TABLE 1-continued

Examples 1-B through 128-A in the following table were prepared from appropriate acid and amine starting materials described previously or commercially available starting materials using procedures described for the synthesis of Examples 1-A and 2-A.

| Ex # | Structure | Chemical Name | m/z[M + H]+ |
|---|---|---|---|
| 127-A | 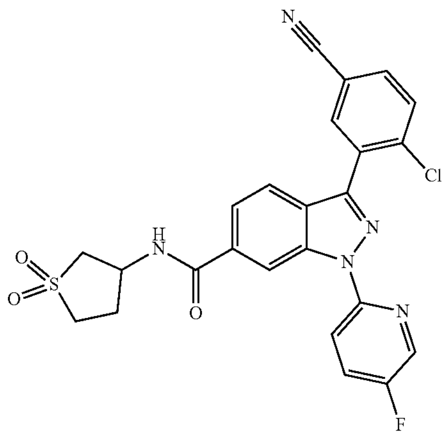 [SMILES: N#Cc1ccc(Cl)c(-c2nn(-c3ccc(F)cn3)c3cc(C(=O)NC4CCS(=O)(=O)C4)ccc23)c1] | 3-(2-chloro-5-cyanophenyl)-N-(1,1-dioxidotetrahydrothiophen-3-yl)-1-(5-fluoropyridin-2-yl)-1H-indazole-6-carboxamide (enantiomer A) | 510.0 |
| 128-A | 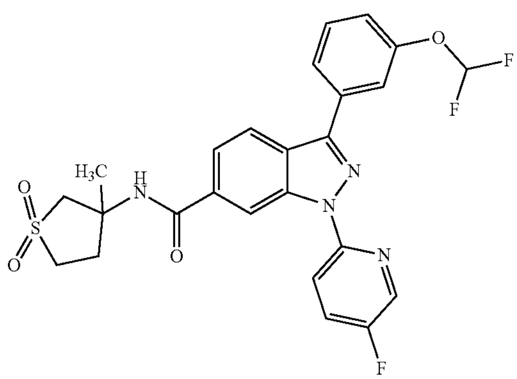 [SMILES: CC1(NC(=O)c2ccc3c(-c4cccc(OC(F)F)c4)nn(-c4ccc(F)cn4)c3c2)CCS(=O)(=O)C1] | 3-[3-(difluoromethoxy)phenyl]-1-(5-fluoropyridin-2-yl)-N-(3-methyl-1,1-dioxidotetrahydrothiophen-3-yl)-1H-indazole-6-carboxamide (enantiomer A) | 531.1 |

Example 129-A 3-(3-Cyanophenyl)-N-1,1-dioxidotetrahydrothiophen-3-yl)-1-(4-fluorophenyl)-1H-indazole-6-carboxamide (Enantiomer A)

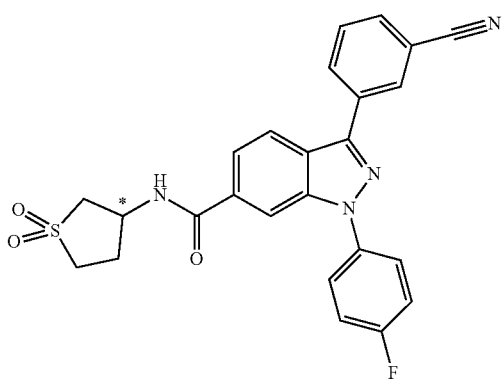 [SMILES: N#Cc1cccc(-c2nn(-c3ccc(F)cc3)c3cc(C(=O)NC4CCS(=O)(=O)C4)ccc23)c1]

A mixture of Int-4-A (20 mg, 0.044 mmol), 3-cyanophenylboronic acid (19.49 mg, 0.133 mmol) and sodium bicarbonate (11.14 mg, 0.133 mmol) in DME (1.0 ml) and water (0.500 ml) was treated with tetrakis(triphenylphosphine) palladium (12.77 mg, 0.011 mmol) and sub-surface sparged with nitrogen for 2 min. The reaction mixture was stirred at heated at 100° C. under a nitrogen atmosphere for 12 h, cooled to rt, and filtered. The filtrate was directly purified by RP-HPLC (ACN/water with 0.05% TFA) followed by preparative-TLC (60% EtOAc/hexanes) to afford the title compound. m/z=475.0 [M+H]+. $^1$H NMR (500 MHz, CDCl$_3$): δ 8.33 (s, 1H), 8.27 (d, J=7.9 Hz, 1H), 8.22 (s, 1H), 8.11 (d, J=8.6 Hz, 1H), 7.73-7.77 (m, 3H), 7.67 (t, J=7.8 Hz, 1H), 7.62 (d, J=8.5 Hz, 1H), 7.29-7.33 (m, 2H), 6.94 (m, 1H), 5.04-5.09 (m, 1H), 3.48 (dd, J=13.8, 7.2 Hz, 1H), 3.29-3.35 (m, 1H), 3.19-3.24 (m, 1H), 3.15-3.19 (m, 1H), 2.63-2.70 (m, 1H), 2.47-2.53 (m, 1H)

TABLE 2

Examples 130-A through 166-A in the following Table were prepared from the appropriate starting materials described previously or commercially starting materials available using procedures described in Example 129-A above. Example 166-A was prepared from mCPBA oxidation of Example 134-A

| Ex # | Structure | Chemical Name | M/Z [M + H]+ |
|---|---|---|---|
| 130-A | 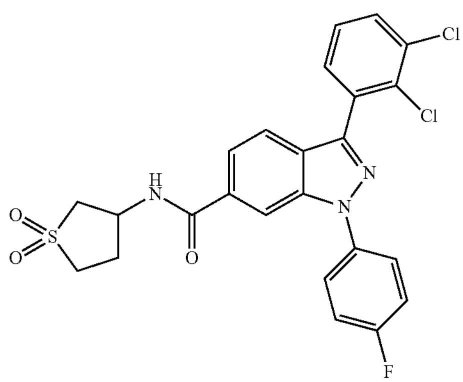 [SMILES: O=C(NC1CCS(=O)(=O)C1)c1ccc2c(-c3cccc(Cl)c3Cl)nn(-c3ccc(F)cc3)c2c1] | 3-(2,3-dichlorophenyl)-N-(1,1-dioxidotetrahydro-thiophen-3-yl)-1-(4-fluorophenyl)-1H-indazole-6-carboxamide (enantiomer A) | 517.8 |
| 131-A | 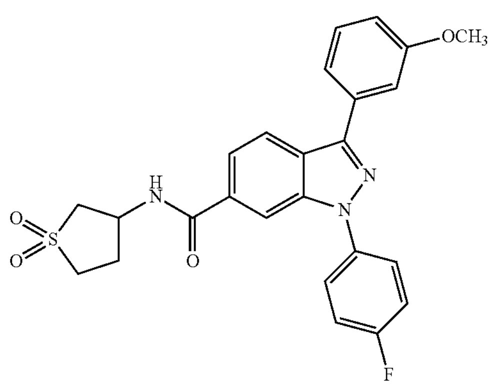 [SMILES: COc1cccc(-c2nn(-c3ccc(F)cc3)c3cc(C(=O)NC4CCS(=O)(=O)C4)ccc23)c1] | N-(1,1-dioxidotetrahydrothiophen-3-yl)-1-(4-fluorophenyl)-3-(3-methoxyphenyl)-1H-indazole-6-carboxamide (enantiomer A) | 480.0 |
| 132-A | 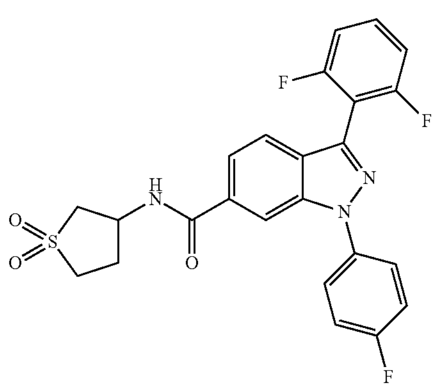 [SMILES: O=C(NC1CCS(=O)(=O)C1)c1ccc2c(-c3c(F)cccc3F)nn(-c3ccc(F)cc3)c2c1] | 3-(2,6-difluorophenyl)-N-(1,1-dioxidotetrahydro-thiophen-3-yl)-1-(4-fluorophenyl)-1H-indazole-6-carboxamide (enantiomer A) | 485.9 |

TABLE 2-continued

Examples 130-A through 166-A in the following Table were prepared from the appropriate starting materials described previously or commercially starting materials available using procedures described in Example 129-A above. Example 166-A was prepared from mCPBA oxidation of Example 134-A

| Ex # | Structure | Chemical Name | M/Z [M + H]⁺ |
|---|---|---|---|
| 133-A | 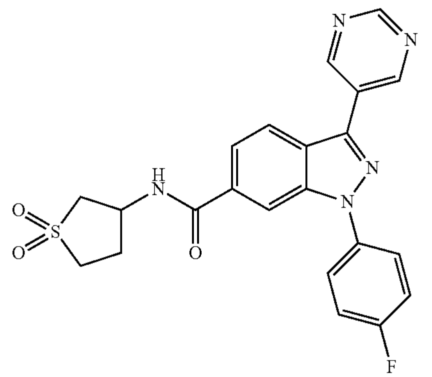 [SMILES: O=C(NC1CCS(=O)(=O)C1)c1ccc2c(-c3cncnc3)nn(-c3ccc(F)cc3)c2c1] | N-(1,1-dioxidotetrahydrothiophen-3-yl)-1-(4-fluorophenyl)-3-pyrimidin-5-yl-1H-indazole-6-carboxamide (enantiomer A) | 452.0 |
| 134-A | 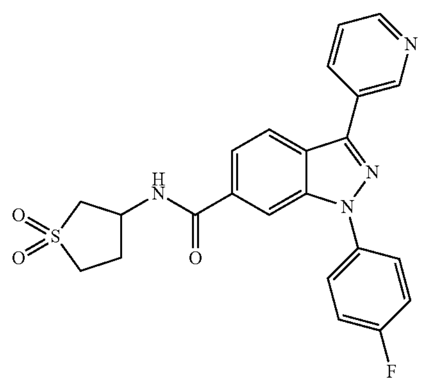 [SMILES: O=C(NC1CCS(=O)(=O)C1)c1ccc2c(-c3cccnc3)nn(-c3ccc(F)cc3)c2c1] | N-(1,1-dioxidotetrahydrothiophen-3-yl)-1-(4-fluorophenyl)-3-pyridin-3-yl-1H-indazole-6-carboxamide (enantiomer A) | 451.1 |
| 135-A | 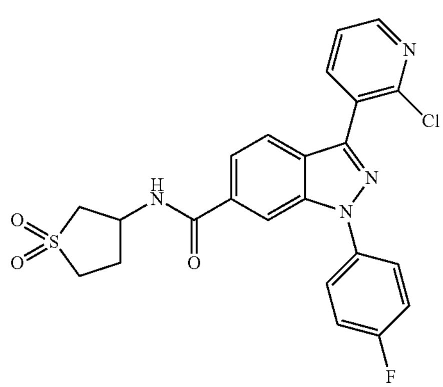 [SMILES: O=C(NC1CCS(=O)(=O)C1)c1ccc2c(-c3cccnc3Cl)nn(-c3ccc(F)cc3)c2c1] | 3-(2-chloropyridin-3-yl)-N-(1,1-dioxidotetrahydrothiophen-3-yl)-1-(4-fluorophenyl)-1H-indazole-6-carboxamide (enantiomer A) | 484.9 |

TABLE 2-continued

Examples 130-A through 166-A in the following Table were prepared from the appropriate starting materials described previously or commercially starting materials available using procedures described in Example 129-A above. Example 166-A was prepared from mCPBA oxidation of Example 134-A

| Ex # | Structure | Chemical Name | M/Z [M + H]+ |
|---|---|---|---|
| 136-A | 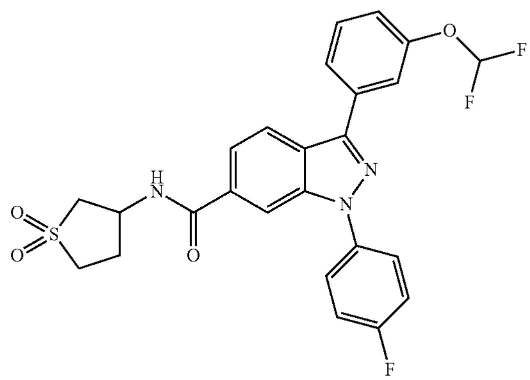 [SMILES: O=C(NC1CCS(=O)(=O)C1)c1ccc2c(-c3cccc(OC(F)F)c3)nn(-c3ccc(F)cc3)c2c1] | 3-[3-(difluoromethoxy)phenyl]-N-(1,1-dioxidotetrahydrothiophen-3-yl)-1-(4-fluorophenyl)-1H-indazole-6-carboxamide (enantiomer A) | 516.0 |
| 137-A | 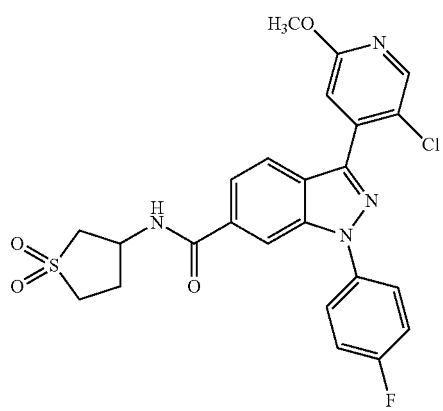 [SMILES: COc1cc(-c2nn(-c3ccc(F)cc3)c3cc(C(=O)NC4CCS(=O)(=O)C4)ccc23)c(Cl)cn1] | 3-(5-chloro-2-methoxypyridin-4-yl)-N-(1,1-dioxidotetrahydrothiophen-3-yl)-1-(4-fluorophenyl)-1H-indazole-6-carboxamide (enantiomer A) | 515.0 |
| 138-A | 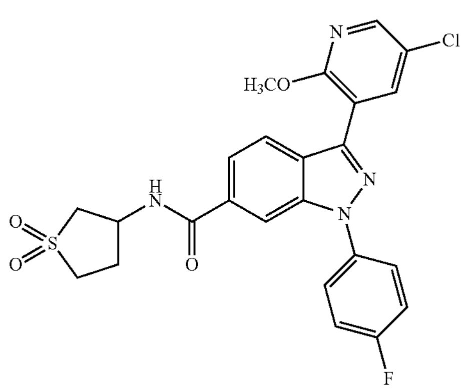 [SMILES: COc1ncc(Cl)cc1-c1nn(-c2ccc(F)cc2)c2cc(C(=O)NC3CCS(=O)(=O)C3)ccc12] | 3-(5-chloro-2-methoxypyridin-3-yl)-N-(1,1-dioxidotetrahydrothiophen-3-yl)-1-(4-fluorophenyl)-1H-indazole-6-carboxamide (enantiomer A) | 515.0 |

TABLE 2-continued

Examples 130-A through 166-A in the following Table were prepared from the appropriate starting materials described previously or commercially starting materials available using procedures described in Example 129-A above. Example 166-A was prepared from mCPBA oxidation of Example 134-A

| Ex # | Structure | Chemical Name | M/Z [M + H]⁺ |
|---|---|---|---|
| 139-A | 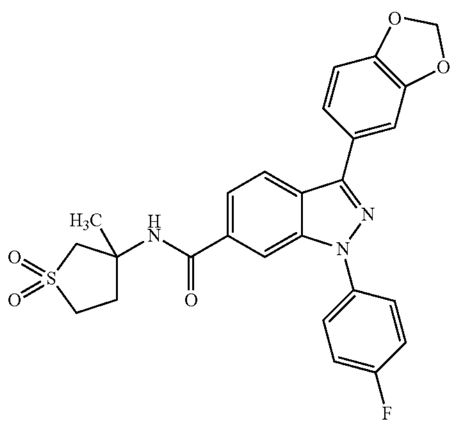 [SMILES: CC1(NC(=O)c2ccc3c(-c4ccc5c(c4)OCO5)nn(-c4ccc(F)cc4)c3c2)CCS(=O)(=O)C1] | 3-(1,3-benzodioxol-5-yl)-1-(4-fluorophenyl)-N-(3-methyl-1,1-dioxidotetrahydrothiophen-3-yl)-1H-indazole-6-carboxamide (enantiomer A) | 507.9 |
| 140-A | 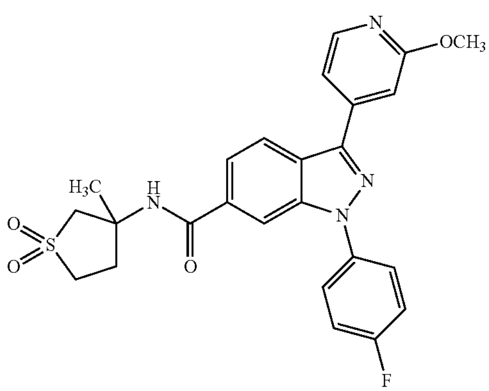 [SMILES: COc1cc(-c2nn(-c3ccc(F)cc3)c3cc(C(=O)NC4(C)CCS(=O)(=O)C4)ccc23)ccn1] | 1-(4-fluorophenyl)-3-(2-methoxypyridin-4-yl)-N-(3-methyl-1,1-dioxidotetrahydrothiophen-3-yl)-1H-indazole-6-carboxamide (enantiomer A) | 495.1 |
| 141-A | 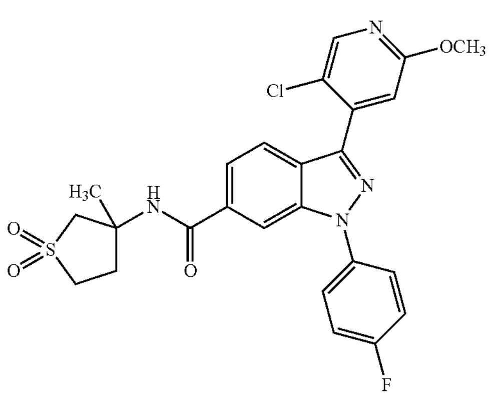 [SMILES: COc1cc(-c2nn(-c3ccc(F)cc3)c3cc(C(=O)NC4(C)CCS(=O)(=O)C4)ccc23)c(Cl)cn1] | 3-(5-chloro-2-methoxypyridin-4-yl)-1-(4-fluorophenyl)-N-(3-methyl-1,1-dioxidotetrahydrothiophen-3-yl)-1H-indazole-6-carboxamide (enantiomer A) | 529.0 |

TABLE 2-continued

*Examples 130-A through 166-A in the following Table were prepared from the appropriate starting materials described previously or commercially starting materials available using procedures described in Example 129-A above. Example 166-A was prepared from mCPBA oxidation of Example 134-A*

| Ex # | Structure | Chemical Name | M/Z [M + H]$^+$ |
|---|---|---|---|
| 142-A | 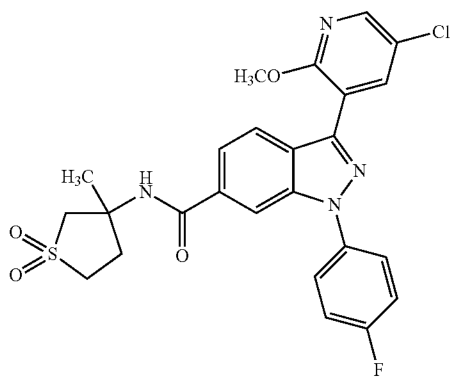 [SMILES: COc1ncc(Cl)cc1-c1nn(-c2ccc(F)cc2)c2cc(C(=O)NC3(C)CCS(=O)(=O)C3)ccc12] | 3-(5-chloro-2-methoxypyridin-3-yl)-1-(4-fluorophenyl)-N-(3-methyl-1,1-dioxidotetrahydrothiophen-3-yl)-1H-indazole-6-carboxamide (enantiomer A) | 529.0 |
| 143-A | 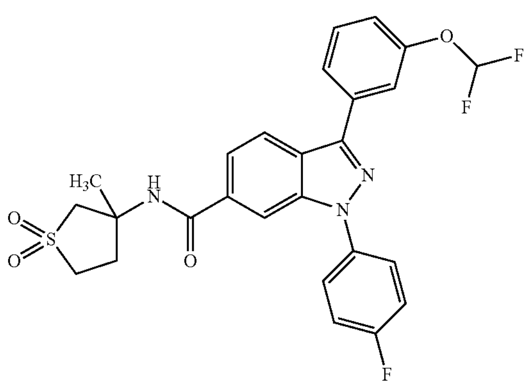 [SMILES: CC1(NC(=O)c2ccc3c(-c4cccc(OC(F)F)c4)nn(-c4ccc(F)cc4)c3c2)CCS(=O)(=O)C1] | 3-[3-(difluoromethoxy)phenyl]-1-(4-fluorophenyl)-N-(3-methyl-1,1-dioxidotetrahydrothiophen-3-yl)-1H-indazole-6-carboxamide (enantiomer A) | 530.1 |
| 144-A | 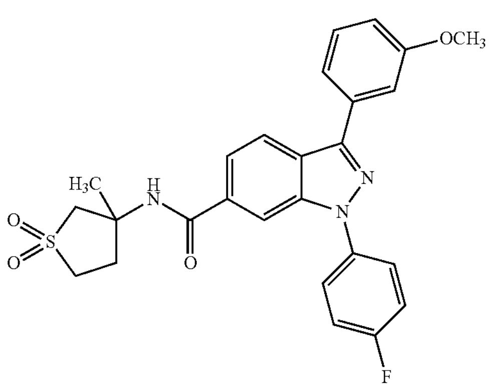 [SMILES: COc1cccc(-c2nn(-c3ccc(F)cc3)c3cc(C(=O)NC4(C)CCS(=O)(=O)C4)ccc23)c1] | 1-(4-fluorophenyl)-3-(3-methoxyphenyl)-N-(3-methyl-1,1-dioxidotetrahydrothiophen-3-yl)-1H-indazole-6-carboxamide (enantiomer A) | 494.1 |

TABLE 2-continued

Examples 130-A through 166-A in the following Table were prepared from the appropriate starting materials described previously or commercially starting materials available using procedures described in Example 129-A above. Example 166-A was prepared from mCPBA oxidation of Example 134-A

| Ex # | Structure | Chemical Name | M/Z [M + H]+ |
|---|---|---|---|
| 145-A | 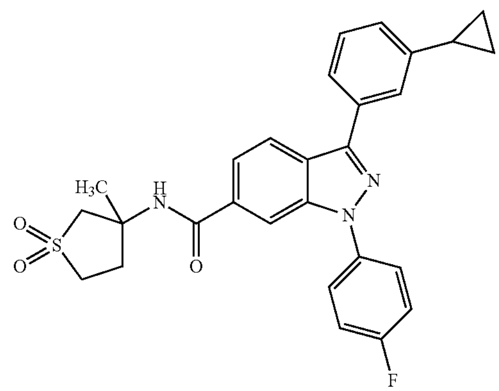 [SMILES: CC1(NC(=O)c2ccc3c(-c4cccc(C5CC5)c4)nn(-c4ccc(F)cc4)c3c2)CCS(=O)(=O)C1] | 3-(3-cyclopropylphenyl)-1-(4-fluorophenyl)-N-(3-methyl-1,1-dioxidotetrahydrothiophen-3-yl)-1H-indazole-6-carboxamide (enantiomer A) | 504.1 |
| 146-A | 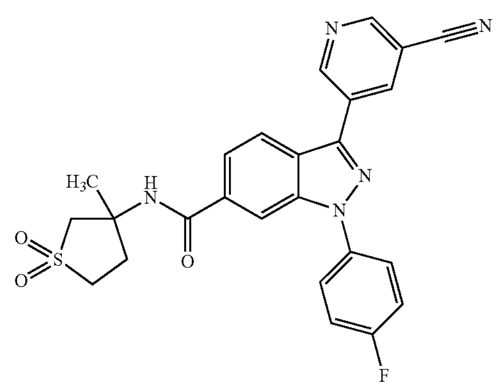 [SMILES: CC1(NC(=O)c2ccc3c(-c4cncc(C#N)c4)nn(-c4ccc(F)cc4)c3c2)CCS(=O)(=O)C1] | 3-(5-cyanopyridin-3-yl)-1-(4-fluorophenyl)-N-(3-methyl-1,1-dioxidotetrahydrothiophen-3-yl)-1H-indazole-6-carboxamide (enantiomer A) | 490.1 |
| 147-A | 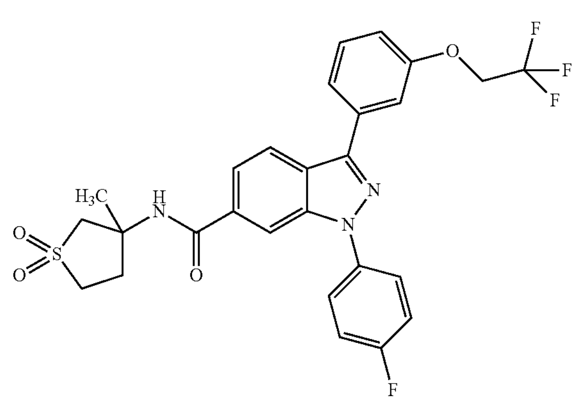 [SMILES: CC1(NC(=O)c2ccc3c(-c4cccc(OCC(F)(F)F)c4)nn(-c4ccc(F)cc4)c3c2)CCS(=O)(=O)C1] | 1-(4-fluorophenyl)-N-(3-methyl-1,1-dioxidotetrahydrothiophen-3-yl)-3-[3-(2,2,2-trifluoroethoxy)phenyl]-1H-indazole-6-carboxamide (enantiomer A) | 562.1 |

TABLE 2-continued

Examples 130-A through 166-A in the following Table were prepared from the appropriate starting materials described previously or commercially starting materials available using procedures described in Example 129-A above. Example 166-A was prepared from mCPBA oxidation of Example 134-A

| Ex # | Structure | Chemical Name | M/Z [M + H]+ |
|---|---|---|---|
| 148 | 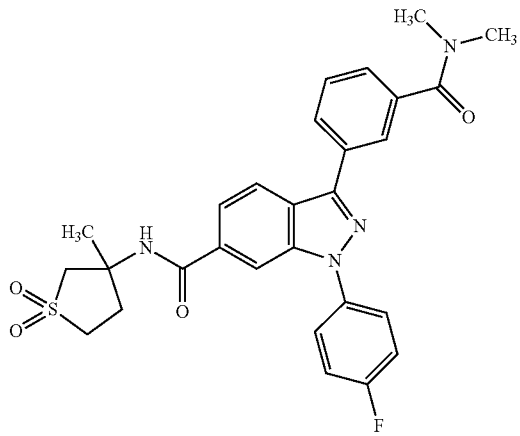 [SMILES: CN(C)C(=O)c1cccc(-c2nn(-c3ccc(F)cc3)c3cc(C(=O)NC4(C)CCS(=O)(=O)C4)ccc23)c1] | 3-[3-(dimethylcarbamoyl)phenyl]-1-(4-fluorophenyl)-N-(3-methyl-1,1-dioxidotetrahydrothiophen-3-yl)-1H-indazole-6-carboxamide (racemic) | 535.3 |
| 149 | 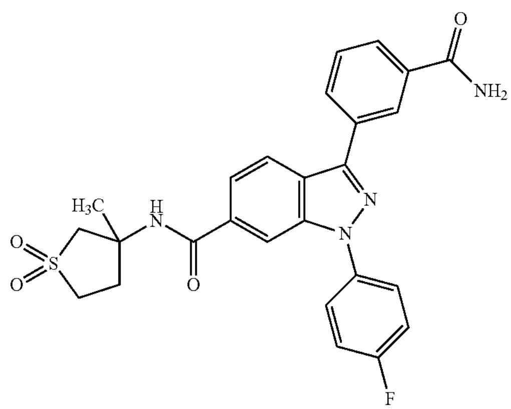 [SMILES: CC1(NC(=O)c2ccc3c(-c4cccc(C(N)=O)c4)nn(-c4ccc(F)cc4)c3c2)CCS(=O)(=O)C1] | 3-(3-carbamoylphenyl)-1-(4-fluorophenyl)-N-(3-methyl-1,1-dioxidotetrahydrothiophen-3-yl)-1H-indazole-6-carboxamide (racemic) | 507.2 |
| 150 | 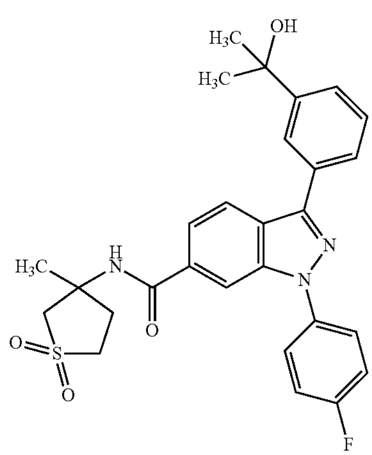 [SMILES: CC1(NC(=O)c2ccc3c(-c4cccc(C(C)(C)O)c4)nn(-c4ccc(F)cc4)c3c2)CCS(=O)(=O)C1] | 1-(4-fluorophenyl)-3-[3-(1-hydroxy-1-methylethyl)phenyl]-N-(3-methyl-1,1-dioxidotetrahydrothiophen-3-yl)-1H-indazole-6-carboxamide (racemic) | 522.3 |

TABLE 2-continued

Examples 130-A through 166-A in the following Table were prepared from the appropriate starting materials described previously or commercially starting materials available using procedures described in Example 129-A above. Example 166-A was prepared from mCPBA oxidation of Example 134-A

| Ex # | Structure | Chemical Name | M/Z [M + H]+ |
|---|---|---|---|
| 151-A | 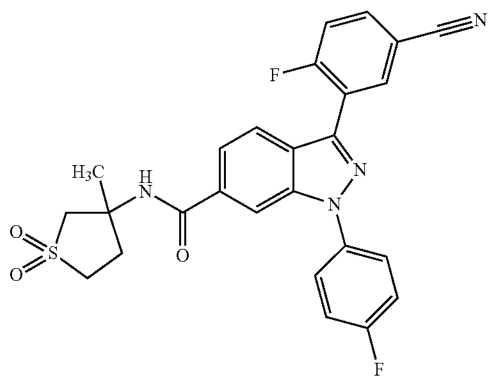 [SMILES: CC1(NC(=O)c2ccc3c(-c4cc(C#N)ccc4F)nn(-c4ccc(F)cc4)c3c2)CCS(=O)(=O)C1] | 3-(5-cyano-2-fluorophenyl)-1-(4-fluorophenyl)-N-(3-methyl-1,1-dioxidotetrahydrothiophen-3-yl)-1H-indazole-6-carboxamide (enantiomer A) | 507.1 |
| 152-A | 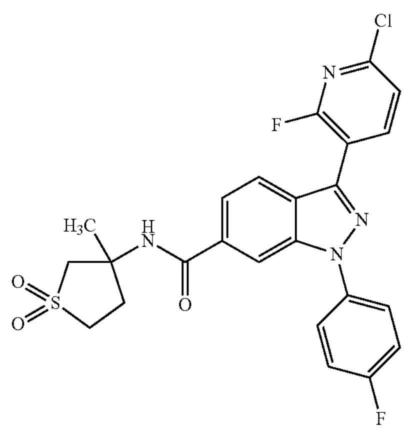 [SMILES: CC1(NC(=O)c2ccc3c(-c4ccc(Cl)nc4F)nn(-c4ccc(F)cc4)c3c2)CCS(=O)(=O)C1] | 3-(6-chloro-2-fluoropyridin-3-yl)-1-(4-fluorophenyl)-N-(3-methyl-1,1-dioxidotetrahydrothiophen-3-yl)-1H-indazole-6-carboxamide (enantiomer A) | 517.0 |
| 153-A | 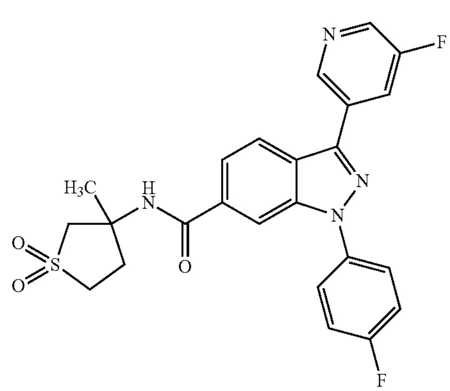 [SMILES: CC1(NC(=O)c2ccc3c(-c4cncc(F)c4)nn(-c4ccc(F)cc4)c3c2)CCS(=O)(=O)C1] | 1-(4-fluorophenyl)-3-(5-fluoropyridin-3-yl)-N-(3-methyl-1,1-dioxidotetrahydrothiophen-3-yl)-1H-indazole-6-carboxamide (enantiomer A) | 483.1 |

TABLE 2-continued

Examples 130-A through 166-A in the following Table were prepared from the appropriate starting materials described previously or commercially starting materials available using procedures described in Example 129-A above. Example 166-A was prepared from mCPBA oxidation of Example 134-A

| Ex # | Structure | Chemical Name | M/Z [M + H]+ |
|---|---|---|---|
| 154-A | 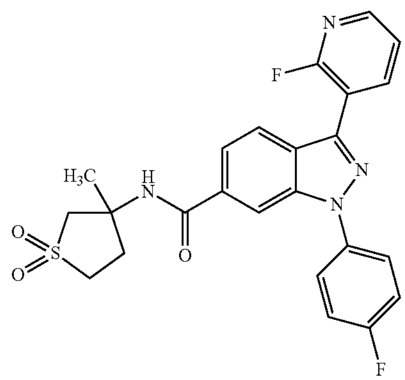 [SMILES: CC1(NC(=O)c2ccc3c(-c4cccnc4F)nn(-c4ccc(F)cc4)c3c2)CCS(=O)(=O)C1] | 1-(4-fluorophenyl)-3-(2-fluoropyridin-3-yl)-N-(3-methyl-1,1-dioxidotetrahydrothiophen-3-yl)-1H-indazole-6-carboxamide (enantiomer A) | 483.1 |
| 155-A | 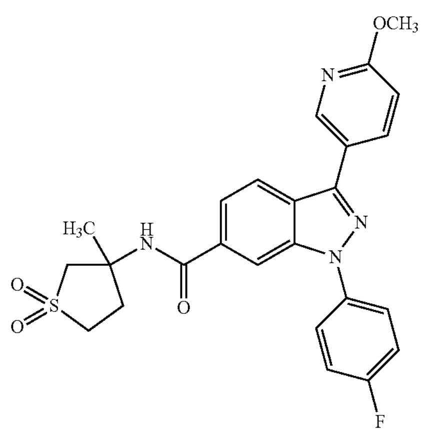 [SMILES: COc1ccc(-c2nn(-c3ccc(F)cc3)c3cc(C(=O)NC4(C)CCS(=O)(=O)C4)ccc23)cn1] | 1-(4-fluorophenyl)-3-(6-methoxypyridin-3-yl)-N-(3-methyl-1,1-dioxidotetrahydrothiophen-3-yl)-1H-indazole-6-carboxamide (enantiomer A) | 495.1 |
| 156-A | 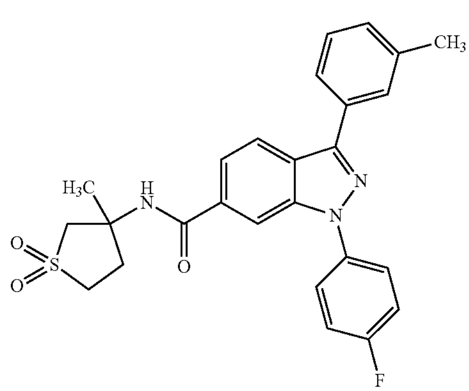 [SMILES: Cc1cccc(-c2nn(-c3ccc(F)cc3)c3cc(C(=O)NC4(C)CCS(=O)(=O)C4)ccc23)c1] | 1-(4-fluorophenyl)-N-(3-methyl-1,1-dioxidotetrahydrothiophen-3-yl)-3-(3-methylphenyl)-1H-indazole-6-carboxamide (enantiomer A) | 478.1 |

TABLE 2-continued

Examples 130-A through 166-A in the following Table were prepared from the appropriate starting materials described previously or commercially starting materials available using procedures described in Example 129-A above. Example 166-A was prepared from mCPBA oxidation of Example 134-A

| Ex # | Structure | Chemical Name | M/Z [M + H]+ |
|---|---|---|---|
| 157-A | 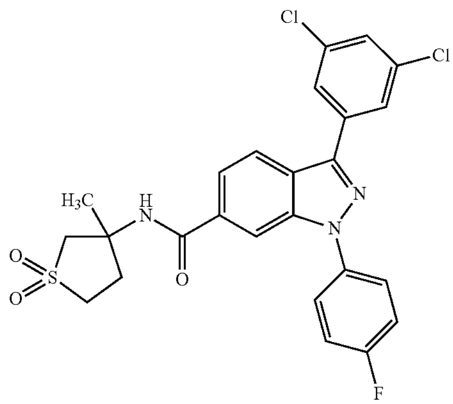 [SMILES: CC1(NC(=O)c2ccc3c(-c4cc(Cl)cc(Cl)c4)nn(-c4ccc(F)cc4)c3c2)CCS(=O)(=O)C1] | 3-(3,5-dichlorophenyl)-1-(4-fluorophenyl)-N-(3-methyl-1,1-dioxidotetrahydrothiophen-3-yl)-1H-indazole-6-carboxamide (enantiomer A) | 532.0 |
| 158-A | 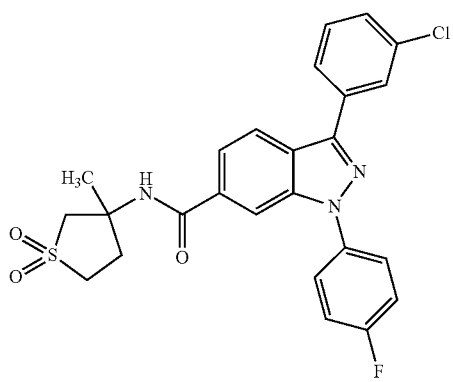 [SMILES: CC1(NC(=O)c2ccc3c(-c4cccc(Cl)c4)nn(-c4ccc(F)cc4)c3c2)CCS(=O)(=O)C1] | 3-(3-chlorophenyl)-1-(4-fluorophenyl)-N-(3-methyl-1,1-dioxidotetrahydrothiophen-3-yl)-1H-indazole-6-carboxamide (enantiomer A) | 498.1 |
| 159-A | 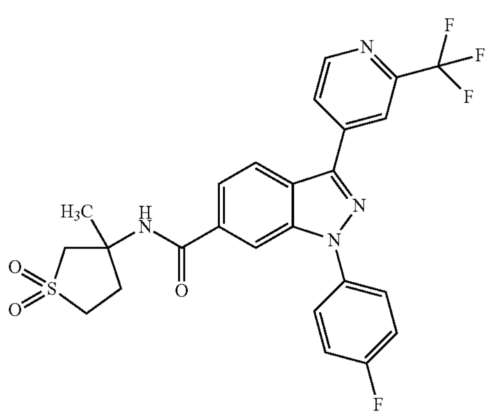 [SMILES: CC1(NC(=O)c2ccc3c(-c4ccnc(C(F)(F)F)c4)nn(-c4ccc(F)cc4)c3c2)CCS(=O)(=O)C1] | 1-(4-fluorophenyl)-N-(3-methyl-1,1-dioxidotetrahydrothiophen-3-yl)-3-[2-(trifluoromethyl)pyridin-4-yl]-1H-indazole-6-carboxamide (enantiomer A) | 533.1 |

TABLE 2-continued

Examples 130-A through 166-A in the following Table were prepared from the appropriate starting materials described previously or commercially starting materials available using procedures described in Example 129-A above. Example 166-A was prepared from mCPBA oxidation of Example 134-A

| Ex # | Structure | Chemical Name | M/Z [M + H]+ |
|---|---|---|---|
| 160-A | 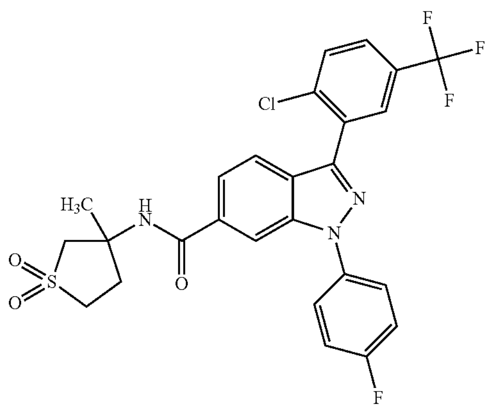 [SMILES: CC1(NC(=O)c2ccc3c(-c4cc(C(F)(F)F)ccc4Cl)nn(-c4ccc(F)cc4)c3c2)CCS(=O)(=O)C1] | 3-[2-chloro-5-(trifluoromethyl)phenyl]-1-(4-fluorophenyl)-N-(3-methyl-1,1-dioxidotetrahydrothiophen-3-yl)-1H-indazole-6-carboxamide (enantiomer A) | 566.1 |
| 161-B | 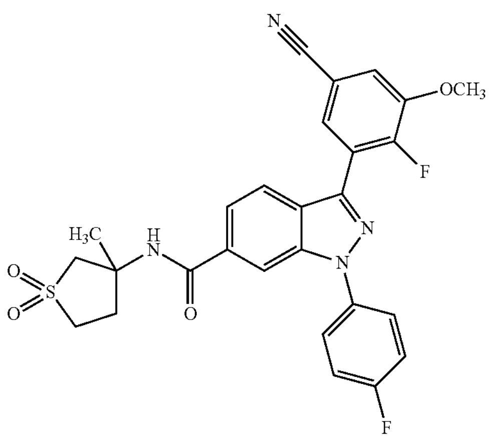 [SMILES: COc1cc(C#N)cc(-c2nn(-c3ccc(F)cc3)c3cc(C(=O)NC4(C)CCS(=O)(=O)C4)ccc23)c1F] | 3-(5-cyano-2-fluoro-3-methoxyphenyl)-1-(4-fluorophenyl)-N-(3-methyl-1,1-dioxidotetrahydrothiophen-3-yl)-1H-indazole-6-carboxamide (enantiomer B) | 537.1 |
| 162-A | 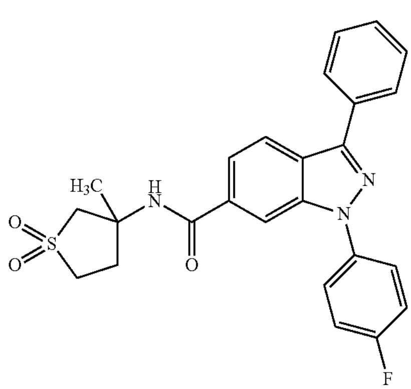 [SMILES: CC1(NC(=O)c2ccc3c(-c4ccccc4)nn(-c4ccc(F)cc4)c3c2)CCS(=O)(=O)C1] | 1-(4-fluorophenyl)-N-(3-methyl-1,1-dioxidotetrahydrothiophen-3-yl)-3-phenyl-1H-indazole-6-carboxamide (enantiomer A) | 464.1 |

TABLE 2-continued

Examples 130-A through 166-A in the following Table were prepared from the appropriate starting materials described previously or commercially starting materials available using procedures described in Example 129-A above. Example 166-A was prepared from mCPBA oxidation of Example 134-A

| Ex # | Structure | Chemical Name | M/Z [M + H]+ |
|---|---|---|---|
| 163 | 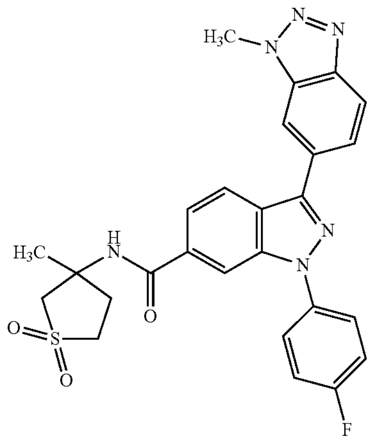 [SMILES: Cn1nnc2ccc(-c3nn(-c4ccc(F)cc4)c4cc(C(=O)NC5(C)CCS(=O)(=O)C5)ccc34)cc21] | 1-(4-fluorophenyl)-3-(1-methyl-1H-benzotriazol-6-yl)-N-(3-methyl-1,1-dioxidotetrahydrothiophen-3-yl)-1H-indazole-6-carboxamide (racemic) | 519.3 |
| 164 | 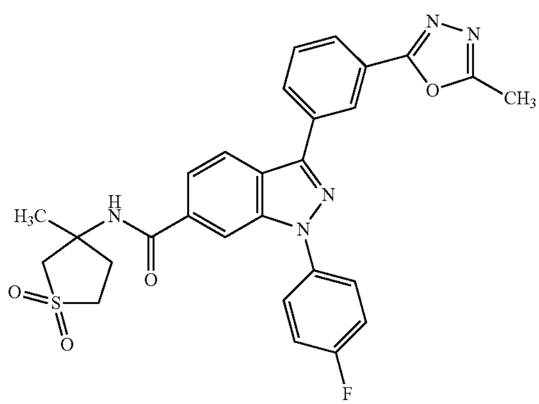 [SMILES: Cc1nnc(-c2cccc(-c3nn(-c4ccc(F)cc4)c4cc(C(=O)NC5(C)CCS(=O)(=O)C5)ccc34)c2)o1] | 1-(4-fluorophenyl)-N-(3-methyl-1,1-dioxidotetrahydrothiophen-3-yl)-3-[3-(5-methyl-1,3,4-oxadiazol-2-yl)phenyl]-1H-indazole-6-carboxamide (racemic) | 546.3 |
| 165 | 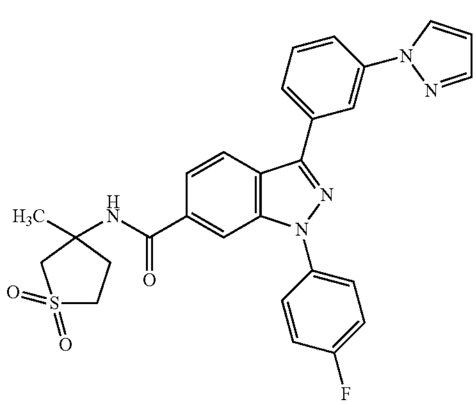 [SMILES: CC1(NC(=O)c2ccc3c(-c4cccc(-n5cccn5)c4)nn(-c4ccc(F)cc4)c3c2)CCS(=O)(=O)C1] | 1-(4-fluorophenyl)-N-(3-methyl-1,1-dioxidotetrahydrothiophen-3-yl)-3-[3-(1H-pyrazol-1-yl)phenyl]-1H-indazole-6-carboxamide (racemic) | 530.3 |

TABLE 2-continued

Examples 130-A through 166-A in the following Table were prepared from the appropriate starting materials described previously or commercially starting materials available using procedures described in Example 129-A above. Example 166-A was prepared from mCPBA oxidation of Example 134-A

| Ex # | Structure | Chemical Name | M/Z [M + H]+ |
|---|---|---|---|
| 166-A | 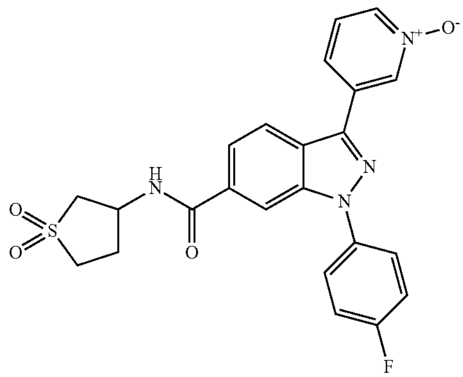 [SMILES: O=C(NC1CCS(=O)(=O)C1)c1ccc2c(-c3ccc[n+]([O-])c3)nn(-c3ccc(F)cc3)c2c1] | 3-(6-((1,1-dioxidotetrahydrothiophen-3-yl)carbamoyl)-1-(4-fluorophenyl)-1H-indazol-3-yl)pyridine 1-oxide (enantiomer A) | 467.0 |

Example 167

(±)-1-Benzyl-3-(2-chlorophenyl-N-(1,1-dioxidotetrahydrothiophen-3-yl)-1-indazole-6-carboxamide

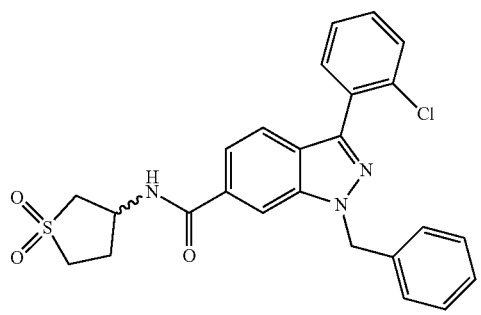 [SMILES: O=C(NC1CCS(=O)(=O)C1)c1ccc2c(-c3ccccc3Cl)nn(Cc3ccccc3)c2c1]

Int-5 (12.2 mg, 0.031 mmol), cesium carbonate (20.4 mg, 0.063 mmol) in DMF (0.5 ml) was treated at rt with benzyl bromide (4.5 µl, 0.038 mmol). The reaction mixture was stirred at rt for 16 h and then at 60° C. for 2 h. The reaction mixture was diluted with aq. DMSO, filtered and the filtrate was purified by RP-HPLC (ACN/water with 0.05% TFA) followed by purification on SiO$_2$ (50 to 100% EtOAc, hexanes) to afford the title compound. m/z=480.1/482.1 [M+H]+. $^1$H NMR (500 MHz, CDCl$_3$): δ 7.94 (s, 1H), 7.75 (d, J=8.5 Hz, 1H), 7.59-7.62 (m, 1H), 7.55-7.57 (m, 1H), 7.45 (d, J=8.5 Hz, 1H), 7.37-7.42 (m, 2H), 7.26-7.33 (m, 5H), 6.89 (s, 1H), 5.71 (s, 2H), 4.98-5.04 (m, 1H), 3.43-3.47 (m, 1H), 3.23-3.29 (m, 1H), 3.16-3.20 (m, 1H), 3.11 (dd, J=13.9, 4.3 Hz, 1H), 2.57-264 (m, 1H), 2.40-2.46 (m, 1H)

TABLE 3

Examples 168 through 170 in the following Table were prepared from the appropriate starting materials described previously or commercially available using procedures similar to those described in Example 167 above.

| Ex | Structure | Chemical Name | M/Z [M + H]+ |
|---|---|---|---|
| 168 | 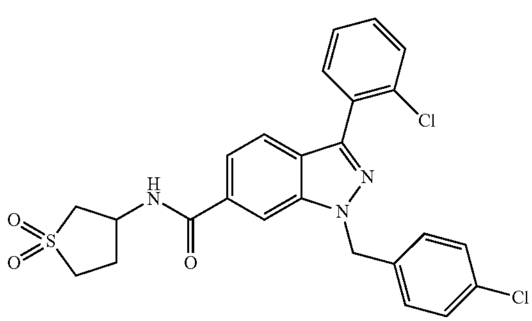 [SMILES: O=C(NC1CCS(=O)(=O)C1)c1ccc2c(-c3ccccc3Cl)nn(Cc3ccc(Cl)cc3)c2c1] | 1-(4-chlorobenzyl)-3-(2-chlorophenyl)-N-(1,1-dioxidotetrahydrothiophen-3-yl)-1H-indazole-6-carboxamide | 514.0 |

TABLE 3-continued

Examples 168 through 170 in the following Table were prepared from the
appropriate starting materials described previously or commercially available using
procedures similar to those described in Example 167 above.

| Ex | Structure | Chemical Name | M/Z [M + H]+ |
|---|---|---|---|
| 169 | 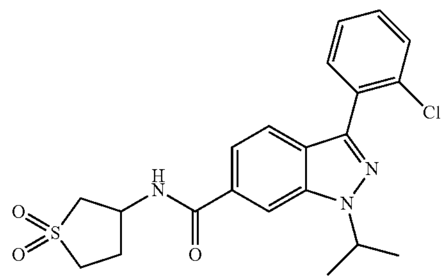 [SMILES: CC(C)n1nc(-c2ccccc2Cl)c2ccc(C(=O)NC3CCS(=O)(=O)C3)cc21] | 3-(2-chlorophenyl)-N-(1,1-dioxidotetrahydrothiophen-3-yl)-1-(1-methylethyl)-1H-indazole-6-carboxamide | 432.0 |
| 170 | 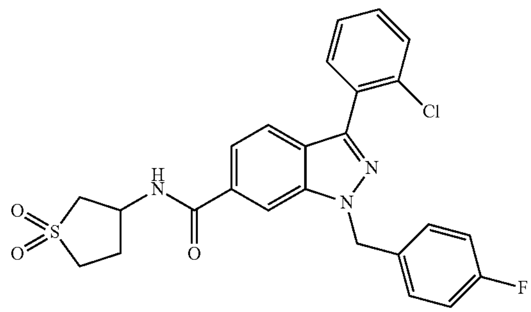 [SMILES: O=C(NC1CCS(=O)(=O)C1)c1ccc2c(-c3ccccc3Cl)nn(Cc3ccc(F)cc3)c2c1] | 3-(2-chlorophenyl)-N-(1,1-dioxidotetrahydrothiophen-3-yl)-1-(4-fluorobenzyl)-1H-indazole-6-carboxamide | 497.9 |

Example 171-A

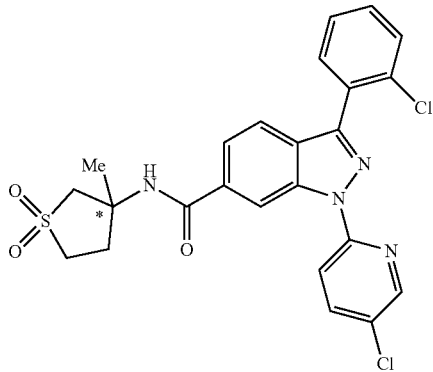 [SMILES: CC1(NC(=O)c2ccc3c(-c4ccccc4Cl)nn(-c4ccc(Cl)cn4)c3c2)CCS(=O)(=O)C1]

3-(2-Chlorophenyl)-1-(5-chloropyridin-2-yl)-N-(3-methyl-1,1-dioxidotetrahydrothiophen-3-yl)-1H-indazole-6-carboxamide (Enantiomer A)

A mixture of 3-(2-chlorophenyl)-1-(5-chloropyridin-2-yl)-1H-indazole-6-carboxylic acid (14.0 mg, 0.036 mmol), Int-2-A (10.2 mg, 0.1 mmol) in DMF (0.5 ml) was treated at rt with HBTU (27.6 mg, 0.1 mmol) and TEA (10 µl, 0.07 mmol). The mixture was stirred at rt for 2 h, and diluted with aq. AcOH and DMSO, and the reaction mixture was directly purified by RP-HPLC (ACN/water with 0.05% TFA) to afford the title compound. m/z=514.9/516.8 [M+H]+. $^1$H NMR (500 MHz, DMSO-d$_6$): δ 9.15 (s, 1H), 8.73 (d, J=2.5 Hz, 1H), 8.63 (s, 1H), 8.16 (dd, J=8.9, 2.6 Hz, 1H), 8.07 (d, J=8.9 Hz, 1H), 7.77 (s, 2H), 7.73-7.77 (m, 2H), 7.62 (td, J=7.7, 1.8 Hz, 1H), 7.57 (t, J=7.5 Hz, 1H), 4.01 (d, J=13.7 Hz, 1H), 3.30-3.42 (m, 2H), 3.23 (d, J=13.7 Hz, 1H), 2.79 (br s, 1H), 2.23 (ddd, J=13.8, 10.5, 8.1 Hz, 1H), 1.61 (s, 3H).

Example 172-A

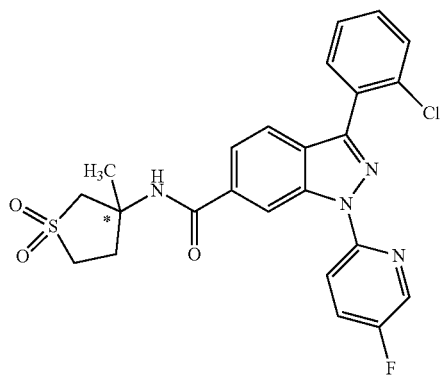 [SMILES: CC1(NC(=O)c2ccc3c(-c4ccccc4Cl)nn(-c4ccc(F)cn4)c3c2)CCS(=O)(=O)C1]

3-(2-chlorophenyl)-1-(5-fluoropyridin-2-yl-N-(3-methyl-1-dioxidotetrahydrothiophen-3-yl)-1H-indazole-6-carboxamide (Enantiomer A)

3-(2-Chlorophenyl)-1-(5-fluoropyridin-2-yl)-1H-indazole-6-carboxylic acid (40 mg, 0.11 mmol) and Int-2-A (20 mg, 0.11 mmol) in DMF (1.0 ml) at rt treated with HBTU (49.5 mg, 0.131 mmol) and TEA (0.033 ml, 0.239 mmol).

The mixture was stirred at rt for 16 h and diluted with aq. DMSO, and the reaction mixture was directly purified by RP-HPLC (ACN/water with 0.05% TFA) to afford the title compound. m/z=499.0/501.0 [M+H]$^+$; $^1$H NMR (500 MHz, DMSO-d): δ 9.12 (s, 1H), 8.68 (d, J=3.0 Hz, 1H), 8.62 (s, 1H), 8.09 (dd, J=9.1, 3.9 Hz, 1H), 8.00 (td, J=86, 2.9 Hz, 1H), 7.71-7.76 (m, 3H), 7.55-7.63 (m, 2H), 4.01 (d, J=13.7 Hz, 1H), 3.29-3.42 (m, 2H), 3.23 (d, J=13.7 Hz, 1H), 2.76-2.81 (m, 1H), 2.23 (ddd, J=13.8, 10.5, 8.1 Hz, 1H), 1.60 (s, 3H).

TABLE 4

Examples 172-B through 178-B in the following Table were prepared from the appropriate starting materials described previously or commercially available using procedures similar to those described in Examples 171-A and 172-A above.

| Ex | Structure | Chemical Name | M/Z [M + H]$^+$ |
|---|---|---|---|
| 172-B | 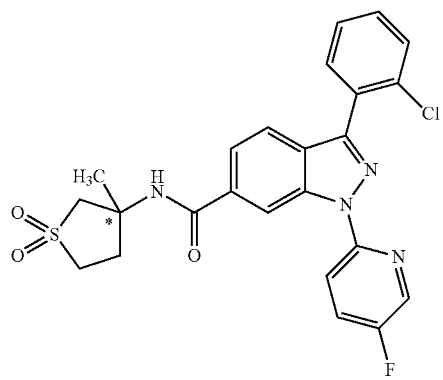 [SMILES: CC1(NC(=O)c2ccc3c(-c4ccccc4Cl)nn(-c4ccc(F)cn4)c3c2)CCS(=O)(=O)C1] | 3-(2-chlorophenyl)-1-(5-fluoropyridin-2-yl)-N-(3-methyl-1,1-dioxidotetrahydrothiophen-3-yl)-1H-indazole-6-carboxamide (enantiomer B) | 499.0 |
| 173-A | 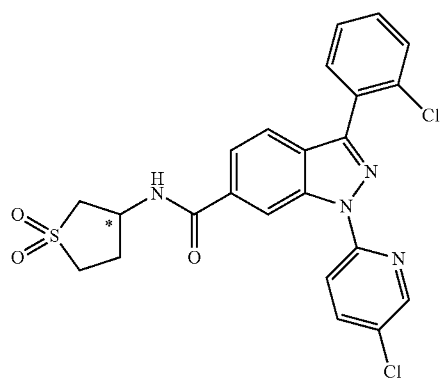 [SMILES: O=C(NC1CCS(=O)(=O)C1)c1ccc2c(-c3ccccc3Cl)nn(-c3ccc(Cl)cn3)c2c1] | 3-(2-chlorophenyl)-1-(5-chloropyridin-2-yl)-N-(1,1-dioxidotetrahydrothiophen-3-yl)-1H-indazole-6-carboxamide (enantiomer A) | 500.9 |
| 174-A | 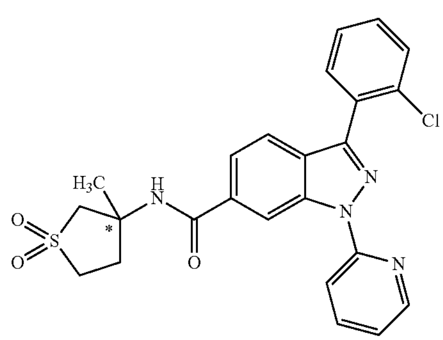 [SMILES: CC1(NC(=O)c2ccc3c(-c4ccccc4Cl)nn(-c4ccccn4)c3c2)CCS(=O)(=O)C1] | 3-(2-chlorophenyl)-N-(3-methyl-1,1-dioxidotetrahydrothiophen-3-yl)-1-pyridin-2-yl-1H-indazole-6-carboxamide (enantiomer A) | 481.0 |

TABLE 4-continued

Examples 172-B through 178-B in the following Table were prepared from the appropriate starting materials described previously or commercially available using procedures similar to those described in Examples 171-A and 172-A above.

| Ex | Structure | Chemical Name | M/Z [M + H]+ |
|---|---|---|---|
| 174-B | 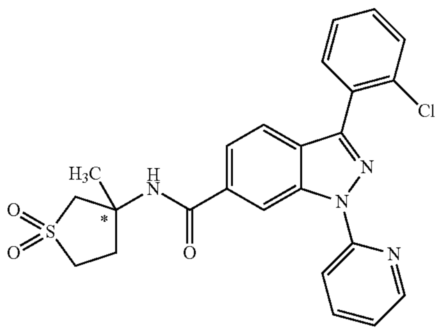 [SMILES: CC1(NC(=O)c2ccc3c(-c4ccccc4Cl)nn(-c4ccccn4)c3c2)CCS(=O)(=O)C1] | 3-(2-chlorophenyl)-N-(3-methyl-1,1-dioxidotetrahydrothiophen-3-yl)-1-pyridin-2-yl-1H-indazole-6-carboxamide (enantiomer B) | 481.0 |
| 175-A | 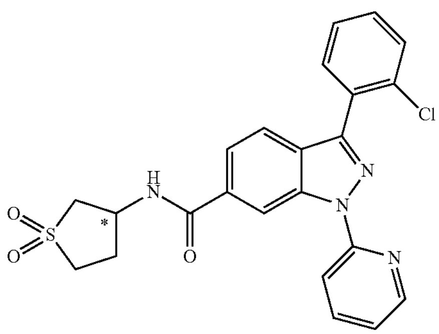 [SMILES: O=C(NC1CCS(=O)(=O)C1)c1ccc2c(-c3ccccc3Cl)nn(-c3ccccn3)c2c1] | 3-(2-chlorophenyl)-N-(1,1-dioxidotetrahydrothiophen-3-yl)-1-pyridin-2-yl-1H-indazole-6-carboxamide (enantiomer A) | 467.0 |
| 176-A | 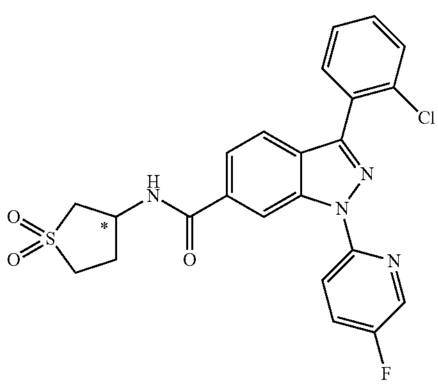 [SMILES: O=C(NC1CCS(=O)(=O)C1)c1ccc2c(-c3ccccc3Cl)nn(-c3ccc(F)cn3)c2c1] | 3-(2-chlorophenyl)-N-(1,1-dioxidotetrahydrothiophen-3-yl)-1-(5-fluoropyridin-2-yl)-1H-indazole-6-carboxamide (enantiomer A) | 485.0 |
| 177-A | 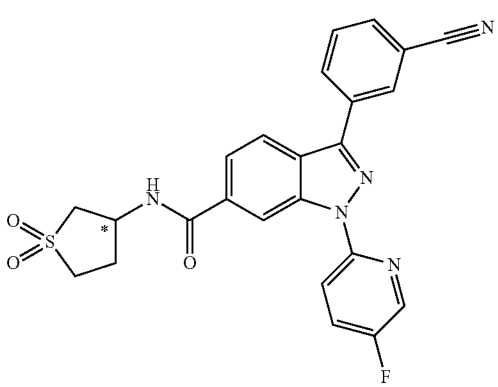 [SMILES: N#Cc1cccc(-c2nn(-c3ccc(F)cn3)c3cc(C(=O)NC4CCS(=O)(=O)C4)ccc23)c1] | 3-(3-cyanophenyl)-N-(1,1-dioxidotetrahydrothiophen-3-yl)-1-(5-fluoropyridin-2-yl)-1H-indazole-6-carboxamide (enantiomer A) | 476.0 |

TABLE 4-continued

Examples 172-B through 178-B in the following Table were prepared from the appropriate starting materials described previously or commercially available using procedures similar to those described in Examples 171-A and 172-A above.

| Ex | Structure | Chemical Name | M/Z [M + H]+ |
|---|---|---|---|
| 178-B | 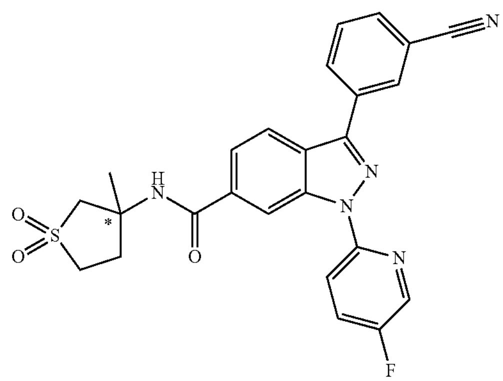 [SMILES: CC1(NC(=O)c2ccc3c(-c4cccc(C#N)c4)nn(-c4ccc(F)cn4)c3c2)CCS(=O)(=O)C1] | 3-(3-cyanophenyl)-1-(5-fluoropyridin-2-yl)-N-(3-methyl-1,1-dioxidotetrahydrothiophen-3-yl)-1H-indazole-6-carboxamide (enantiomer B) | 490.1 |

Example 179

3-(2-Chlorophenyl)-N-(3-methyl-1,1-dioxidotetrahydrothiophen-3-yl)-1-(thiazol-4-yl)-1H-indazole-6-carboxamide

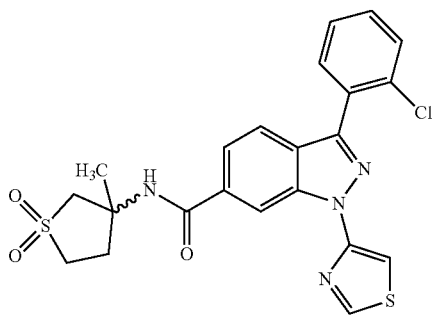 [SMILES: CC1(NC(=O)c2ccc3c(-c4ccccc4Cl)nn(-c4cscn4)c3c2)CCS(=O)(=O)C1]

A mixture of Int-22 (42.8 mg, 0.106 mmol), 4-bromothiazole (52.1 mg, 0.318 mmol), (+/−)-trans-1,2-diaminocyclohexane (12.10 mg, 0.106 mmol), copper (1) iodide (10.09 mg, 0.053 mmol) and TPP (67.5 mg, 0.318 mmol) in dioxane (2.0 ml) was sub-surface sparged with nitrogen for 2 min. The reaction mixture was heated at 100° C. under a nitrogen atmosphere for 12 h. The mixture was cooled to rt, diluted with aq. AcOH-1 and DMSO, and the reaction mixture was directly purified by RP-HPLC (15~100% ACN in water with 0.05% TFA) to afford the title compound. m/z=486.9/488.8 [M+H]+, $^1$H NMR (500 MHz, CDCl$_3$): δ 8.94 (d, J=2.3 Hz, 1H), 8.85-8.86 (min, 1H), 7.75 (d, J=8.4 Hz, 1H), 7.65 (d, J=7.3 Hz, 1H), 7.59 (d, J=8.4 Hz, 3H), 7.42-7.48 (m, 2H), 6.74 (b s, 1H), 3.75 (d, J=13.9 Hz, 1H), 3.46-3.52 (m, 1H), 3.26-3.31 (m, 1H), 3.16-3.20 (m, 1H), 3.10-3.15 (m, 1H), 2.25-2.31 (m, 1H), 1.80 (s, 3H).

TABLE 5

Examples 180 through 190 in the following Table were prepared from the appropriate starting materials described previously or commercially available using procedures similar to those described in Example 179 above.

| Ex # | Structure | Chemical Name | m/z [M + H]+ |
|---|---|---|---|
| 180 | 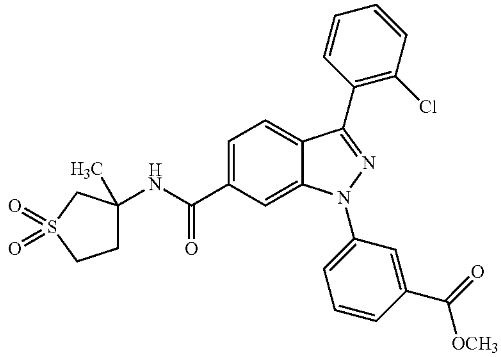 [SMILES: COC(=O)c1cccc(-n2nc(-c3ccccc3Cl)c3ccc(C(=O)NC4(C)CCS(=O)(=O)C4)cc32)c1] | methyl 3-{3-(2-chlorophenyl)-6-[(3-methyl-1,1-dioxidotetrahydrodioxidotetrahydrodioxidotetrahydrodioxidotetrahydro-thiophen-3-yl)carbamoyl]-1H-indazol-1-yl}benzoate (racemic) | 538.0 |

TABLE 5-continued

Examples 180 through 190 in the following Table were prepared from the
appropriate starting materials described previously or commercially available using
procedures similar to those described in Example 179 above.

| Ex # | Structure | Chemical Name | m/z [M + H]+ |
|---|---|---|---|
| 181 | 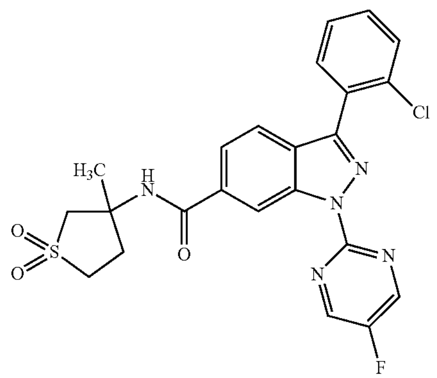 [SMILES: CC1(NC(=O)c2ccc3c(-c4ccccc4Cl)nn(-c4ncc(F)cn4)c3c2)CCS(=O)(=O)C1] | 3-(2-chlorophenyl)-1-(5-fluoropyrimidin-2-yl)-N-(3-methyl-1,1-dioxidotetradioxidotetradioxido-tetradioxidotetra-hydrothiophen-3-yl)-1H-indazole-6-carboxamide (racemic) | 500.0 |
| 182 | 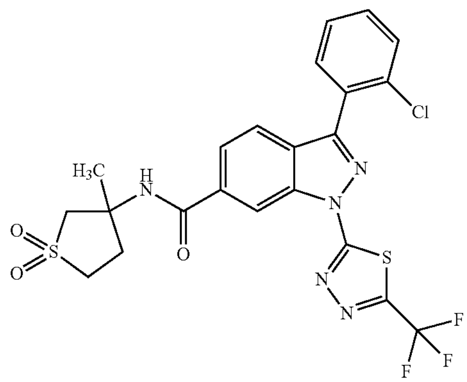 [SMILES: CC1(NC(=O)c2ccc3c(-c4ccccc4Cl)nn(-c4nnc(C(F)(F)F)s4)c3c2)CCS(=O)(=O)C1] | 3-(2-chlorophenyl)-N-(3-methyl-1,1-dioxidotetrahydrothiophen-3-yl)-1-[5-(trifluoromethyl)-1,3,4-thiadiazol-2-yl]-1H-indazole-6-carboxamide (racemic) | 556.2 |
| 183 | 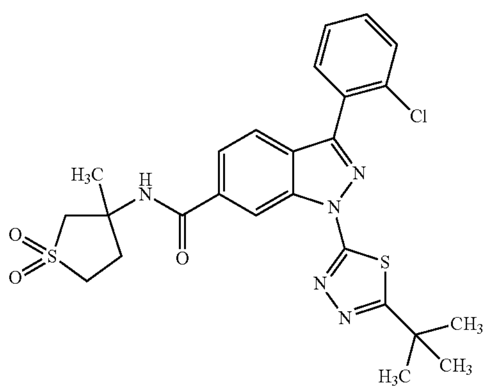 [SMILES: CC1(NC(=O)c2ccc3c(-c4ccccc4Cl)nn(-c4nnc(C(C)(C)C)s4)c3c2)CCS(=O)(=O)C1] | 1-(5-tert-butyl-1,3,4-thiadiazol-2-yl)-3-(2-chlorophenyl)-N-(3-methyl-1,1-dioxidotetrahydrothiophen-3-yl)-1H-indazole-6-carboxamide (racemic) | 544.3 |
| 184 | 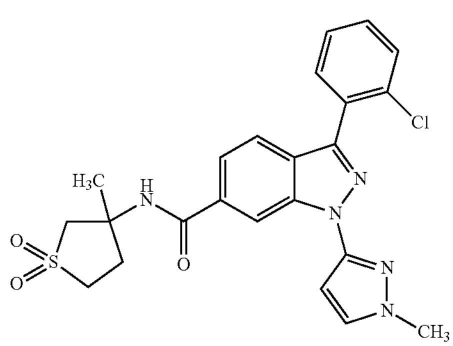 [SMILES: Cn1ccc(-n2nc(-c3ccccc3Cl)c3ccc(C(=O)NC4(C)CCS(=O)(=O)C4)cc32)n1] | 3-(2-chlorophenyl)-N-(3-methyl-1,1-dioxidotetrahydrothiophen-3-yl)-1-(1-methyl-1H-pyrazol-3-yl)-1H-indazole-6-carboxamide (racemic) | 484.2 |

TABLE 5-continued

Examples 180 through 190 in the following Table were prepared from the appropriate starting materials described previously or commercially available using procedures similar to those described in Example 179 above.

| Ex # | Structure | Chemical Name | m/z [M + H]+ |
| --- | --- | --- | --- |
| 185 | 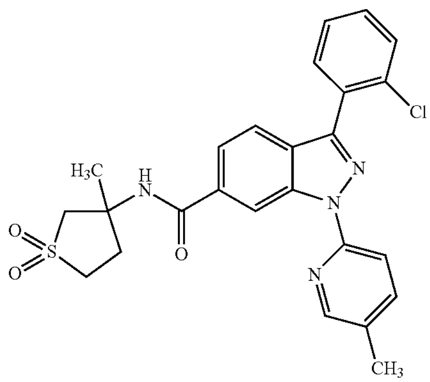 [SMILES: Cc1ccc(-n2nc(-c3ccccc3Cl)c3ccc(C(=O)NC4(C)CCS(=O)(=O)C4)cc32)nc1] | 3-(2-chloophenyl)-N-(3-methyl-1,1-dioxidotetrahydrothiophen-3-yl)-1-(5-methylpyridin-2-yl)-1H-indazole-6-carboxamide (racemic) | 495.1 |
| 186 | 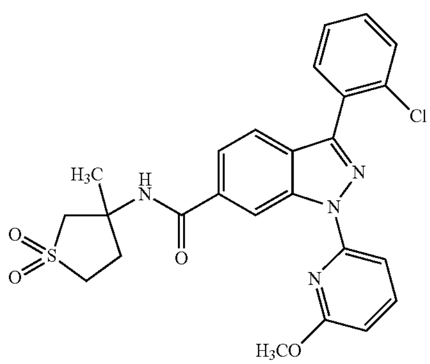 [SMILES: COc1cccc(-n2nc(-c3ccccc3Cl)c3ccc(C(=O)NC4(C)CCS(=O)(=O)C4)cc32)n1] | 3-(2-chlorophenyl)-1-(6-methoxypyridin-2-yl)-N-(3-methyl-1,1-dioxidotetrahydrothiophen-3-yl)-1H-indazole-6-carboxamide (racemic) | 511.1 |
| 187 | 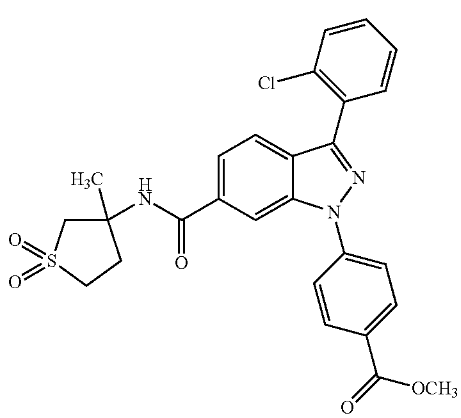 [SMILES: COC(=O)c1ccc(-n2nc(-c3ccccc3Cl)c3ccc(C(=O)NC4(C)CCS(=O)(=O)C4)cc32)cc1] | methyl 4-{3-(2-chlorophenyl)-6-[(3-methyl-1,1-dioxidotetrahydrothiophen-3-yl)carbamoyl]-1H-indazol-1-yl}benzoate (racemic) | 538.1 |

TABLE 5-continued

Examples 180 through 190 in the following Table were prepared from the appropriate starting materials described previously or commercially available using procedures similar to those described in Example 179 above.

| Ex # | Structure | Chemical Name | m/z [M + H]+ |
|---|---|---|---|
| 188 | 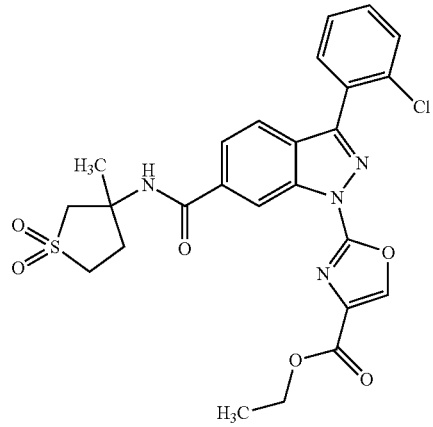 [SMILES: CCOC(=O)c1coc(-n2nc(-c3ccccc3Cl)c3ccc(C(=O)NC4(C)CCS(=O)(=O)C4)cc32)n1] | ethyl 2-{3-(2-chlorophenyl)-6-[(3-methyl-1,1-dioxidotetrahydrothiophen-3-yl)carbamoyl]-1H-indazol-1-yl}-1,3-oxazole-4-carboxylate (racemic) | 543.2 |
| 189 | 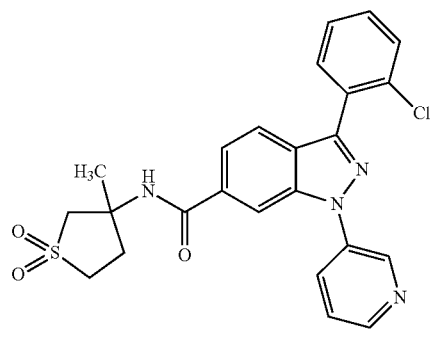 [SMILES: CC1(NC(=O)c2ccc3c(-c4ccccc4Cl)nn(-c4cccnc4)c3c2)CCS(=O)(=O)C1] | 3-(2-chlorophenyl)-N-(3-methyl-1,1-dioxidotetrahydrothiophen-3-yl)-1-pyridin-3-yl-1H-indazole-6-carboxamide (racemic) | 481.2 |
| 190 | 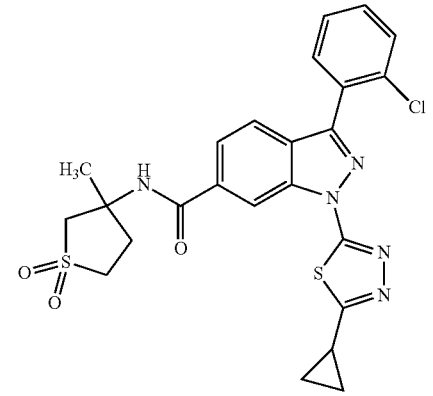 [SMILES: CC1(NC(=O)c2ccc3c(-c4ccccc4Cl)nn(-c4nnc(C5CC5)s4)c3c2)CCS(=O)(=O)C1] | 3-(2-chlorophenyl)-1-(5-cyclopropyl-1,3,4-thiadiazol-2-yl)-N-(3-methyl-1,1-dioxidotetrahydrothiophen-3-yl)-1H-indazole-6-carboxamide (racemic) | 528.2 |

Example 191

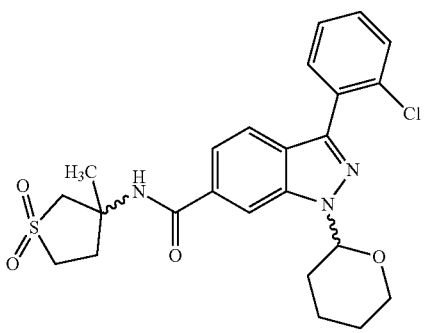 [SMILES: CC1(NC(=O)c2ccc3c(-c4ccccc4Cl)nn(C4CCCCO4)c3c2)CCS(=O)(=O)C1]

3-(2-Chlorophenyl)-N-(3-methyl-1,1-dioxidotetrahydrothiophen-3-yl)-1-(tetrahydro-2H-pyran-2-yl)-1H-indazole-6-carboxamide Int-22; 60 mg, 0.149 mmol) and p-TsOH (1.413 mg, 7.43 μmol) were dissolved in THF (2 mL) and treated with 3,4-dihydro-2H-pyran (0.136 ml, 1.486 mmol). The reaction mixture was heated at 80° C. for 3 h, cooled to rt and directly purified by preparative RP-HPLC (ACN/water) to afford the title compound as a mixture of diastereomers m/z=488.1 [M+H]$^+$.

Assays

Insect Cell Expression and Membrane Preparation

Sf-9 insect cells were maintained in Grace's insect cell culture medium with 10% heated-inactivated fetal bovine serum, 1% Pluronic F-68 and 0.14 μg/m Kanamycine sulfate in Erlenmeyer flasks at 28° C. in a shaker incubator. After infection with untagged hDGAT2 baculovirus at multiplicity of infection (MOI) 0.1 for 48 hours, cells were harvested. Cell pellets were suspended in buffer containing 10 mM Tris-HC (pH 7.5), 1 mM EDTA (pH 8.0), 250 mM sucrose and Complete Protease Inhibitor Cocktail (Roche Diagnostics Corp., Indianapolis, Ill.), and sonicated on ice. Membrane fractions were isolated by ultracentrifugation (100,000×g pellet), resuspended in the same buffer, and frozen (–80° C.) for later use. The protein concentration was determined with the BCA Protein Assay kit (Pierce Biotechnology Inc., Rockford, Ill.). Expression of protein levels was analyzed by immunoblotting with goat polyclonal DGAT2 antibody C-15 and donkey anti-goat IgG HRP (Santa Cruz Biotechnology, Inc., Santa Cruz, Calif.) followed by detection with ECL reagent (GE Healthcare, Piscataway, N.J.).

LC/MS/MS Analysis Method

LC/MS/MS analyses were performed using Thermal Fisher's LX4-TSQ Vantage system. This system consists of an Agilent binary high-performance liquid chromatography (HPLC) pumps and a TSQ Vantage triple quadrupole MS/MS instrument. For each sample, 2 μL samples from the top organic layer of in-plate liquid-liquid extraction were injected onto a Thermo Betabasic C4 column (2.1 mm×20 mm, 5 μm particle size). The samples were then eluted using the following conditions; mobile phase: MeOH/water with 0.1% ammonium format=92/8 (v/v), flow rate: 1 mL/min, temperature: 25 C. Data was acquired in positive mode using a heated electrospray ionization (HESI) interface. The operational parameters for the TSQ Vantage MS/MS instrument were a spray voltage of 3000 V, capillary temperature of 280° C., vaporizer temperature 400° C., shealth gas 60 arbitrary unit, Aux gas 40 arbitrary units, S-lens 113 and collision gas 0.16 Pascals. Standard reference material (SRM) chromatograms of triolein (Q1: 902.9>Q3:602.3) and internal standard (Q1: 902.9>Q3:602.3) were collected for 40 sec. The peak area was integrated by Xcalibur Quan software. The ratio between the triolein generated in the reaction and spiked in internal standard was used to generate percentage inhibition and $IC_{50}$ values. Compound percentage inhibition was calculated by the following formula: Inhibition %=1–[(compound response–low control)/(high control–low control)]×100%. Potent compounds were titrated and $IC_{50}$ were calculated by 4 parameter sigmoidal curve fitting formula.

DGAT2 Enzymatic Activity Assay

DGAT2 activity was determined by measuring the amount of enzymatic product triolein (1,2,3-Tri(cis-9-octadecenoyl) glycerol) using the membrane prep mentioned above. The assay was carried out in deep well 384 plates in a final volume of 40 μL at room temperature. The assay mixture contained the following: assay buffer (100 mM Tris.Cl, pH 7.0, 20 mM $MgCl_2$, 5% ethanol), 25 μM of diolein, 10 μM of oleoyl-CoA and 10 ng/μL of DGAT2 membrane.

TABLE 6

$IC_{50}$ values for inhibition of DGAT2

| Ex. # | Human DGAT2 $IC_{50}$ (nM) |
|---|---|
| 1-A | 4.5 |
| 2-A | 12 |
| 1-B | 8.3 |
| 2-B | 303 |
| 3 | 155 |
| 4 | 67 |
| 5 | 45 |
| 6 | 686 |
| 7 | 164 |
| 8 | 554 |
| 9 | 531 |
| 10 | 608 |
| 11 | 38 |
| 12 | 85 |
| 13 | 48 |
| 14 | 78 |
| 15 | 77 |
| 16 | 120 |
| 17 | 83 |
| 18 | 64 |
| 19 | 585 |
| 20 | 148 |
| 21 | 873 |
| 22 | 102 |
| 23 | 403 |
| 24 | 61 |
| 25 | 558 |
| 26 | 446 |
| 27 | 301 |
| 28 | 93 |
| 29 | 65 |
| 30 | 48 |
| 31 | 320 |
| 32 | 495 |
| 33 | 654 |
| 34 | 75 |
| 35 | 415 |
| 36 | 889 |
| 37 | 221 |
| 38 | 368 |
| 39 | 96 |
| 40 | 445 |
| 41 | 519 |

TABLE 6-continued

IC$_{50}$ values for inhibition of DGAT2

| Ex. # | Human DGAT2 IC$_{50}$ (nM) |
|---|---|
| 42 | 26 |
| 43 | 11 |
| 44 | 176 |
| 45 | 424 |
| 46 | 49 |
| 47 | 47 |
| 48 | 96 |
| 49 | 79 |
| 50 | 34 |
| 51 | 184 |
| 52 | 413 |
| 53 | 32 |
| 54 | 121 |
| 55 | 383 |
| 56 | 22 |
| 57 | 669 |
| 58-A | 668 |
| 58-B | 608 |
| 59 | 461 |
| 60 | 16 |
| 61 | 73 |
| 62 | 580 |
| 63 | 405 |
| 64 | 132 |
| 65 | 170 |
| 66 | 68 |
| 67 | 40 |
| 68 | 310 |
| 69 | 8.0 |
| 70 | 607 |
| 71 | 526 |
| 72 | 22 |
| 73 | 534 |
| 74 | 16 |
| 75 | 357 |
| 76 | 205 |
| 77 | 59 |
| 78 | 353 |
| 79 | 772 |
| 80 | 127 |
| 81 | 88 |
| 82 | 36 |
| 83 | 276 |
| 84 | 156 |
| 85 | 432 |
| 86 | 505 |
| 87 | 198 |
| 88 | 15 |
| 89 | 125 |
| 90 | 90 |
| 91 | 572 |
| 92 | 372 |
| 93 | 503 |
| 94 | 772 |
| 95 | 606 |
| 96 | 43 |
| 97 | 155 |
| 98 | 45 |
| 99 | 6.1 |
| 100 | 12 |
| 101 | 136 |
| 102 | 179 |
| 103 | 31 |
| 104 | 180 |
| 105 | 139 |
| 106 | 832 |
| 107 | 305 |
| 108 | 393 |
| 109 | 532 |
| 110 | 134 |
| 111 | 194 |
| 112 | 593 |
| 113 | 41 |
| 114 | 627 |
| 115 | 578 |
| 116 | 359 |
| 117 | 7.0 |
| 118 | 5.5 |
| 119-A | 8.4 |
| 120-A | 4.2 |
| 121-A | 132 |
| 119-B | 2.5 |
| 121-B | 61 |
| 122-A | 96 |
| 123 | 3.8 |
| 117-B | 6.4 |
| 124 | 4.4 |
| 125-A | 4.2 |
| 125-B | 3.0 |
| 126-A | 11 |
| 127-A | 8.2 |
| 128-A | 3.3 |
| 129-A | 10 |
| 130-A | 3.6 |
| 131-A | 3.0 |
| 132-A | 25 |
| 133-A | 846 |
| 134-A | 212 |
| 135-A | 65 |
| 136-A | 1.4 |
| 137-A | 5.4 |
| 139-A | 229 |
| 139-A | 158 |
| 140-A | 455 |
| 141-A | 4.8 |
| 142-A | 430 |
| 143-A | 1.6 |
| 144-A | 5.8 |
| 145-A | 2.1 |
| 146-A | 63 |
| 147-A | 5.7 |
| 148- | 855 |
| 149 | 249 |
| 150 | 311 |
| 151-A | 4.5 |
| 152-A | 4.5 |
| 153-A | 90 |
| 154-A | 17 |
| 155-A | 353 |
| 156-A | 11 |
| 157-A | 61 |
| 158-A | 31 |
| 159-A | 469 |
| 160-A | 6.9 |
| 161-B | 28 |
| 162-A | 157 |
| 163 | 340 |
| 164 | 28 |
| 165 | 7.0 |
| 166-A | 843 |
| 167 | 383 |
| 168 | 455 |
| 169 | 364 |
| 170 | 179 |
| 171-A | 15 |
| 172-A | 39 |
| 173-A | 23 |
| 174-A | 71 |
| 174-B | 75 |
| 175-A | 338 |
| 176-A | 252 |
| 172-B | 56 |
| 177-B | 86 |
| 178-B | 32 |
| 179 | 285 |
| 180 | 222 |
| 181 | 391 |
| 182 | 371 |

TABLE 6-continued
IC$_{50}$ values for inhibition of DGAT2
| Ex. # | Human DGAT2 IC$_{50}$ (nM) |
|---|---|
| 183 | 460 |
| 184 | 201 |
| 185 | 9.5 |
| 186 | 322 |
| 187 | 644 |
| 188 | 95 |
| 189 | 409 |
| 190 | 45 |
| 191 | 182 |
What is claimed is:
1. A compound having structural Formula I-c':
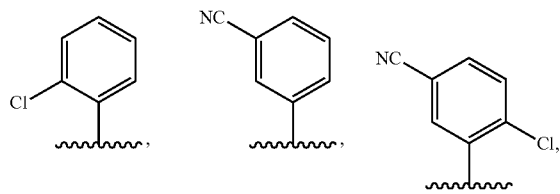
or a pharmaceutically acceptable salt thereof wherein:
R$^1$ is
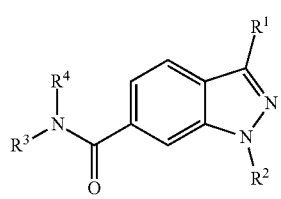
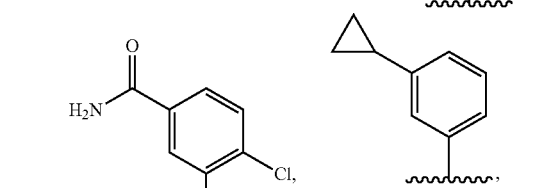
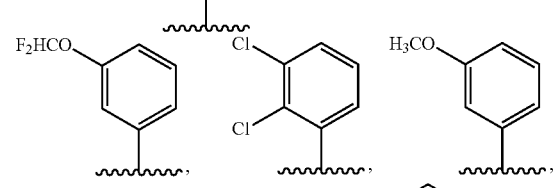
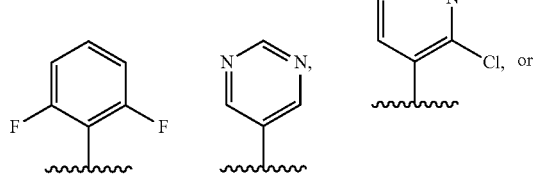
R$^2$ is
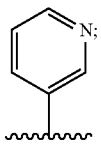
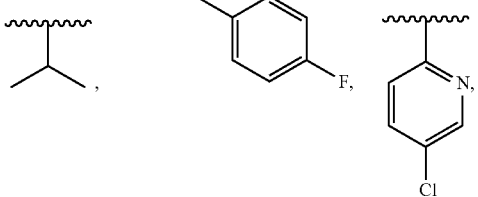
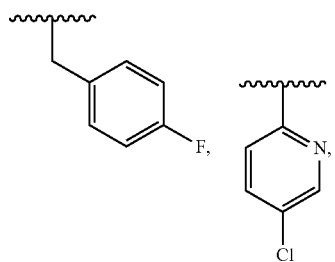
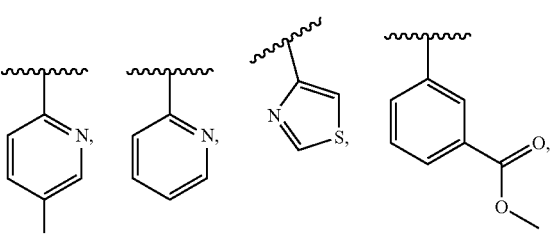
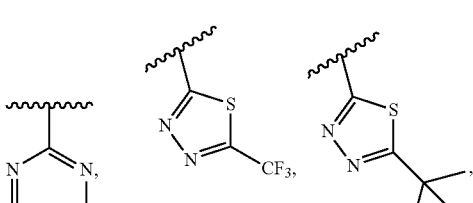
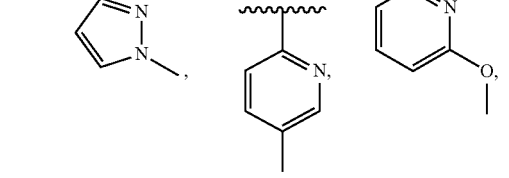

221
-continued
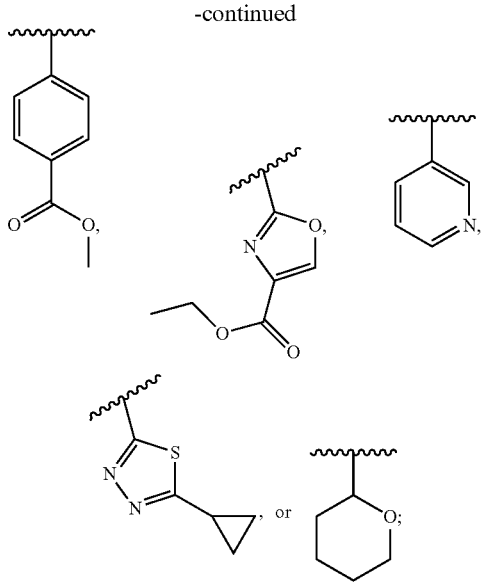
R³ is
222
-continued
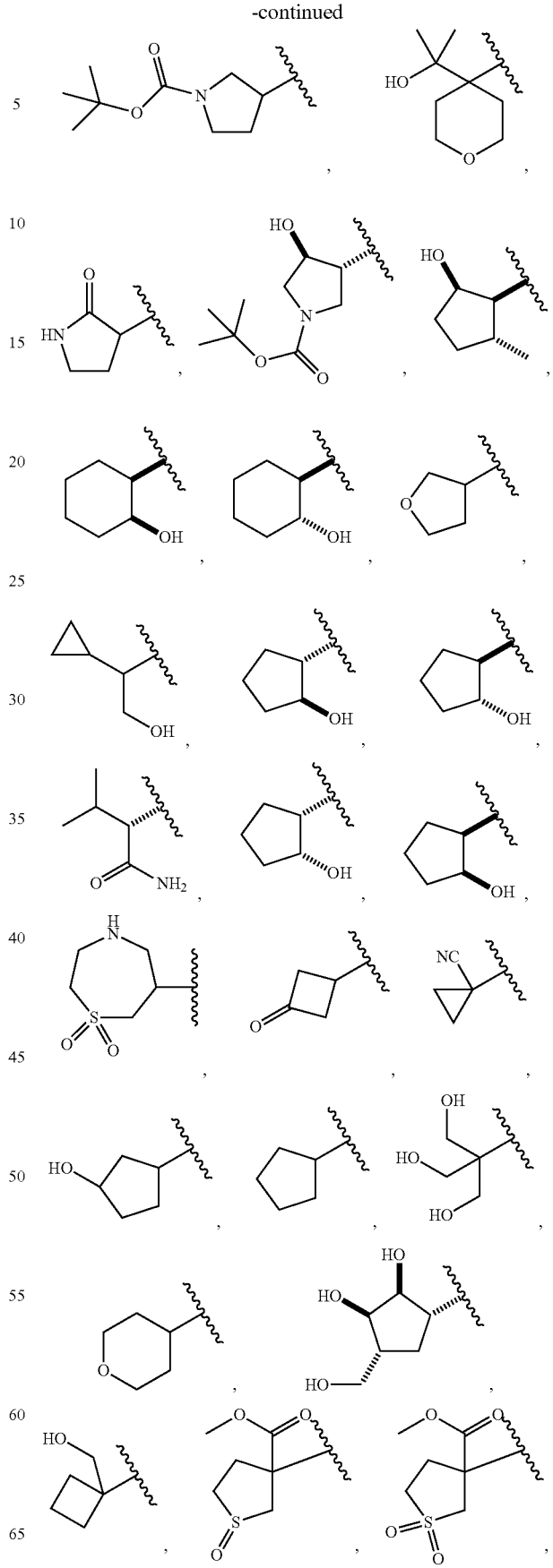

223
-continued
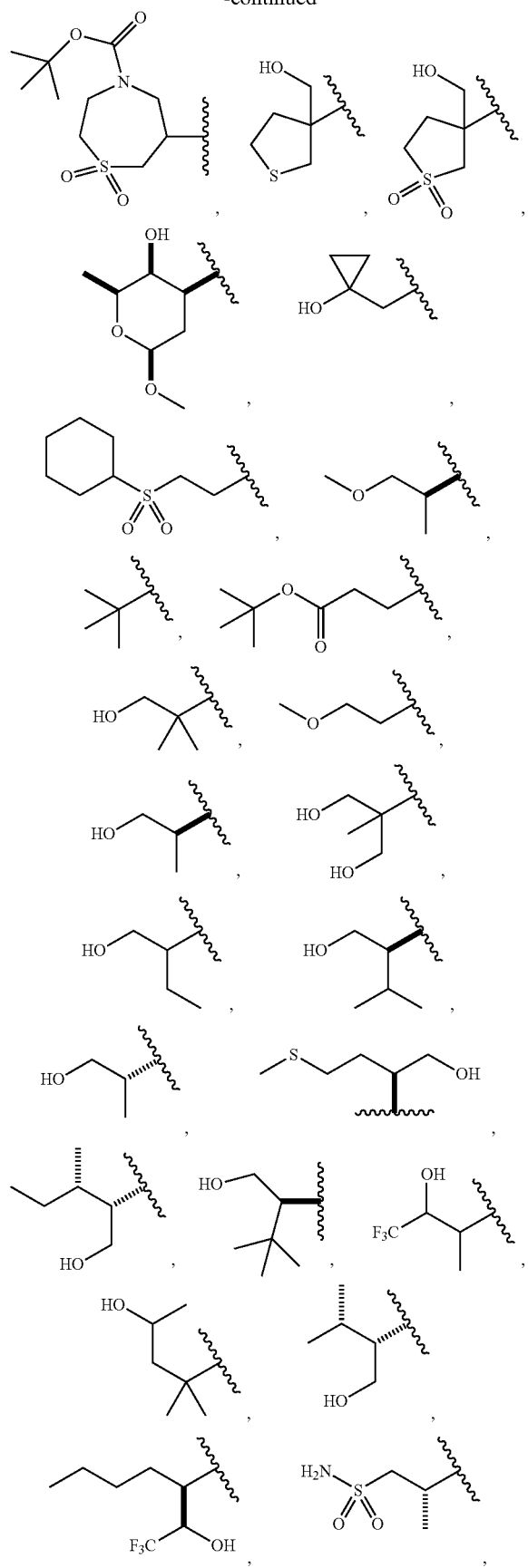
224
-continued
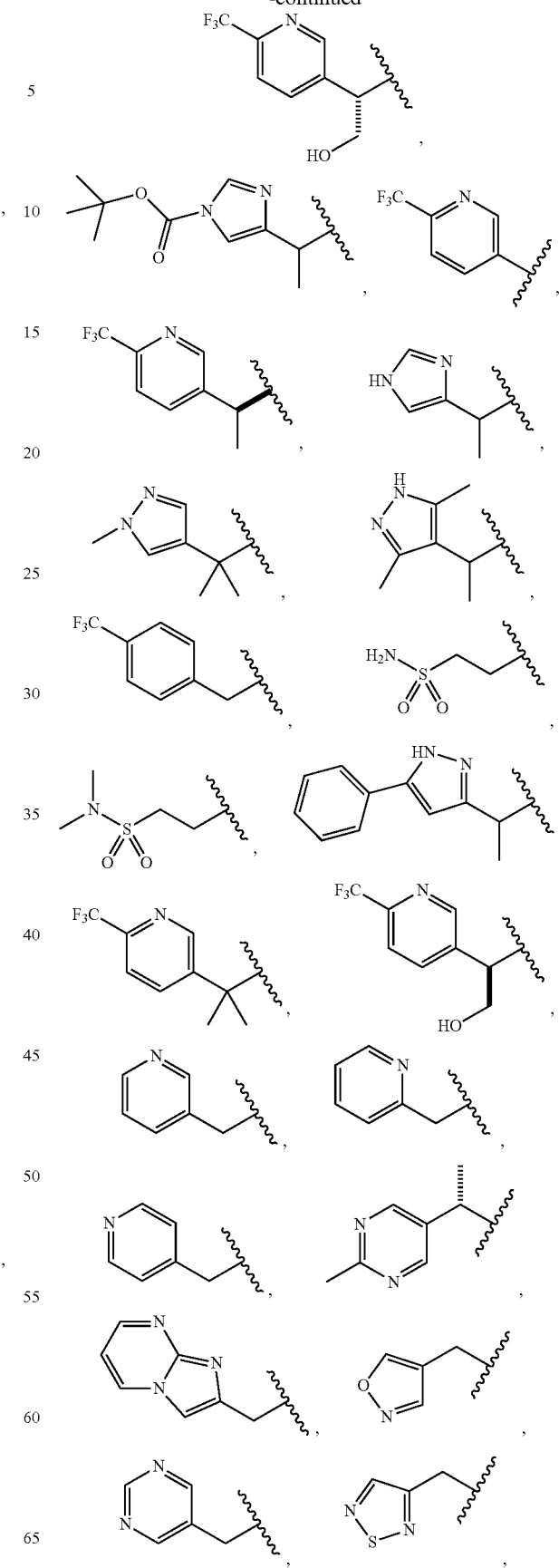

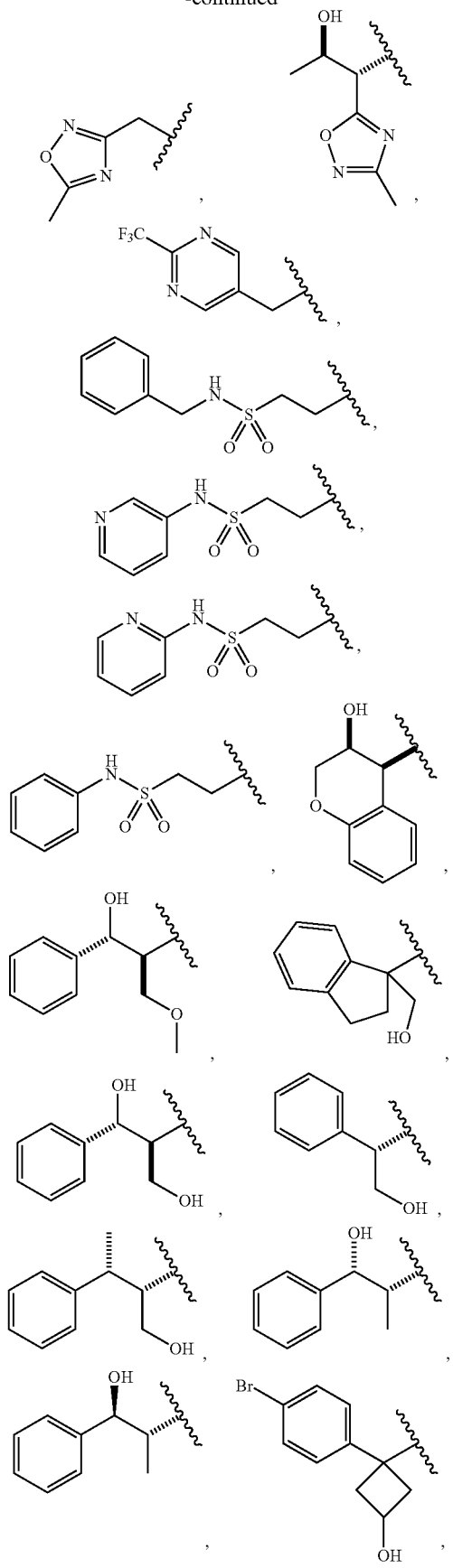
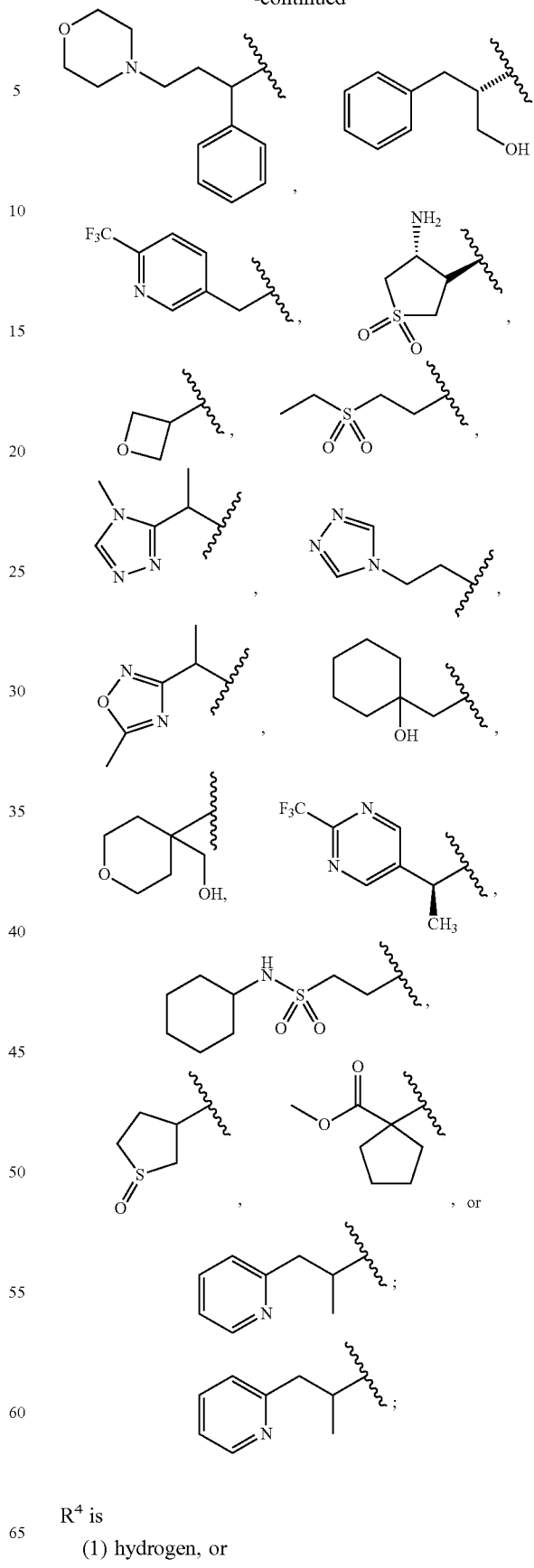
R⁴ is
(1) hydrogen, or
(2) $(C_{1-3})$alkyl, or R³ and R⁴ combine along with the nitrogen atom to which they are attached to form a 4- to 7-membered mono- or 6- to 10-membered bicyclic heterocyclyl ring, containing 1 or 2 heteroatoms independently selected from N, O and S, wherein the heterocyclyl ring is unsubstituted or substituted by 1-3 R⁶; and R⁶ is
(1) (C₁₋₃)alkyl,
(2) halo(C₁₋₃)alkyl-,
(3) oxo,
(4) (C₃₋₆)cycloalkyl,
(5) —C(O)O—(C₁₋₄)alkyl,
(6) NH₂,
(7) hydroxy,
(8) phenyl unsubstituted or substituted by halo,
(9) hydroxy(C₁₋₃)alkyl-,
(10) cyano,
(11) halo, or
(12) —S(O)₂—(C₁₋₃)alkyl.

2. The compound of claim 1 wherein R³ and R⁴ combine along with the nitrogen atom to which they are attached to form

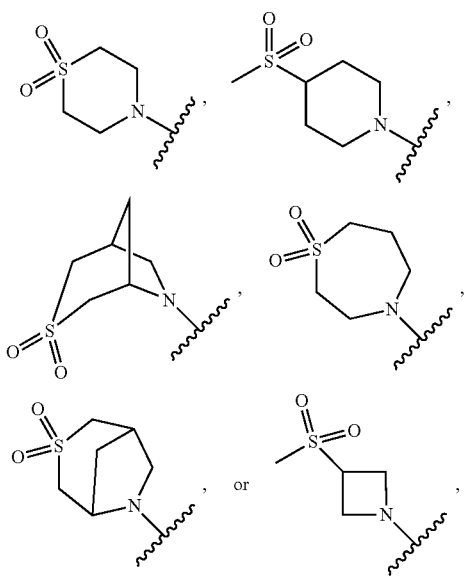

or a pharmaceutically acceptable salt thereof.

3. The compound of claim 1, wherein R² is

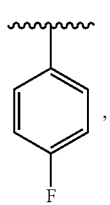

or a pharmaceutically acceptable salt thereof.

4. The compound of claim 1, wherein R³ is

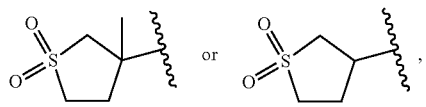

or a pharmaceutically acceptable salt thereof.

5. A compound of claim 1, selected from the group consisting of
(1) 3-(2-Chlorophenyl)-1-(4-fluorophenyl)-N-(3-methyl-1,1-dioxidotetrahydrothiophen-3-yl)-1H-indazole-6-carboxamide,
(2) 3-(2-Chlorophenyl)-N-(1,1-dioxidotetrahydrothiophen-3-yl)-1-(4-fluorophenyl)-1H-indazole-6-carboxamide,
(3) 3-(2-chlorophenyl)-1-(4-fluorophenyl)-N-{1-[1-oxido-6-(trifluoromethyl)pyridin-3-yl]ethyl}-1H-indazole-6-carboxamide,
(4) 3-(2-chlorophenyl)-1-(4-fluorophenyl)-N-{1-[2-(trifluoromethyl)pyrimidin-5-yl]ethyl}-1H-indazole-6-carboxamide,
(5) 3-(2-chlorophenyl)-1-(4-fluorophenyl)-N-{(1S)-2-hydroxy-1-[6-(trifluoromethyl)pyridin-3-yl]ethyl}-1H-indazole-6-carboxamide,
(6) 3-(2-chlorophenyl)-1-(4-fluorophenyl)-N-(1-methyl-2-oxopyrrolidin-3-yl)-1H-indazole-6-carboxamide,
(7) tert-butyl 4-[1-({[3-(2-chlorophenyl)-1-(4-fluorophenyl)-1H-indazol-6-yl]carbonyl}amino)ethyl]-1H-imidazole-1-carboxylate,
(8) N-[(3R,4R)-4-amino-1,1-dioxidotetrahydrothiophen-3-yl]-3-(2-chlorophenyl)-1-(4-fluorophenyl)-1H-indazole-6-carboxamide,
(9) 3-(2-chlorophenyl)-1-(4-fluorophenyl)-N-[4-hydroxy-1,1-dioxidotetrahydrothiophen-3-yl]-1H-indazole-6-carboxamide,
(10) 3-(2-chlorophenyl)-1-(4-fluorophenyl)-N-[6-(trifluoromethyl)pyridin-3-yl]-1H-indazole-6-carboxamide,
(11) 3-(2-chlorophenyl)-1-(4-fluorophenyl)-N-{(1R)-1-[6-(trifluoromethyl)pyridin-3-yl]ethyl}-1H-indazole-6-carboxamide,
(12) 3-(2-chlorophenyl)-1-(4-fluorophenyl)-N-[(1S)-2-methoxy-1-methylethyl]-1H-indazole-6-carboxamide,
(13) 3-(2-chlorophenyl)-1-(4-fluorophenyl)-N-{(1S)-1-[6-(trifluoromethyl)pyridin-3-yl]ethyl}-1H-indazole-6-carboxamide,
(14) 3-(2-chlorophenyl)-1-(4-fluorophenyl)-N-[1-(1H-imidazol-4-yl)ethyl]-1H-indazole-6-carboxamide,
(15) N-tert-butyl-3-(2-chlorophenyl)-1-(4-fluorophenyl)-1H-indazole-6-carboxamide,
(16) 3-(2-chlorophenyl)-1-(4-fluorophenyl)-N-[1-methyl-1-(1-methyl-1H-pyrazol-4-yl)ethyl]-1H-indazole-6-carboxamide,
(17) 3-(2-chlorophenyl)-N-[1-(3,5-dimethyl-1H-pyrazol-4-yl)ethyl]-1-(4-fluorophenyl)-1H-indazole-6-carboxamide,
(18) 3-(2-chlorophenyl)-1-(4-fluorophenyl)-N-{[6-(trifluoromethyl)pyridin-3-yl]methyl}-1H-indazole-6-carboxamide,
(19) tert-butyl N-{[3-(2-chlorophenyl)-1-(4-fluorophenyl)-1H-indazol-6-yl]carbonyl}-beta-alaninate,
(20) 3-(2-chlorophenyl)-1-(4-fluorophenyl)-N-(2-sulfamoylethyl)-1H-indazole-6-carboxamide,
(21) 3-(2-chlorophenyl)-1-(4-fluorophenyl)-N-oxetan-3-yl-1H-indazole-6-carboxamide,

(22) 3-(2-chlorophenyl)-1-(4-fluorophenyl)-N-(1-methyl-5-oxopyrrolidin-3-yl)-1H-indazole-6-carboxamide,
(23) 3-(2-chlorophenyl)-6-[(3,3-dioxido-3-thia-6-azabicyclo[3.2.1]oct-6-yl)carbonyl]-1-(4-fluorophenyl)-1H-indazole,
(24) 3-(2-chlorophenyl)-N-(1,1-dioxidotetrahydro-2H-thiopyran-4-yl)-1-(4-fluorophenyl)-1H-indazole-6-carboxamide,
(25) 3-(2-chlorophenyl)-N-[2-(dimethylsulfamoyl)ethyl]-1-(4-fluorophenyl)-1H-indazole-6-carboxamide,
(26) 3-(2-chlorophenyl)-N-[2-(ethylsulfonyl)ethyl]-1-(4-fluorophenyl)-1H-indazole-6-carboxamide,
(27) 3-(2-chlorophenyl)-1-(4-fluorophenyl)-N-methyl-N-[1-(5-phenyl-1H-pyrazol-3-yl)ethyl]-1H-indazole-6-carboxamide,
(28) 3-(2-chlorophenyl)-1-(4-fluorophenyl)-N-{1-methyl-1-[6-(trifluoromethyl)pyridin-3-yl]ethyl}-1H-indazole-6-carboxamide,
(29) 3-(2-chlorophenyl)-N-[(1,1-dioxidotetrahydrothiophen-3-yl)methyl]-1-(4-fluorophenyl)-1H-indazole-6-carboxamide,
(30) 3-(2-chlorophenyl)-1-(4-fluorophenyl)-N-{(1R)-2-hydroxy-1-[6-(trifluoromethyl)pyridin-3-yl]ethyl}-1H-indazole-6-carboxamide,
(31) 3-(2-chlorophenyl)-1-(4-fluorophenyl)-N-(pyridin-3-ylmethyl)-1H-indazole-6-carboxamide,
(32) 3-(2-chlorophenyl)-1-(4-fluorophenyl)-N-(pyridin-2-ylmethyl)-1H-indazole-6-carboxamide,
(33) 3-(2-chlorophenyl)-1-(4-fluorophenyl)-N-(pyridin-4-ylmethyl)-1H-indazole-6-carboxamide,
(34) 3-(2-chlorophenyl)-1-(4-fluorophenyl)-N-[(1S)-1-(2-methylpyrimidin-5-yl)ethyl]-1H-indazole-6-carboxamide,
(35) 3-(2-chlorophenyl)-1-(4-fluorophenyl)-N-(imidazo[1,2-a]pyrimidin-2-ylmethyl)-1H-indazole-6-carboxamide,
(36) 3-(2-chlorophenyl)-1-(4-fluorophenyl)-N-[1-(4-methyl-4H-1,2,4-triazol-3-yl)ethyl]-1H-indazole-6-carboxamide,
(37) 3-(2-chlorophenyl)-1-(4-fluorophenyl)-N-(isoxazol-4-ylmethyl)-1H-indazole-6-carboxamide,
(38) 3-(2-chlorophenyl)-1-(4-fluorophenyl)-N-(pyrimidin-5-ylmethyl)-1H-indazole-6-carboxamide,
(39) 3-(2-chlorophenyl)-1-(4-fluorophenyl)-N-[2-(4H-1,2,4-triazol-4-yl)ethyl]-1H-indazole-6-carboxamide,
(40) 3-(2-chlorophenyl)-1-(4-fluorophenyl)-N-(1,2,5-thiadiazol-3-ylmethyl)-1H-indazole-6-carboxamide,
(41) 3-(2-chlorophenyl)-1-(4-fluorophenyl)-N-[1-(5-methyl-1,2,4-oxadiazol-3-yl)ethyl]-1H-indazole-6-carboxamide,
(42) 3-(2-chlorophenyl)-1-(4-fluorophenyl)-N-(2-hydroxy-1,1-dimethylethyl)-1H-indazole-6-carboxamide,
(43) 3-(2-chlorophenyl)-1-(4-fluorophenyl)-N-[1-(hydroxymethyl)cyclopentyl]-1H-indazole-6-carboxamide,
(44) 3-(2-chlorophenyl)-1-(4-fluorophenyl)-N-[(1-hydroxycyclohexyl)methyl]-1H-indazole-6-carboxamide,
(45) 3-(2-chlorophenyl)-1-(4-fluorophenyl)-N-(2-methoxyethyl)-1H-indazole-6-carboxamide,
(46) 3-(2-chlorophenyl)-1-(4-fluorophenyl)-N-[2-hydroxy-1-(hydroxymethyl)-1-methylethyl]-1H-indazole-6-carboxamide,
(47) 3-(2-chlorophenyl)-1-(4-fluorophenyl)-N-[4-(hydroxymethyl)tetrahydro-2H-pyran-4-yl]-1H-indazole-6-carboxamide,
(48) 3-(2-chlorophenyl)-1-(4-fluorophenyl)-N-[(1R,2S)-2-hydroxy-1-(3-methyl-1,2,4-oxadiazol-5-yl)propyl]-1H-indazole-6-carboxamide,
(49) 3-(2-chlorophenyl)-1-(4-fluorophenyl)-N-{[2-(trifluoromethyl)pyrimidin-5-yl]methyl}-1H-indazole-6-carboxamide,
(50) 3-(2-chlorophenyl)-1-(4-fluorophenyl)-N-{(1S)-1-[2-(trifluoromethyl)pyrimidin-5-yl]ethyl}-1H-indazole-6-carboxamide,
(51) 3-(2-chlorophenyl)-1-(4-fluorophenyl)-N-[(1R)-1-methyl-2-sulfamoylethyl]-1H-indazole-6-carboxamide,
(52) 3-(2-chlorophenyl)-1-(4-fluorophenyl)-N-(2-oxopyrrolidin-3-yl)-1H-indazole-6-carboxamide,
(53) 3-(2-chlorophenyl)-N-[2-(cyclohexylsulfamoyl)ethyl]-1-(4-fluorophenyl)-1H-indazole-6-carboxamide,
(54) N-[2-(benzylsulfamoyl)ethyl]-3-(2-chlorophenyl)-1-(4-fluorophenyl)-1H-indazole-6-carboxamide,
(55) 3-(2-chlorophenyl)-1-(4-fluorophenyl)-N-[2-(pyridin-2-ylsulfamoyl)ethyl]-1H-indazole-6-carboxamide,
(56) 3-(2-chlorophenyl)-1-(4-fluorophenyl)-N-[2-(phenylsulfamoyl)ethyl]-1H-indazole-6-carboxamide,
(57) 3-(2-chlorophenyl)-N-(2,5-dioxopyrrolidin-3-yl)-1-(4-fluorophenyl)-1H-indazole-6-carboxamide,
(58) 3-(2-chlorophenyl)-1-(4-fluorophenyl)-N-(1-oxido-tetrahydrothiophen-3-yl)-1H-indazole-6-carboxamide,
(59) methyl 3-({[3-(2-chlorophenyl)-1-(4-fluorophenyl)-1H-indazol-6-yl]carbonyl}) amino)tetra-hydrothiophene-3-carboxylate,
(60) 3-(2-chlorophenyl)-1-(4-fluorophenyl)-N-[2-(pyridin-3-ylsulfamoyl)ethyl]-1H-indazole-6-carboxamide,
(61) 3-(2-chlorophenyl)-1-(4-fluorophenyl)-N-[1-(hydroxymethyl)cyclopropyl]-1H-indazole-6-carboxamide,
(62) ethyl 1-({[3-(2-chlorophenyl)-1-(4-fluorophenyl)-1H-indazol-6-yl]carbonyl}amino)cyclopropanecarboxylate,
(63) methyl 1-({[3-(2-chlorophenyl)-1-(4-fluorophenyl)-1H-indazol-6-yl]carbonyl}amino)cyclopentanecarboxylate,
(64) 3-(2-chlorophenyl)-N-(3,3-difluorocyclopentyl)-1-(4-fluorophenyl)-1H-indazole-6-carboxamide,
(65) 3-(2-chlorophenyl)-1-(4-fluorophenyl)-N-[1-(hydroxymethyl)propyl]-1H-indazole-6-carboxamide,
(66) 3-(2-chlorophenyl)-1-(4-fluorophenyl)-N-2-hydroxycyclohexyl]-1H-indazole-6-carboxamide (cis),
(67) 3-(2-chlorophenyl)-1-(4-fluorophenyl)-N-2-hydroxycyclohexyl]-1H-indazole-6-carboxamide (trans),
(68) 3-(2-chlorophenyl)-1-(4-fluorophenyl)-N-[(1S)-2-hydroxy-1-methylethyl]-1H-indazole-6-carboxamide,
(69) 3-(2-chlorophenyl)-1-(4-fluorophenyl)-N-[(1S)-1-(hydroxymethyl)-2-methylpropyl]-1H-indazole-6-carboxamide,
(70) 3-(2-chlorophenyl)-1-(4-fluorophenyl)-N-[4-(1-hydroxy-1-methylethyl)tetrahydro-2H-pyran-4-yl]-1H-indazole-6-carboxamide,
(71) 3-(2-chlorophenyl)-1-(4-fluorophenyl)-N-[3-hydroxy-3,4-dihydro-2H-chromen-4-yl]-1H-indazole-6-carboxamide,
(72) 3-(2-chlorophenyl)-1-(4-fluorophenyl)-N-[2-hydroxy-5-methylcyclopentyl]-1H-indazole-6-carboxamide,
(73) 3-(2-chlorophenyl)-1-(4-fluorophenyl)-N-[1-(2,2,2-trifluoro-1-hydroxyethyl)pentyl]-1H-indazole-6-carboxamide,

(74) 3-(2-chlorophenyl)-1-(4-fluorophenyl)-N-[2-hydroxy-1-(methoxymethyl)-2-phenylethyl]-1H-indazole-6-carboxamide,
(75) 3-(2-chlorophenyl)-1-(4-fluorophenyl)-N-[1-(hydroxymethyl)-2,3-dihydro-1H-inden-1-yl]-1H-indazole-6-carboxamide,
(76) tert-butyl 3-({[3-(2-chlorophenyl)-1-(4-fluorophenyl)-1H-indazol-6-yl]carbonyl}amino)-4-hydroxypyrrolidine-1-carboxylate,
(77) 3-(2-chlorophenyl)-1-(4-fluorophenyl)-N-(tetrahydrofuran-3-yl)-1H-indazole-6-carboxamide,
(78) 3-(2-chlorophenyl)-N-(1-cyclopropyl-2-hydroxyethyl)-1-(4-fluorophenyl)-1H-indazole-6-carboxamide,
(79) 3-(2-chlorophenyl)-1-(4-fluorophenyl)-N-[2-hydroxy-1-methylethyl]-1H-indazole-6-carboxamide,
(80) 3-(2-chlorophenyl)-1-(4-fluorophenyl)-N-[2-hydroxy-1-(hydroxymethyl)-2-phenylethyl]-1H-indazole-6-carboxamide,
(81) 3-(2-chlorophenyl)-1-(4-fluorophenyl)-N-(3,3,3-trifluoro-2-hydroxy-1-methylpropyl)-1H-indazole-6-carboxamide,
(82) 3-(2-chlorophenyl)-1-(4-fluorophenyl)-N-[2-hydroxy-1-phenylethyl]-1H-indazole-6-carboxamide,
(83) 3-(2-chlorophenyl)-1-(4-fluorophenyl)-N-(3-hydroxycyclopentyl)-1H-indazole-6-carboxamide,
(84) 3-(2-chlorophenyl)-N-cyclopentyl-1-(4-fluorophenyl)-1H-indazole-6-carboxamide,
(85) 3-(2-chlorophenyl)-1-(4-fluorophenyl)-N-[2-hydroxy-1,1-bis(hydroxymethyl)ethyl]-1H-indazole-6-carboxamide,
(86) 3-(2-chlorophenyl)-1-(4-fluorophenyl)-N-(tetrahydro-2H-pyran-4-yl)-1H-indazole-6-carboxamide,
(87) 3-(2-chlorophenyl)-N-[2,3-dihydroxy-4-(hydroxymethyl)cyclopentyl]-1-(4-fluorophenyl)-1H-indazole-6-carboxamide,
(88) 3-(2-chlorophenyl)-1-(4-fluorophenyl)-N-[1-(hydroxymethyl)cyclobutyl]-1H-indazole-6-carboxamide,
(89) methyl 3-({[3-(2-chlorophenyl)-1-(4-fluorophenyl)-1H-indazol-6-yl]carbonyl}amino)tetra-hydrothiophene-3-carboxylate 1-oxide,
(90) methyl 3-({[3-(2-chlorophenyl)-1-(4-fluorophenyl)-1H-indazol-6-yl]carbonyl}amino)tetra-hydrothiophene-3-carboxylate 1,1-dioxide,
(91) tert-butyl 6-({[3-(2-chlorophenyl)-1-(4-fluorophenyl)-1H-indazol-6-yl]carbonyl}) amino)-1,4-thiazepane-4-carboxylate 1,1-dioxide,
(92) 3-(2-chlorophenyl)-1-(4-fluorophenyl)-N-[3-(hydroxymethyl)-1,1-dioxidotetrahydrothiophen-3-yl]-1H-indazole-6-carboxamide,
(93) 3-(2-chlorophenyl)-1-(4-fluorophenyl)-N-[(1S)-1-(hydroxymethyl)-3-(methylsulfanyl)propyl]-1H-indazole-6-carboxamide,
(94) 3-(2-chlorophenyl)-1-(4-fluorophenyl)-N-[2-hydroxycyclopentyl]-1H-indazole-6-carboxamide,
(95) N-[1-carbamoyl-2-methylpropyl]-3-(2-chlorophenyl)-1-(4-fluorophenyl)-1H-indazole-6-carboxamide,
(96) 3-(2-chlorophenyl)-1-(4-fluorophenyl)-N-[2-hydroxycyclopentyl]-1H-indazole-6-carboxamide,
(97) 3-(2-chlorophenyl)-1-(4-fluorophenyl)-N-[(1S,2S)-2-hydroxycyclopentyl]-1H-indazole-6-carboxamide,
(98) 3-(2-chlorophenyl)-1-(4-fluorophenyl)-N-[3-(hydroxymethyl)tetrahydrothiophen-3-yl]-1H-indazole-6-carboxamide,
(99) 3-(2-chlorophenyl)-1-(4-fluorophenyl)-N-[(1S)-1-(hydroxymethyl)-2,2-dimethylpropyl]-1H-indazole-6-carboxamide,
(100) tert-butyl (3 S)-3-({[3-(2-chlorophenyl)-1-(4-fluorophenyl)-1H-indazol-6-yl]carbonyl}amino)pyrrolidine-1-carboxylate,
(101) tert-butyl (3R)-3-({[3-(2-chlorophenyl)-1-(4-fluorophenyl)-1H-indazol-6-yl]carbonyl}amino)pyrrolidine-1-carboxylate,
(102) 3-(2-chlorophenyl)-N-(1,1-dioxido-1,4-thiazepan-6-yl)-1-(4-fluorophenyl)-1H-indazole-6-carboxamide,
(103) 3-(2-chlorophenyl)-1-(4-fluorophenyl)-N-[(1S,2 S)-1-(hydroxymethyl)-2-methylbutyl]-1H-indazole-6-carboxamide,
(104) 3-(2-chlorophenyl)-1-(4-fluorophenyl)-N-(3-oxocyclobutyl)-1H-indazole-6-carboxamide,
(105) 3-(2-chlorophenyl)-N-(1-cyanocyclopropyl)-1-(4-fluorophenyl)-1H-indazole-6-carboxamide,
(106) 3-(2-chlorophenyl)-1-(4-fluorophenyl)-N-[(1R,2S)-2-hydroxy-1-methyl-2-phenylethyl]-1H-indazole-6-carboxamide,
(107) 3-(2-chlorophenyl)-1-(4-fluorophenyl)-N-[(1R,2R)-2-hydroxy-1-methyl-2-phenylethyl]-1H-indazole-6-carboxamide,
(108) N-[1-(4-bromophenyl)-3-hydroxycyclobutyl]-3-(2-chlorophenyl)-1-(4-fluorophenyl)-1H-indazole-6-carboxamide,
(109) 3-(2-chlorophenyl)-1-(4-fluorophenyl)-N-(3-morpholin-4-yl-1-phenylpropyl)-1H-indazole-6-carboxamide,
(110) N-[(1S)-1-benzyl-2-hydroxyethyl]-3-(2-chlorophenyl)-1-(4-fluorophenyl)-1H-indazole-6-carboxamide,
(111) 3-(2-chlorophenyl)-1-(4-fluorophenyl)-N-((2S,3S,4S,6S)-3-hydroxy-6-methoxy-2-methyltetrahydro-2H-pyran-4-yl)-1H-indazole-6-carboxamide,
(112) 3-(2-chlorophenyl)-1-(4-fluorophenyl)-N-(1-methyl-2-pyridin-2-ylethyl)-1H-indazole-6-carboxamide,
(113) 3-(2-chlorophenyl)-1-(4-fluorophenyl)-N-(3-hydroxy-1,1-dimethylbutyl)-1H-indazole-6-carboxamide,
(114) 3-(2-chlorophenyl)-1-(4-fluorophenyl)-N-[(1-hydroxycyclopropyl)methyl]-1H-indazole-6-carboxamide,
(115) 3-(2-chlorophenyl)-1-(4-fluorophenyl)-N-[(1R,2S)-2-hydroxycyclopentyl]-1H-indazole-6-carboxamide,
(167) 1-Benzyl-3-(2-chlorophenyl)-N-(1,1-dioxidotetrahydrothiophen-3-yl)-1H-indazole-6-carboxamide,
(168) 1-(4-chlorobenzyl)-3-(2-chlorophenyl)-N-(1,1-dioxidotetrahydrothiophen-3-yl)-1H-indazole-6-carboxamide,
(169) 3-(2-chlorophenyl)-N-(1,1-dioxidotetrahydrothiophen-3-yl)-1-(1-methylethyl)-1H-indazole-6-carboxamide,
(170) 3-(2-chlorophenyl)-N-(1,1-dioxidotetrahydrothiophen-3-yl)-1-(4-fluorobenzyl)-1H-indazole-6-carboxamide,
(171) 3-(2-chlorophenyl)-1-(5-chloropyridin-2-yl)-N-(3-methyl-1,1-dioxidotetrahydrothiophen-3-yl)-1H-indazole-6-carboxamide,
(172) 3-(2-chlorophenyl)-1-(5-fluoropyridin-2-yl)-N-(3-methyl-1,1-dioxidotetrahydrothiophen-3-yl)-1H-indazole-6-carboxamide,
(173) 3-(2-chlorophenyl)-1-(5-chloropyridin-2-yl)-N-(1,1-dioxidotetrahydrothiophen-3-yl)-1H-indazole-6-carboxamide,
(174) 3-(2-chlorophenyl)-N-(3-methyl-1,1-dioxidotetrahydrothiophen-3-yl)-1-pyridin-2-yl-1H-indazole-6-carboxamide, (175) 3-(2-chlorophenyl)-N-(1,1-dioxidotetrahydrothiophen-3-yl)-1-pyridin-2-yl-1H-indazole-6-carboxamide,
(176) 3-(2-chlorophenyl)-N-(1,1-dioxidotetrahydrothiophen-3-yl)-1-(5-fluoropyridin-2-yl)-1H-indazole-6-carboxamide,
(179) 3-(2-Chlorophenyl)-N-(3-methyl-1,1-dioxidotetrahydrothiophen-3-yl)-1-(thiazol-4-yl)-1H-indazole-6-carboxamide,
(180) methyl 3-{3-(2-chlorophenyl)-6-[(3-methyl-1,1-dioxidotetrahydrodioxidotetrahydrodioxidotetrahydrodioxidotetrahydro-thiophen-3-yl)carbamoyl]-1H-indazol-1-yl}benzoate,
(181) 3-(2-chlorophenyl)-1-(5-fluoropyrimidin-2-yl)-N-(3-methyl-1,1-dioxidotetradioxidotetradioxidotetradioxidotetra-hydrothiophen-3-yl)-1H-indazole-6-carboxamide,
(182) 3-(2-chlorophenyl)-N-(3-methyl-1,1-dioxidotetrahydrothiophen-3-yl)-1-[5-(trifluoromethyl)-1,3,4-thiadiazol-2-yl]-1H-indazole-6-carboxamide,
(183) 1-(5-tert-butyl-1,3,4-thiadiazol-2-yl)-3-(2-chlorophenyl)-N-(3-methyl-1,1-dioxidotetrahydrothiophen-3-yl)-1H-indazole-6-carboxamide,
(184) 3-(2-chlorophenyl)-N-(3-methyl-1,1-dioxidotetrahydrothiophen-3-yl)-1-(1-methyl-1H-pyrazol-3-yl)-1H-indazole-6-carboxamide,
(185) 3-(2-chlorophenyl)-N-(3-methyl-1,1-dioxidotetrahydrothiophen-3-yl)-1-(5-methylpyridin-2-yl)-1H-indazole-6-carboxamide,
(186) 3-(2-chlorophenyl)-1-(6-methoxypyridin-2-yl)-N-(3-methyl-1,1-dioxidotetrahydrothiophen-3-yl)-1H-indazole-6-carboxamide,
(187) methyl 4-{3-(2-chlorophenyl)-6-[(3-methyl-1,1-dioxidotetrahydrothiophen-3-yl)carbamoyl]-1H-indazol-1-yl}benzoate,
(188) ethyl 2-{3-(2-chlorophenyl)-6-[(3-methyl-1,1-dioxidotetrahydrothiophen-3-yl)carbamoyl]-1H-indazol-1-yl}-1,3-oxazole-4-carboxylate,
(189) 3-(2-chlorophenyl)-N-(3-methyl-1,1-dioxidotetrahydrothiophen-3-yl)-1-pyridin-3-yl-1H-indazole-6-carboxamide,
(190) 3-(2-chlorophenyl)-1-(5-cyclopropyl-1,3,4-thiadiazol-2-yl)-N-(3-methyl-1,1-dioxidotetrahydrothiophen-3-yl)-1H-indazole-6-carboxamide, and
(191) 3-(2-Chlorophenyl)-N-(3-methyl-1,1-dioxidotetrahydrothiophen-3-yl)-1-(tetrahydro-2H-pyran-2-yl)-1H-indazole-6-carboxamide, or a pharmaceutically acceptable salt thereof.

6. A compound of claim 1, selected from the group consisting of
(116) 3-(3-cyanophenyl)-N-(1,1-dioxidotetrahydrothiophen-3-yl)-1-(4-fluorophenyl)-1H-indazole-6-carboxamide,
(117) 3-(3-cyanophenyl)-1-(4-fluorophenyl)-N-(3-methyl-1,1-dioxidotetrahydrothiophen-3-yl)-1H-indazole-6-carboxamide,
(118) 3-(2-chloro-5-cyanophenyl)-1-(4-fluorophenyl)-N-[1-(hydroxymethyl)cyclobutyl]-1H-indazole-6-carboxamide,
(119) 3-(2-chloro-5-cyanophenyl)-1-(4-fluorophenyl)-N-(3-methyl-1,1-dioxidotetrahydrothiophen-3-yl)-1H-indazole-6-carboxamide,
(120) 3-(2-chloro-5-cyanophenyl)-N-(1,1-dioxidotetrahydrothiophen-3-yl)-1-(4-fluorophenyl)-1H-indazole-6-carboxamide,
(121) 3-(5-carbamoyl-2-chlorophenyl)-1-(4-fluorophenyl)-N-(3-methyl-1,1-dioxidotetrahydrothiophen-3-yl)-1H-indazole-6-carboxamide,
(122) 3-(5-carbamoyl-2-chlorophenyl)-N-(1,1-dioxidotetrahydrothiophen-3-yl)-1-(4-fluorophenyl)-1H-indazole-6-carboxamide,
(123) 3-(2-chloro-5-cyanophenyl)-1-(4-fluorophenyl)-N-[(1S)-1-(hydroxymethyl)-2-methylpropyl]-1H-indazole-6-carboxamide,
(124) 3-(3-cyclopropylphenyl)-1-(5-fluoropyridin-2-yl)-N-[(1S)-1-(hydroxymethyl)-2-methylpropyl]-1H-indazole-6-carboxamide,
(125) 3-(3-cyclopropylphenyl)-1-(5-fluoropyridin-2-yl)-N-(3-methyl-1,1-dioxidotetrahydrothiophen-3-yl)-1H-indazole-6-carboxamide,
(126) 3-(3-cyclopropylphenyl)-N-(1,1-dioxidotetrahydrothiophen-3-yl)-1-(5-fluoropyridin-2-yl)-1H-indazole-6-carboxamide,
(127) 3-(2-chloro-5-cyanophenyl)-N-(1,1-dioxidotetrahydrothiophen-3-yl)-1-(5-fluoropyridin-2-yl)-1H-indazole-6-carboxamide,
(128) 3-[3-(difluoromethoxy)phenyl]-1-(5-fluoropyridin-2-yl)-N-(3-methyl-1,1-dioxidotetrahydrothiophen-3-yl)-1H-indazole-6-carboxamide,
(129) 3-(3-Cyanophenyl)-N-(1,1-dioxidotetrahydrothiophen-3-yl)-1-(4-fluorophenyl)-1H-indazole-6-carboxamide,
(130) 3-(2,3-dichlorophenyl)-N-(1,1-dioxidotetrahydrothiophen-3-yl)-1-(4-fluorophenyl)-1H-indazole-6-carboxamide,
(131) N-(1,1-dioxidotetrahydrothiophen-3-yl)-1-(4-fluorophenyl)-3-(3-methoxyphenyl)-1H-indazole-6-carboxamide,
(132) 3-(2,6-difluorophenyl)-N-(1,1-dioxidotetrahydrothiophen-3-yl)-1-(4-fluorophenyl)-1H-indazole-6-carboxamide,
(133) N-(1,1-dioxidotetrahydrothiophen-3-yl)-1-(4-fluorophenyl)-3-pyrimidin-5-yl-1H-indazole-6-carboxamide,
(134) N-(1,1-dioxidotetrahydrothiophen-3-yl)-1-(4-fluorophenyl)-3-pyridin-3-yl-1H-indazole-6-carboxamide,
(135) 3-(2-chloropyridin-3-yl)-N-(1,1-dioxidotetrahydrothiophen-3-yl)-1-(4-fluorophenyl)-1H-indazole-6-carboxamide,
(136) 3-[3-(difluoromethoxy)phenyl]-N-(1,1-dioxidotetrahydrothiophen-3-yl)-1-(4-fluorophenyl)-1H-indazole-6-carboxamide,
(137) 3-(5-chloro-2-methoxypyridin-4-yl)-N-(1,1-dioxidotetrahydrothiophen-3-yl)-1-(4-fluorophenyl)-1H-indazole-6-carboxamide,
(138) 3-(5-chloro-2-methoxypyridin-3-yl)-N-(1,1-dioxidotetrahydrothiophen-3-yl)-1-(4-fluorophenyl)-1H-indazole-6-carboxamide,
(139) 3-(1,3-benzodioxol-5-yl)-1-(4-fluorophenyl)-N-(3-methyl-1,1-dioxidotetrahydrothiophen-3-yl)-1H-indazole-6-carboxamide,
(140) 1-(4-fluorophenyl)-3-(2-methoxypyridin-4-yl)-N-(3-methyl-1,1-dioxidotetrahydrothiophen-3-yl)-1H-indazole-6-carboxamide,
(141) 3-(5-chloro-2-methoxypyridin-4-yl)-1-(4-fluorophenyl)-N-(3-methyl-1,1-dioxidotetrahydrothiophen-3-yl)-1H-indazole-6-carboxamide,
(142) 3-(5-chloro-2-methoxypyridin-3-yl)-1H-(4-fluorophenyl)-N-(3-methyl-1,1-dioxidotetrahydrothiophen-3-yl)-1H-indazole-6-carboxamide, (143) 3-[3-(difluoromethoxy)phenyl]-1-(4-fluorophenyl)-N-(3-methyl-1,1-dioxidotetrahydrothiophen-3-yl)-1H-indazole-6-carboxamide,
(144) 1-(4-fluorophenyl)-3-(3-methoxyphenyl)-N-(3-methyl-1,1-dioxidotetrahydrothiophen-3-yl)-1H-indazole-6-carboxamide,
(145) 3-(3-cyclopropylphenyl)-1-(4-fluorophenyl)-N-(3-methyl-1,1-dioxidotetrahydrothiophen-3-yl)-1H-indazole-6-carboxamide,
(146) 3-(5-cyanopyridin-3-yl)-1-(4-fluorophenyl)-N-(3-methyl-1,1-dioxidotetrahydrothiophen-3-yl)-1H-indazole-6-carboxamide,
(147) 1-(4-fluorophenyl)-N-(3-methyl-1,1-dioxidotetrahydrothiophen-3-yl)-3-[3-(2,2,2-trifluoroethoxy)phenyl]-1H-indazole-6-carboxamide,
(148) 3-[3-(dimethylcarbamoyl)phenyl]-1-(4-fluorophenyl)-N-(3-methyl-1,1-dioxidotetrahydrothiophen-3-yl)-1H-indazole-6-carboxamide,
(149) 3-(3-carbamoylphenyl)-1-(4-fluorophenyl)-N-(3-methyl-1,1-dioxidotetrahydrothiophen-3-yl)-1H-indazole-6-carboxamide,
(150) 1-(4-fluorophenyl)-3-[3-(1-hydroxy-1-methylethyl)phenyl]-N-(3-methyl-1,1-dioxidotetrahydrothiophen-3-yl)-1H-indazole-6-carboxamide,
(151) 3-(5-cyano-2-fluorophenyl)-1-(4-fluorophenyl)-N-(3-methyl-1,1-dioxidotetrahydrothiophen-3-yl)-1H-indazole-6-carboxamide,
(152) 3-(6-chloro-2-fluoropyridin-3-yl)-1-(4-fluorophenyl)-N-(3-methyl-1,1-dioxidotetrahydrothiophen-3-yl)-1H-indazole-6-carboxamide,
(153) 1-(4-fluorophenyl)-3-(5-fluoropyridin-3-yl)-N-(3-methyl-1,1-dioxidotetrahydrothiophen-3-yl)-1H-indazole-6-carboxamide,
(154) 1-(4-fluorophenyl)-3-(2-fluoropyridin-3-yl)-N-(3-methyl-1,1-dioxidotetrahydrothiophen-3-yl)-1H-indazole-6-carboxamide,
(155) 1-(4-fluorophenyl)-3-(6-methoxypyridin-3-yl)-N-(3-methyl-1,1-dioxidotetrahydrothiophen-3-yl)-1H-indazole-6-carboxamide,
(156) 1-(4-fluorophenyl)-N-(3-methyl-1,1-dioxidotetrahydrothiophen-3-yl)-3-(3-methylphenyl)-1H-indazole-6-carboxamide,
(157) 3-(3,5-dichlorophenyl)-1-(4-fluorophenyl)-N-(3-methyl-1,1-dioxidotetrahydrothiophen-3-yl)-1H-indazole-6-carboxamide,
(158) 3-(3-chlorophenyl)-1-(4-fluorophenyl)-N-(3-methyl-1,1-dioxidotetrahydrothiophen-3-yl)-1H-indazole-6-carboxamide,
(159) 1-(4-fluorophenyl)-N-(3-methyl-1,1-dioxidotetrahydrothiophen-3-yl)-3-[2-(trifluoromethyl)pyridin-4-yl]-1H-indazole-6-carboxamide,
(160) 3-[2-chloro-5-(trifluoromethyl)phenyl]-1-(4-fluorophenyl)-N-(3-methyl-1,1-dioxidotetrahydrothiophen-3-yl)-1H-indazole-6-carboxamide,
(161) 3-(5-cyano-2-fluoro-3-methoxyphenyl)-1-(4-fluorophenyl)-N-(3-methyl-1,1-dioxidotetrahydrothiophen-3-yl)-1H-indazole-6-carboxamide,
(162) 1-(4-fluorophenyl)-N-(3-methyl-1,1-dioxidotetrahydrothiophen-3-yl)-3-phenyl-1H-indazole-6-carboxamide,
(163) 1-(4-fluorophenyl)-3-(1-methyl-1H-benzotriazol-6-yl)-N-(3-methyl-1,1-dioxidotetrahydrothiophen-3-yl)-1H-indazole-6-carboxamide,
(164) 1-(4-fluorophenyl)-N-(3-methyl-1,1-dioxidotetrahydrothiophen-3-yl)-3-[3-(5-methyl-1,3,4-oxadiazol-2-yl)phenyl]-1H-indazole-6-carboxamide,
(165) 1-(4-fluorophenyl)-N-(3-methyl-1,1-dioxidotetrahydrothiophen-3-yl)-3-[3-(1H-pyrazol-1-yl)phenyl]-1H-indazole-6-carboxamide,
(166) 3-(6-((1,1-dioxidotetrahydrothiophen-3-yl)carbamoyl)-1-(4-fluorophenyl)-1H-indazol-3-yl)pyridine 1-oxide,
(177) 3-(3-cyanophenyl)-N-(1,1-dioxidotetrahydrothiophen-3-yl)-1-(5-fluoropyridin-2-yl)-1H-indazole-6-carboxamide, and
(178) -(3-cyanophenyl)-1-(5-fluoropyridin-2-yl)-N-(3-methyl-1,1-dioxidotetrahydrothiophen-3-yl)-1H-indazole-6-carboxamide,
or a pharmaceutically acceptable salt thereof.

7. A pharmaceutical composition comprising the compound of claim 1, or a pharmaceutically acceptable salt thereof, and a pharmaceutically acceptable carrier.

8. A method of treating atherosclerosis, hepatic steatosis, atherosclerosis, type-2 diabetes mellitus, obesity, hyperlipidemia, non-alcoholic steatohepatitis or hypercholesterolemia in a patient in need of treatment comprising the administration to the patient of a therapeutically effective amount of a compound having the structural Formula I',

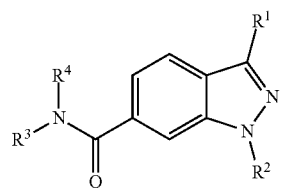

or a pharmaceutically acceptable salt thereof, wherein:
$R^1$ is
(1) 6-membered aryl unsubstituted or substituted by 1-3 $R^5$, or
(2) 5-, 6- or 9-membered heteroaryl or 9-membered bicyclic heterocycle, containing 1, 2 or 3 heteroatoms independently selected from N, O, and S, wherein the heteroaryl is unsubstituted or substituted by 1-3 $R^5$;
$R^2$ is
(1) 6-membered aryl unsubstituted or substituted by 1-3 $R^7$,
(2) 5- or 6-membered heteroaryl containing 1, 2 or 3 heteroatoms independently selected from N, O, and S, wherein the heteroaryl is unsubstituted or substituted by 1-3 $R^7$,
(3) $(C_{1-6})$alkyl,
(4) 4- to 6-membered heterocyclyl containing 1 or 2 heteroatoms independently selected from N, O and S, or
(5) —$CH_{2-6}$-membered aryl, wherein the aryl is unsubstituted or substituted by 1-3 $R^7$;
$R^3$ is
(1) 4- to 7-membered heterocyclyl containing 1 or 2 heteroatoms independently selected from N, O and S,
(2) 5- or 6-membered heteroaryl containing 1, 2 or 3 heteroatoms independently selected from N, O, and S,
(3) —$(C_{1-6})$alkyl-heteroaryl, wherein the heteroaryl is a 5- or 6-membered heteroaryl containing 1, 2 or 3 heteroatoms independently selected from N, O and S, (4) —$(C_{1-6})$alkyl-6-membered aryl,
(5) —$(C_{1-6})$alkyl-heterocyclyl, wherein the heterocyclyl is a 3- to 6-membered ring containing 1 or 2 heteroatoms independently selected from N, O and S,
(6) $(C_{1-6})$alkyl,
(7) —$(C_{1-6})$alkyl-C(O)O—$(C_{1-4})$alkyl,
(8) —$(C_{1-6})$alkyl-S(O)$_2$—NR$^{9a}$R$^{9b}$,
(9) —$(C_{1-6})$alkyl-S(O)$_2$—$(C_{1-3})$alkyl,
(10) —$(C_{1-3})$alkyl-heteroaryl, wherein the heteroaryl is a 8- to 10-membered fused ring, and wherein the heteroaryl contains 1, 2, 3, or 4 heteroatoms independently selected from N, O, and S,
(11) —$(C_{1-6})$alkyl-S(O)$_2$—$(C_{3-6})$cycloalkyl,
(12) —$(C_{1-6})$alkyl-S(O)$_2$—NR$^{9a}$—$(C_{3-6})$cycloalkyl,
(13) —$(C_{1-6})$alkyl-$(C_{3-6})$cycloalkyl,
(14) $(C_{3-6})$cycloalkyl, or
(15) 9- to 10-membered fused aryl,
wherein each aryl, heteroaryl, cycloalkyl, or heterocyclyl are unsubstituted or substituted by 1-3 R$^6$, and wherein each alkyl is unsubstituted or substituted by 1-3 R$^8$;

R$^4$ is
(1) hydrogen,
(2) $(C_{1-3})$alkyl,
or R$^3$ and R$^4$ combine along with the nitrogen atom to which they are attached to form a 4- to 7-membered mono- or 6- to 10-membered bicyclic heterocyclyl ring containing 1 or 2 heteroatoms independently selected from N, O and S, wherein the heterocyclyl ring is unsubstituted or substituted by 1-3 R$^6$;

R$^5$ is
(1) cyano,
(2) halo,
(3) $(C_{1-6})$alkyl,
(4) —C(O)NH$_2$,
(5) —C(O)NR$^{10a}$R$^{10b}$,
(6) $(C_{3-6})$cycloalkyl,
(7) hydroxy,
(8) hydroxy$(C_{1-3})$alkyl-,
(9) $(C_{1-6})$alkoxy-,
(10) -NR$^{10a}$R$^{10b}$
(11) 5-membered heteroaryl containing 1, 2 or 3 heteroatoms independently selected from N, O, and S, wherein the heteroaryl is unsubstituted or substituted by 1-2 R$^7$;
(12) halo$(C_{1-6})$alkyl-, or
(13) halo$(C_{1-6})$alkoxy-;

R$^6$ is
(1) $(C_{1-3})$alkyl,
(2) halo$(C_{1-3})$alkyl-,
(3) oxo,
(4) $(C_{3-6})$cycloalkyl,
(5) —C(O)O—$(C_{1-4})$alkyl,
(6) NH$_2$,
(7) hydroxy,
(8) phenyl unsubstituted or substituted by halo,
(9) hydroxy$(C_{1-3})$alkyl-,
(10) $(C_{1-6})$alkoxy-,
(11) halo$(C_{1-6})$alkoxy-,
(12) cyano, or
(13) halo;

R$^7$ is
(1) $(C_{1-6})$alkyl,
(2) halo,
(3) $(C_{1-3})$alkoxy-,
(4) halo$(C_{1-3})$alkyl-,
(5) $(C_{3-6})$cycloalkyl, or
(6) —C(O)O—$(C_{1-3})$alkyl;

R$^8$ is
(1) $(C_{1-3})$alkyl,
(2) hydroxy$(C_{1-3})$alkyl-,
(3) $(C_{1-3})$alkoxy-,
(4) hydroxy,
(5) halo$(C_{1-3})$alkyl-,
(6) $(C_{1-3})$alkyl-S—,
(7) —C(O)—NR$^{9a}$R$^{9b}$, or
(8) phenyl;

R$^{9a}$ and R$^{9b}$ are independently
(1) hydrogen,
(2) $(C_{1-3})$alkyl,
(3) —$(C_{1-3})$alkyl-phenyl,
(4) 5- or 6-membered heteroaryl containing 1, 2, or 3 heteroatoms independently selected from N, O, and S, or
(5) phenyl;

R$^{10a}$ and R$^{10b}$ are independently
(1) hydrogen, or
(2) $(C_{1-3})$alkyl.

9. The method according to claim 8 for treating non-alcoholic steatohepatitis.

* * * * *